(12) United States Patent
Dahmann et al.

(10) Patent No.: US 8,093,266 B2
(45) Date of Patent: Jan. 10, 2012

(54) RHO KINASE INHIBITORS

(75) Inventors: Georg Dahmann, Attenweiler (DE);
Eugene Richard Hickey, Danbury, CT (US); Xiang Li, Danbury, CT (US); Wang Mao, Milford, CT (US); Daniel R. Marshall, Sandy Hook, CT (US); Tina M. Morwick, New Milford, CT (US); Robert Sibley, North Haven, CT (US); Roger John Snow, Danbury, CT (US); Ronald J. Sorcek, Bethel, CT (US); Frank Wu, Ridgefield, CT (US); Erick Richard Roush Young, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 215 days.

(21) Appl. No.: 12/521,817

(22) PCT Filed: Jan. 2, 2008

(86) PCT No.: PCT/US2008/050014
§ 371 (c)(1),
(2), (4) Date: Aug. 10, 2009

(87) PCT Pub. No.: WO2008/086047
PCT Pub. Date: Jul. 17, 2008

(65) Prior Publication Data
US 2010/0041645 A1 Feb. 18, 2010

Related U.S. Application Data

(60) Provisional application No. 60/878,625, filed on Jan. 3, 2007.

(51) Int. Cl.
*A61K 31/472* (2006.01)
*A61K 31/4365* (2006.01)
*A61K 31/17* (2006.01)
*C07D 217/22* (2006.01)
*C07D 211/34* (2006.01)
*C07C 233/64* (2006.01)
*C07C 275/28* (2006.01)

(52) U.S. Cl. ............ 514/310; 514/302; 514/239.5; 514/596; 514/617; 546/143; 546/226; 564/161; 564/192

(58) Field of Classification Search ........ 514/239.5, 514/302, 596, 617, 310; 564/161, 192, 50; 546/143, 226
See application file for complete search history.

(56) References Cited

FOREIGN PATENT DOCUMENTS

| EP | 1256574 A1 | 11/2002 |
|---|---|---|
| EP | 1403255 A1 | 3/2004 |
| JP | 11130751 | 5/1999 |

OTHER PUBLICATIONS

Loirand et al. Circulation Research 2006, 98, 322-334-217.*
Tawara et al. Yakugaku Zasshi 2007, 127(3), Abstract, p. 501.*
Schafer et al. Drug Discovery Today 2008, 13 (21/22), 913-916.*
Horig et al. Journal of Translational Medicine 2004, 2(44).*
Lorthioir et al. Analytical Chemistry 2001, 73, 963-970.*
International Search Report, Form PCT/ISA/210, for corresponding PCT/US2008/050014, date of mailing: May 8, 2008.

* cited by examiner

*Primary Examiner* — Jason M Nolan
(74) *Attorney, Agent, or Firm* — Michael P. Morris; Edward S. Lazer

(57) ABSTRACT

Substituted amide and urea derivatives useful as inhibitors of Rho kinase are described, which inhibitors can be useful in the treatment of various disorders such as cardiovascular diseases, cancer, neurological diseases, renal diseases, bronchial asthma, erectile dysfunction and glaucoma.

11 Claims, No Drawings

RHO KINASE INHIBITORS

FIELD OF THE INVENTION

This invention relates to substituted amide and urea derivatives which are useful as inhibitors of Rho kinase and are thus useful for treating a variety of diseases and disorders that are mediated or sustained through the activity of Rho kinase, including cardiovascular diseases, cancer, neurological diseases, renal diseases, bronchial asthma, erectile dysfunction, and glaucoma. This invention also relates to pharmaceutical compositions comprising these compounds, methods of using these compounds in the treatment of various diseases and disorders, processes for preparing these compounds and intermediates useful in these processes.

BACKGROUND

Rho kinase (ROCK) is a member of the serine-threonine protein kinase family. ROCK exists in two isoforms, ROCK1 and ROCK2. ROCK has been identified as an effector molecule of RhoA, a small GTP-binding protein (G protein) that plays a key role in multiple cellular signaling pathways. ROCK and RhoA are ubiquitously expressed across tissues. The RhoA/ROCK signaling pathway is involved in a number of cellular functions, such as actin organization, cell adhesion, cell migration, and cytokinesis. It is also directly involved in regulating smooth muscle contraction. Upon activation of its receptor, RhoA is activated, and, in turn, it activates ROCK. Activated ROCK phosphorylates the myosin-binding subunit of myosin light chain phosphatase, which inhibits activity of the phosphatase and leads to contraction. Contraction of the smooth muscle in the vasculature increases blood pressure, leading to hypertension.

There is considerable evidence in the literature that the RhoA/ROCK signaling pathway plays an important role in signal transduction initiated by several vasoactive factors, for example angiotensin II, urotension II, endothelin-1, serotonin, norepinephrine and platelet-derived growth factor (PDGF). Many of these factors are implicated in the pathogenesis of cardiovascular disease.

Additional studies in the literature, some using the known ROCK inhibitors fasudil or Y-27632 further illustrate the link between ROCK and cardiovascular disease. For example, ROCK expression and activity have been shown to be elevated in spontaneously hypertensive rats, suggesting a link to the development of hypertension in these animals. The ROCK inhibitor Y-27632 was shown to significantly decrease blood pressure in three rat models of hypertension, including the spontaneously hypertensive rat, renal hypertensive rat and deoxycortisone acetate salt hypertensive rat models, while having only a minor effect on blood pressure in control rats. This reinforces the link between ROCK and hypertension.

Other studies suggest a link between ROCK and atherosclerosis. For example, gene transfer of a dominant negative form of ROCK suppressed neointimal formation following balloon injury in porcine femoral arteries. In a similar model, ROCK inhibitor Y-27632 also inhibited neointimal formation in rats. In a porcine model of IL-1 beta-induced coronary stenosis, long term treatment with the ROCK inhibitor fasudil was shown to progressively reduce coronary stenosis, as well as promote a regression of coronary constrictive remodeling.

Additional investigations suggest that a ROCK inhibitor would be useful in treating other cardiovascular diseases. For example, in a rat stroke model, fasudil was shown to reduce both the infarct size and neurologic deficit. The ROCK inhibitor Y-27632 was shown to improve ventricular hypertrophy and function in a model of congestive heart failure in Dahl salt-sensitive rats.

Other animal or clinical studies have implicated ROCK in additional diseases including coronary vasospasm, cerebral vasospasm, ischemia/reperfusion injury, pulmonary hypertension, angina, renal disease and erectile dysfunction.

In another study, it has been demonstrated that inhibition of the RhoA/ROCK signaling pathway allows formation of multiple competing lamellipodia that disrupt the productive migration of monocytes. It has also been reported that small molecule inhibitors of Rho kinase are capable of inhibiting MCP-1 mediated chemotaxis in vitro. Due to the dependence of immune cell migration upon the RhoA/ROCK signaling pathway one would anticipate inhibition of Rho kinase should also provide benefit for diseases such as rheumatoid arthritis, psoriasis, and inflammatory bowel disease.

The above studies provide evidence for a link between ROCK and cardiovascular diseases including hypertension, atherosclerosis, restenosis, stroke, heart failure, coronary vasospasm, cerebral vasospasm, ischemia/reperfusion injury, pulmonary hypertension and angina, as well as renal disease and erectile dysfunction. Given the demonstrated effect of ROCK on smooth muscle, ROCK inhibitors may also be useful in other diseases involving smooth muscle hyper-reactivity, including asthma and glaucoma. Furthermore, Rho kinase has been indicated as a drug target for the treatment of various other diseases, including airway inflammation and hyperresponsiveness, cancer, as well as neurological disorders, such as spinal-cord injury, Alzheimer disease, multiple sclerosis, stroke and neuropathic pain.

There remains an unmet medical need for new drugs to treat cardiovascular disease. A study published in 2003 estimated that almost 29% of the adult U.S. population had hypertension in 1999-2000 (I. Hajjar et al., JAMA, 2003, 290, 199-206). Furthermore, 69% of the hypertensive individuals studied during this period did not have their hypertension controlled at the time their blood pressure was measured. This figure was worse in patients with diabetes and hypertension where 75% of those patients studied did not have their blood pressure controlled to the target level. Another more recent study showed similar results, with less than one-third of hypertensive patients studied having blood pressure controlled to the target level (V. Andros, Am. J. Manag. Care, 2005, 11, S215-S219). Therefore, despite the number of medications available to treat hypertension, including diuretics, beta blockers, angiotensin converting enzyme inhibitors, angiotensin blockers and calcium channel blockers, hypertension remains poorly controlled or resistant to current medication for many patients. If not adequately treated, hypertension can lead to other cardiovascular diseases and organ failure including coronary artery disease, stroke, myocardial infarction, cardiac failure, renal failure and peripheral artery disease.

Although there are many reports of ROCK inhibitors under investigation, fasudil is the only marketed ROCK inhibitor at this time. An i.v. formulation was approved in Japan for treatment of cerebral vasospasm. There remains a need for new therapeutics, including ROCK inhibitors, for the treatment of cardiovascular diseases, cancer, neurological diseases, renal diseases, bronchial asthma, erectile dysfunction, and glaucoma.

BRIEF SUMMARY OF THE INVENTION

In a general aspect, the present invention is directed to the compounds of the formula I:

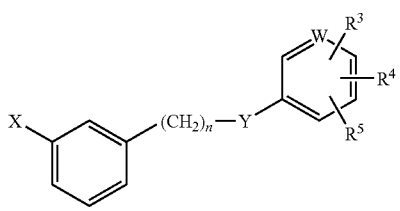

wherein X, Y, n, and $R^3$-$R^5$ are as defined herein, as well as the tautomers, pharmaceutically acceptable salts and solvates thereof. It has been found that the compounds of formula I have valuable pharmacological properties, particularly on inhibiting activity on Rho kinase.

In another aspect, the present invention is directed to a method of inhibiting Rho kinase activity in a patient comprising administering to the patient a compound of the present invention as described above.

In another aspect, the present invention is directed to a method for treating a disease or disorder associated with the activation of Rho kinase which method comprises administering to a patient in need of such treatment a compound of the present invention as described above.

In another aspect, the present invention is directed to a method of treating a cardiovascular or related disease which method comprises administering to a patient in need of such treatment a compound of the present invention as described above. Examples of such diseases that may be treated include, for example, hypertension, atherosclerosis, restenosis, stroke, heart failure, cardiac failure, renal failure, coronary artery disease, peripheral artery disease, coronary vasospasm, cerebral vasospasm, ischemia/reperfusion injury, pulmonary hypertension, angina, erectile dysfunction and renal disease.

In another aspect, the present invention is directed to a method of treating diseases involving smooth muscle hyper reactivity including asthma and glaucoma, which method comprises administering to a patient in need of such treatment a compound of the present invention as described above.

In another aspect, the present invention is directed to a method of treating diseases mediated at least partially by Rho kinase including spinal-cord injury, Alzheimer's disease, multiple sclerosis, stroke, neuropathic pain, rheumatoid arthritis, psoriasis and inflammatory bowel disease, which method comprises administering to a patient in need of such treatment a compound of the present invention as described above.

In yet additional aspects, the present invention is directed at pharmaceutical compositions comprising the above-mentioned compounds, processes for preparing the above-mentioned compounds and intermediates used in these processes.

DETAILED DESCRIPTION OF THE INVENTION

In one embodiment, there are compounds of the formula I

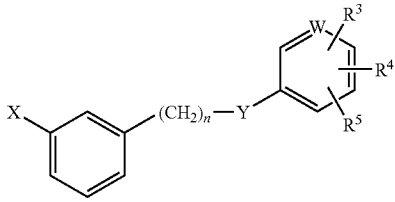

wherein:

X is —C(O)NR$^1$R$^2$ or —NHC(O)R$^1$;
Y is —N(R$^8$)C(O)NR$^9$—, —N(R$^8$)C(O)— or —C(O)N(R$^8$)—;
W is C or N;
n is 1 or 2;
R$^1$ is selected from:

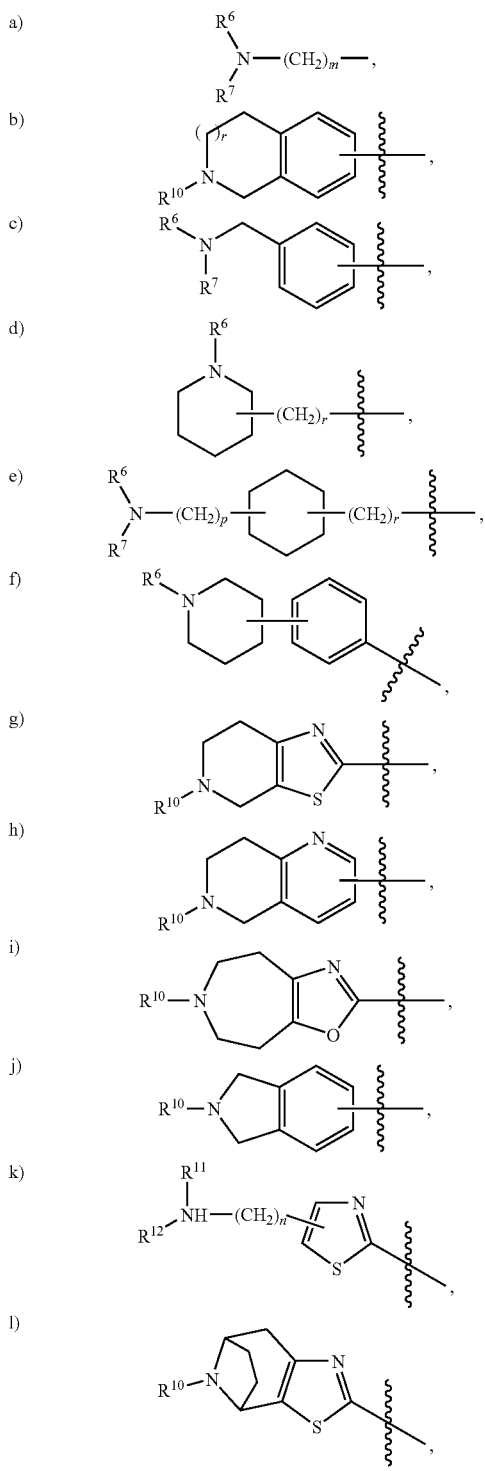

-continued

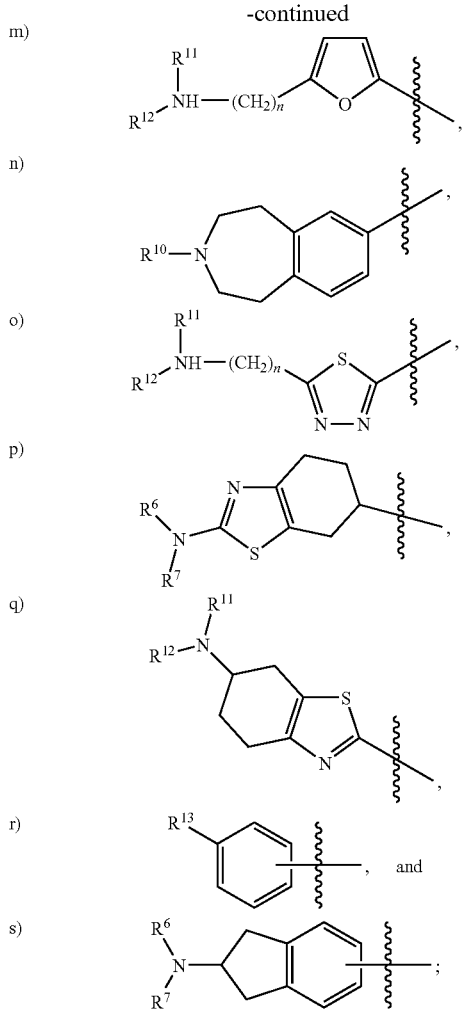

m)
n)
o)
p)
q)
r) and
s)

$R^2$ is selected from H, $C_{1-6}$alkyl and methoxy$C_{2-4}$alkyl;
$R^3$, $R^4$, and $R^5$ are independently selected from:
H, $C_{1-6}$alkyl, $C_{2-6}$alkenyl, $C_{2-6}$alkynyl, $C_{1-6}$alkoxy, $C_{1-6}$alkoxy$C_{1-6}$alkyl, Cl, F, Br, —CN, —CH$_2$CN, —CF$_3$, —OCHF$_2$, —OCF$_3$, —C(O)NH$_2$, —C(O)C$_{1-3}$alkyl, —NHC(O)NH$_2$, and —SC$_{1-3}$alkyl; or
$R^3$ and $R^4$, together with the benzene ring they are bonded to, form a quinoline ring;
$R^6$ and $R^7$ are independently selected from H and $C_{1-6}$alkyl;
$R^8$ and $R^9$ are independently selected from H, $C_{1-3}$alkyl and benzyl;
$R^{10}$ is selected from H, $C_{1-6}$alkyl, —CH$_2$pyridyl, —CH$_2$CO$_2$C$_{1-4}$alkyl, —CH$_2$C(O)NH$_2$, —CH$_2$CH$_2$OC$_{1-4}$alkyl, —CH$_2$CH$_2$CN, —CH$_2$CHF$_2$, —(CH$_2$)$_{1-2}$CF$_3$, —CH$_2$CH$_2$F, —CH(CO$_2$Me)CH$_2$CO$_2$C$_{1-4}$alkyl, and benzyl wherein said benzyl group is optionally substituted with one to two groups selected from $R^3$ and $R^4$;
$R^{11}$ and $R^{12}$ are independently selected from H and $C_{1-6}$alkyl; or $R^{11}$ and $R^{12}$, together with the nitrogen they are attached to, form a morpholine ring, a 4-methyl-1-piperazinyl ring, a thiomorpholine ring, optionally with a dioxo substituent at the sulfur atom, or a 1,3-dihydroisoindole ring;
$R^{13}$ is selected from —(CH$_2$)$_r$N(R$^6$)(R$^7$), —OCH$_2$CH$_2$(4-morpholinyl), —CH$_2$CH$_2$(1-pyrrolidinyl), —CH$_2$(1-pyrazolyl) and —CH$_2$-(5-methyl-4H-[1,2,4]triazol-3-yl);
m is 3-6;
r is 0-2; and
p is 0-1;

with the proviso that if Y=—C(O)NR$^8$— and n=1, then X is not —C(O)NR$^1$R$^2$ and if Y is —N(R$^8$)C(O)NR$^9$—, then n is not 2.

In another embodiment there are compounds of formula (I) wherein:
X is —C(O)NR$^1$R$^2$ or —NHC(O)R$^1$;
Y is —N(R$^8$)C(O)NR$^9$—, —N(R$^8$)C(O)— or —C(O)N(R$^8$)—;
W is C;
n is 1 or 2;
$R^1$ is selected from:

a) 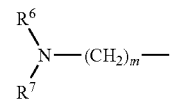

b) 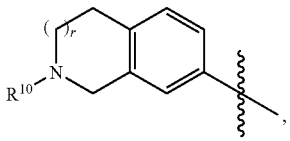

c) 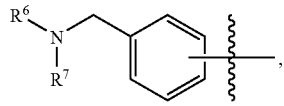

d) 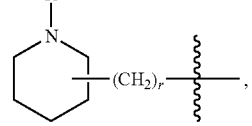

e) 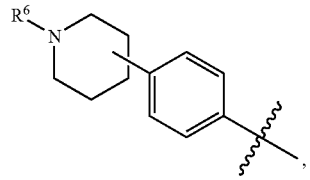

f) 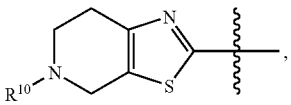

g) 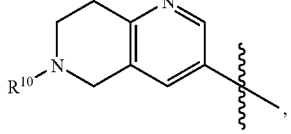

h) 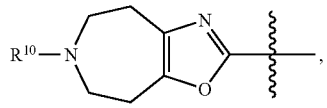

i) 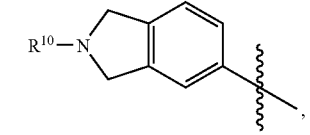

j) 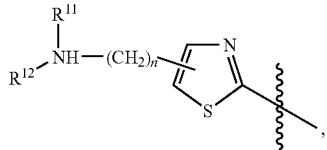

k) 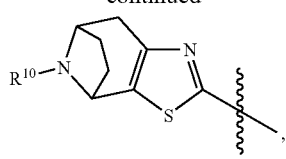

l) 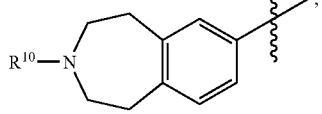

m) 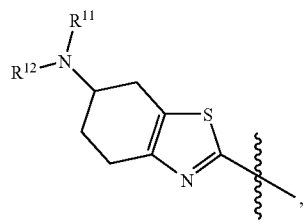

n) 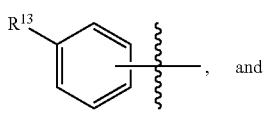, and o) 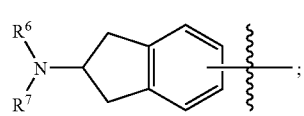;

$R^2$ is H;

$R^3$, $R^4$, and $R^5$ are independently selected from:
H, $C_{1-6}$alkyl, $C_{2-6}$alkenyl, $C_{2-6}$alkynyl, $C_{1-6}$alkoxy, $C_{1-6}$alkoxy$C_{1-6}$alkyl, Cl, F, Br, —CN, —CH$_2$CN, —CF$_3$, —OCHF$_2$, —OCF$_3$, —C(O)NH$_2$, —C(O)C$_{1-3}$alkyl, —NHC(O)NH$_2$, and —SC$_{1-3}$alkyl;

$R^6$ and $R^7$ are independently selected from H and $C_{1-6}$alkyl, or $R^6$ and $R^7$, together with the nitrogen to which they are bound, may form a morpholine ring;

$R^8$ and $R^9$ are H;

$R^{10}$ is selected from H, $C_{1-6}$alkyl, —CH$_2$pyridyl, —CH$_2$CO$_2$C$_{1-4}$alkyl, —CH$_2$C(O)NH$_2$, —CH$_2$CH$_2$OC$_{1-4}$alkyl, —CH$_2$CH$_2$CN, —CH$_2$CHF$_2$, —(CH$_2$)$_{1-2}$CF$_3$, —CH$_2$CH$_2$F, —CH(CO$_2$Me)CH$_2$CO$_2$C$_{1-4}$alkyl, and benzyl wherein said benzyl group is optionally substituted with one to two groups selected from $R^3$ and $R^4$;

$R^{11}$ and $R^{12}$ are independently selected from H and $C_{1-6}$alkyl; or $R^{11}$ and $R^{12}$, together with the nitrogen they are attached to, form a morpholine ring, a 4-methyl-1-piperazinyl ring, a thiomorpholine ring, optionally with a dioxo substituent at the sulfur atom, or a 1,3-dihydroisoindole ring;

$R^{13}$ is selected from —(CH$_2$)$_n$N(R$^6$)(R$^7$), —CH$_2$CH$_2$(1-pyrrolidinyl), —CH$_2$(1-pyrazolyl) and —CH$_2$-(5-methyl-4H-[1,2,4]triazol-3-yl);

m is 3-6; and
r is 0-2;
with the proviso that if Y═—C(O)NR$^8$— and n=1, then X is not —C(O)NR$^1$R$^2$ and if Y is —N(R$^8$)C(O)NR$^9$—, then n is not 2.

In a further embodiment there are compounds of formula (I) wherein:
X is —C(O)NR$^1$R$^2$ or —NHC(O)R$^1$;
Y is —N(R$^8$)C(O)NR$^9$—, —N(R$^8$)C(O)— or —C(O)N(R$^8$)—;
W is C;
n is 1 or 2;
$R^1$ is selected from:

a) 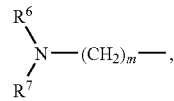

b) 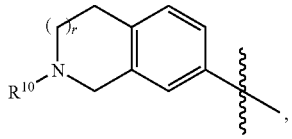

c) 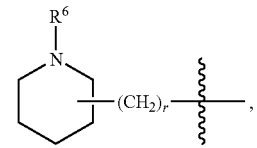

d) 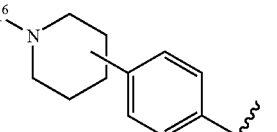

e) 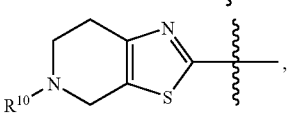

f) 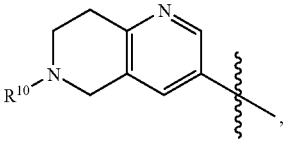

g) 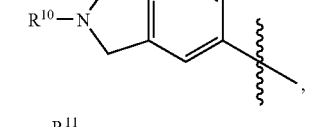

h) 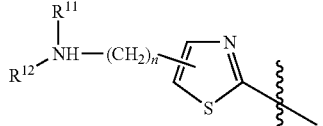

i) 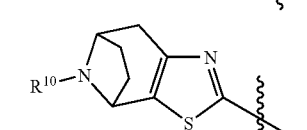

j) 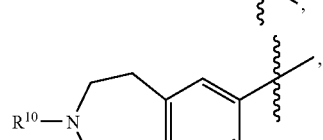

k) 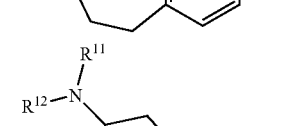

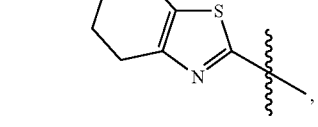

l) 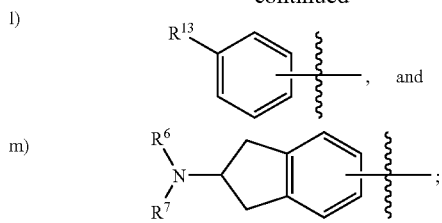, and m) 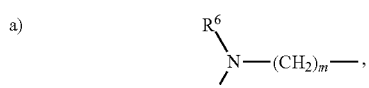;

$R^2$ is H;

$R^3$, $R^4$, and $R^5$ are independently selected from:
H, $C_{1-6}$alkyl, $C_{2-6}$alkenyl, $C_{2-6}$alkynyl, $C_{1-6}$alkoxy, $C_{1-6}$alkoxy$C_{1-6}$alkyl, Cl, F, Br, —CN, —CH$_2$CN, —CF$_3$, —OCHF$_2$, —OCF$_3$, —C(O)NH$_2$, —C(O)C$_{1-3}$alkyl, —NHC(O)NH$_2$, and —SC$_{1-3}$alkyl;

$R^6$ and $R^7$ are independently selected from H and $C_{1-6}$alkyl;

$R^8$ and $R^9$ are H;

$R^{10}$ is selected from H, $C_{1-6}$alkyl, —CH$_2$pyridyl, —CH$_2$CO$_2$C$_{1-4}$alkyl, —CH$_2$C(O)NH$_2$, —CH$_2$CH$_2$OC$_{1-4}$alkyl, —CH$_2$CH$_2$CN, —CH$_2$CHF$_2$, —(CH$_2$)$_{1-2}$CF$_3$, —CH$_2$CH$_2$F, —CH(CO$_2$Me)CH$_2$CO$_2$C$_{1-4}$alkyl, and benzyl wherein said benzyl group is optionally substituted with one to two groups selected from $R^3$ and $R^4$;

$R^{11}$ and $R^{12}$ are independently selected from H and $C_{1-6}$alkyl; or $R^{11}$ and $R^{12}$, together with the nitrogen they are attached to, form a morpholine ring, a 4-methyl-1-piperazinyl ring, a thiomorpholine ring, optionally with a dioxo substituent at the sulfur atom, or a 1,3-dihydroisoindole ring;

$R^{13}$ is selected from —OCH$_2$CH$_2$(4-morpholinyl), —CH$_2$CH$_2$(1-pyrrolidinyl), —CH$_2$(1-pyrazolyl) and —CH$_2$-(5-methyl-4H-[1,2,4]triazol-3-yl);

m is 3-6; and r is 0-2;

with the proviso that if Y=—C(O)NR$^8$— and n=1, then X is not —C(O)NR$^1$R$^2$ and if Y is —N(R$^8$)C(O)NR$^9$—, then n is not 2.

In an additional embodiment there are compounds of formula (I) wherein:

X is —C(O)NR$^1$R$^2$ or —NHC(O)R$^1$;

Y is —N(R$^8$)C(O)NR$^9$—, —N(R$^8$)C(O)— or —C(O)N(R$^8$)—;

W is C;

n is 1 or 2;

$R^1$ is selected from:

a) 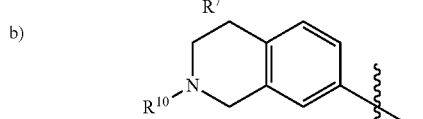

b) 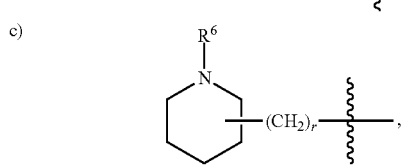, c)

d) 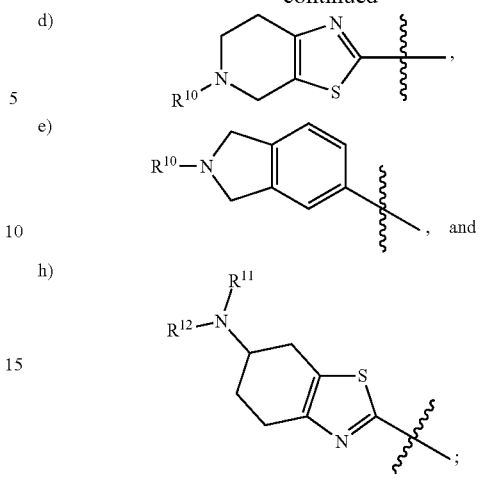, e) , and h)

$R^2$ is H;

$R^3$, $R^4$, and $R^5$ are independently selected from:
H, $C_{1-6}$alkyl, $C_{2-6}$alkenyl, $C_{2-6}$alkynyl, $C_{1-6}$alkoxy, $C_{1-6}$alkoxy$C_{1-6}$alkyl, Cl, F, Br, —CN, —CH$_2$CN, —CF$_3$, —OCHF$_2$, —OCF$_3$, —C(O)NH$_2$, —C(O)C$_{1-3}$alkyl, —NHC(O)NH$_2$, and —SC$_{1-3}$alkyl;

$R^6$ and $R^7$ are independently selected from H and $C_{1-6}$alkyl;

$R^3$ and $R^9$ are H;

$R^{10}$ is selected from H, $C_{1-6}$alkyl, —CH$_2$pyridyl, —CH$_2$CO$_2$C$_{1-4}$alkyl, —CH$_2$C(O)NH$_2$, —CH$_2$CH$_2$OC$_{1-4}$alkyl, —CH$_2$CH$_2$CN, —CH$_2$CHF$_2$, —(CH$_2$)$_{1-2}$CF$_3$, —CH$_2$CH$_2$F, —CH(CO$_2$Me)CH$_2$CO$_2$C$_{1-4}$alkyl, and benzyl wherein said benzyl group is optionally substituted with one to two groups selected from $R^3$ and $R^4$;

$R^{11}$ and $R^{12}$ are independently selected from H and $C_{1-6}$alkyl; or $R^{11}$ and $R^{12}$, together with the nitrogen they are attached to, form a morpholine ring, a 4-methyl-1-piperazinyl ring, a thiomorpholine ring, optionally with a dioxo substituent at the sulfur atom, or a 1,3-dihydroisoindole ring;

$R^{13}$ is selected from —OCH$_2$CH$_2$(4-morpholinyl), —CH$_2$CH$_2$(1-pyrrolidinyl), —CH$_2$(1-pyrazolyl) and —CH$_2$-(5-methyl-4H-[1,2,4]triazol-3-yl);

m is 3-6; and r is 0-2;

with the proviso that if Y=—C(O)NR$^8$— and n=1, then X is not —C(O)NR$^1$R$^2$ and if Y is —N(R$^8$)C(O)NR$^9$—, then n is not 2.

In another embodiment there are compounds of formula (I) wherein:

X is —C(O)NR$^1$R$^2$;

Y is —NHC(O)—;

W is C;

n is 1;

$R^1$ is

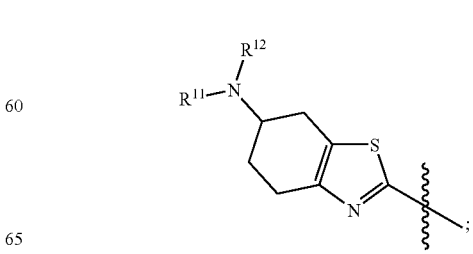;

$R^2$ is H;

$R^3$, $R^4$, and $R^5$ are independently selected from:
H, $C_{1-6}$alkyl, $C_{2-6}$alkenyl, $C_{2-6}$alkynyl, $C_{1-6}$alkoxy, $C_{1-6}$alkoxy$C_{1-6}$alkyl, Cl, F, Br, —CN, —CH$_2$CN, —CF$_3$, —OCHF$_2$, —OCF$_3$, —C(O)NH$_2$, —C(O)C$_{1-3}$alkyl, —NHC(O)NH$_2$, and —SC$_{1-3}$alkyl; and $R^{11}$ and $R^{12}$ are independently selected from H and $C_{1-6}$alkyl; or $R^{11}$ and $R^{12}$, together with the nitrogen they are attached to, form a morpholine ring, a 4-methyl-1-piperazinyl ring, a thiomorpholine ring, optionally with a dioxo substituent at the sulfur atom, or a 1,3-dihydroisoindole ring.

In still a further embodiment of the invention, there are compounds of the formula (I) selected from the group below, or a tautomer or a salt thereof, including preferably a pharmaceutically acceptable salt thereof:

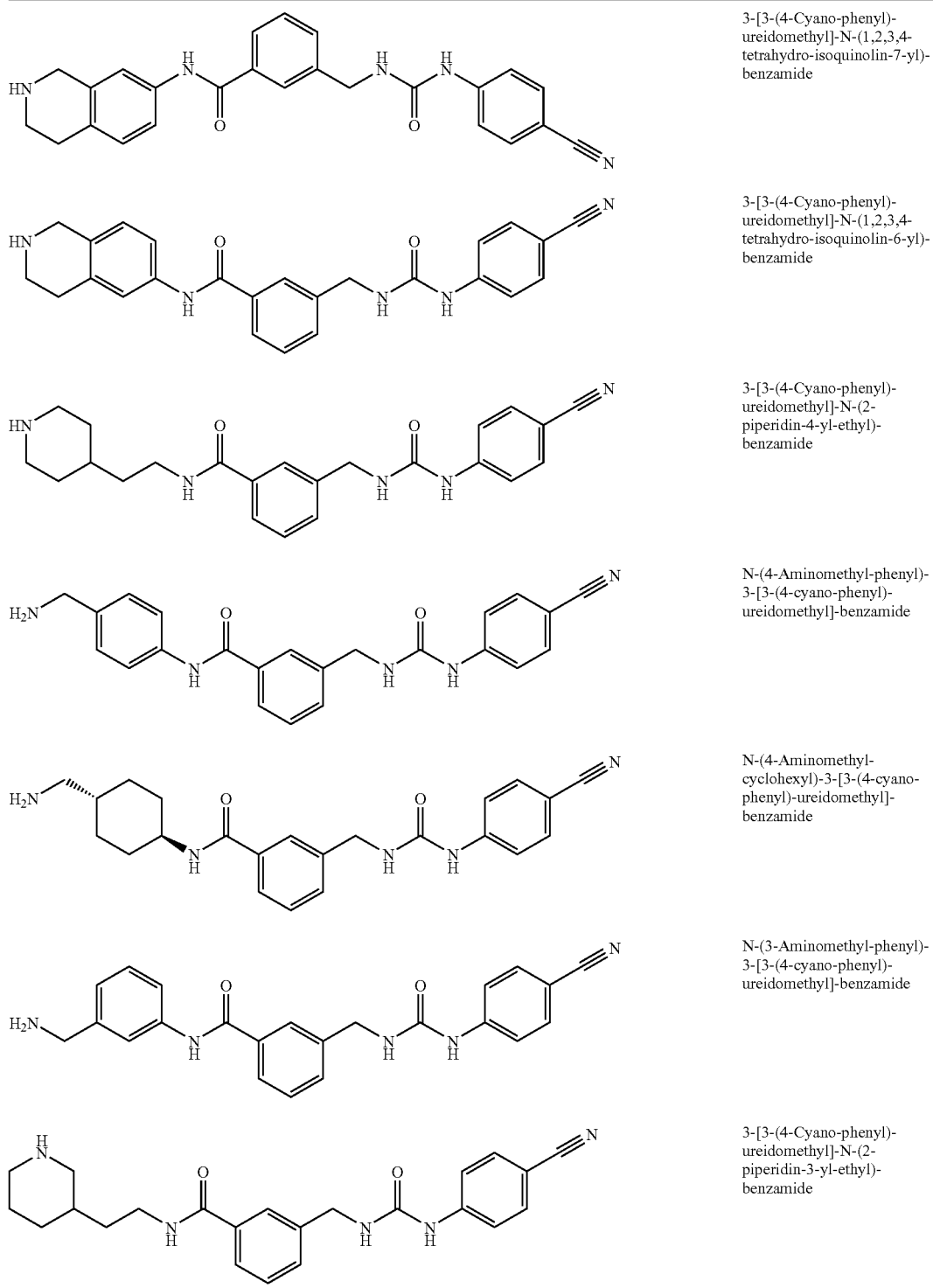

3-[3-(4-Cyano-phenyl)-ureidomethyl]-N-(1,2,3,4-tetrahydro-isoquinolin-7-yl)-benzamide 3-[3-(4-Cyano-phenyl)-ureidomethyl]-N-(1,2,3,4-tetrahydro-isoquinolin-6-yl)-benzamide 3-[3-(4-Cyano-phenyl)-ureidomethyl]-N-(2-piperidin-4-yl-ethyl)-benzamide N-(4-Aminomethyl-phenyl)-3-[3-(4-cyano-phenyl)-ureidomethyl]-benzamide N-(4-Aminomethyl-cyclohexyl)-3-[3-(4-cyano-phenyl)-ureidomethyl]-benzamide N-(3-Aminomethyl-phenyl)-3-[3-(4-cyano-phenyl)-ureidomethyl]-benzamide 3-[3-(4-Cyano-phenyl)-ureidomethyl]-N-(2-piperidin-3-yl-ethyl)-benzamide -continued

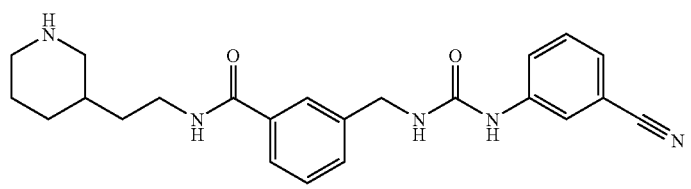
3-[3-(3-Cyano-phenyl)-ureidomethyl]-N-(2-piperidin-3-yl-ethyl)-benzamide

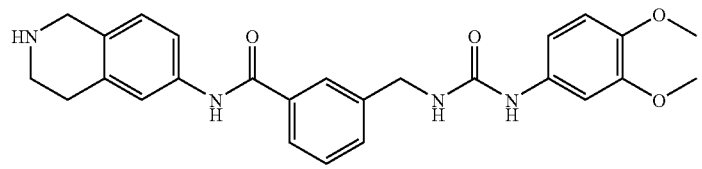
3-[3-(3,4-Dimethoxy-phenyl)-ureidomethyl]-N-(1,2,3,4-tetrahydro-isoquinolin-6-yl)-benzamide

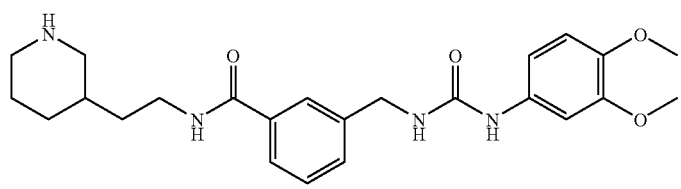
3-[3-(3,4-Dimethoxy-phenyl)-ureidomethyl]-N-(2-piperidin-3-yl-ethyl)-benzamide

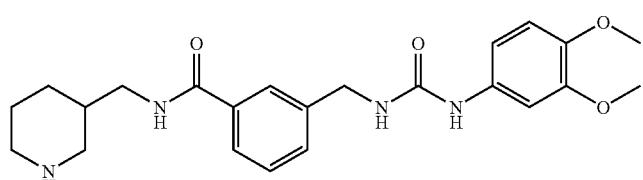
3-[3-(3,4-Dimethoxy-phenyl)-ureidomethyl]-N-piperidin-3-ylmethyl-benzamide

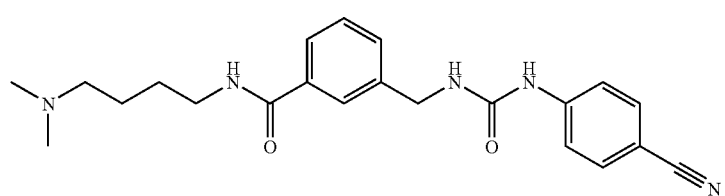
3-[3-(4-Cyano-phenyl)-ureidomethyl]-N-(4-dimethylamino-butyl)-benzamide

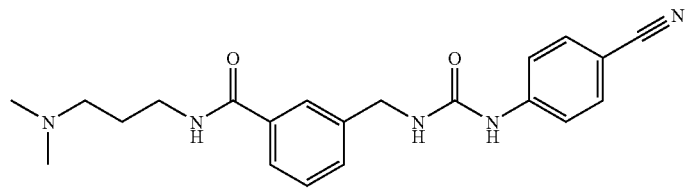
3-[3-(4-Cyano-phenyl)-ureidomethyl]-N-(3-dimethylamino-propyl)-benzamide

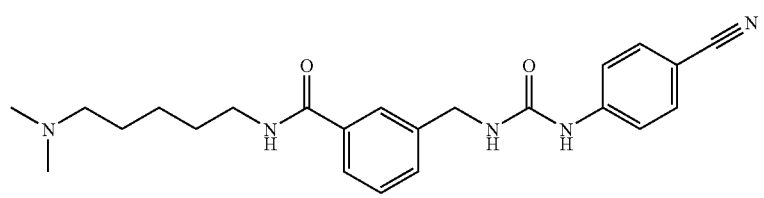
3-[3-(4-Cyano-phenyl)-ureidomethyl]-N-(5-dimethylamino-pentyl)-benzamide

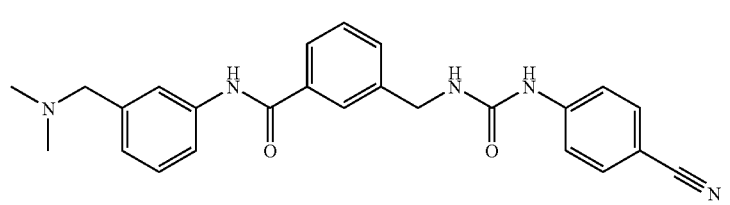
3-[3-(4-Cyano-phenyl)-ureidomethyl]-N-(3-dimethylaminomethyl-phenyl)-benzamide

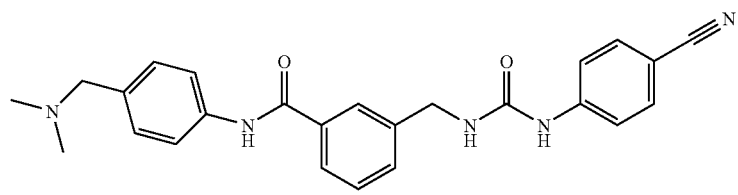
3-[3-(4-Cyano-phenyl)-ureidomethyl]-N-(4-dimethylaminomethyl-phenyl)-benzamide

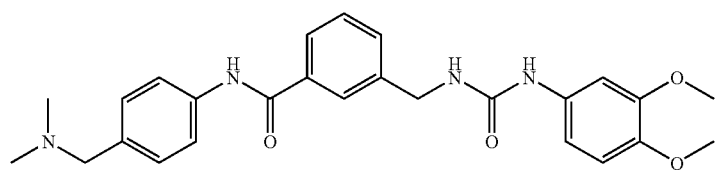
3-[3-(3,4-Dimethoxy-phenyl)-ureidomethyl]-N-(4-dimethylaminomethyl-phenyl)-benzamide

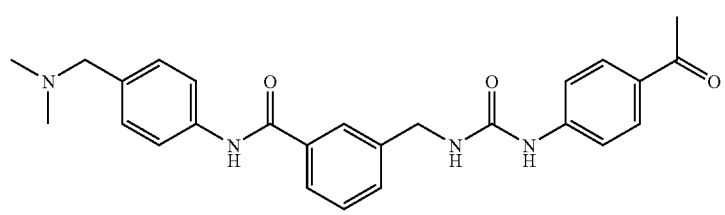
3-[3-(4-Acetyl-phenyl)-ureidomethyl]-N-(4-dimethylaminomethyl-phenyl)-benzamide

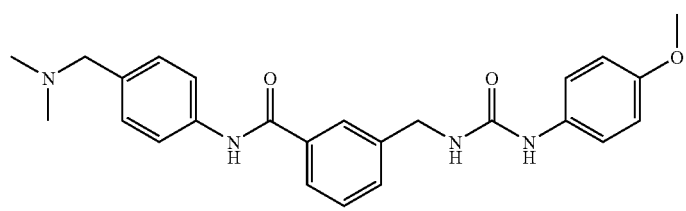
N-(4-Dimethylaminomethyl-phenyl)-3-[3-(4-methoxy-phenyl)-ureidomethyl]-benzamide

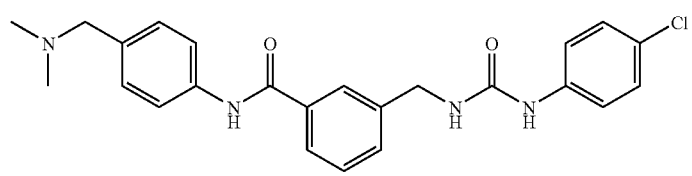
3-[3-(4-Chloro-phenyl)-ureidomethyl]-N-(4-dimethylaminomethyl-phenyl)-benzamide

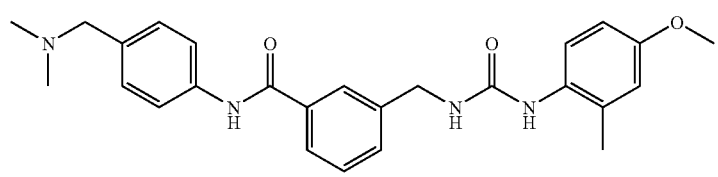
N-(4-Dimethylaminomethyl-phenyl)-3-[3-(4-methoxy-2-methyl-phenyl)-ureidomethyl]-benzamide

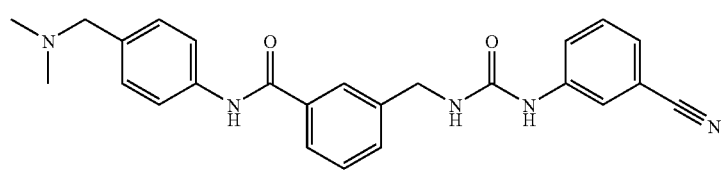
3-[3-(3-Cyano-phenyl)-ureidomethyl]-N-(4-dimethylaminomethyl-phenyl)-benzamide

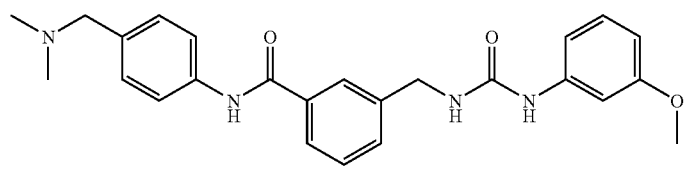
N-(4-Dimethylaminomethyl-phenyl)-3-[3-(3-methoxy-phenyl)-ureidomethyl]-benzamide -continued

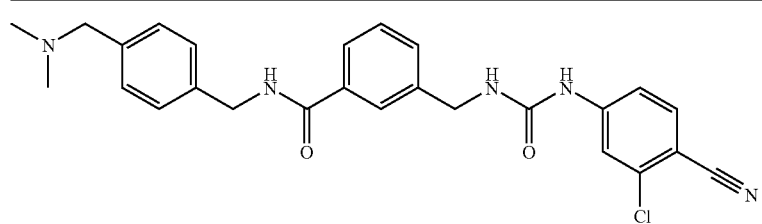 3-[3-(3-Chloro-4-cyano-phenyl)-ureidomethyl]-N-(3-dimethylaminomethyl-benzyl)-benzamide

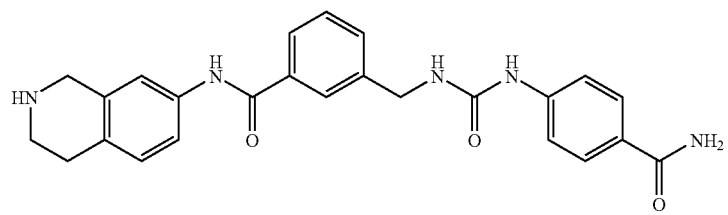 3-[3-(4-Amido-phenyl)-ureidomethyl]-N-(1,2,3,4-tetrahydro-isoquinolin-7-yl)-benzamide

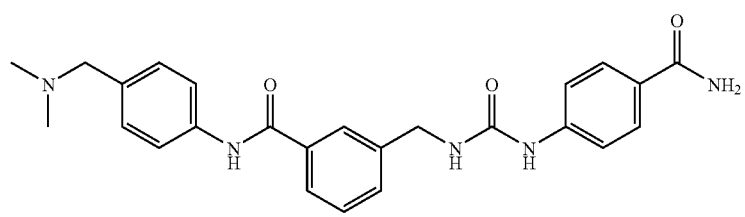 3-[3-(4-Amido-phenyl)-ureidomethyl]-N-(4-dimethylaminomethyl-phenyl)-benzamide

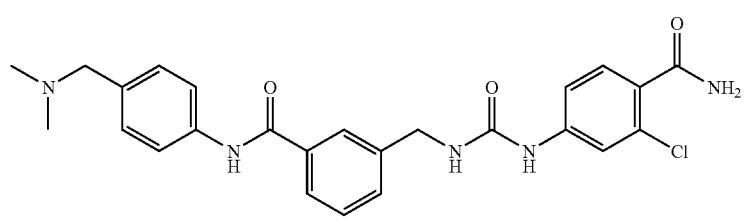 3-[3-(3-Chloro-4-amido-phenyl)-ureidomethyl]-N-(4-dimethylaminomethyl-phenyl)-benzamide

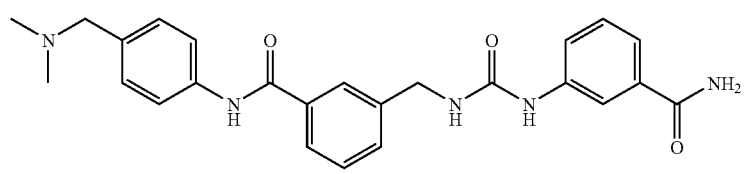 3-[3-(3-Amido-phenyl)-ureidomethyl]-N-(4-dimethylaminomethyl-phenyl)-benzamide

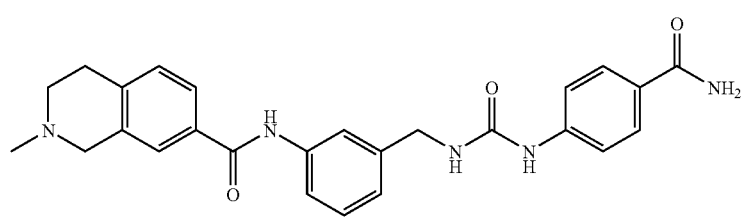 2-Methyl-1,2,3,4-tetrahydro-isoquinoline-7-carboxylic acid {3-[3-(4-amido-phenyl)-ureidomethyl]-phenyl}-amide

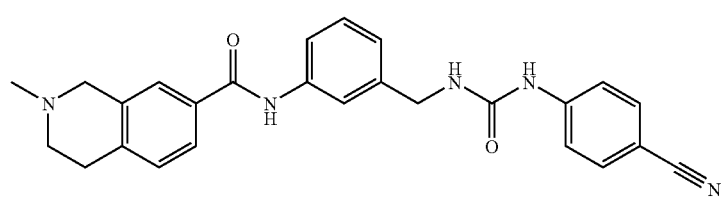 2-Methyl-1,2,3,4-tetrahydro-isoquinoline-7-carboxylic acid {3-[3-(4-cyano-phenyl)-ureidomethyl]-phenyl}-amide -continued

| | |
|---|---|
| 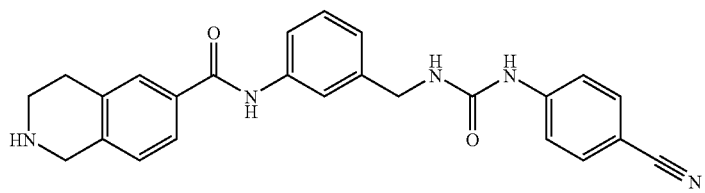 | 1,2,3,4-Tetrahydro-isoquinoline-6-carboxylic acid {3-[3-(4-cyano-phenyl)-ureidomethyl]-phenyl}-amide |
| 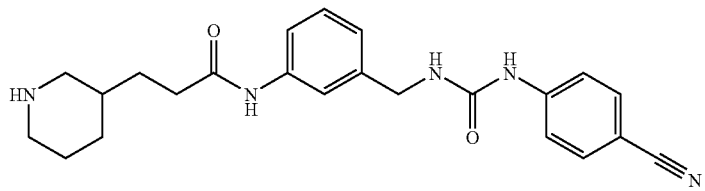 | N-{3-[3-(4-Cyano-phenyl)-ureidomethyl]-phenyl}-3-piperidin-3-yl-propionamide |
| 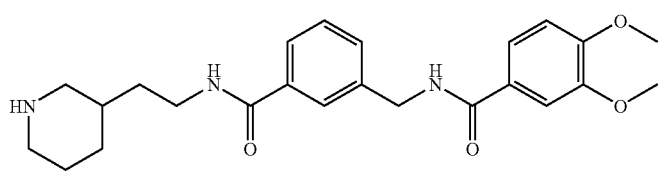 | 3,4-Dimethoxy-N-[3-(2-piperidin-3-yl-ethylcarbamoyl)-benzyl]-benzamide |
| 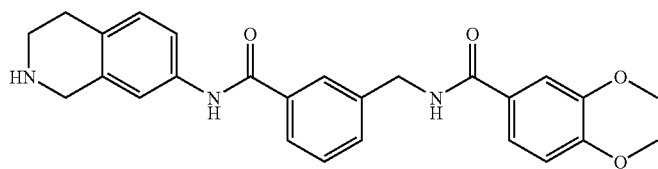 | 3,4-Dimethoxy-N-[3-(1,2,3,4-tetrahydro-isoquinolin-7-ylcarbamoyl)-benzyl]-benzamide |
| 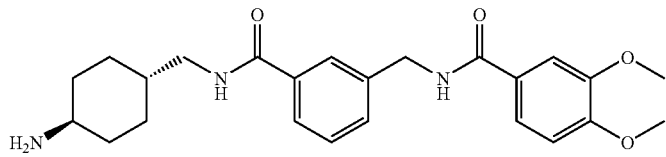 | N-{3-[(4-Amino-cyclohexylmethyl)-carbamoyl]-benzyl}-3,4-dimethoxy-benzamide |
| 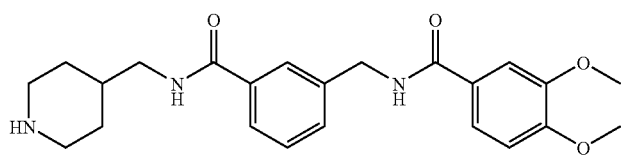 | 3,4-Dimethoxy-N-{3-[(piperidin-4-ylmethyl)-carbamoyl]-benzyl}-benzamide |
| 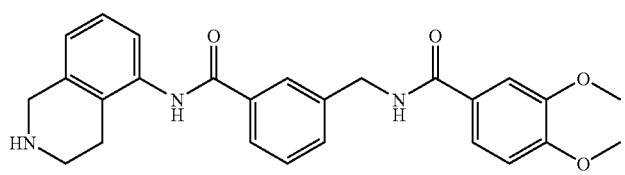 | 3,4-Dimethoxy-N-[3-(1,2,3,4-tetrahydro-isoquinolin-5-ylcarbamoyl)-benzyl]-benzamide |
| 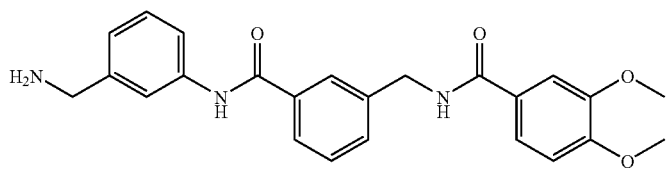 | N-[3-(3-Aminomethyl-phenylcarbamoyl)-benzyl]-3,4-dimethoxy-benzamide |
| 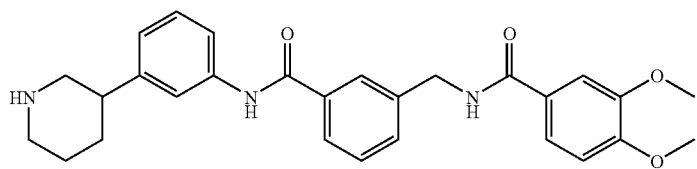 | 3,4-Dimethoxy-N-[3-(3-piperidin-3-yl-phenylcarbamoyl)-benzyl]-benzamide |

-continued

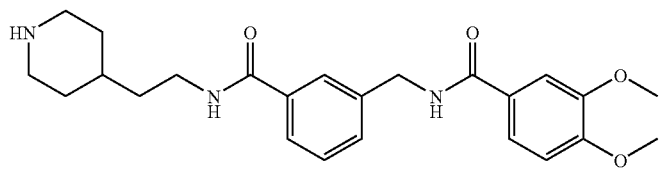

3,4-Dimethoxy-N-[3-(2-piperidin-4-yl-ethylcarbamoyl)-benzyl]-benzamide

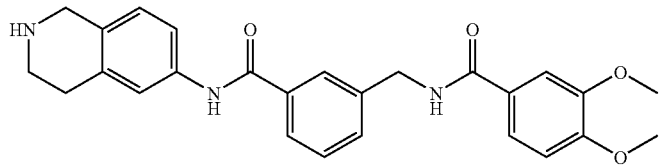

3,4-Dimethoxy-N-[3-(1,2,3,4-tetrahydro-isoquinolin-6-ylcarbamoyl)-benzyl]-benzamide

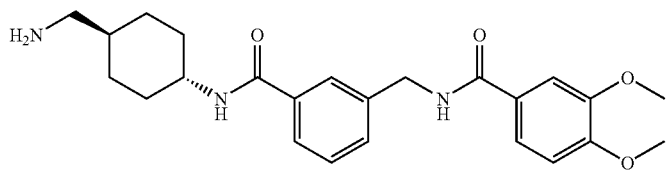

N-[3-(4-Aminomethyl-cyclohexylcarbamoyl)-benzyl]-3,4-dimethoxy-benzamide

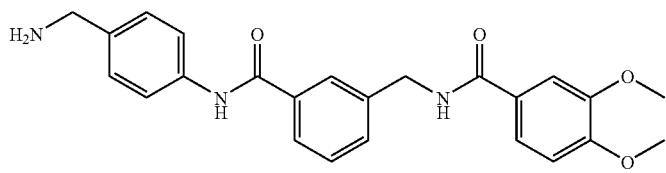

N-[3-(4-Aminomethyl-phenylcarbamoyl)-benzyl]-3,4-dimethoxy-benzamide

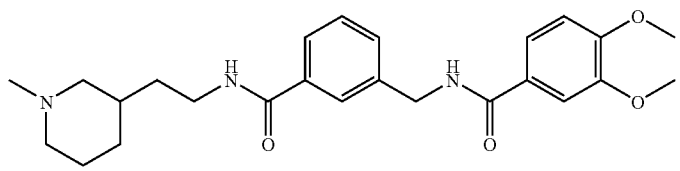

3,4-Dimethoxy-N-{3-[2-(1-methyl-piperidin-3-yl)-ethylcarbamoyl]-benzyl}-benzamide

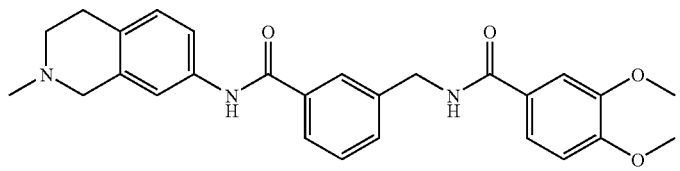

3,4-Dimethoxy-N-[3-(2-methyl-1,2,3,4-tetrahydro-isoquinolin-7-ylcarbamoyl)-benzyl]-benzamide

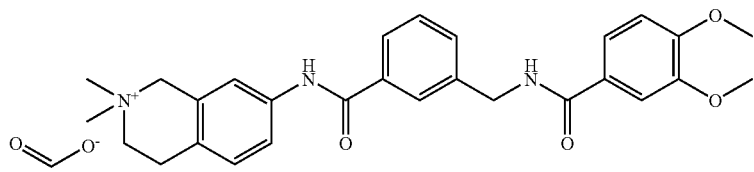

7-{3-[(3,4-dimethoxy-benzoylamino)-methyl]-benzoylamino}-2,2-dimethyl-1,2,3,4-tetrahydro-isoquinolinium formate

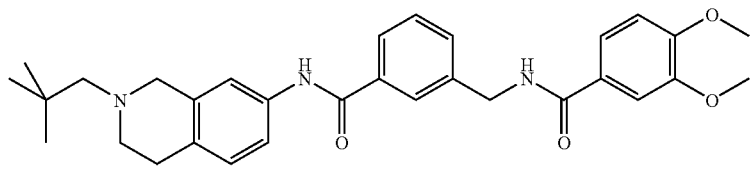

N-{3-[2-(2,2-Dimethyl-propyl)-1,2,3,4-tetrahydro-isoquinolin-7-ylcarbamoyl]-benzyl}-3,4-dimethoxy-benzamide

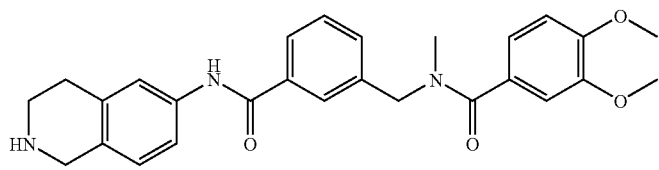

3,4-Dimethoxy-N-methyl-N-[3-(1,2,3,4-tetrahydro-isoquinolin-6-ylcarbamoyl)-benzyl]-benzamide -continued

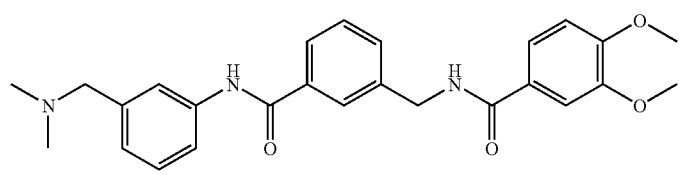

N-[3-(3-Dimethylaminomethyl-phenylcarbamoyl)-benzyl]-3,4-dimethoxy-benzamide

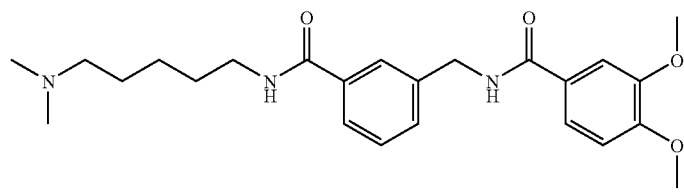

N-[3-(5-Dimethylamino-pentylcarbamoyl)-benzyl]-3,4-dimethoxy-benzamide

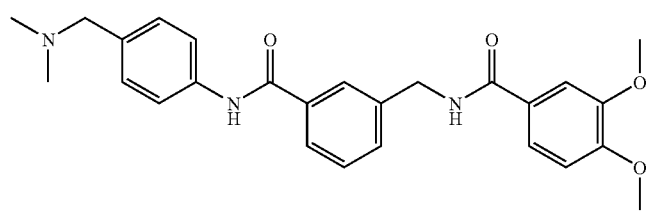

N-[3-(4-Dimethylaminomethyl-phenylcarbamoyl)-benzyl]-3,4-dimethoxy-benzamide

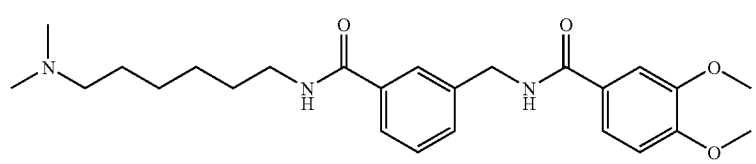

N-[3-(6-Dimethylamino-hexylcarbamoyl)-benzyl]-3,4-dimethoxy-benzamide

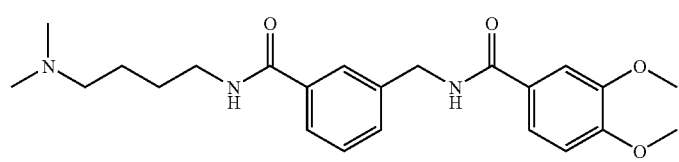

N-[3-(4-Dimethylamino-butylcarbamoyl)-benzyl]-3,4-dimethoxy-benzamide

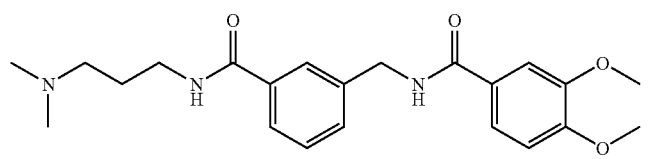

N-[3-(3-Dimethylamino-propylcarbamoyl)-benzyl]-3,4-dimethoxy-benzamide

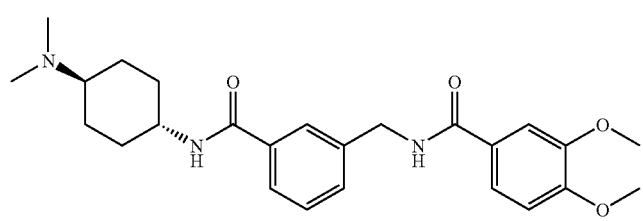

N-[3-(4-Dimethylamino-cyclohexylcarbamoyl)-benzyl]-3,4-dimethoxy-benzamide

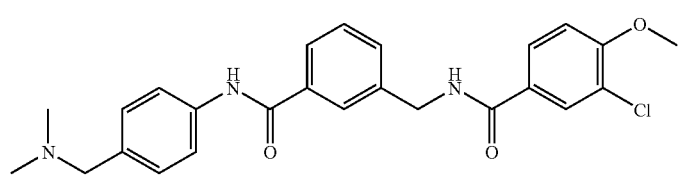

3-Chloro-N-[3-(4-dimethylaminomethyl-phenylcarbamoyl)-benzyl]-4-methoxy-benzamide -continued

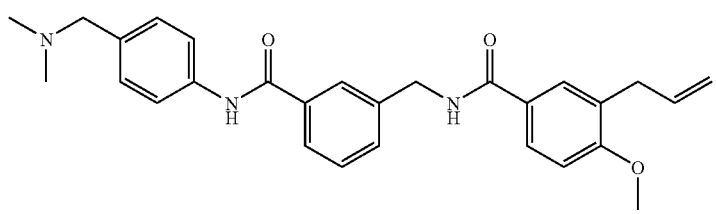
3-Allyl-N-[3-(4-dimethylaminomethyl-phenylcarbamoyl)-benzyl]-4-methoxy-benzamide

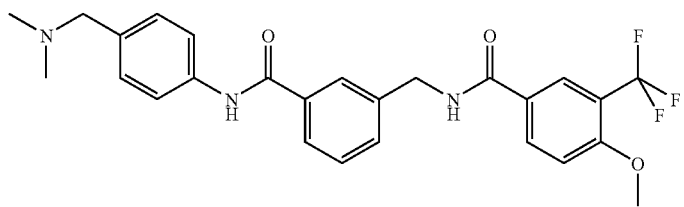
N-[3-(4-Dimethylaminomethyl-phenylcarbamoyl)-benzyl]-4-methoxy-3-trifluoromethyl-benzamide

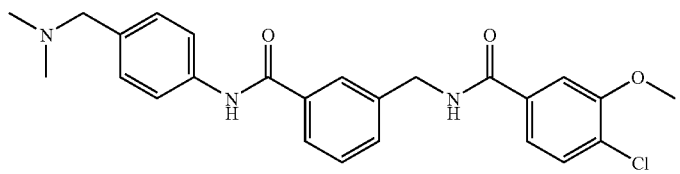
4-Chloro-N-[3-(4-dimethylaminomethyl-phenylcarbamoyl)-benzyl]-3-methoxy-benzamide

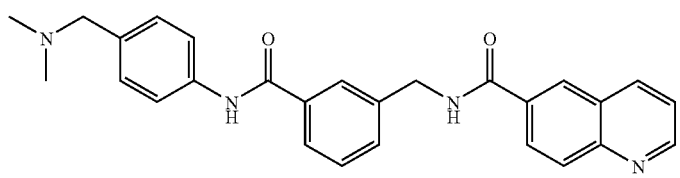
Quinoline-6-carboxylic acid 3-(4-dimethylaminomethyl-phenylcarbamoyl)-benzylamide

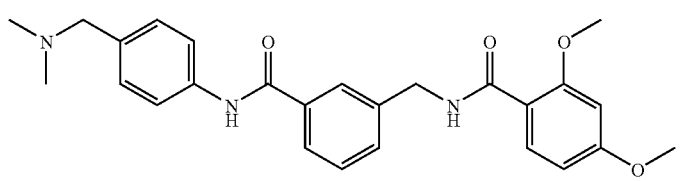
N-[3-(4-Dimethylaminomethyl-phenylcarbamoyl)-benzyl]-2,4-dimethoxy-benzamide

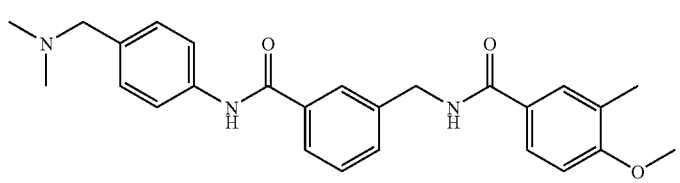
N-[3-(4-Dimethylaminomethyl-phenylcarbamoyl)-benzyl]-4-methoxy-3-methyl-benzamide

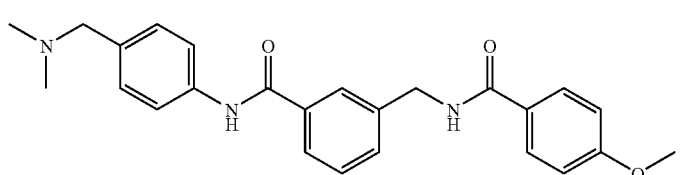
N-[3-(4-Dimethylaminomethyl-phenylcarbamoyl)-benzyl]-4-methoxy-benzamide

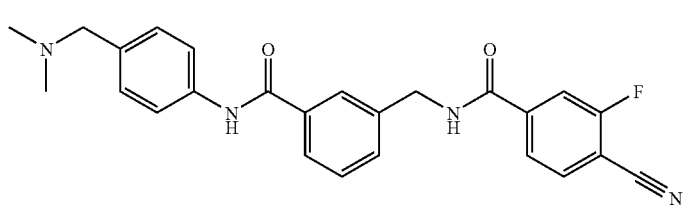
4-Cyano-N-[3-(4-dimethylaminomethyl-phenylcarbamoyl)-benzyl]-3-fluoro-benzamide -continued

| | |
|---|---|
| 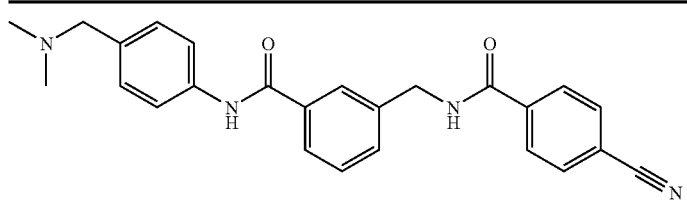 | 4-Cyano-N-[3-(4-dimethylaminomethyl-phenylcarbamoyl)-benzyl]-benzamide |
| 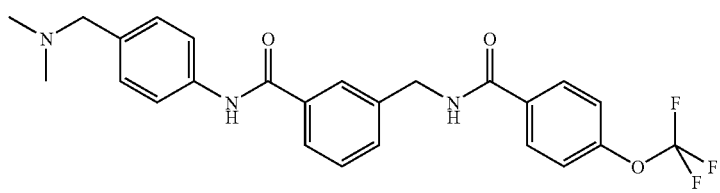 | N-[3-(4-Dimethylaminomethyl-phenylcarbamoyl)-benzyl]-4-trifluoromethoxy-benzamide |
| 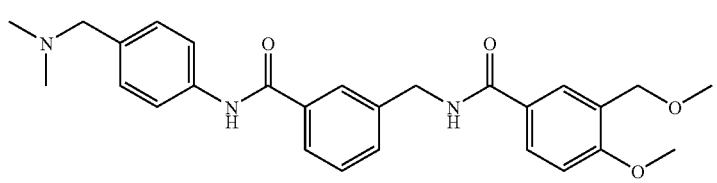 | N-[3-(4-Dimethylaminomethyl-phenylcarbamoyl)-benzyl]-4-methoxy-3-methoxymethyl-benzamide |
| 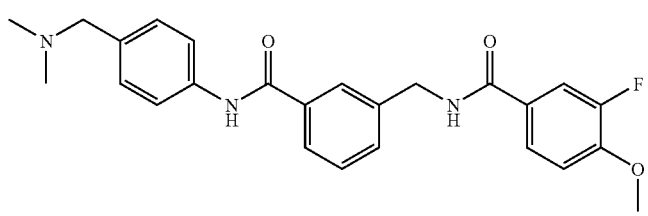 | N-[3-(4-Dimethylaminomethyl-phenylcarbamoyl)-benzyl]-3-fluoro-4-methoxy-benzamide |
| 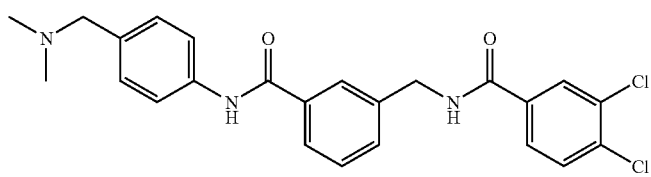 | 3,4-Dichloro-N-[3-(4-dimethylaminomethyl-phenylcarbamoyl)-benzyl]-benzamide |
| 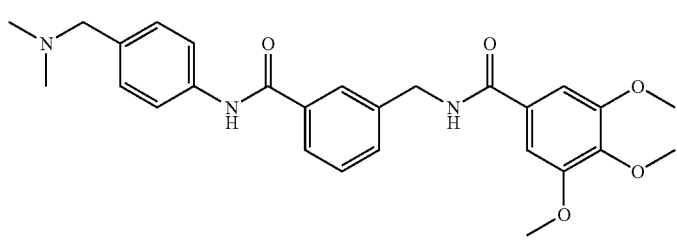 | N-[3-(4-Dimethylaminomethyl-phenylcarbamoyl)-benzyl]-3,4,5-trimethoxy-benzamide |
| 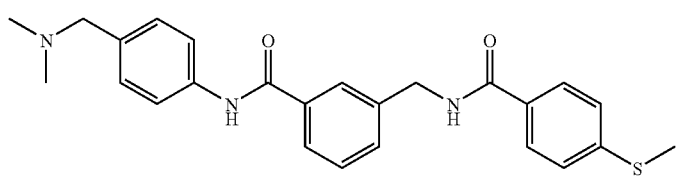 | N-[3-(4-Dimethylaminomethyl-phenylcarbamoyl)-benzyl]-4-methylsulfanyl-benzamide |
| 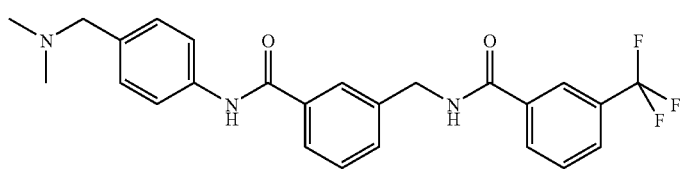 | N-[3-(4-Dimethylaminomethyl-phenylcarbamoyl)-benzyl]-3-trifluoromethyl-benzamide |

-continued

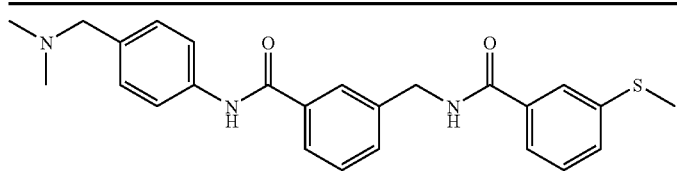

N-[3-(4-Dimethylaminomethyl-phenylcarbamoyl)-benzyl]-3-methylsulfanyl-benzamide

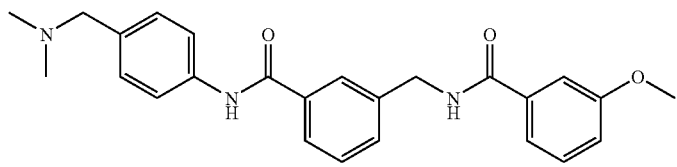

N-[3-(4-Dimethylaminomethyl-phenylcarbamoyl)-benzyl]-3-methoxy-benzamide

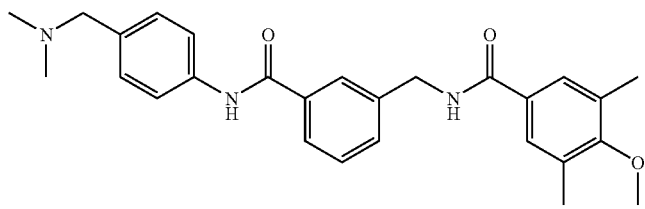

N-[3-(4-Dimethylaminomethyl-phenylcarbamoyl)-benzyl]-4-methoxy-3,5-dimethyl-benzamide

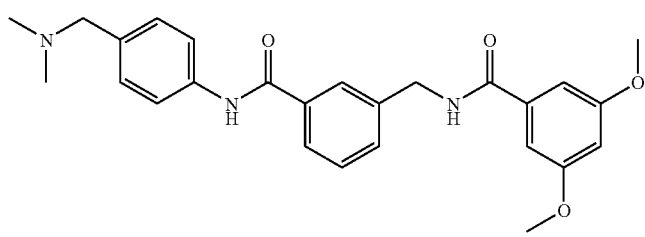

N-[3-(4-Dimethylaminomethyl-phenylcarbamoyl)-benzyl]-3,5-dimethoxy-benzamide

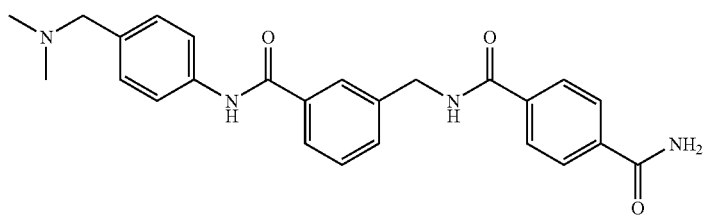

N-[3-(4-Dimethylaminomethyl-phenylcarbamoyl)-benzyl]-terephthalamide

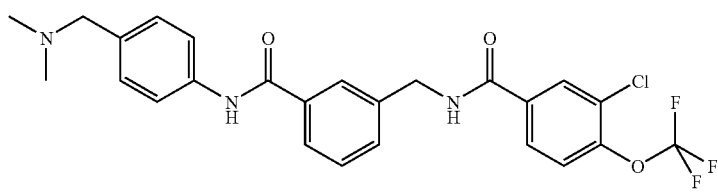

3-Chloro-N-[3-(4-dimethylaminomethyl-phenylcarbamoyl)-benzyl]-4-trifluoromethoxy-benzamide

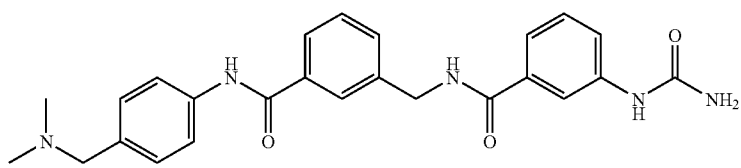

N-[3-(4-Dimethylaminomethyl-phenylcarbamoyl)-benzyl]-3-ureido-benzamide

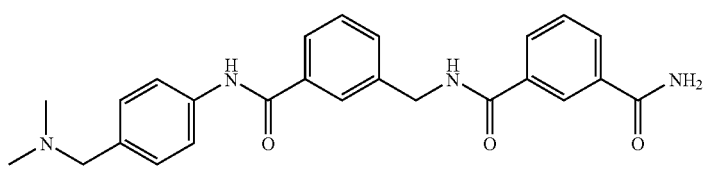

N-[3-(4-Dimethylaminomethyl-phenylcarbamoyl)-benzyl]-isophthalamide

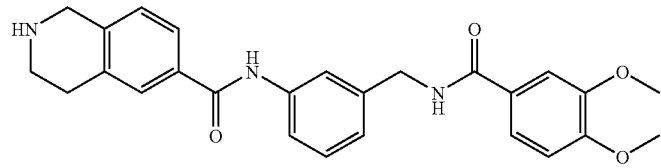
1,2,3,4-Tetrahydro-isoquinoline-6-carboxylic acid {3-[(3,4-dimethoxy-benzoylamino)-methyl]-phenyl}-amide

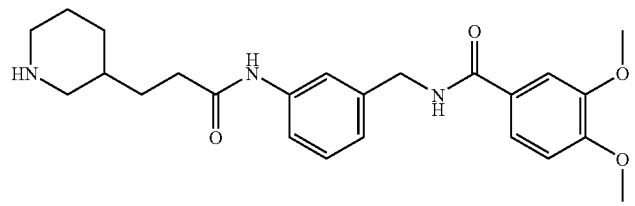
3,4-Dimethoxy-N-[3-(3-piperidin-3-yl-propionylamino)-benzyl]-benzamide

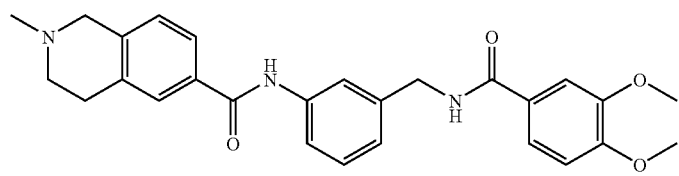
2-Methyl-1,2,3,4-tetrahydro-isoquinoline-6-carboxylic acid {3-[(3,4-dimethoxy-benzoylamino)-methyl]-phenyl}-amide

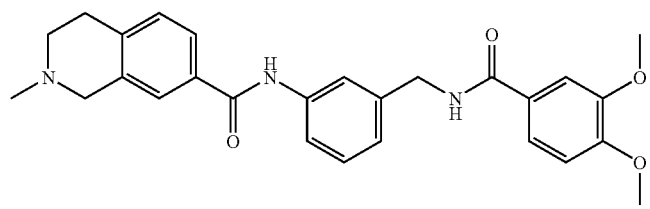
2-Methyl-1,2,3,4-tetrahydro-isoquinoline-7-carboxylic acid {3-[(3,4-dimethoxy-benzoylamino)-methyl]-phenyl}-amide

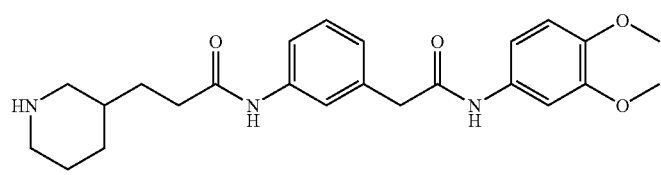
N-{3-[(3,4-Dimethoxy-phenylcarbamoyl)-methyl]-phenyl}-3-piperidin-3-yl-propionamide

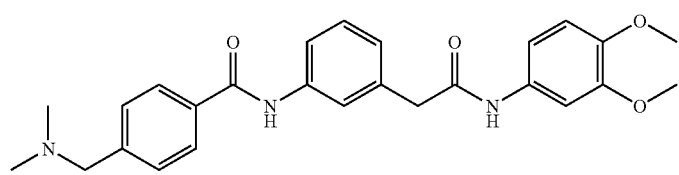
N-{3-[(3,4-Dimethoxy-phenylcarbamoyl)-methyl]-phenyl}-4-dimethylaminomethyl-benzamide

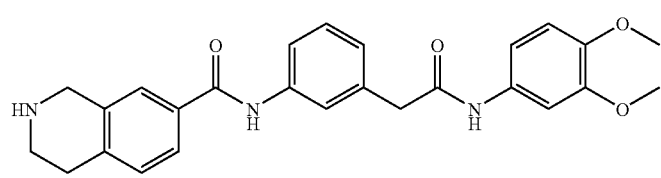
1,2,3,4-Tetrahydro-isoquinoline-7-carboxylic acid {3-[(3,4-dimethoxy-phenylcarbamoyl)-methyl]-phenyl}-amide

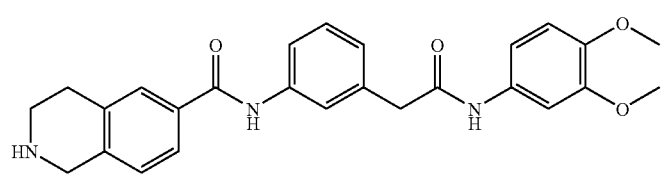
1,2,3,4-Tetrahydro-isoquinoline-6-carboxylic acid {3-[(3,4-dimethoxy-phenylcarbamoyl)-methyl]-phenyl}-amide

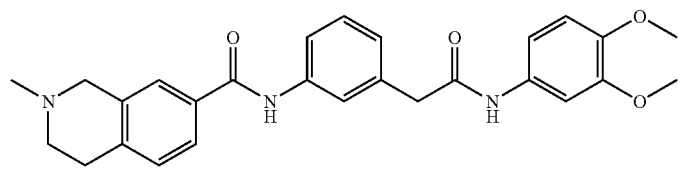

2-Methyl-1,2,3,4-tetrahydro-isoquinoline-7-carboxylic acid {3-[(3,4-dimethoxy-phenylcarbamoyl)-methyl]-phenyl}-amide

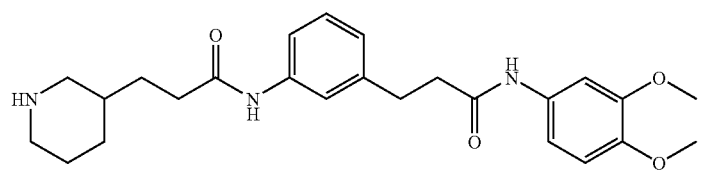

N-(3,4-Dimethoxy-phenyl)-3-[3-(3-piperidin-3-yl-propionylamino)-phenyl]-propionamide

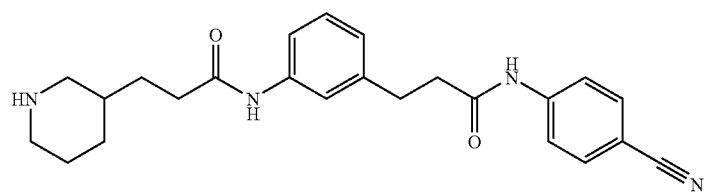

N-(4-Cyano-phenyl)-3-[3-(3-piperidin-3-yl-propionylamino)-phenyl]-propionamide

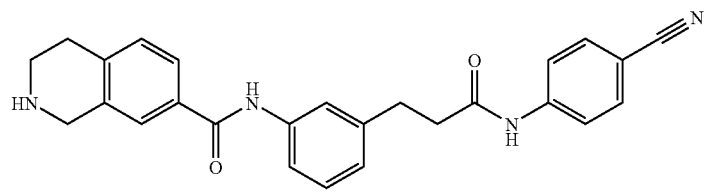

1,2,3,4-Tetrahydro-isoquinoline-7-carboxylic acid {3-[2-(4-cyano-phenylcarbamoyl)-ethyl]-phenyl}-amide

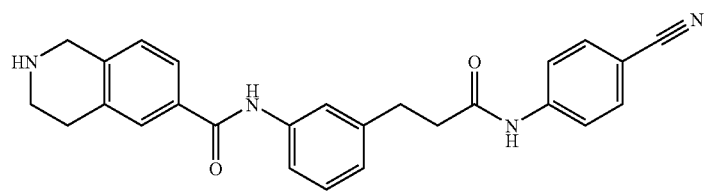

1,2,3,4-Tetrahydro-isoquinoline-6-carboxylic acid {3-[2-(4-cyano-phenylcarbamoyl)-ethyl]-phenyl}-amide

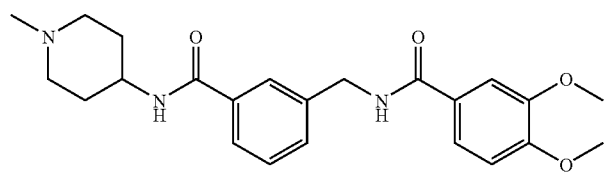

3,4-Dimethoxy-N-[3-(1-methyl-piperidin-4-ylcarbamoyl)-benzyl]-benzamide

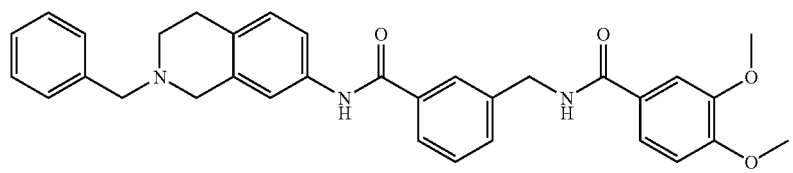

N-[3-(2-Benzyl-1,2,3,4-tetrahydro-isoquinolin-7-ylcarbamoyl)-benzyl]-3,4-dimethoxy-benzamide

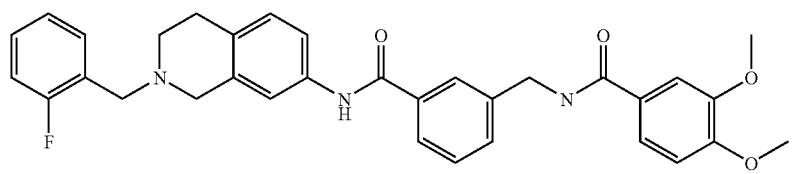

N-{3-[2-(2-Fluoro-benzyl)-1,2,3,4-tetrahydro-isoquinolin-7-ylcarbamoyl]-benzyl}-3,4-dimethoxy-benzamide

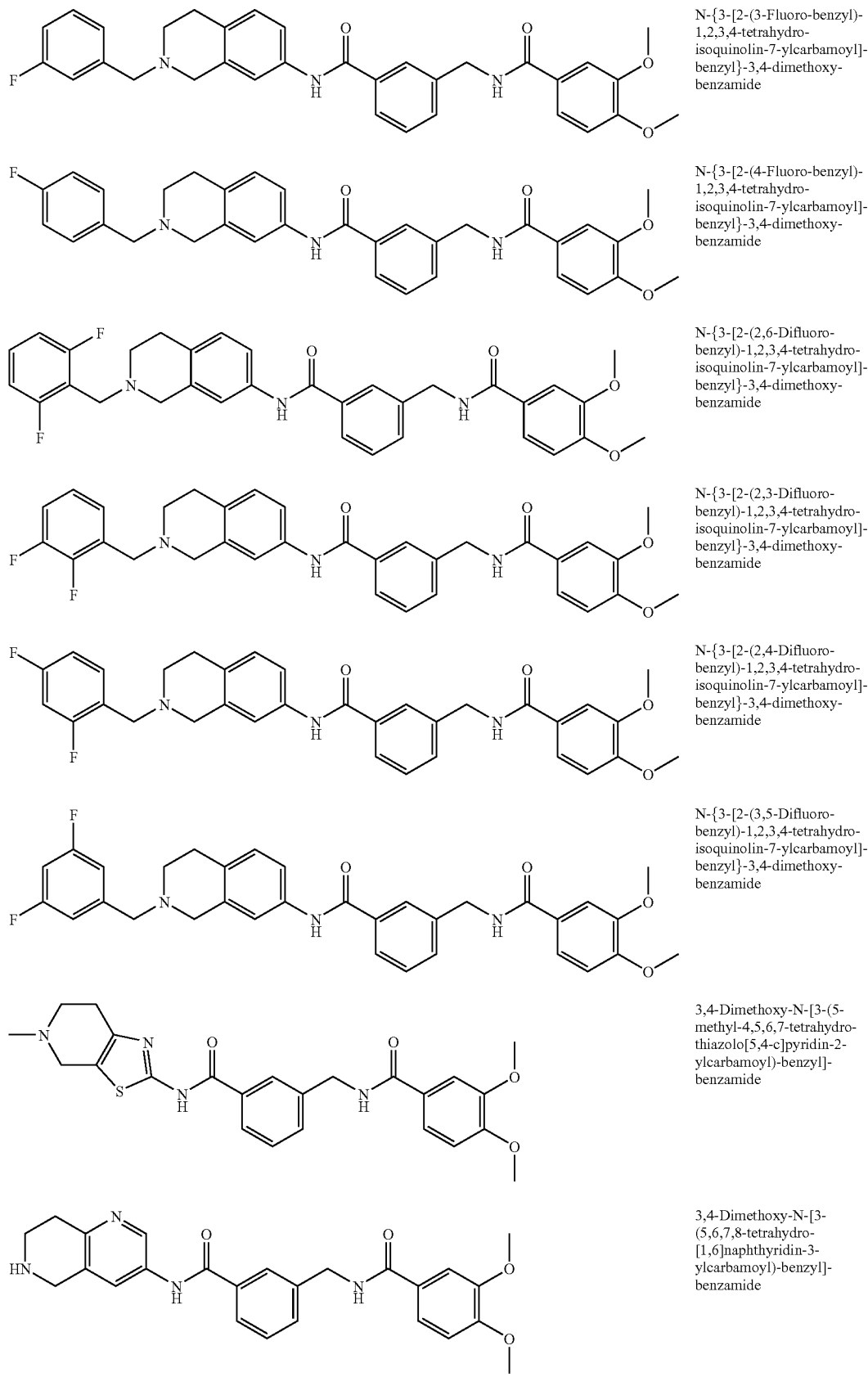

N-{3-[2-(3-Fluoro-benzyl)-1,2,3,4-tetrahydro-isoquinolin-7-ylcarbamoyl]-benzyl}-3,4-dimethoxy-benzamide N-{3-[2-(4-Fluoro-benzyl)-1,2,3,4-tetrahydro-isoquinolin-7-ylcarbamoyl]-benzyl}-3,4-dimethoxy-benzamide N-{3-[2-(2,6-Difluoro-benzyl)-1,2,3,4-tetrahydro-isoquinolin-7-ylcarbamoyl]-benzyl}-3,4-dimethoxy-benzamide N-{3-[2-(2,3-Difluoro-benzyl)-1,2,3,4-tetrahydro-isoquinolin-7-ylcarbamoyl]-benzyl}-3,4-dimethoxy-benzamide N-{3-[2-(2,4-Difluoro-benzyl)-1,2,3,4-tetrahydro-isoquinolin-7-ylcarbamoyl]-benzyl}-3,4-dimethoxy-benzamide N-{3-[2-(3,5-Difluoro-benzyl)-1,2,3,4-tetrahydro-isoquinolin-7-ylcarbamoyl]-benzyl}-3,4-dimethoxy-benzamide 3,4-Dimethoxy-N-[3-(5-methyl-4,5,6,7-tetrahydro-thiazolo[5,4-c]pyridin-2-ylcarbamoyl)-benzyl]-benzamide 3,4-Dimethoxy-N-[3-(5,6,7,8-tetrahydro-[1,6]naphthyridin-3-ylcarbamoyl)-benzyl]-benzamide -continued

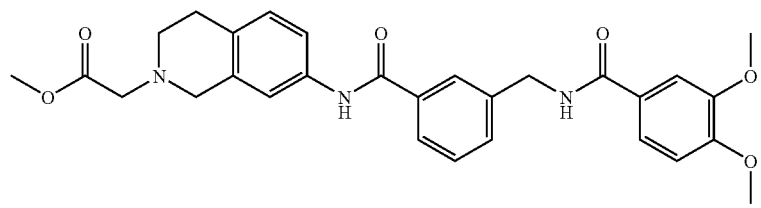
(7-{3-[(3,4-Dimethoxy-benzoylamino)-methyl]-benzoylamino}-3,4-dihydro-1H-isoquinolin-2-yl)-acetic acid methyl ester

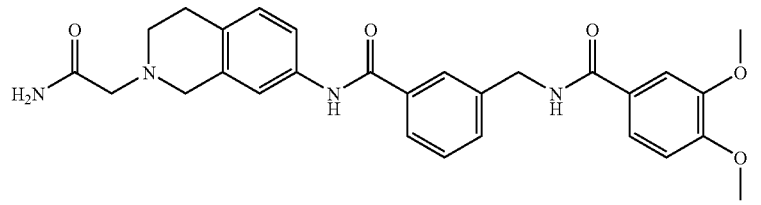
N-[3-(2-Carbamoylmethyl-1,2,3,4-tetrahydro-isoquinolin-7-ylcarbamoyl)-benzyl]-3,4-dimethoxy-benzamide

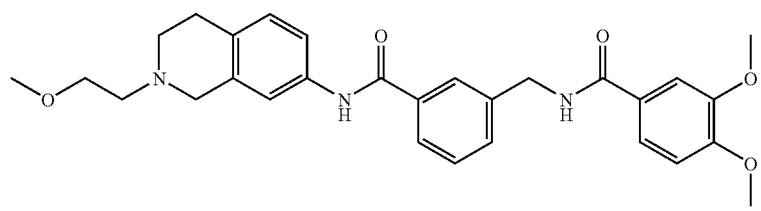
3,4-Dimethoxy-N-{3-[2-(2-methoxy-ethyl)-1,2,3,4-tetrahydro-isoquinolin-7-ylcarbamoyl]-benzyl}-benzamide,

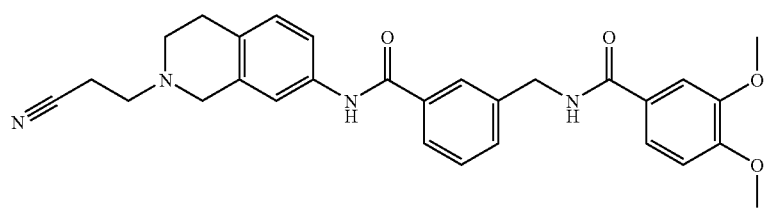
N-{3-[2-(2-Cyano-ethyl)-1,2,3,4-tetrahydro-isoquinolin-7-ylcarbamoyl]-benzyl}-3,4-dimethoxy-benzamide

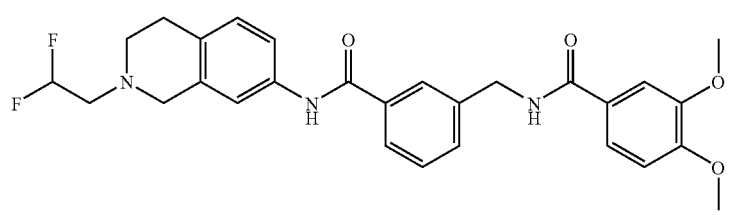
N-{3-[2-(2,2-Difluoro-ethyl)-1,2,3,4-tetrahydro-isoquinolin-7-ylcarbamoyl]-benzyl}-3,4-dimethoxy-benzamide

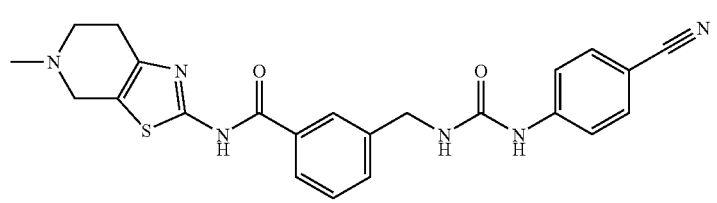
3-[3-(4-Cyano-phenyl)-ureidomethyl]-N-(5-methyl-4,5,6,7-tetrahydro-thiazolo[5,4-c]pyridin-2-yl)-benzamide

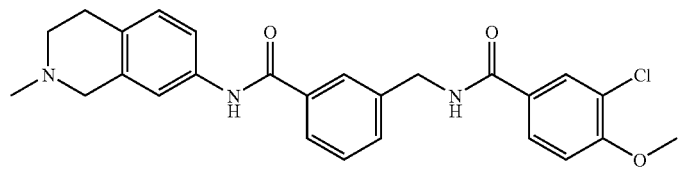
3-Chloro-4-methoxy-N-[3-(2-methyl-1,2,3,4-tetrahydro-isoquinolin-7-ylcarbamoyl)-benzyl]-benzamide

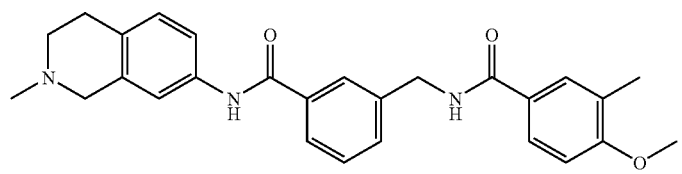
4-Methoxy-3-methyl-N-[3-(2-methyl-1,2,3,4-tetrahydro-isoquinolin-7-ylcarbamoyl)-benzyl]-benzamide

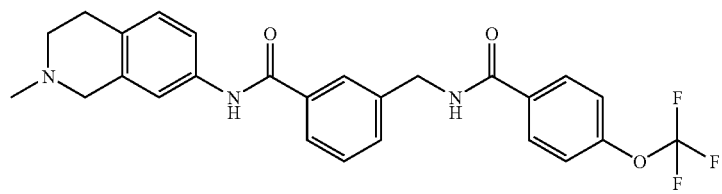 4-Trifluoromethoxy-N-[3-(2-methyl-1,2,3,4-tetrahydro-isoquinolin-7-ylcarbamoyl)-benzyl]-benzamide

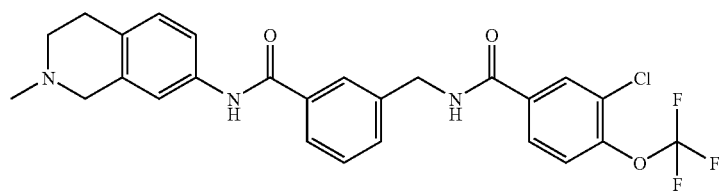 3-Chloro-N-[3-(2-methyl-1,2,3,4-tetrahydro-isoquinolin-7-ylcarbamoyl)-benzyl]-4-trifluoromethoxy-benzamide

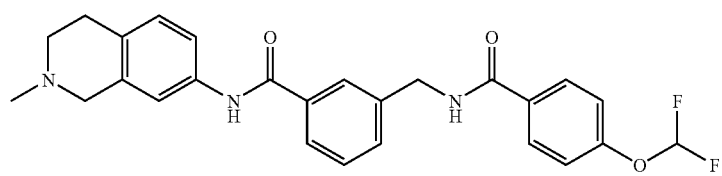 4-Difluoromethoxy-N-[3-(2-methyl-1,2,3,4-tetrahydro-isoquinolin-7-ylcarbamoyl)-benzyl]-benzamide

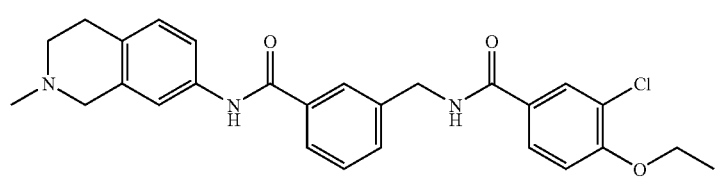 3-Chloro-4-ethoxy-N-[3-(2-methyl-1,2,3,4-tetrahydro-isoquinolin-7-ylcarbamoyl)-benzyl]-benzamide

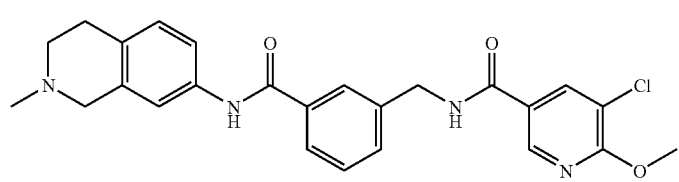 5-Chloro-6-methoxy-N-[3-(2-methyl-1,2,3,4-tetrahydro-isoquinolin-7-ylcarbamoyl)-benzyl]-nicotinamide

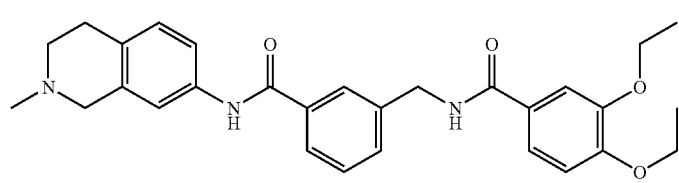 3,4-Diethoxy-N-[3-(2-methyl-1,2,3,4-tetrahydro-isoquinolin-7-ylcarbamoyl)-benzyl]-benzamide

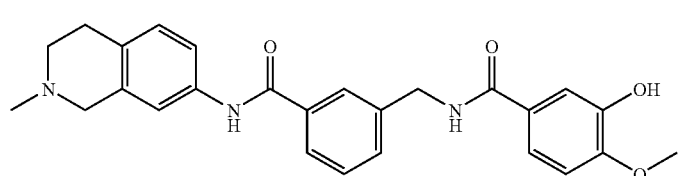 3-Hydroxy-4-methoxy-N-[3-(2-methyl-1,2,3,4-tetrahydro-isoquinolin-7-ylcarbamoyl)-benzyl]-benzamide

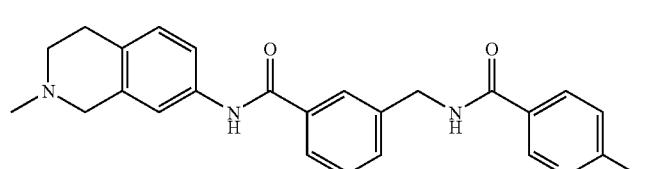 6-Hydroxy-N-{3-(2-methyl-1,2,3,4-tetrahydro-isoquinolin-7-ylcarbamoyl)-benzyl}-nicotinamide -continued

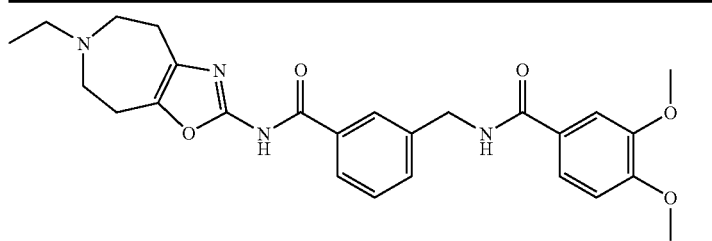
N-[3-(6-Ethyl-5,6,7,8-tetrahydro-4H-oxazolo[4,5-d]azepin-2-ylcarbamoyl)-benzyl]-3,4-dimethoxy-benzamide

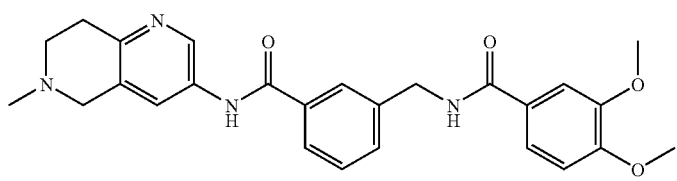
3,4-Dimethoxy-N-[3-(6-methyl-5,6,7,8-tetrahydro-[1,6]naphthyridin-3-ylcarbamoyl)-benzyl]-benzamide

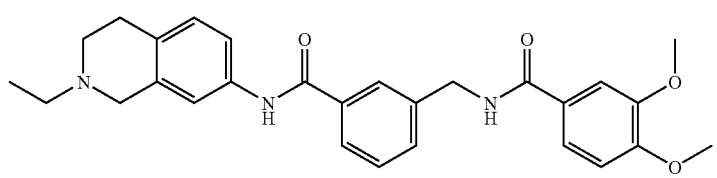
N-[3-(2-Ethyl-1,2,3,4-tetrahydro-isoquinolin-7-ylcarbamoyl)-benzyl]-3,4-dimethoxy-benzamide

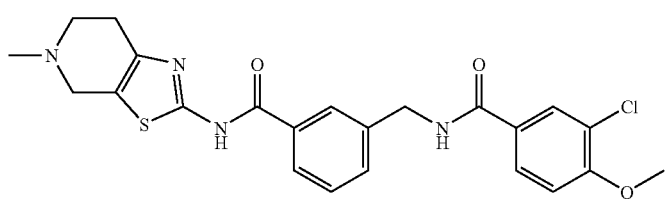
3-Chloro-4-methoxy-N-[3-(5-methyl-4,5,6,7-tetrahydro-thiazolo[5,4-c]pyridin-2-ylcarbamoyl)-benzyl]-benzamide

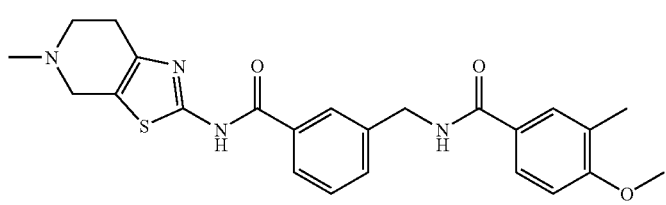
4-Methoxy-3-methyl-N-[3-(5-methyl-4,5,6,7-tetrahydro-thiazolo[5,4-c]pyridin-2-ylcarbamoyl)-benzyl]-benzamide

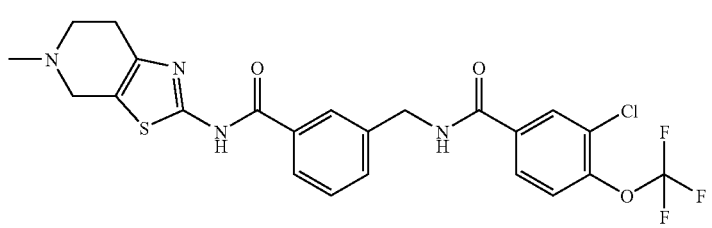
3-Chloro-N-[3-(5-methyl-4,5,6,7-tetrahydro-thiazolo[5,4-c]pyridin-2-ylcarbamoyl)-benzyl]-4-trifluoromethoxy-benzamide

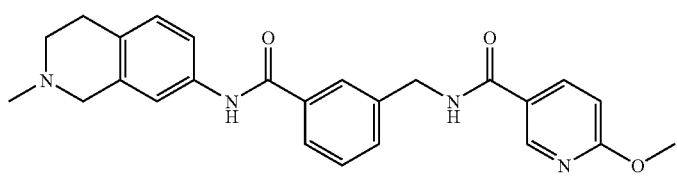
6-Methoxy-N-[3-(2-methyl-1,2,3,4-tetrahydro-isoquinolin-7-ylcarbamoyl)-benzyl]-nicotinamide

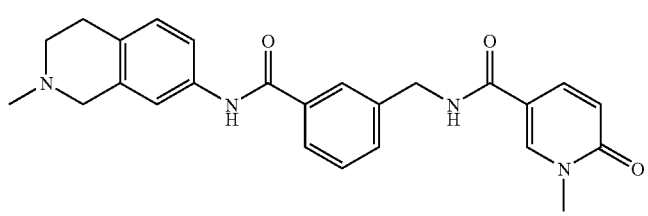
1-Methyl-6-oxo-1,6-dihydro-pyridine-3-carboxylic acid 3-(2-methyl-1,2,3,4-tetrahydro-isoquinolin-7-ylcarbamoyl)-benzylamide

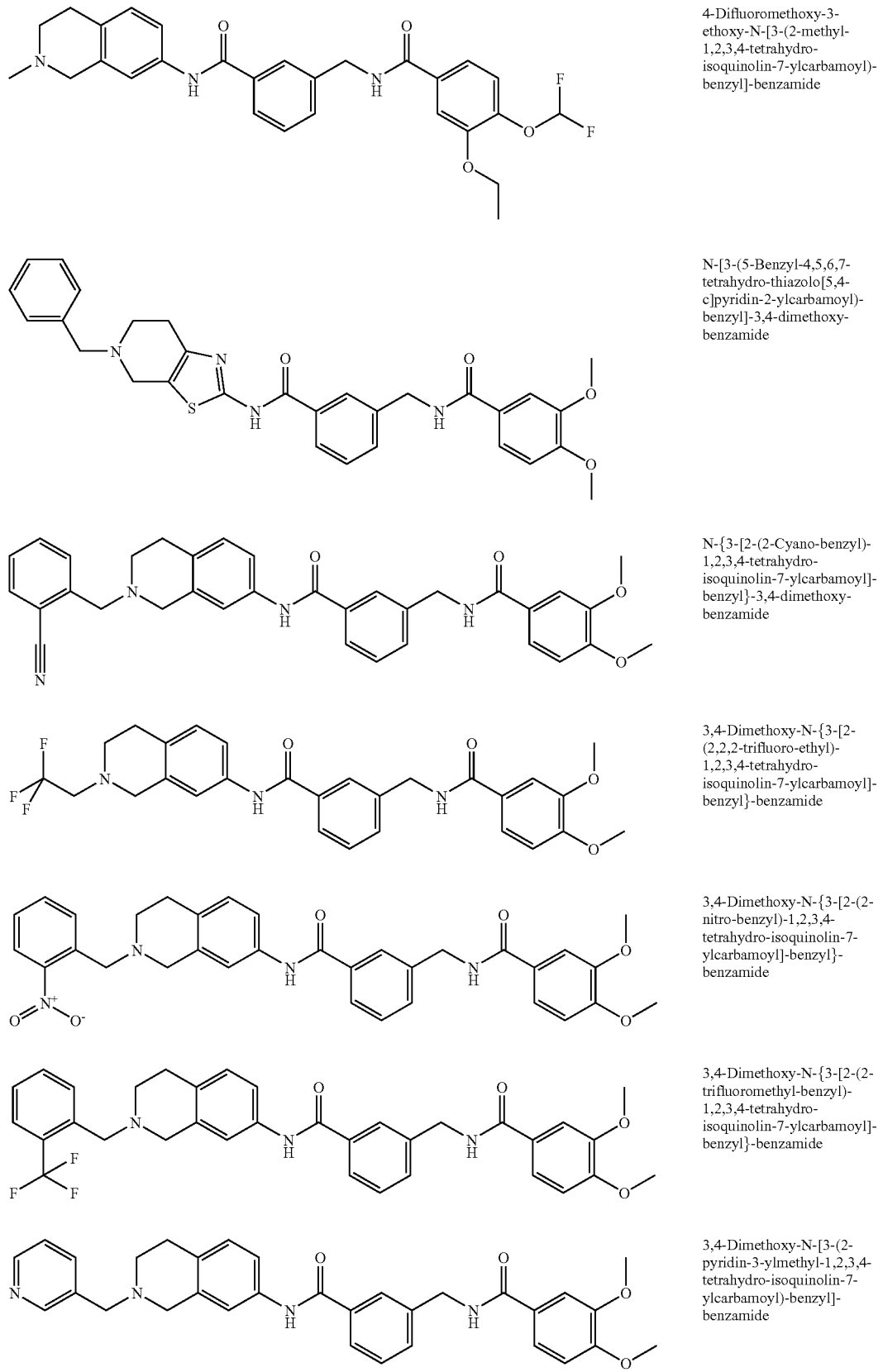

| | |
|---|---|
| | 4-Difluoromethoxy-3-ethoxy-N-[3-(2-methyl-1,2,3,4-tetrahydro-isoquinolin-7-ylcarbamoyl)-benzyl]-benzamide |
| | N-[3-(5-Benzyl-4,5,6,7-tetrahydro-thiazolo[5,4-c]pyridin-2-ylcarbamoyl)-benzyl]-3,4-dimethoxy-benzamide |
| | N-{3-[2-(2-Cyano-benzyl)-1,2,3,4-tetrahydro-isoquinolin-7-ylcarbamoyl]-benzyl}-3,4-dimethoxy-benzamide |
| | 3,4-Dimethoxy-N-{3-[2-(2,2,2-trifluoro-ethyl)-1,2,3,4-tetrahydro-isoquinolin-7-ylcarbamoyl]-benzyl}-benzamide |
| | 3,4-Dimethoxy-N-{3-[2-(2-nitro-benzyl)-1,2,3,4-tetrahydro-isoquinolin-7-ylcarbamoyl]-benzyl}-benzamide |
| | 3,4-Dimethoxy-N-{3-[2-(2-trifluoromethyl-benzyl)-1,2,3,4-tetrahydro-isoquinolin-7-ylcarbamoyl]-benzyl}-benzamide |
| | 3,4-Dimethoxy-N-[3-(2-pyridin-3-ylmethyl-1,2,3,4-tetrahydro-isoquinolin-7-ylcarbamoyl)-benzyl]-benzamide |

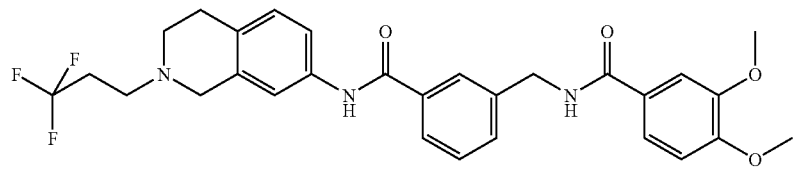
3,4-Dimethoxy-N-{3-[2-(3,3,3-trifluoro-propyl)-1,2,3,4-tetrahydro-isoquinolin-7-ylcarbamoyl]-benzyl}-benzamide

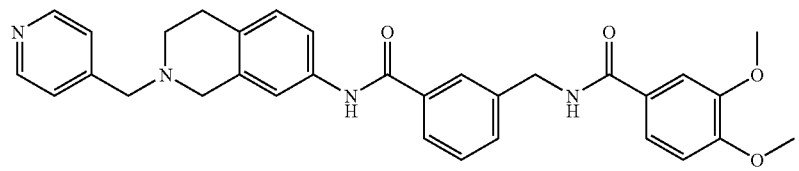
3,4-Dimethoxy-N-[3-(2-pyridin-4-ylmethyl-1,2,3,4-tetrahydro-isoquinolin-7-ylcarbamoyl)-benzyl]-benzamide

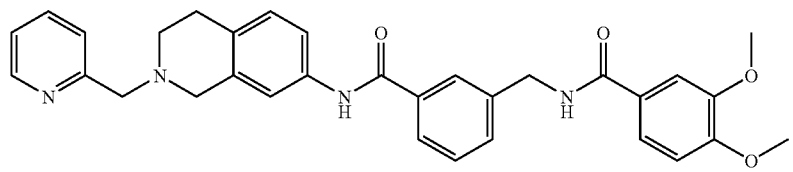
3,4-Dimethoxy-N-[3-(2-pyridin-2-ylmethyl-1,2,3,4-tetrahydro-isoquinolin-7-ylcarbamoyl)-benzyl]-benzamide

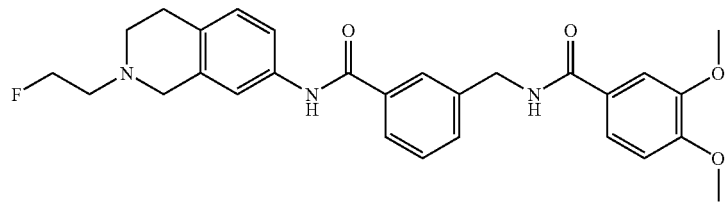
N-{3-[2-(2-Fluoro-ethyl)-1,2,3,4-tetrahydro-isoquinolin-7-ylcarbamoyl]-benzyl}-3,4-dimethoxy-benzamide

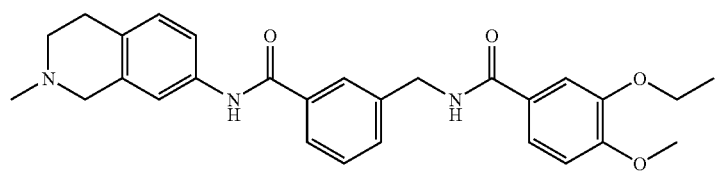
3-Ethoxy-4-methoxy-N-[3-(2-methyl-1,2,3,4-tetrahydro-isoquinolin-7-ylcarbamoyl)-benzyl]-benzamide

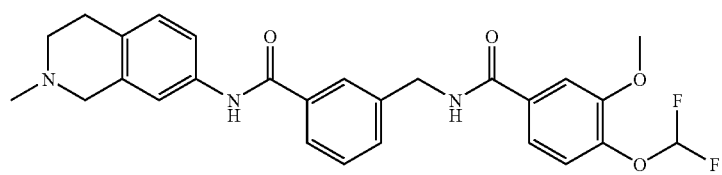
4-Difluoromethoxy-3-methoxy-N-[3-(2-methyl-1,2,3,4-tetrahydro-isoquinolin-7-ylcarbamoyl)-benzyl]-benzamide

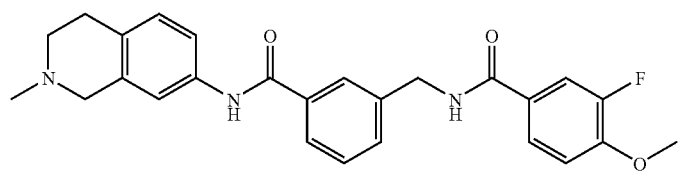
3-Fluoro-4-methoxy-N-[3-(2-methyl-1,2,3,4-tetrahydro-isoquinolin-7-ylcarbamoyl)-benzyl]-benzamide

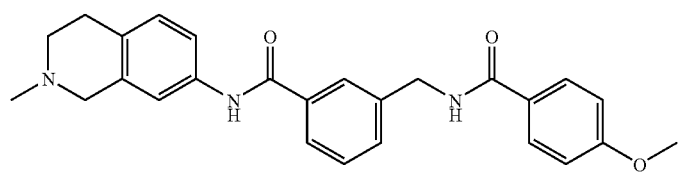
4-Methoxy-N-[3-(2-methyl-1,2,3,4-tetrahydro-isoquinolin-7-ylcarbamoyl)-benzyl]-benzamide

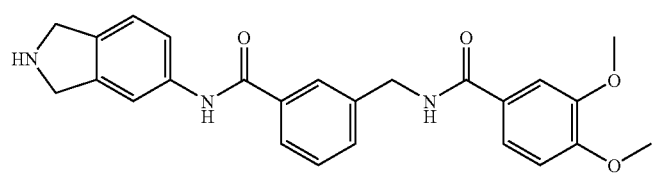
N-[3-(2,3-Dihydro-1H-isoindol-5-ylcarbamoyl)-benzyl]-3,4-dimethoxy-benzamide

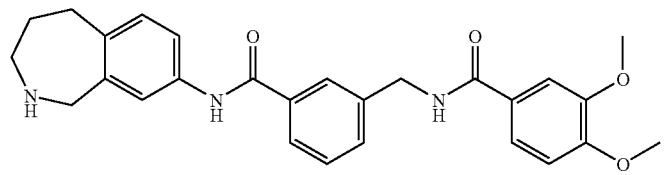

3,4-Dimethoxy-N-[3-(2,3,4,5-tetrahydro-1H-benzo[c]azepin-8-ylcarbamoyl)-benzyl]-benzamide

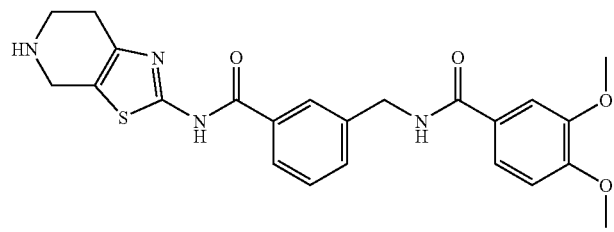

3,4-Dimethoxy-N-[3-(4,5,6,7-tetrahydro-thiazolo[5,4-c]pyridin-2-ylcarbamoyl)-benzyl]-benzamide

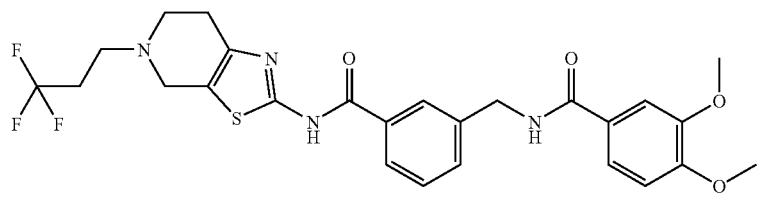

3,4-Dimethoxy-N-{3-[5-(3,3,3-trifluoro-propyl)-4,5,6,7-tetrahydro-thiazolo[5,4-c]pyridin-2-ylcarbamoyl]-benzyl}-benzamide,

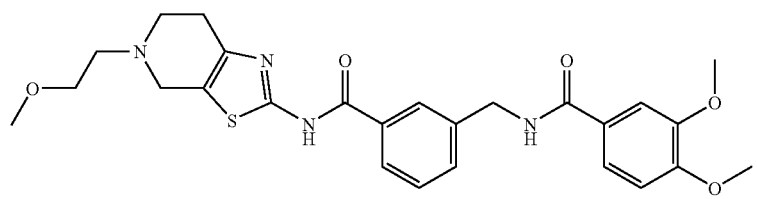

3,4-Dimethoxy-N-{3-[5-(2-methoxy-ethyl)-4,5,6,7-tetrahydro-thiazolo[5,4-c]pyridin-2-ylcarbamoyl]-benzyl}-benzamide

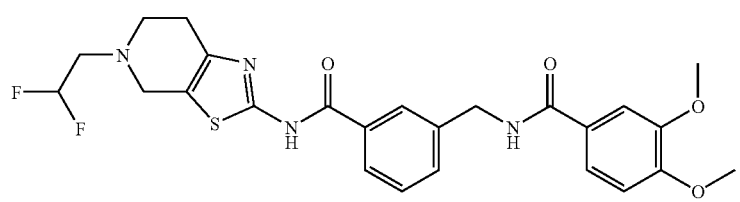

N-{3-[5-(2,2-Difluoro-ethyl)-4,5,6,7-tetrahydro-thiazolo[5,4-c]pyridin-2-ylcarbamoyl]-benzyl}-3,4-dimethoxy-benzamide

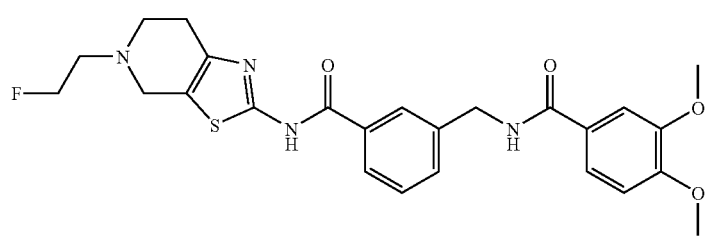

N-{3-[5-(2-Fluoro-ethyl)-4,5,6,7-tetrahydro-thiazolo[5,4-c]pyridin-2-ylcarbamoyl]-benzyl}-3,4-dimethoxy-benzamide

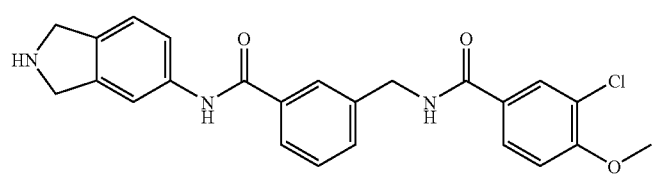

3-Chloro-N-[3-(2,3-dihydro-1H-isoindol-5-ylcarbamoyl)-benzyl]-4-methoxy-benzamide

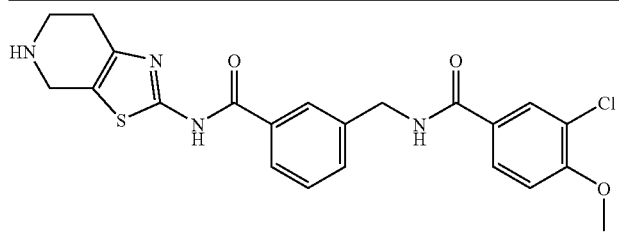

3-Chloro-4-methoxy-N-[3-(4,5,6,7-tetrahydro-thiazolo[5,4-c]pyridin-2-ylcarbamoyl)-benzyl]-benzamide

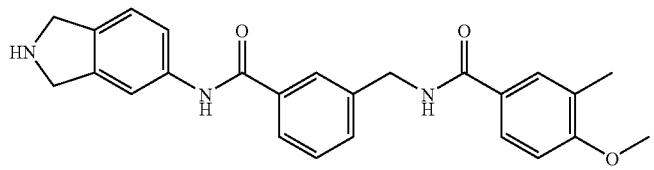

N-[3-(2,3-Dihydro-1H-isoindol-5-ylcarbamoyl)-benzyl]-4-methoxy-3-methyl-benzamide

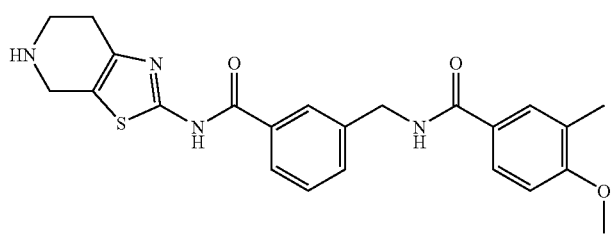

4-Methoxy-3-methyl-N-[3-(4,5,6,7-tetrahydro-thiazolo[5,4-c]pyridin-2-ylcarbamoyl)-benzyl]-benzamide

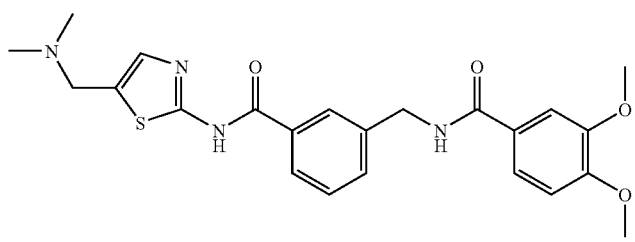

N-[3-(5-Dimethylaminomethyl-thiazol-2-ylcarbamoyl)-benzyl]-3,4-dimethoxy-benzamide

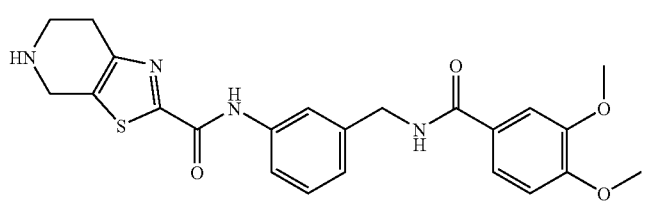

4,5,6,7-Tetrahydro-thiazolo[5,4-c]pyridine-2-carboxylic acid {3-[(3,4-dimethoxy-benzoylamino)-methyl]-phenyl}-amide

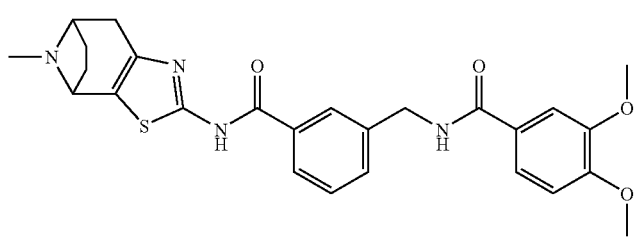

3,4-Dimethoxy-N-[3-(11-methyl-3-thia-5,11-diaza-tricyclo[6.2.1.0$^{2,6}$]undeca-2(6),4-dien-4-ylcarbamoyl)-benzyl]-benzamide

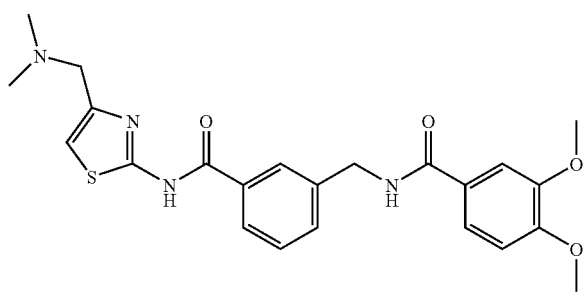

N-[3-(4-Dimethylaminomethyl-thiazol-2-ylcarbamoyl)-benzyl]-3,4-dimethoxy-benzamide

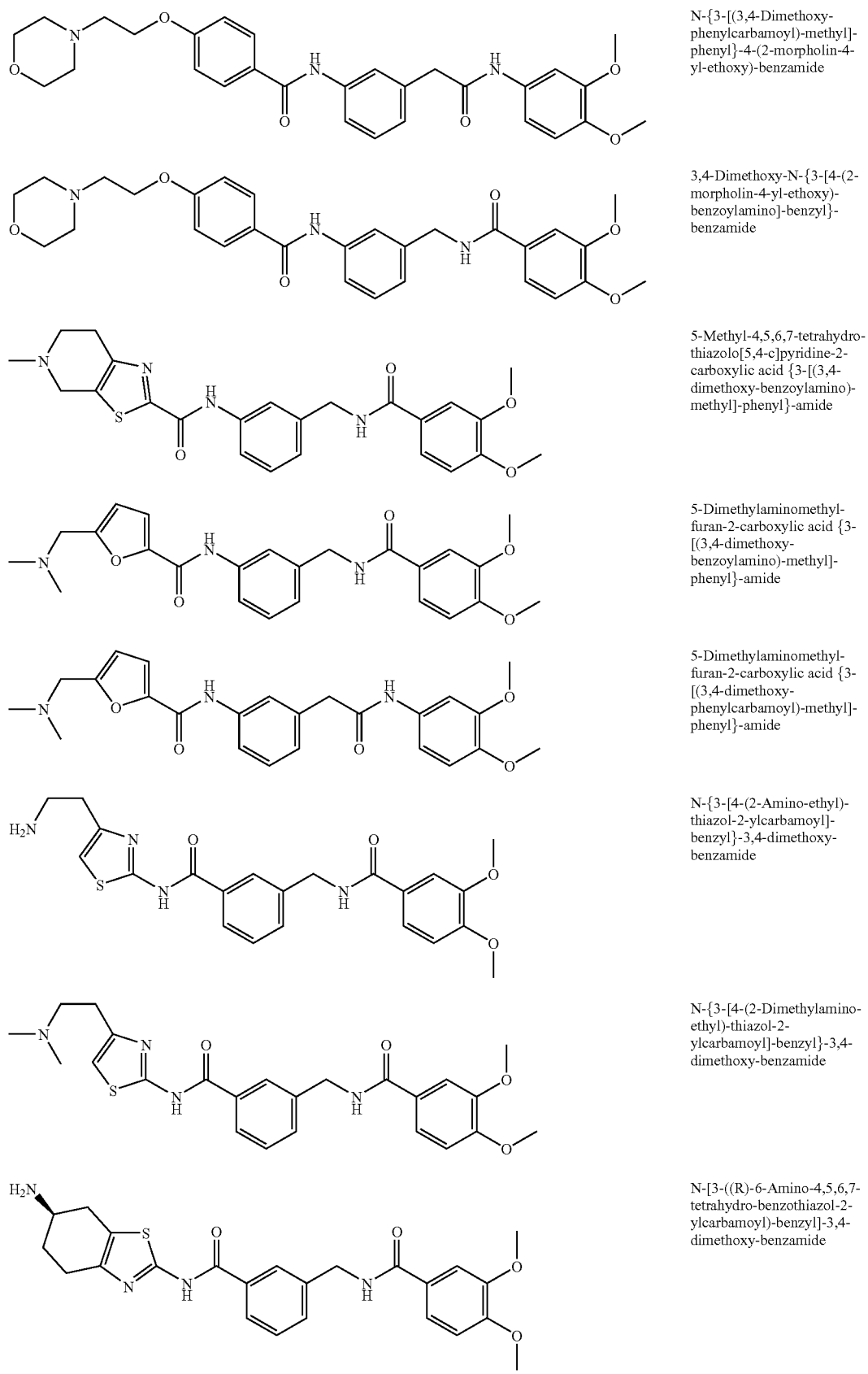

N-{3-[(3,4-Dimethoxy-phenylcarbamoyl)-methyl]-phenyl}-4-(2-morpholin-4-yl-ethoxy)-benzamide 3,4-Dimethoxy-N-{3-[4-(2-morpholin-4-yl-ethoxy)-benzoylamino]-benzyl}-benzamide 5-Methyl-4,5,6,7-tetrahydro-thiazolo[5,4-c]pyridine-2-carboxylic acid {3-[(3,4-dimethoxy-benzoylamino)-methyl]-phenyl}-amide 5-Dimethylaminomethyl-furan-2-carboxylic acid {3-[(3,4-dimethoxy-benzoylamino)-methyl]-phenyl}-amide 5-Dimethylaminomethyl-furan-2-carboxylic acid {3-[(3,4-dimethoxy-phenylcarbamoyl)-methyl]-phenyl}-amide N-{3-[4-(2-Amino-ethyl)-thiazol-2-ylcarbamoyl]-benzyl}-3,4-dimethoxy-benzamide N-{3-[4-(2-Dimethylamino-ethyl)-thiazol-2-ylcarbamoyl]-benzyl}-3,4-dimethoxy-benzamide N-[3-((R)-6-Amino-4,5,6,7-tetrahydro-benzothiazol-2-ylcarbamoyl)-benzyl]-3,4-dimethoxy-benzamide

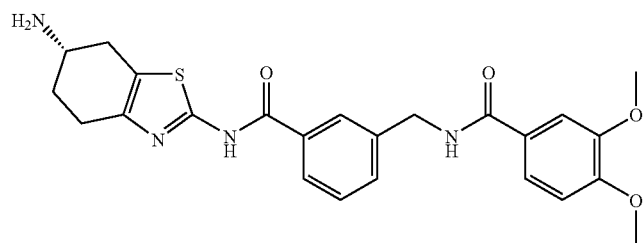
N-[3-((S)-6-Amino-4,5,6,7-tetrahydro-benzothiazol-2-ylcarbamoyl)-benzyl]-3,4-dimethoxy-benzamide

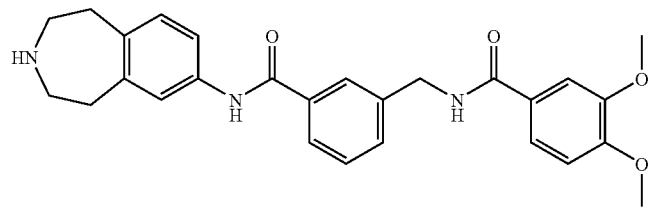
3,4-Dimethoxy-N-[3-(2,3,4,5-tetrahydro-1H-benzo[d]azepin-7-ylcarbamoyl)-benzyl]-benzamide

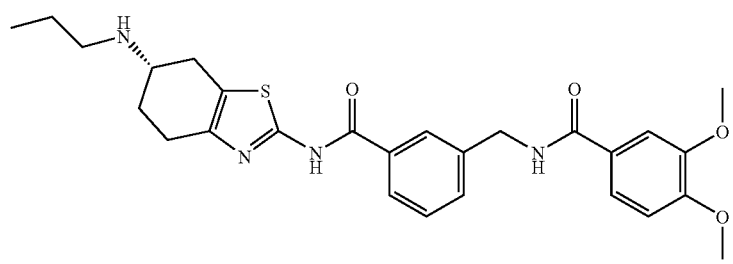
3,4-Dimethoxy-N-[3-((S)-6-propylamino-4,5,6,7-tetrahydro-benzothiazol-2-ylcarbamoyl)-benzyl]-benzamide

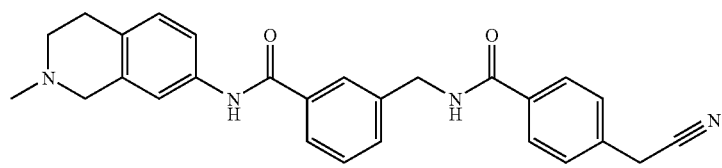
4-Methylcyano-N-[3-(2-methyl-1,2,3,4-tetrahydro-isoquinolin-7-ylcarbamoyl)-benzyl]-benzamide

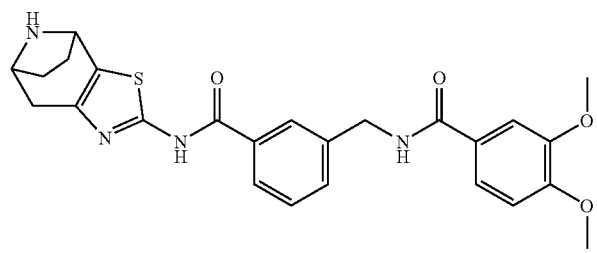
3,4-Dimethoxy-N-[3-(3-thia-5,11-diaza-tricyclo[6.2.1.0$^{2,6}$]undeca-2(6),4-dien-4-ylcarbamoyl)-benzyl]-benzamide

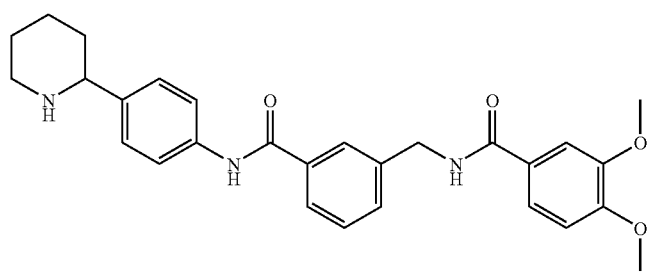
3,4-Dimethoxy-N-[3-(4-piperidin-2-yl-phenylcarbamoyl)-benzyl]-benzamide -continued

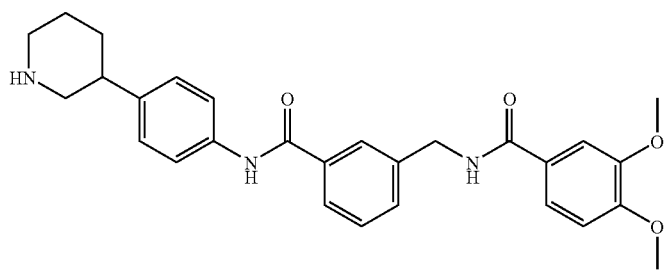

3,4-Dimethoxy-N-[3-(4-piperidin-2-yl-phenylcarbamoyl)-benzyl]-benzamide

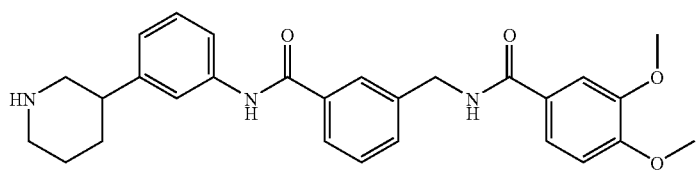

3,4-Dimethoxy-N-[3-(3-piperidin-3-yl-phenylcarbamoyl)-benzyl]-benzamide

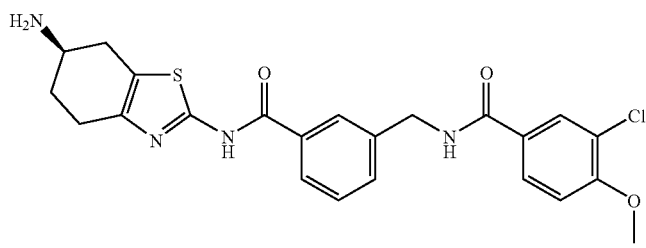

N-[3-((R)-6-Amino-4,5,6,7-tetrahydro-benzothiazol-2-ylcarbamoyl)-benzyl]-3-chloro-4-methoxy-benzamide

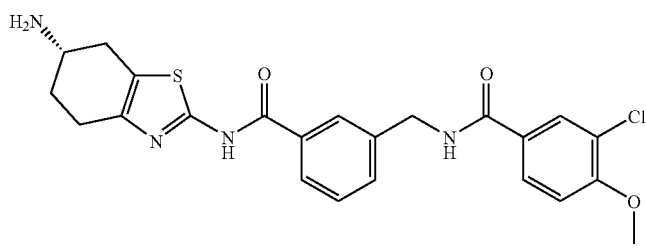

N-[3-((S)-6-Amino-4,5,6,7-tetrahydro-benzothiazol-2-ylcarbamoyl)-benzyl]-3-chloro-4-methoxy-benzamide

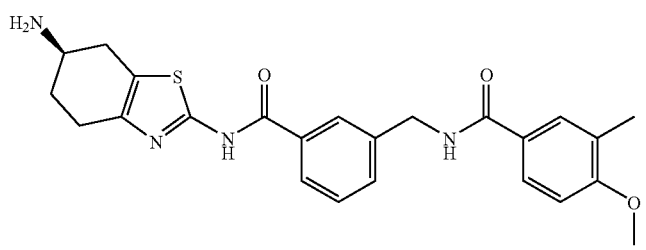

N-[3-((R)-6-Amino-4,5,6,7-tetrahydro-benzothiazol-2-ylcarbamoyl)-benzyl]-4-methoxy-3-methyl-benzamide

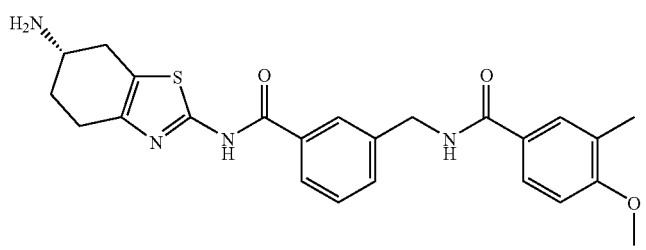

N-[3-((S)-6-Amino-4,5,6,7-tetrahydro-benzothiazol-2-ylcarbamoyl)-benzyl]-4-methoxy-3-methyl-benzamide

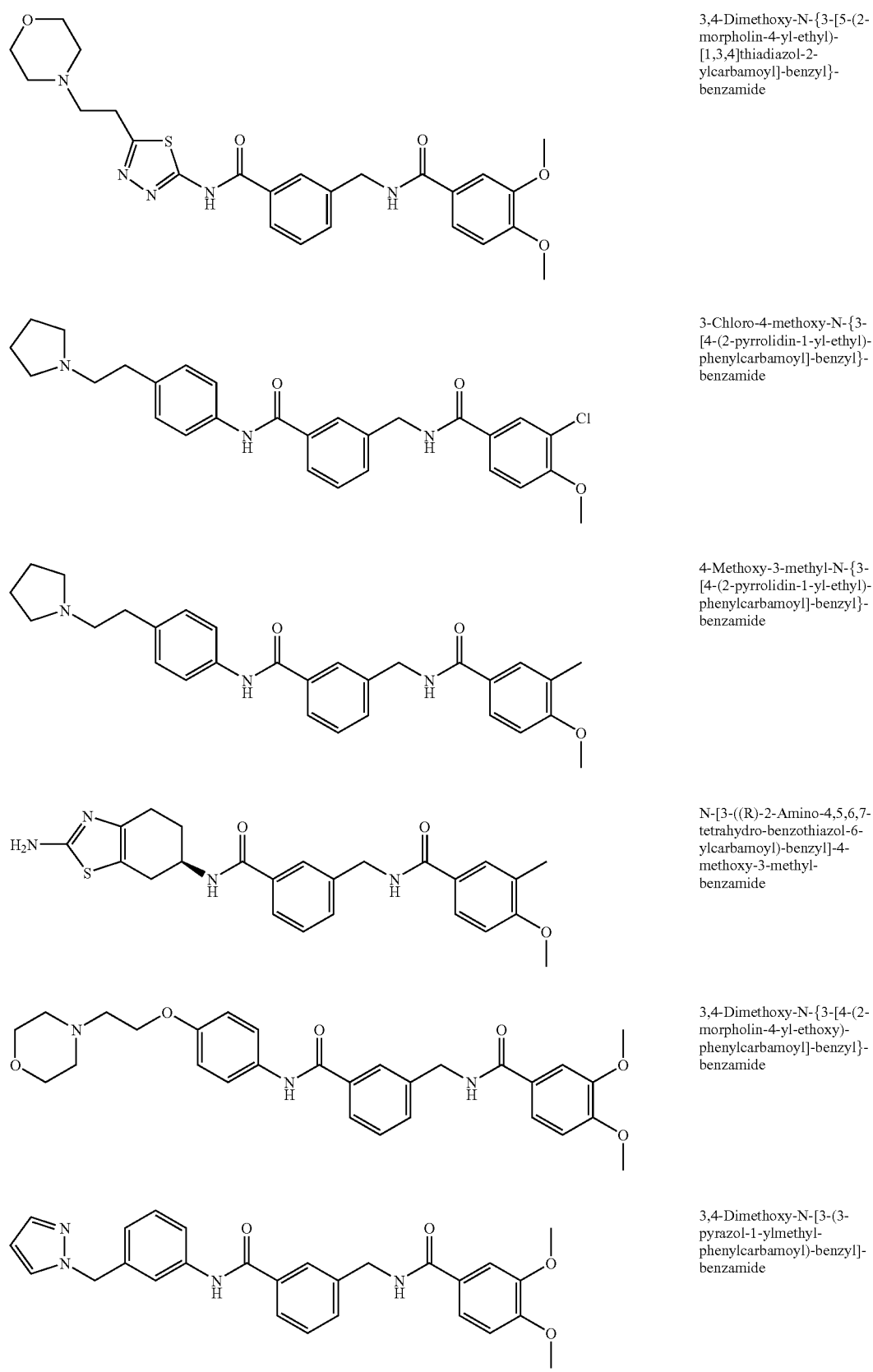

3,4-Dimethoxy-N-{3-[5-(2-morpholin-4-yl-ethyl)-[1,3,4]thiadiazol-2-ylcarbamoyl]-benzyl}-benzamide 3-Chloro-4-methoxy-N-{3-[4-(2-pyrrolidin-1-yl-ethyl)-phenylcarbamoyl]-benzyl}-benzamide 4-Methoxy-3-methyl-N-{3-[4-(2-pyrrolidin-1-yl-ethyl)-phenylcarbamoyl]-benzyl}-benzamide N-[3-((R)-2-Amino-4,5,6,7-tetrahydro-benzothiazol-6-ylcarbamoyl)-benzyl]-4-methoxy-3-methyl-benzamide 3,4-Dimethoxy-N-{3-[4-(2-morpholin-4-yl-ethoxy)-phenylcarbamoyl]-benzyl}-benzamide 3,4-Dimethoxy-N-[3-(3-pyrazol-1-ylmethyl-phenylcarbamoyl)-benzyl]-benzamide

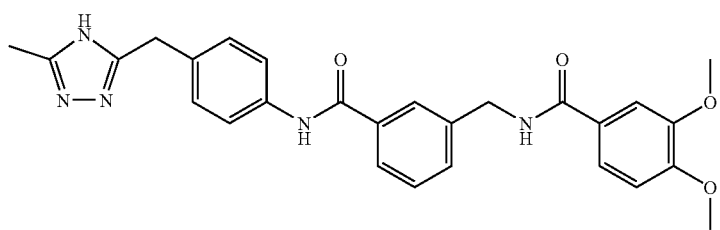

3,4-Dimethoxy-N-{3-[4-(5-methyl-4H-[1,2,4]triazol-3-ylmethyl)-phenylcarbamoyl]-benzyl}-benzamide

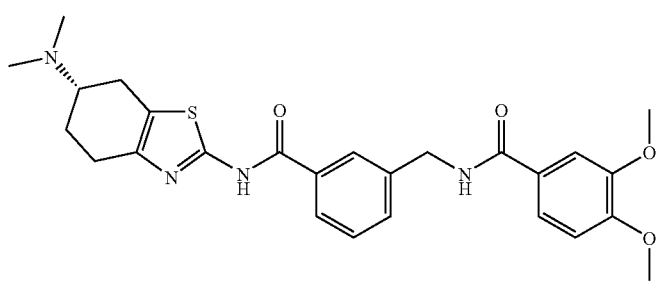

N-[3-((S)-6-Dimethylamino-4,5,6,7-tetrahydro-benzothiazol-2-ylcarbamoyl)-benzyl]-3,4-dimethoxy-benzamide

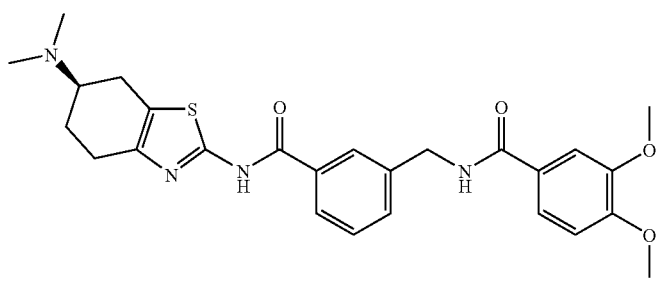

N-[3-((R)-6-Dimethylamino-4,5,6,7-tetrahydro-benzothiazol-2-ylcarbamoyl)-benzyl]-3,4-dimethoxy-benzamide

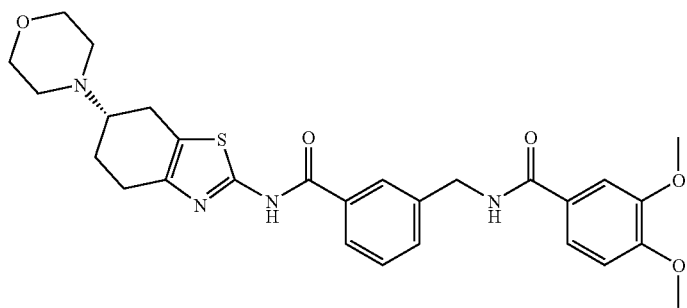

3,4-Dimethoxy-N-[3-((S)-6-morpholin-4-yl-4,5,6,7-tetrahydro-benzothiazol-2-ylcarbamoyl)-benzyl]-benzamide

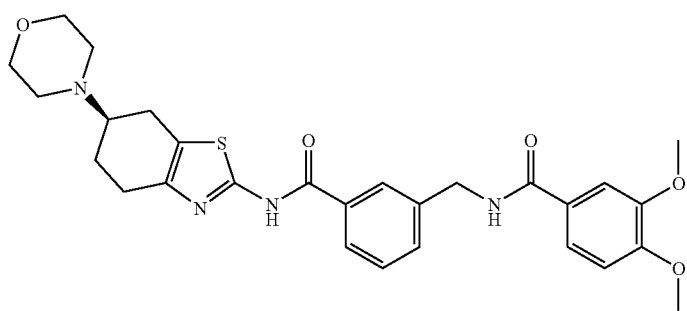

3,4-Dimethoxy-N-[3-((R)-6-morpholin-4-yl-4,5,6,7-tetrahydro-benzothiazol-2-ylcarbamoyl)-benzyl]-benzamide -continued

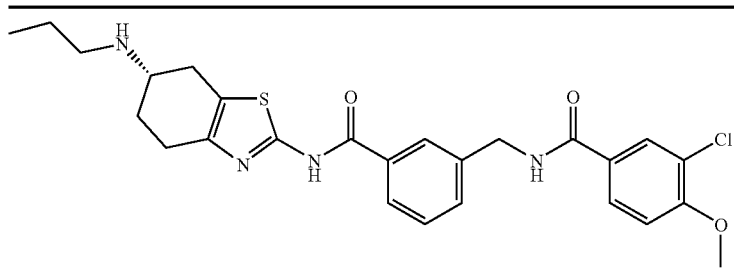

3-Chloro-4-methoxy-N-[3-((S)-6-propylamino-4,5,6,7-tetrahydro-benzothiazol-2-ylcarbamoyl)-benzyl]-benzamide

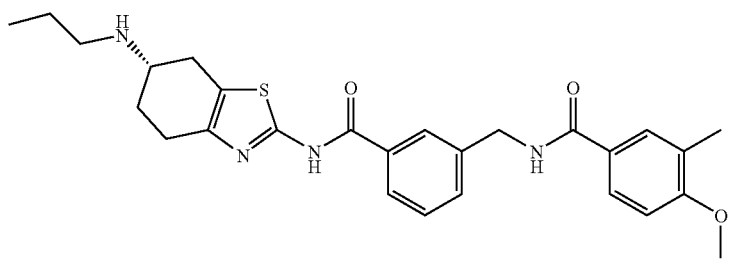

4-Methoxy-3-methyl-N-[3-((S)-6-propylamino-4,5,6,7-tetrahydro-benzothiazol-2-ylcarbamoyl)-benzyl]-benzamide

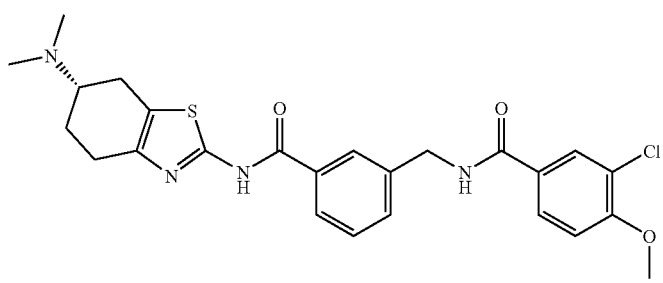

3-Chloro-N-[3-((S)-6-dimethylamino-4,5,6,7-tetrahydro-benzothiazol-2-ylcarbamoyl)-benzyl]-4-methoxy-benzamide

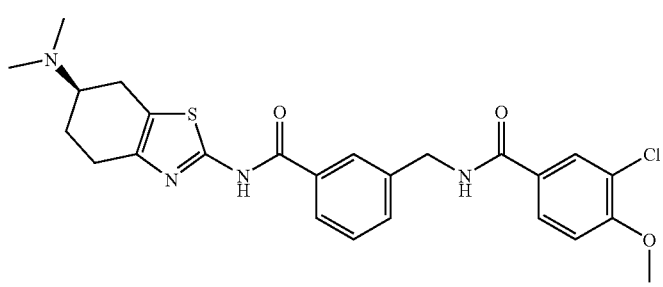

3-Chloro-N-[3-((R)-6-dimethylamino-4,5,6,7-tetrahydro-benzothiazol-2-ylcarbamoyl)-benzyl]-4-methoxy-benzamide

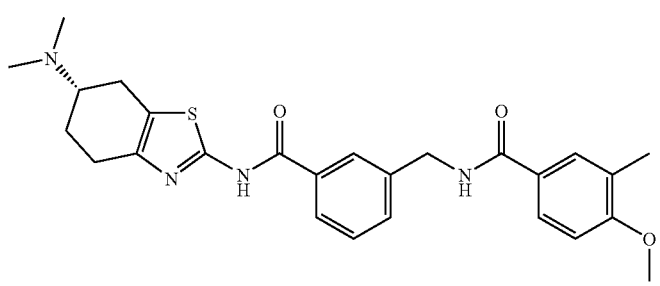

N-[3-((S)-6-Dimethylamino-4,5,6,7-tetrahydro-benzothiazol-2-ylcarbamoyl)-benzyl]-4-methoxy-3-methyl-benzamide

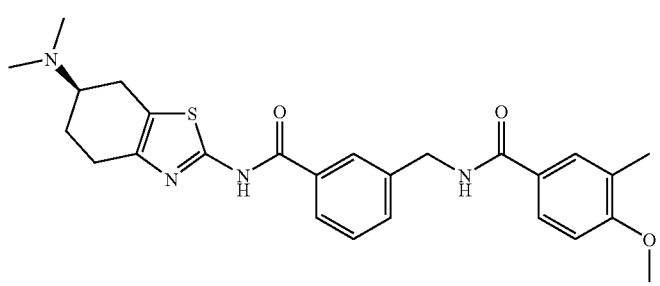

N-[3-((R)-6-Dimethylamino-4,5,6,7-tetrahydro-benzothiazol-2-ylcarbamoyl)-benzyl]-4-methoxy-3-methyl-benzamide

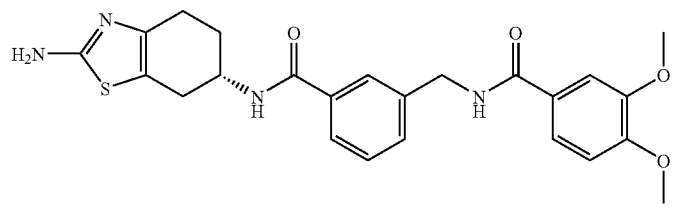

N-[3-((S)-2-Amino-4,5,6,7-tetrahydro-benzothiazol-6-ylcarbamoyl)-benzyl]-3,4-dimethoxy-benzamide

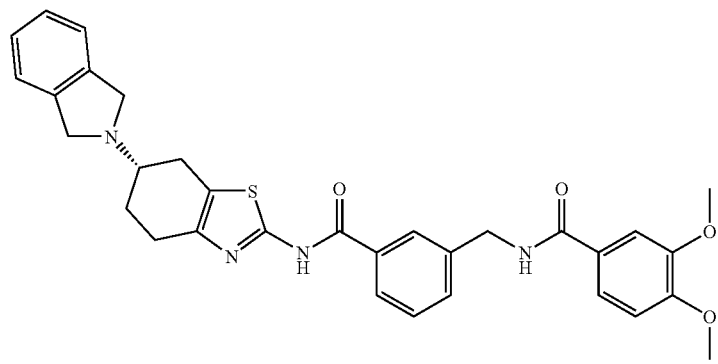

N-{3-[(S)-6-(1,3-Dihydro-isoindol-2-yl)-4,5,6,7-tetrahydro-benzothiazol-2-ylcarbamoyl]-benzyl}-3,4-dimethoxy-benzamide

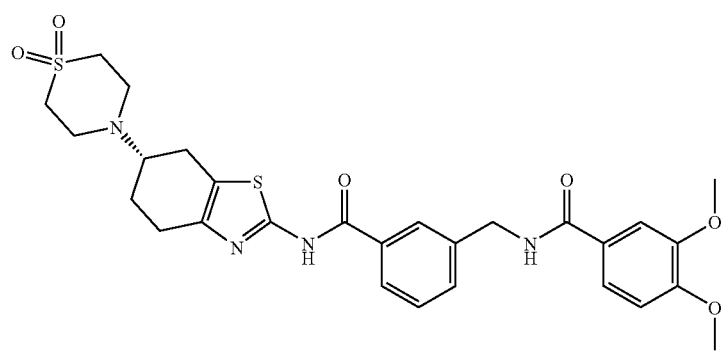

N-{3-[(S)-6-(1,1-Dioxo-thiomorpholin-4-yl)-4,5,6,7-tetrahydro-benzothiazol-2-ylcarbamoyl]-benzyl}-3,4-dimethoxy-benzamide

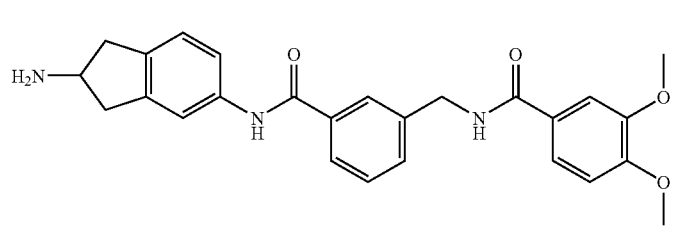

N-[3-(2-Amino-indan-5-ylcarbamoyl)-benzyl]-3,4-dimethoxy-benzamide

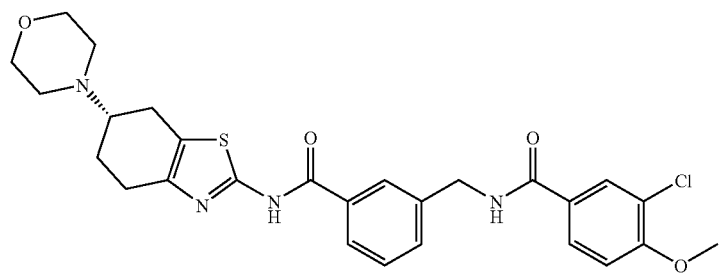

3-Chloro-4-methoxy-N-[3-((S)-6-morpholin-4-yl-4,5,6,7-tetrahydro-benzothiazol-2-ylcarbamoyl)-benzyl]-benzamide

| | |
|---|---|
| 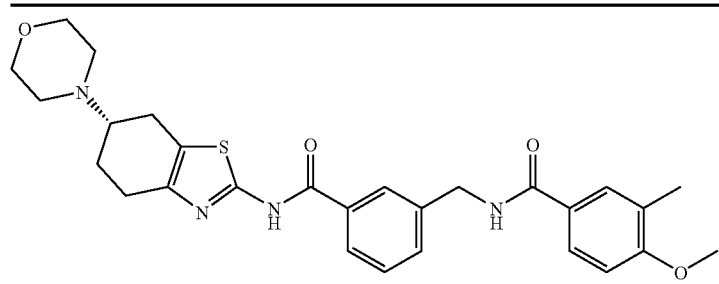 | 4-Methoxy-3-methyl-N-[3-((S)-6-morpholin-4-yl-4,5,6,7-tetrahydro-benzothiazol-2-ylcarbamoyl)-benzyl]-benzamide |
| 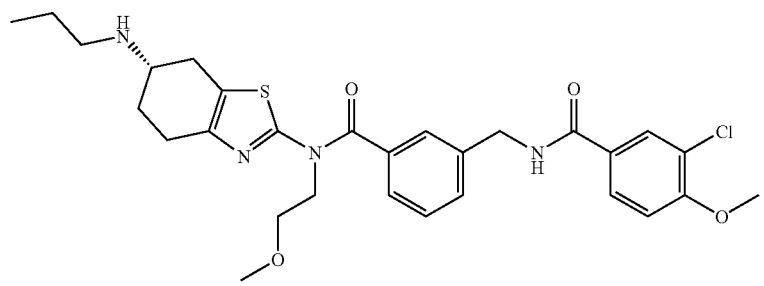 | 3-Chloro-4-methoxy-N-{3-[(2-methoxy-ethyl)-((S)-6-propylamino-4,5,6,7-tetrahydro-benzothiazol-2-yl)-carbamoyl]-benzyl}-benzamide |
| 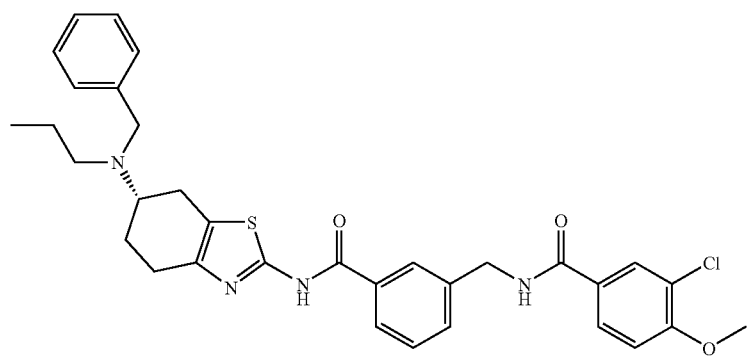 | N-{3-[(S)-6-(Benzyl-propyl-amino)-4,5,6,7-tetrahydro-benzothiazol-2-ylcarbamoyl]-benzyl}-3-chloro-4-methoxy-benzamide |
| 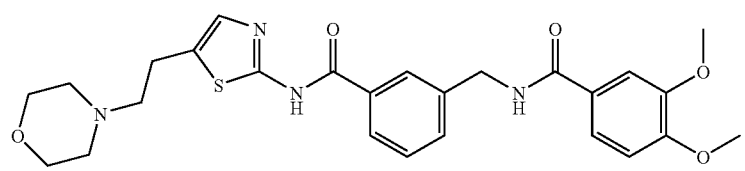 | 3,4-Dimethoxy-N-{3-[5-(2-morpholin-4-yl-ethyl)-thiazol-2-ylcarbamoyl]-benzyl}-benzamide |
| 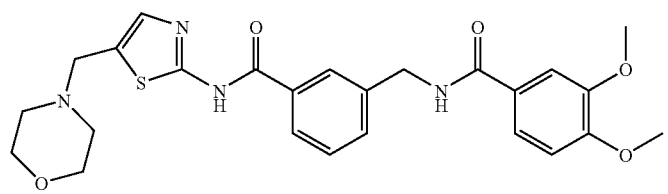 | 3,4-Dimethoxy-N-[3-(5-morpholin-4-ylmethyl-thiazol-2-ylcarbamoyl)-benzyl]-benzamide |
| 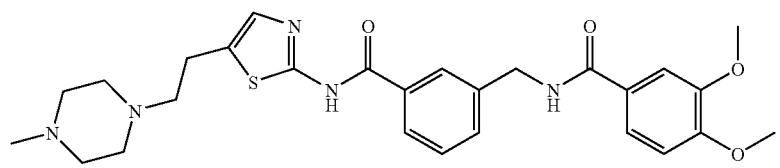 | 3,4-Dimethoxy-N-(3-{5-[2-(4-methyl-piperazin-1-yl)-ethyl]-thiazol-2-ylcarbamoyl}-benzyl)-benzamide |
| 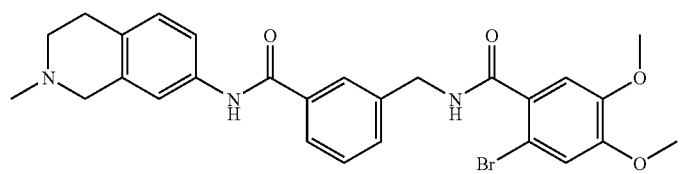 | 2-Bromo-4,5-dimethoxy-N-[3-(2-methyl-1,2,3,4-tetrahydro-isoquinolin-7-ylcarbamoyl)-benzyl]-benzamide |

-continued

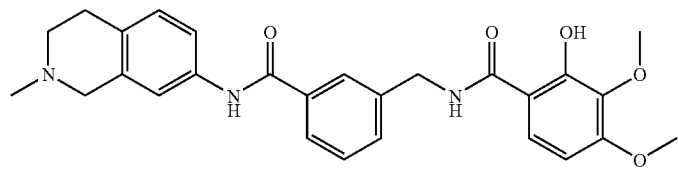
2-Hydroxy-3,4-dimethoxy-N-[3-(2-methyl-1,2,3,4-tetrahydro-isoquinolin-7-ylcarbamoyl)-benzyl]-benzamide

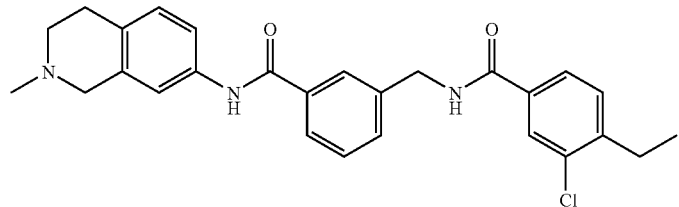
3-Chloro-4-ethyl-N-[3-(2-methyl-1,2,3,4-tetrahydro-isoquinolin-7-ylcarbamoyl)-benzyl]-benzamide

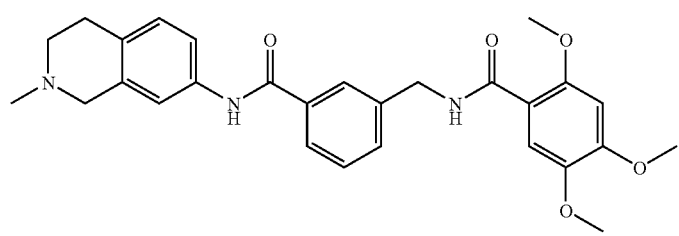
2,4,5-Trimethoxy-N-[3-(2-methyl-1,2,3,4-tetrahydro-isoquinolin-7-ylcarbamoyl)-benzyl]-benzamide

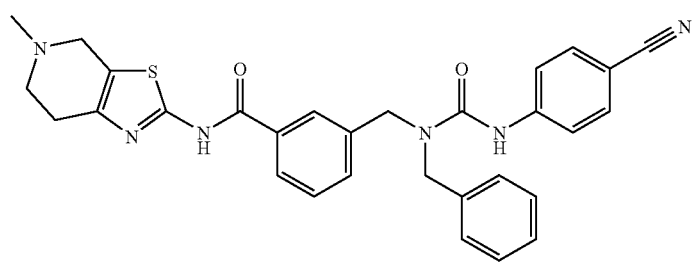
3-[1-Benzyl-3-(4-cyano-phenyl)-ureidomethyl]-N-(5-methyl-4,5,6,7-tetrahydro-thiazolo[5,4-c]pyridin-2-yl)-benzamide

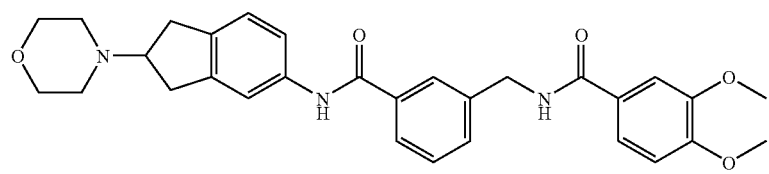
3,4-Dimethoxy-N-[3-(2-morpholin-4-yl-indan-5-ylcarbamoyl)-benzyl]-benzamide

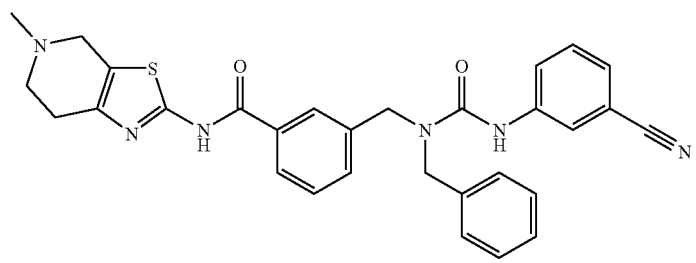
3-[1-Benzyl-3-(3-cyano-phenyl)-ureidomethyl]-N-(5-methyl-4,5,6,7-tetrahydro-thiazolo[5,4-c]pyridin-2-yl)-benzamide

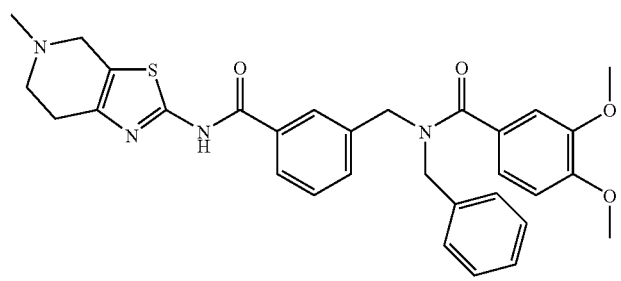
N-Benzyl-3,4-dimethoxy-N-[3-(5-methyl-4,5,6,7-tetrahydro-thiazolo[5,4-c]pyridin-2-ylcarbamoyl)-benzyl]-benzamide

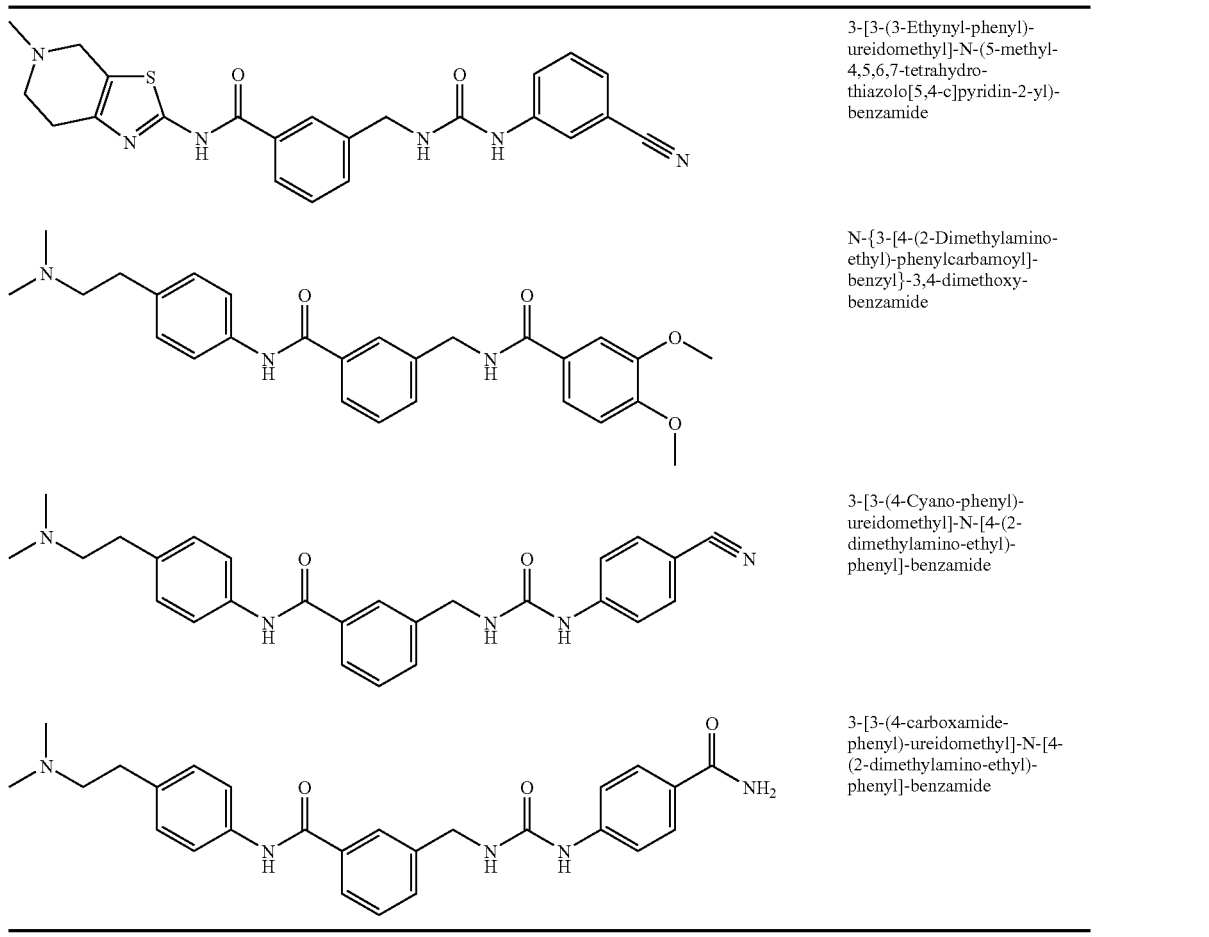

| | |
|---|---|
| | 3-[3-(3-Ethynyl-phenyl)-ureidomethyl]-N-(5-methyl-4,5,6,7-tetrahydro-thiazolo[5,4-c]pyridin-2-yl)-benzamide |
| | N-{3-[4-(2-Dimethylamino-ethyl)-phenylcarbamoyl]-benzyl}-3,4-dimethoxy-benzamide |
| | 3-[3-(4-Cyano-phenyl)-ureidomethyl]-N-[4-(2-dimethylamino-ethyl)-phenyl]-benzamide |
| | 3-[3-(4-carboxamide-phenyl)-ureidomethyl]-N-[4-(2-dimethylamino-ethyl)-phenyl]-benzamide |

In an additional embodiment of the invention, there are compounds of the formula (I) selected from the group below, or a tautomer thereof or a salt thereof, preferably a pharmaceutically acceptable salt thereof:

3-[3-(4-Cyano-phenyl)-ureidomethyl]-N-(1,2,3,4-tetrahydro-isoquinolin-7-yl)-benzamide;
3-[3-(4-Cyano-phenyl)-ureidomethyl]-N-(2-piperidin-4-yl-ethyl)-benzamide;
3-[3-(4-Cyano-phenyl)-ureidomethyl]-N-(2-piperidin-3-yl-ethyl)-benzamide;
3-[3-(3-Cyano-phenyl)-ureidomethyl]-N-(2-piperidin-3-yl-ethyl)-benzamide;
3-[3-(3,4-Dimethoxy-phenyl)-ureidomethyl]-N-(2-piperidin-3-yl-ethyl)-benzamide;
3-[3-(3,4-Dimethoxy-phenyl)-ureidomethyl]-N-piperidin-3-ylmethyl-benzamide;
3-[3-(4-Cyano-phenyl)-ureidomethyl]-N-(4-dimethylamino-butyl)-benzamide;
3-[3-(4-Cyano-phenyl)-ureidomethyl]-N-(3-dimethylamino-propyl)-benzamide;
3-[3-(4-Cyano-phenyl)-ureidomethyl]-N-(5-dimethylamino-pentyl)-benzamide;
3-[3-(4-Amido-phenyl)-ureidomethyl]-N-(1,2,3,4-tetrahydro-isoquinolin-7-yl)-benzamide;
2-Methyl-1,2,3,4-tetrahydro-isoquinoline-7-carboxylic acid {3-[3-(4-amido-phenyl)-ureidomethyl]-phenyl}-amide;
2-Methyl-1,2,3,4-tetrahydro-isoquinoline-7-carboxylic acid {3-[3-(4-cyano-phenyl)-ureidomethyl]-phenyl}-amide;
N-{3-[3-(4-Cyano-phenyl)-ureidomethyl]-phenyl}-3-piperidin-3-yl-propionamide;
3,4-Dimethoxy-N-[3-(2-piperidin-3-yl-ethylcarbamoyl)-benzyl]-benzamide;
3,4-Dimethoxy-N-[3-(1,2,3,4-tetrahydro-isoquinolin-7-ylcarbamoyl)-benzyl]-benzamide;
3,4-Dimethoxy-N-{3-[(piperidin-4-ylmethyl)-carbamoyl]-benzyl}-benzamide;
3,4-Dimethoxy-N-[3-(2-piperidin-4-yl-ethylcarbamoyl)-benzyl]-benzamide;
3,4-Dimethoxy-N-{3-[2-(1-methyl-piperidin-3-yl)-ethylcarbamoyl]-benzyl}-benzamide;
3,4-Dimethoxy-N-[3-(2-methyl-1,2,3,4-tetrahydro-isoquinolin-7-ylcarbamoyl)-benzyl]-benzamide;
N-{3-[2-(2,2-Dimethyl-propyl)-1,2,3,4-tetrahydro-isoquinolin-7-ylcarbamoyl]-benzyl}-3,4-dimethoxy-benzamide;
N-[3-(5-Dimethylamino-pentylcarbamoyl)-benzyl]-3,4-dimethoxy-benzamide;
N-[3-(6-Dimethylamino-hexylcarbamoyl)-benzyl]-3,4-dimethoxy-benzamide;
N-[3-(4-Dimethylamino-butylcarbamoyl)-benzyl]-3,4-dimethoxy-benzamide;
N-[3-(3-Dimethylamino-propylcarbamoyl)-benzyl]-3,4-dimethoxy-benzamide;
3,4-Dimethoxy-N-[3-(3-piperidin-3-yl-propionylamino)-benzyl]-benzamide;
2-Methyl-1,2,3,4-tetrahydro-isoquinoline-6-carboxylic acid {3-[(3,4-dimethoxy-benzoylamino)-methyl]-phenyl}-amide;

2-Methyl-1,2,3,4-tetrahydro-isoquinoline-7-carboxylic acid {3-[(3,4-dimethoxy-benzoylamino)-methyl]-phenyl}-amide;
N-{3-[(3,4-Dimethoxy-phenylcarbamoyl)-methyl]-phenyl}-3-piperidin-3-yl-propionamide;
1,2,3,4-Tetrahydro-isoquinoline-7-carboxylic acid {3-[(3,4-dimethoxy-phenylcarbamoyl)-methyl]-phenyl}-amide;
2-Methyl-1,2,3,4-tetrahydro-isoquinoline-7-carboxylic acid {3-[(3,4-dimethoxy-phenylcarbamoyl)-methyl]-phenyl}-amide;
N-(3,4-Dimethoxy-phenyl)-3-[3-(3-piperidin-3-yl-propionylamino)-phenyl]-propionamide
N-(4-Cyano-phenyl)-3-[3-(3-piperidin-3-yl-propionylamino)-phenyl]-propionamide;
1,2,3,4-Tetrahydro-isoquinoline-7-carboxylic acid {3-[2-(4-cyano-phenylcarbamoyl)-ethyl]-phenyl}-amide;
3,4-Dimethoxy-N-[3-(1-methyl-piperidin-4-ylcarbamoyl)-benzyl]-benzamide;
N-[3-(2-Benzyl-1,2,3,4-tetrahydro-isoquinolin-7-ylcarbamoyl)-benzyl]-3,4-dimethoxy-benzamide;
N-{3-[2-(2-Fluoro-benzyl)-1,2,3,4-tetrahydro-isoquinolin-7-ylcarbamoyl]-benzyl}-3,4-dimethoxy-benzamide;
N-{3-[2-(3-Fluoro-benzyl)-1,2,3,4-tetrahydro-isoquinolin-7-ylcarbamoyl]-benzyl}-3,4-dimethoxy-benzamide;
N-{3-[2-(4-Fluoro-benzyl)-1,2,3,4-tetrahydro-isoquinolin-7-ylcarbamoyl]-benzyl}-3,4-dimethoxy-benzamide;
N-{3-[2-(2,6-Difluoro-benzyl)-1,2,3,4-tetrahydro-isoquinolin-7-ylcarbamoyl]-benzyl}-3,4-dimethoxy-benzamide;
N-{3-[2-(2,3-Difluoro-benzyl)-1,2,3,4-tetrahydro-isoquinolin-7-ylcarbamoyl]-benzyl}-3,4-dimethoxy-benzamide;
N-{3-[2-(2,4-Difluoro-benzyl)-1,2,3,4-tetrahydro-isoquinolin-7-ylcarbamoyl]-benzyl}-3,4-dimethoxy-benzamide;
N-{3-[2-(3,5-Difluoro-benzyl)-1,2,3,4-tetrahydro-isoquinolin-7-ylcarbamoyl]-benzyl}-3,4-dimethoxy-benzamide;
3,4-Dimethoxy-N-[3-(5-methyl-4,5,6,7-tetrahydro-thiazolo[5,4-c]pyridin-2-ylcarbamoyl)-benzyl]-benzamide;
(7-{3-[(3,4-Dimethoxy-benzoylamino)-methyl]-benzoylamino}-3,4-dihydro-1H-isoquinolin-2-yl)-acetic acid methyl ester;
N-[3-(2-Carbamoylmethyl-1,2,3,4-tetrahydro-isoquinolin-7-ylcarbamoyl)-benzyl]-3,4-dimethoxy-benzamide;
3,4-Dimethoxy-N-{3-[2-(2-methoxy-ethyl)-1,2,3,4-tetrahydro-isoquinolin-7-ylcarbamoyl]-benzyl}-benzamide;
N-{3-[2-(2-Cyano-ethyl)-1,2,3,4-tetrahydro-isoquinolin-7-ylcarbamoyl]-benzyl}-3,4-dimethoxy-benzamide;
N-{3-[2-(2,2-Difluoro-ethyl)-1,2,3,4-tetrahydro-isoquinolin-7-ylcarbamoyl]-benzyl}-3,4-dimethoxy-benzamide;
3-[3-(4-Cyano-phenyl)-ureidomethyl]-N-(5-methyl-4,5,6,7-tetrahydro-thiazolo[5,4-c]pyridin-2-yl)-benzamide;
3-Chloro-4-methoxy-N-[3-(2-methyl-1,2,3,4-tetrahydro-isoquinolin-7-ylcarbamoyl)-benzyl]-benzamide;
4-Methoxy-3-methyl-N-[3-(2-methyl-1,2,3,4-tetrahydro-isoquinolin-7-ylcarbamoyl)-benzyl]-benzamide;
4-Trifluoromethoxy-N-[3-(2-methyl-1,2,3,4-tetrahydro-isoquinolin-7-ylcarbamoyl)-benzyl]-benzamide;
3-Chloro-N-[3-(2-methyl-1,2,3,4-tetrahydro-isoquinolin-7-ylcarbamoyl)-benzyl]-4-trifluoromethoxy-benzamide;
4-Difluoromethoxy-N-[3-(2-methyl-1,2,3,4-tetrahydro-isoquinolin-7-ylcarbamoyl)-benzyl]-benzamide;
3-Chloro-4-ethoxy-N-[3-(2-methyl-1,2,3,4-tetrahydro-isoquinolin-7-ylcarbamoyl)-benzyl]-benzamide;
5-Chloro-6-methoxy-N-[3-(2-methyl-1,2,3,4-tetrahydro-isoquinolin-7-ylcarbamoyl)-benzyl]-nicotinamide;
3,4-Diethoxy-N-[3-(2-methyl-1,2,3,4-tetrahydro-isoquinolin-7-ylcarbamoyl)-benzyl]-benzamide;
3-Hydroxy-4-methoxy-N-[3-(2-methyl-1,2,3,4-tetrahydro-isoquinolin-7-ylcarbamoyl)-benzyl]-benzamide;
6-Hydroxy-N-[3-(2-methyl-1,2,3,4-tetrahydro-isoquinolin-7-ylcarbamoyl)-benzyl]-nicotinamide;
N-[3-(2-Ethyl-1,2,3,4-tetrahydro-isoquinolin-7-ylcarbamoyl)-benzyl]-3,4-dimethoxy-benzamide;
3-Chloro-4-methoxy-N-[3-(5-methyl-4,5,6,7-tetrahydro-thiazolo[5,4-c]pyridin-2-ylcarbamoyl)-benzyl]-benzamide;
4-Methoxy-3-methyl-N-[3-(5-methyl-4,5,6,7-tetrahydro-thiazolo[5,4-c]pyridin-2-ylcarbamoyl)-benzyl]-benzamide;
3-Chloro-N-[3-(5-methyl-4,5,6,7-tetrahydro-thiazolo[5,4-c]pyridin-2-ylcarbamoyl)-benzyl]-4-trifluoromethoxy-benzamide;
6-Methoxy-N-[3-(2-methyl-1,2,3,4-tetrahydro-isoquinolin-7-ylcarbamoyl)-benzyl]-nicotinamide;
1-Methyl-6-oxo-1,6-dihydro-pyridine-3-carboxylic acid 3-(2-methyl-1,2,3,4-tetrahydro-isoquinolin-7-ylcarbamoyl)-benzylamide;
4-Difluoromethoxy-3-ethoxy-N-[3-(2-methyl-1,2,3,4-tetrahydro-isoquinolin-7-ylcarbamoyl)-benzyl]-benzamide;
N-[3-(5-Benzyl-4,5,6,7-tetrahydro-thiazolo[5,4-c]pyridin-2-ylcarbamoyl)-benzyl]-3,4-dimethoxy-benzamide;
N-{3-[2-(2-Cyano-benzyl)-1,2,3,4-tetrahydro-isoquinolin-7-ylcarbamoyl]-benzyl}-3,4-dimethoxy-benzamide;
3,4-Dimethoxy-N-{3-[2-(2,2,2-trifluoro-ethyl)-1,2,3,4-tetrahydro-isoquinolin-7-ylcarbamoyl]-benzyl}-benzamide;
3,4-Dimethoxy-N-{3-[2-(2-nitro-benzyl)-1,2,3,4-tetrahydro-isoquinolin-7-ylcarbamoyl]-benzyl}-benzamide;
3,4-Dimethoxy-N-{3-[2-(2-trifluoromethyl-benzyl)-1,2,3,4-tetrahydro-isoquinolin-7-ylcarbamoyl]-benzyl}-benzamide;
3,4-Dimethoxy-N-[3-(2-pyridin-3-ylmethyl-1,2,3,4-tetrahydro-isoquinolin-7-ylcarbamoyl)-benzyl]-benzamide;
3,4-Dimethoxy-N-{3-[2-(3,3,3-trifluoro-propyl)-1,2,3,4-tetrahydro-isoquinolin-7-ylcarbamoyl]-benzyl}-benzamide;
3,4-Dimethoxy-N-[3-(2-pyridin-4-ylmethyl-1,2,3,4-tetrahydro-isoquinolin-7-ylcarbamoyl)-benzyl]-benzamide;
3,4-Dimethoxy-N-[3-(2-pyridin-2-ylmethyl-1,2,3,4-tetrahydro-isoquinolin-7-ylcarbamoyl)-benzyl]-benzamide;
N-{3-[2-(2-Fluoro-ethyl)-1,2,3,4-tetrahydro-isoquinolin-7-ylcarbamoyl]-benzyl}-3,4-dimethoxy-benzamide;
3-Ethoxy-4-methoxy-N-[3-(2-methyl-1,2,3,4-tetrahydro-isoquinolin-7-ylcarbamoyl)-benzyl]-benzamide;
4-Difluoromethoxy-3-methoxy-N-[3-(2-methyl-1,2,3,4-tetrahydro-isoquinolin-7-ylcarbamoyl)-benzyl]-benzamide;
3-Fluoro-4-methoxy-N-[3-(2-methyl-1,2,3,4-tetrahydro-isoquinolin-7-ylcarbamoyl)-benzyl]-benzamide;
4-Methoxy-N-[3-(2-methyl-1,2,3,4-tetrahydro-isoquinolin-7-ylcarbamoyl)-benzyl]-benzamide;
N-[3-(2,3-Dihydro-1H-isoindol-5-ylcarbamoyl)-benzyl]-3,4-dimethoxy-benzamide;
3,4-Dimethoxy-N-[3-(4,5,6,7-tetrahydro-thiazolo[5,4-c]pyridin-2-ylcarbamoyl)-benzyl]-benzamide;
3,4-Dimethoxy-N-{3-[5-(3,3,3-trifluoro-propyl)-4,5,6,7-tetrahydro-thiazolo[5,4-c]pyridin-2-ylcarbamoyl]-benzyl}-benzamide;
3,4-Dimethoxy-N-{3-[5-(2-methoxy-ethyl)-4,5,6,7-tetrahydro-thiazolo[5,4-c]pyridin-2-ylcarbamoyl]-benzyl}-benzamide;
N-{3-[5-(2,2-Difluoro-ethyl)-4,5,6,7-tetrahydro-thiazolo[5,4-c]pyridin-2-ylcarbamoyl]-benzyl}-3,4-dimethoxy-benzamide;
N-{3-[5-(2-Fluoro-ethyl)-4,5,6,7-tetrahydro-thiazolo[5,4-c]pyridin-2-ylcarbamoyl]-benzyl}-3,4-dimethoxy-benzamide;
3-Chloro-N-[3-(2,3-dihydro-1H-isoindol-5-ylcarbamoyl)-benzyl]-4-methoxy-benzamide;

3-Chloro-4-methoxy-N-[3-(4,5,6,7-tetrahydro-thiazolo[5,4-c]pyridin-2-ylcarbamoyl)-benzyl]-benzamide;
N-[3-(2,3-Dihydro-1H-isoindol-5-ylcarbamoyl)-benzyl]-4-methoxy-3-methyl-benzamide;
4-Methoxy-3-methyl-N-[3-(4,5,6,7-tetrahydro-thiazolo[5,4-c]pyridin-2-ylcarbamoyl)-benzyl]-benzamide;
4,5,6,7-Tetrahydro-thiazolo[5,4-c]pyridine-2-carboxylic acid {3-[(3,4-dimethoxy-benzoylamino)-methyl]-phenyl}-amide;
5-Methyl-4,5,6,7-tetrahydro-thiazolo[5,4-c]pyridine-2-carboxylic acid {3-[(3,4-dimethoxy-benzoylamino)-methyl]-phenyl}-amide;
N-[3-((R)-6-Amino-4,5,6,7-tetrahydro-benzothiazol-2-ylcarbamoyl)-benzyl]-3,4-dimethoxy-benzamide;
N-[3-((S)-6-Amino-4,5,6,7-tetrahydro-benzothiazol-2-ylcarbamoyl)-benzyl]-3,4-dimethoxy-benzamide;
3,4-Dimethoxy-N-[3-((S)-6-propylamino-4,5,6,7-tetrahydro-benzothiazol-2-ylcarbamoyl)-benzyl]-benzamide;
4-Methylcyano-N-[3-(2-methyl-1,2,3,4-tetrahydro-isoquinolin-7-ylcarbamoyl)-benzyl]-benzamide;
N-[3-((R)-6-Amino-4,5,6,7-tetrahydro-benzothiazol-2-ylcarbamoyl)-benzyl]-3-chloro-4-methoxy-benzamide;
N-[3-((S)-6-Amino-4,5,6,7-tetrahydro-benzothiazol-2-ylcarbamoyl)-benzyl]-3-chloro-4-methoxy-benzamide;
N-[3-((R)-6-Amino-4,5,6,7-tetrahydro-benzothiazol-2-ylcarbamoyl)-benzyl]-4-methoxy-3-methyl-benzamide;
N-[3-((S)-6-Amino-4,5,6,7-tetrahydro-benzothiazol-2-ylcarbamoyl)-benzyl]-4-methoxy-3-methyl-benzamide;
N-[3-((S)-6-Dimethylamino-4,5,6,7-tetrahydro-benzothiazol-2-ylcarbamoyl)-benzyl]-3,4-dimethoxy-benzamide;
N-[3-((R)-6-Dimethylamino-4,5,6,7-tetrahydro-benzothiazol-2-ylcarbamoyl)-benzyl]-3,4-dimethoxy-benzamide;
3,4-Dimethoxy-N-[3-((S)-6-morpholin-4-yl-4,5,6,7-tetrahydro-benzothiazol-2-ylcarbamoyl)-benzyl]-benzamide;
3,4-Dimethoxy-N-[3-((R)-6-morpholin-4-yl-4,5,6,7-tetrahydro-benzothiazol-2-ylcarbamoyl)-benzyl]-benzamide;
3-Chloro-4-methoxy-N-[3-((S)-6-propylamino-4,5,6,7-tetrahydro-benzothiazol-2-ylcarbamoyl)-benzyl]-benzamide;
4-Methoxy-3-methyl-N-[3-((S)-6-propylamino-4,5,6,7-tetrahydro-benzothiazol-2-ylcarbamoyl)-benzyl]-benzamide;
3-Chloro-N-[3-((S)-6-dimethylamino-4,5,6,7-tetrahydro-benzothiazol-2-ylcarbamoyl)-benzyl]-4-methoxy-benzamide;
3-Chloro-N-[3-((R)-6-dimethylamino-4,5,6,7-tetrahydro-benzothiazol-2-ylcarbamoyl)-benzyl]-4-methoxy-benzamide;
N-[3-((S)-6-Dimethylamino-4,5,6,7-tetrahydro-benzothiazol-2-ylcarbamoyl)-benzyl]-4-methoxy-3-methyl-benzamide;
N-[3-((R)-6-Dimethylamino-4,5,6,7-tetrahydro-benzothiazol-2-ylcarbamoyl)-benzyl]-4-methoxy-3-methyl-benzamide;
N-{3-[(S)-6-(1,3-Dihydro-isoindol-2-yl)-4,5,6,7-tetrahydro-benzothiazol-2-ylcarbamoyl]-benzyl}-3,4-dimethoxy-benzamide;
N-{3-[(S)-6-(1,1-Dioxo-thiomoypholin-4-yl)-4,5,6,7-tetrahydro-benzothiazol-2-ylcarbamoyl]-benzyl}-3,4-dimethoxy-benzamide;
N-[3-(2-Amino-indan-5-ylcarbamoyl)-benzyl]-3,4-dimethoxy-benzamide;
3-Chloro-4-methoxy-N-[3-((S)-6-morpholin-4-yl-4,5,6,7-tetrahydro-benzothiazol-2-ylcarbamoyl)-benzyl]-benzamide;
4-Methoxy-3-methyl-N-[3-((S)-6-morpholin-4-yl-4,5,6,7-tetrahydro-benzothiazol-2-ylcarbamoyl)-benzyl]-benzamide;
3-Chloro-4-methoxy-N-{3-[(2-methoxy-ethyl)-((S)-6-propylamino-4,5,6,7-tetrahydro-benzothiazol-2-yl)-carbamoyl]-benzyl}-benzamide;
N-{3-[(S)-6-(Benzyl-propyl-amino)-4,5,6,7-tetrahydro-benzothiazol-2-ylcarbamoyl]-benzyl}-3-chloro-4-methoxy-benzamide;
2-Bromo-4,5-dimethoxy-N-[3-(2-methyl-1,2,3,4-tetrahydro-isoquinolin-7-ylcarbamoyl)-benzyl]-benzamide;
2-Hydroxy-3,4-dimethoxy-N-[3-(2-methyl-1,2,3,4-tetrahydro-isoquinolin-7-ylcarbamoyl)-benzyl]-benzamide;
3-Chloro-4-ethyl-N-[3-(2-methyl-1,2,3,4-tetrahydro-isoquinolin-7-ylcarbamoyl)-benzyl]-benzamide;
2,4,5-Trimethoxy-N-[3-(2-methyl-1,2,3,4-tetrahydro-isoquinolin-7-ylcarbamoyl)-benzyl]-benzamide;
3-[1-Benzyl-3-(4-cyano-phenyl)-ureidomethyl]-N-(5-methyl-4,5,6,7-tetrahydro-thiazolo[5,4-c]pyridin-2-yl)-benzamide;
3,4-Dimethoxy-N-[3-(2-morpholin-4-yl-indan-5-ylcarbamoyl)-benzyl]-benzamide;
3-[1-Benzyl-3-(3-cyano-phenyl)-ureidomethyl]-N-(5-methyl-4,5,6,7-tetrahydro-thiazolo[5,4-c]pyridin-2-yl)-benzamide;
N-Benzyl-3,4-dimethoxy-N-[3-(5-methyl-4,5,6,7-tetrahydro-thiazolo[5,4-c]pyridin-2-ylcarbamoyl)-benzyl]-benzamide;
3-[3-(3-Ethynyl-phenyl)-ureidomethyl]-N-(5-methyl-4,5,6,7-tetrahydro-thiazolo[5,4-c]pyridin-2-yl)-benzamide;
N-{3-[4-(2-Dimethylamino-ethyl)-phenylcarbamoyl]-benzyl}-3,4-dimethoxy-benzamide;
3-[3-(4-Cyano-phenyl)-ureidomethyl]-N-[4-(2-dimethylamino-ethyl)-phenyl]-benzamide; and
3-[3-(4-carboxamide-phenyl)-ureidomethyl]-N-[4-(2-dimethylamino-ethyl)-phenyl]-benzamide.

In another embodiment of the invention, there are compounds of the formula (I) selected from the group below, or a tautomer thereof or a salt thereof, preferably a pharmaceutically acceptable salt thereof:
N-[3-((R)-6-Amino-4,5,6,7-tetrahydro-benzothiazol-2-ylcarbamoyl)-benzyl]-3,4-dimethoxy-benzamide;
N-[3-((S)-6-Amino-4,5,6,7-tetrahydro-benzothiazol-2-ylcarbamoyl)-benzyl]-3,4-dimethoxy-benzamide;
3,4-Dimethoxy-N-[3-((S)-6-propylamino-4,5,6,7-tetrahydro-benzothiazol-2-ylcarbamoyl)-benzyl]-benzamide;
N-[3-((R)-6-Amino-4,5,6,7-tetrahydro-benzothiazol-2-ylcarbamoyl)-benzyl]-3-chloro-4-methoxy-benzamide;
N-[3-((S)-6-Amino-4,5,6,7-tetrahydro-benzothiazol-2-ylcarbamoyl)-benzyl]-3-chloro-4-methoxy-benzamide;
N-[3-((R)-6-Amino-4,5,6,7-tetrahydro-benzothiazol-2-ylcarbamoyl)-benzyl]-4-methoxy-3-methyl-benzamide;
N-[3-((S)-6-Amino-4,5,6,7-tetrahydro-benzothiazol-2-ylcarbamoyl)-benzyl]-4-methoxy-3-methyl-benzamide;
N-[3-((S)-6-Dimethylamino-4,5,6,7-tetrahydro-benzothiazol-2-ylcarbamoyl)-benzyl]-3,4-dimethoxy-benzamide;
N-[3-((R)-6-Dimethylamino-4,5,6,7-tetrahydro-benzothiazol-2-ylcarbamoyl)-benzyl]-3,4-dimethoxy-benzamide;
3,4-Dimethoxy-N-[3-((S)-6-morpholin-4-yl-4,5,6,7-tetrahydro-benzothiazol-2-ylcarbamoyl)-benzyl]-benzamide;
3,4-Dimethoxy-N-[3-((R)-6-morpholin-4-yl-4,5,6,7-tetrahydro-benzothiazol-2-ylcarbamoyl)-benzyl]-benzamide;
3-Chloro-4-methoxy-N-[3-((S)-6-propylamino-4,5,6,7-tetrahydro-benzothiazol-2-ylcarbamoyl)-benzyl]-benzamide;

4-Methoxy-3-methyl-N-[3-((S)-6-propylamino-4,5,6,7-tetrahydro-benzothiazol-2-ylcarbamoyl)-benzyl]-benzamide;

3-Chloro-N-[3-((S)-6-dimethylamino-4,5,6,7-tetrahydro-benzothiazol-2-ylcarbamoyl)-benzyl]-4-methoxy-benzamide;

3-Chloro-N-[3-((R)-6-dimethylamino-4,5,6,7-tetrahydro-benzothiazol-2-ylcarbamoyl)-benzyl]-4-methoxy-benzamide;

N-[3-((S)-6-Dimethylamino-4,5,6,7-tetrahydro-benzothiazol-2-ylcarbamoyl)-benzyl]-4-methoxy-3-methyl-benzamide;

N-[3-((R)-6-Dimethylamino-4,5,6,7-tetrahydro-benzothiazol-2-ylcarbamoyl)-benzyl]-4-methoxy-3-methyl-benzamide;

N-{3-[(S)-6-(1,3-Dihydro-isoindol-2-yl)-4,5,6,7-tetrahydro-benzothiazol-2-ylcarbamoyl]-benzyl}-3,4-dimethoxy-benzamide;

N-{3-[(S)-6-(1,1-Dioxo-thiomorpholin-4-yl)-4,5,6,7-tetrahydro-benzothiazol-2-ylcarbamoyl]-benzyl}-3,4-dimethoxy-benzamide;

3-Chloro-4-methoxy-N-[3-((S)-6-morpholin-4-yl-4,5,6,7-tetrahydro-benzothiazol-2-ylcarbamoyl)-benzyl]-benzamide;

4-Methoxy-3-methyl-N-[3-((S)-6-morpholin-4-yl-4,5,6,7-tetrahydro-benzothiazol-2-ylcarbamoyl)-benzyl]-benzamide; and N-{3-[(S)-6-(Benzyl-propyl-amino)-4,5,6,7-tetrahydro-benzothiazol-2-ylcarbamoyl]-benzyl}-3-chloro-4-methoxy-benzamide.

Although every attempt has been made to use IUPAC nomenclature, in the event that such nomenclature is in conflict with the structure, it should be understood that the compound is defined by the structure.

The invention includes the use of any compounds as described above comprising one or more asymmetric carbon atoms which may occur as racemates and racemic mixtures, single enantiomers, diastereomeric mixtures and individual diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods for using all such tautomers.

All terms as used herein in this specification, unless otherwise stated, shall be understood in their ordinary meaning as known in the art. For example, "$C_{1-6}$alkyl" is a saturated aliphatic hydrocarbon monovalent radical containing 1-6 carbons, such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. For the purposes of this invention "$C_{2-6}$alkenyl" refers to a unsaturated hydrocarbon monovalent radical containing 2-6 carbons and a double bond, such as —CH=CH$_2$ and —CH=CH—CH$_3$. For the purposes of this invention "$C_{2-6}$ alkynyl" refers to a unsaturated hydrocarbon monovalent radical containing 2-6 carbons and a triple bond, such as —CH≡CH and —CH≡C—CH$_3$. All alkyl, alkenyl and alkynyl groups shall be understood as being branched or unbranched, cyclized or uncyclized where structurally possible and unless otherwise specified. Other more specific definitions are as follows:

Carbocycles include hydrocarbon rings containing from three to twelve carbon atoms. These carbocycles may be either aromatic or non-aromatic ring systems, monocyclic or polycyclic. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure. Unless otherwise stated, heterocycles include but are not limited to, for example pyrrolidinyl, pyrrolinyl, morpholinyl, thiomorpholinyl, thiomorpholinyl sulfoxide, thiomorpholinyl sulfone, dioxalanyl, piperidinyl, piperazinyl, tetrahydrofuranyl, tetrahydropyranyl, tetrahydrofuranyl, 1,3-dioxolanone, 1,3-dioxanone, 1,4-dioxanyl, piperidinonyl, tetrahydropyrimidonyl, pentamethylene sulfide, pentamethylene sulfoxide, pentamethylene sulfone, tetramethylene sulfide, tetramethylene sulfoxide and tetramethylene sulfone.

The term "heteroaryl" shall be understood to mean an aromatic 5-8 membered monocyclic or 8-11 membered bicyclic ring containing 1-4 heteroatoms such as N,O and S. Unless otherwise stated, such heteroaryls include thienyl, furanyl, isoxazolyl, oxazolyl, thiazolyl, thiadiazolyl, tetrazolyl, pyrazolyl, pyrrolyl, imidazolyl, pyridinyl, pyrimidinyl, pyrazinyl, pyridazinyl, pyranyl, quinoxalinyl, indolyl, benzimidazolyl, benzoxazolyl, benzothiazolyl, benzothienyl, quinolinyl, quinazolinyl, naphthyridinyl, indazolyl, triazolyl, pyrazolo[3,4-b]pyrimidinyl, purinyl, pyrrolo[2,3-b]pyridinyl, pyrazolo[3,4-b]pyridinyl, tubercidinyl, oxazo[4,5-b]pyridinyl and imidazo[4,5-b]pyridinyl.

The term "heteroatom" as used herein shall be understood to mean atoms other than carbon, such as O, N, S and P.

In all alkyl groups or carbon chains one or more carbon atoms can be optionally replaced by heteroatoms: O, S or N. It shall be understood that if N is not substituted then it is NH, and it shall also be understood that the heteroatoms may replace either terminal carbon atoms or internal carbon atoms within a branched or unbranched carbon chain. Such groups can be substituted as described herein by groups such as oxo to result in definitions, such as, but not limited to: alkoxycarbonyl, acyl, amido and thioxo.

The term "aryl" as used herein shall be understood to mean aromatic carbocycle, such as phenyl or naphthyl or heteroaryl as defined above. Each aryl or heteroaryl unless otherwise specified includes it's partially or fully hydrogenated derivative. For example, quinolinyl may include decahydroquinolinyl and tetrahydroquinolinyl, naphthyl may include hydrogenated derivatives, such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl, likewise, —S—R$^a$ may be represented as phenyl-S(O)$_m$— when R$^a$ is phenyl and where m is 0, 1 or 2.

The term "halogen" as used in the present specification shall be understood to mean bromine, chlorine, fluorine or iodine, preferably fluorine or chlorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

The compounds of the invention are only those which are contemplated to be "chemically stable" as will be appreciated by those skilled in the art. For example, a compound which would have a "dangling valency", or a "carbanion" are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, formic, benzoic, malonic, naphthalene-2-sulfonic and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C$_1$-C$_4$ alkyl)$_4$$^+$ salts.

In addition, within the scope of the invention is the use of prodrugs of compounds of formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

GENERAL SYNTHETIC METHODS

The compounds of the invention may be prepared by the general methods and examples presented below, and methods known to those of ordinary skill in the art. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carbocylic acid and an amine in the presence of 1-(3-dimethylaminopropyl)-3-ethylcarbodiimide (EDC) and 1-hydroxybenzotriazole. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization.

The methods described below and in the Synthetic Examples section may be used to prepare the compounds of formula I.

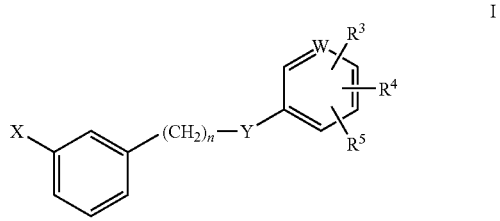

In the schemes below, R' represents R$^3$-R$^5$ in formula I. R$^1$-R$^5$ shall have the meanings defined in the detailed description of formula I.

Compounds of formula I having X=—C(O)NR$^1$R$^2$, Y=—NHC(O)NH— and n=1 may be prepared as shown in Scheme 1.

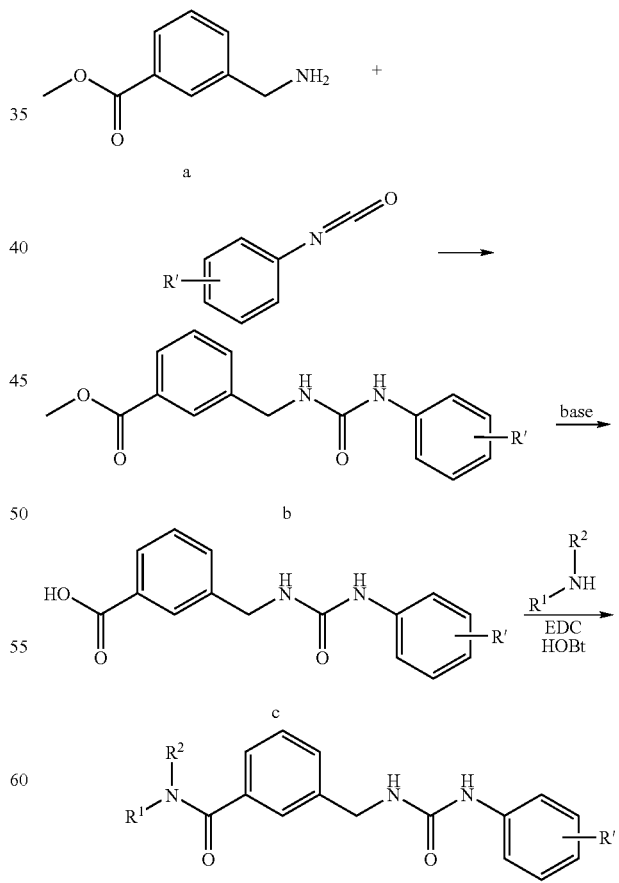

As illustrated in Scheme 1, the amino ester a is treated with an isocyanate in a suitable solvent. The product b is then hydrolyzed to carboxylic acid c, which is subjected to standard coupling conditions with an amine to provide compounds of formula I. Modification of $R^1$ or $R^2$ by methods known in the art and methods illustrated in the Synthetic Examples section can provide additional desired compounds of formula I. Compounds having $R^8$ and/or $R^9$ being alkyl may be prepared by methods known in the art, for example by treating I (Y=—NHC(O)NH—) with an iodo- or bromoalkane in the presence of a suitable base or beginning the synthesis in Scheme I with an N-alkyl intermediate a.

Alternatively, compounds of formula I having X=—C(O)NR$^1$R$^2$, Y=—NHC(O)NH— and n=1 can be synthesized as shown in Scheme 2.

tected, for example by treatment with acid for the Boc-protecting group, and the resulting amine, f, is then treated with an isocyanate to produce the desired compound of formula I. Modification of compound I by methods known in the art and methods illustrated in the Synthetic Examples section can provide additional desired compounds of formula I.

Compounds of formula I having X=—NHC(O)R$^1$, Y=—NHC(O)NH— and n=1 can be synthesized as shown in Scheme 3.

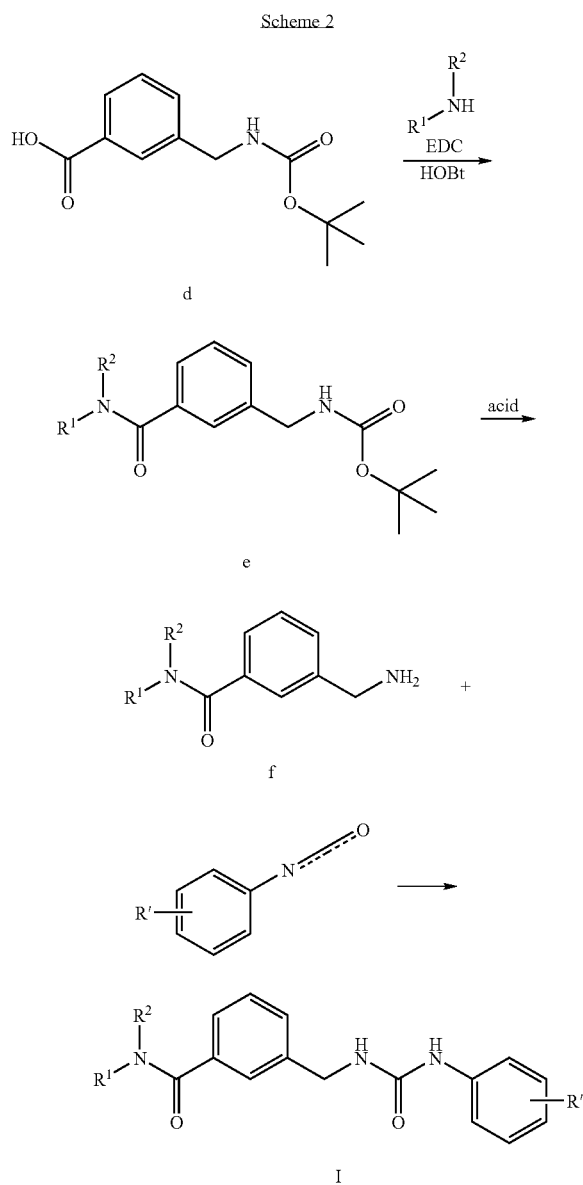

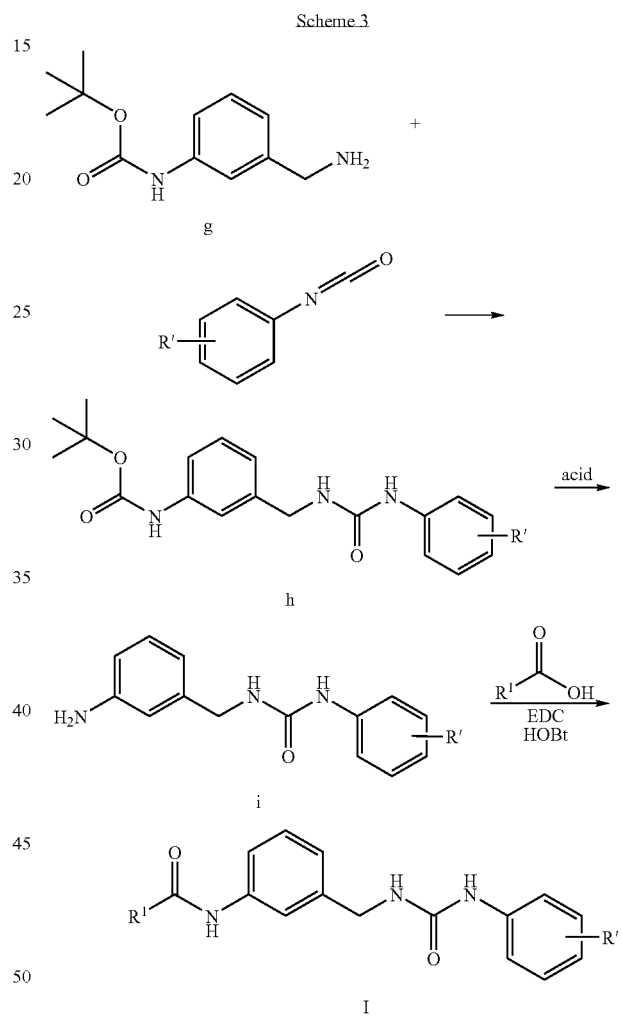

As illustrated in Scheme 2, the amino acid d, protected with a suitable protecting group, such as the Boc-group shown, is coupled to an amine using standard peptide coupling conditions in a suitable solvent. The intermediate e is then depro- As illustrated in Scheme 3, the suitably protected aminomethylaniline g is treated with an isocyanate in a suitable solvent to provide h. This intermediate is then deprotected, for example with a suitable acid for the Boc-protecting group shown, providing i, which is subjected to standard coupling with an acid to provide compounds of formula I having X=—NHC(O)R$^1$, Y=—NHC(O)NH— and n=1. Modification of this product by methods known in the art and methods illustrated in the Synthetic Examples section can provide additional desired compounds of formula I.

A method for synthesis of compounds of formula I having X=—C(O)NR$^1$R$^2$, Y=—NHC(O)— and n=1 is shown in Scheme 4.

Scheme 4

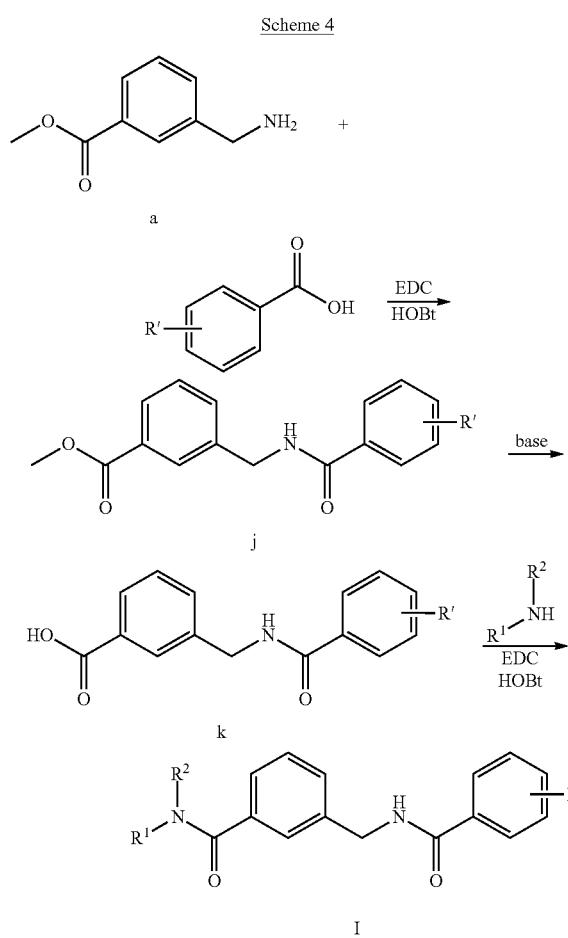

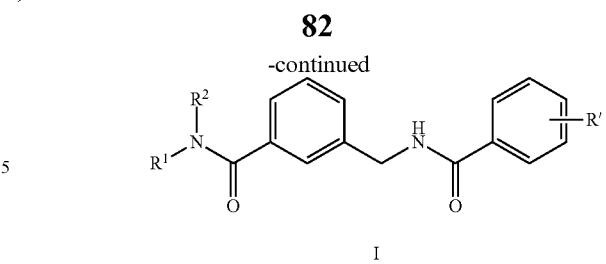

As illustrated in Scheme 4, the amino ester a is coupled to a benzoic acid analog using standard peptide coupling conditions in a suitable solvent. The ester of intermediate j is then hydrolyzed giving carboxylic acid k, which is subjected to a second coupling with an amine under similar coupling conditions to provide compounds of formula I having X=—C(O)NR$^1$R$^2$, Y=—NHC(O)— and n=1. Modification of this product by methods known in the art and methods illustrated in the Synthetic Examples section can provide additional desired compounds of formula III. For example, treatment with an iodo- or bromoalkane in the presence of a suitable base provides the corresponding compound I with R$^8$=alkyl.

An alternate approach that may be used to prepare compounds of formula I having X=—C(O)NR$^1$R$^2$, Y=—NHC(O)— and n=1 is illustrated in Scheme 5.

Scheme 5

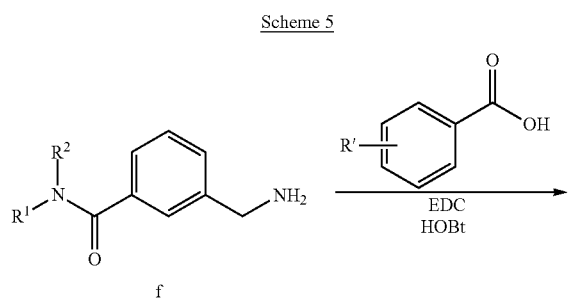

In Scheme 5, reagent f is prepared as described in Scheme 2 and subsequently coupled to a suitable acid. Again, modification of the initial product I can provide additional desired compounds of formula I having X=—C(O)NR$^1$R$^2$, Y=—NHC(O)— and n=1.

Compounds of formula I having X=—NHC(O)R$^1$—, Y=—NHC(O)— and n=1 can be obtained as shown in Scheme 6.

Scheme 6

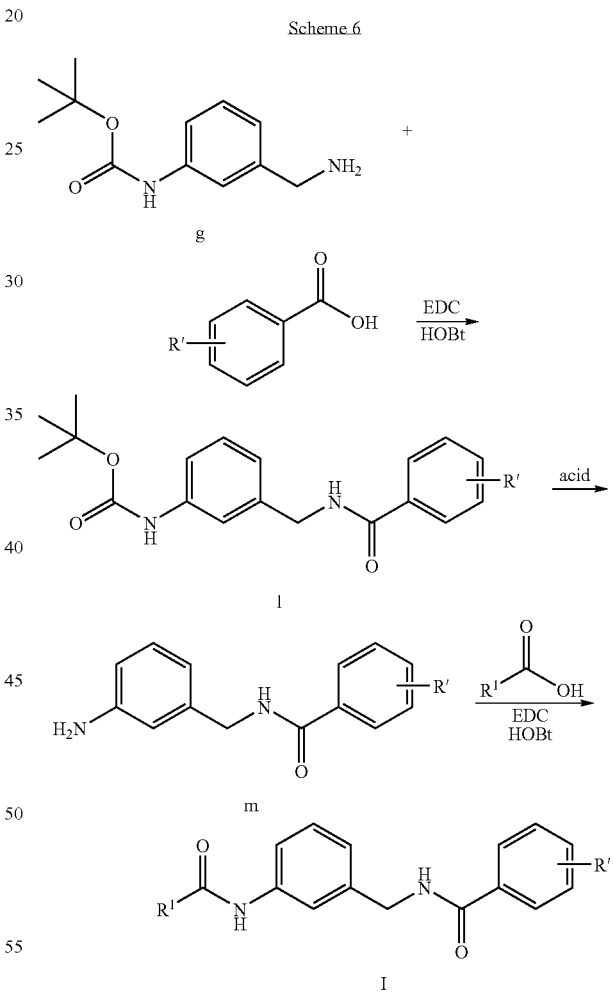

As shown in Scheme 6, g is coupled to a carboxylic acid using standard conditions to produce 1. Deprotection of intermediate 1, for example by using a suitable acid to remove the Boc protecting group, provides m which is subjected to a second coupling reaction to give compounds of formula I. Modification of the initial product I by methods known in the art and methods illustrated in the Synthetic Examples section can provide additional desired compounds of formula I having X=—NHC(O)R$^1$—, Y=—NHC(O)— and n=1.

Compounds of formula I having X=—NHC(O)R¹—, Y=—C(O)NH— and n=1 can be obtained as shown in Scheme 7.

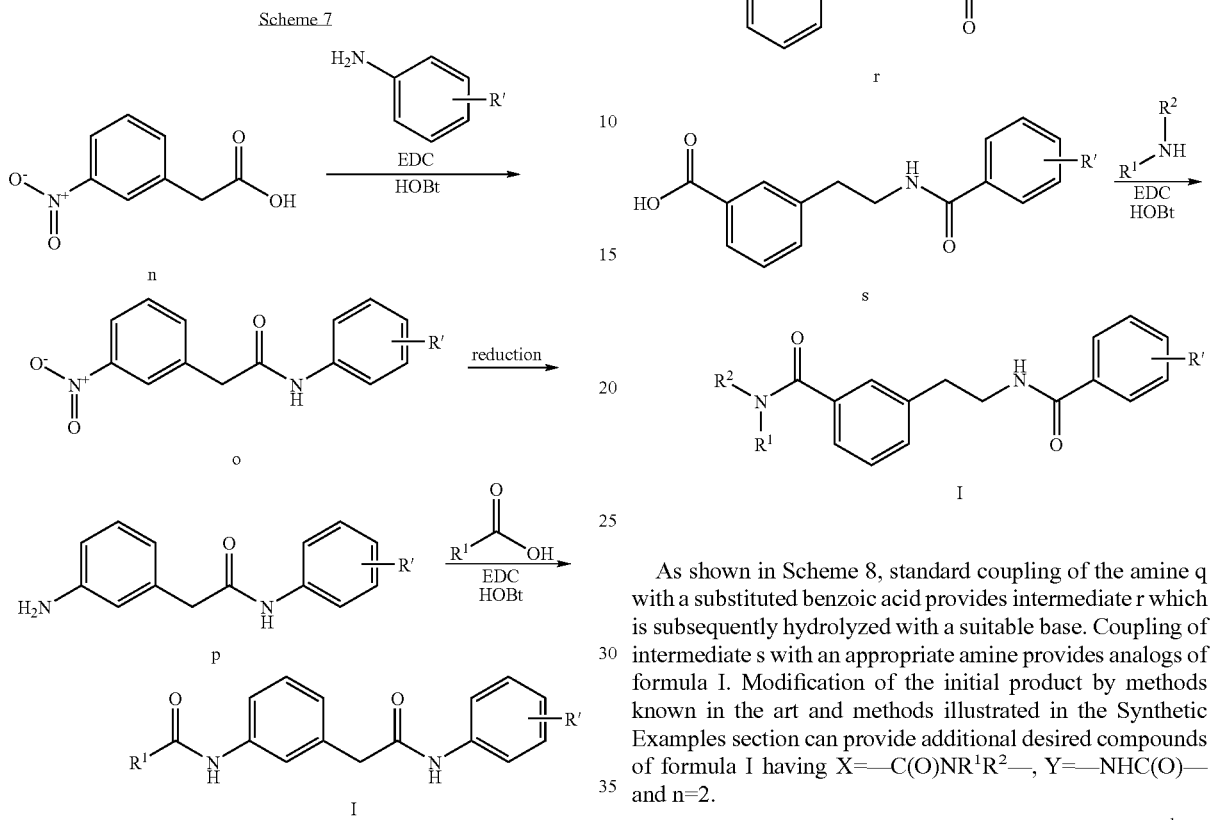

As shown in Scheme 7, standard coupling of 3-nitrophenylacetic acid n with an optionally substituted aniline, provides o, which is subsequently reduced to p, using methods known in the art, for example by treatment with a hydrogen source such as ammonium formate in the presence of a palladium catalyst. A second coupling with a suitable acid provides analogs of formula I. Modification of the initial product by methods known in the art and methods illustrated in the Synthetic Examples section can provide additional desired compounds of formula I having X=—NHC(O)R¹—, Y=—C(O)NH— and n=1.

Compounds of formula I having X=—C(O)NR¹R²—, Y=—NHC(O)— and n=2 can be prepared as shown in Scheme 8.

As shown in Scheme 8, standard coupling of the amine q with a substituted benzoic acid provides intermediate r which is subsequently hydrolyzed with a suitable base. Coupling of intermediate s with an appropriate amine provides analogs of formula I. Modification of the initial product by methods known in the art and methods illustrated in the Synthetic Examples section can provide additional desired compounds of formula I having X=—C(O)NR¹R²—, Y=—NHC(O)— and n=2.

Compounds of formula I having X=—NHC(O)R¹—, Y=—NHC(O)— and n=2 can be prepared as shown in Scheme 9.

85

-continued

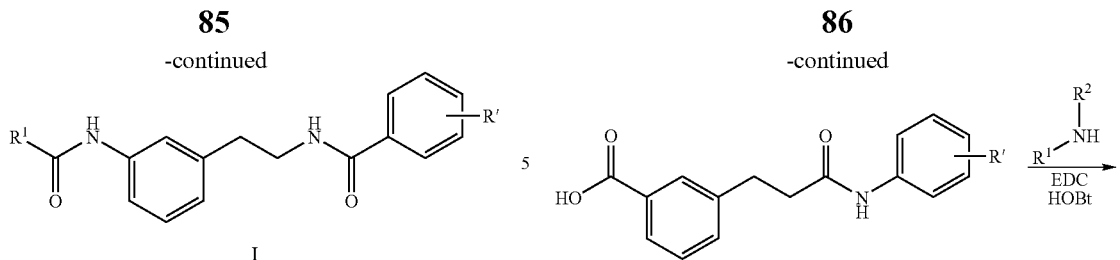

I

As shown in Scheme 9, standard coupling of the amine t with a substituted benzoic acid provides intermediate u which is subsequently hydrogenated to v. Coupling of intermediate v with a suitable acid provides analogs of formula I. Modification of the initial product by methods known in the art and methods illustrated in the Synthetic Examples section can provide additional desired compounds of formula I having X=—NHC(O)R$^1$—, Y=—NHC(O)— and n=2.

Compounds of formula I having X=—C(O)NR$^1$R$^2$—, Y=—C(O)NH— and n=2 can be prepared as shown in Scheme 10.

Scheme 10

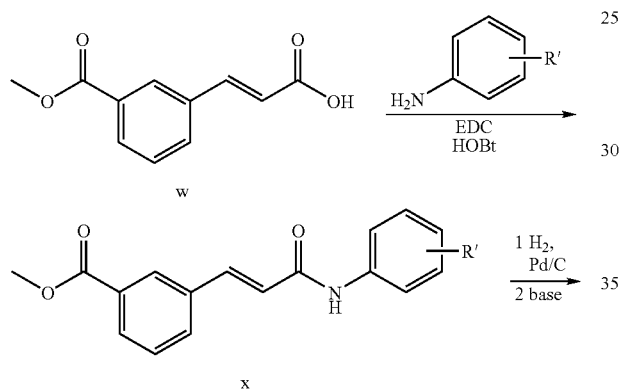

86

-continued

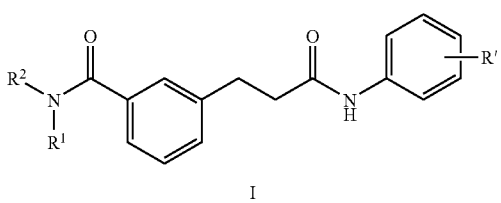

y

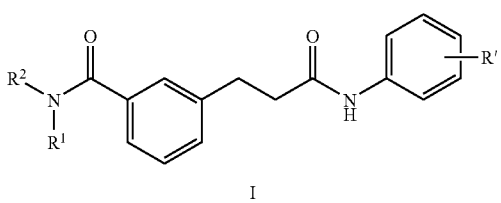

I

As shown in Scheme 10, standard coupling of carboxylic acid w with an aniline provides intermediate x, which can be hydrogenated then hydrolyzed with a suitable base to provide y. Coupling of intermediate y with a suitable amine provides analogs of formula I. Modification of the product by methods known in the art and methods illustrated in the Synthetic Examples section can provide additional desired compounds of formula I having X=—C(O)NR$^1$R$^2$—, Y=—C(O)NH— and n=2.

Compounds of formula I having X=—NHC(O)R$^1$—, Y=—C(O)NH— and n=2 can be obtained as shown in Scheme 11.

Scheme 11

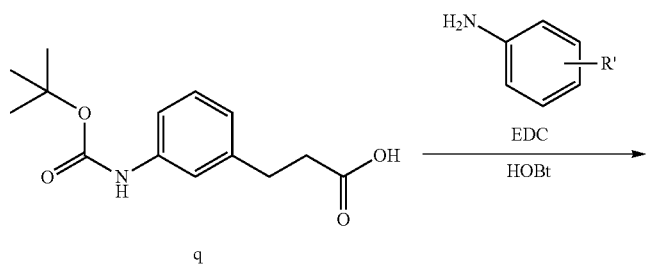

q

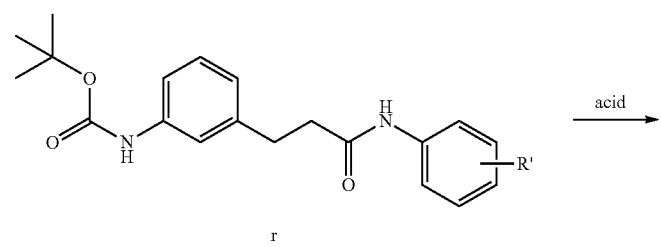

r

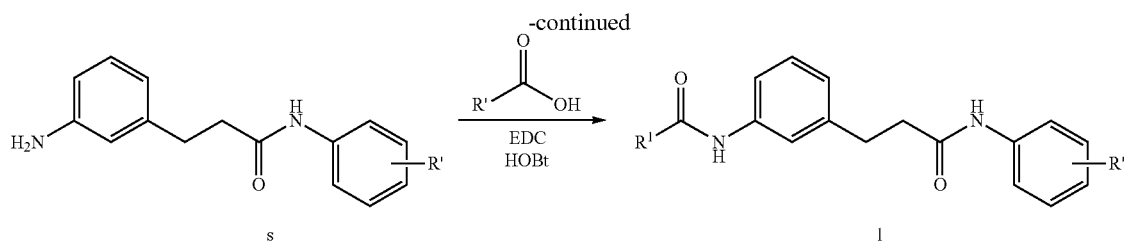

As shown in Scheme 11, standard coupling of an amine-protected aminophenylpropionic acid such as q with an aniline, provides intermediate r which is subsequently deprotected, for example with a suitable acid for the Boc protecting group shown. Coupling of intermediate s provides analogs of formula I. Modification of the product by methods known in the art and methods illustrated in the Synthetic Examples section can provide additional desired compounds of formula I having X=—NHC(O)R$^1$—, Y=—C(O)NH— and n=2.

SYNTHETIC EXAMPLES

For purposes of this invention the term "ppt" is an abbreviation for precipitate, "min" is an abbreviation for minute(s) and "h" is an abbreviation for hour(s).

Example 1

Synthesis of 3-[3-(4-cyano-phenyl)-ureidomethyl]-N-(1,2,3,4-tetrahydro-isoquinolin-7-yl)-benzamide) (1)

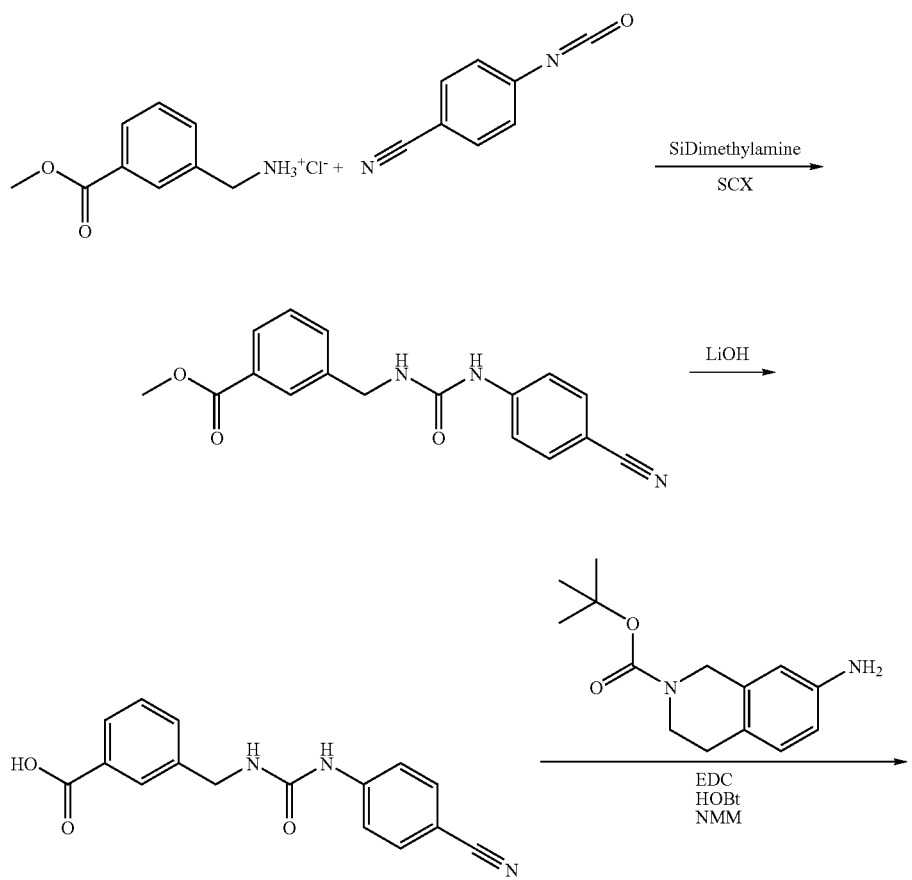

-continued

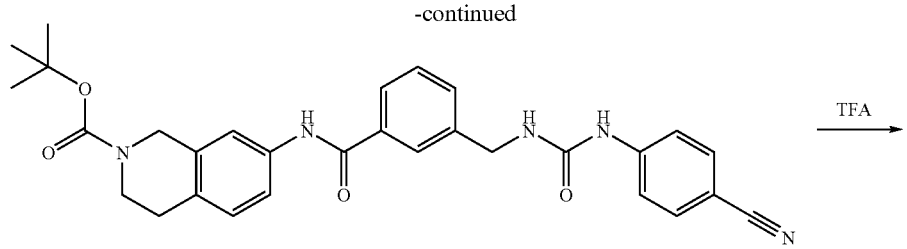

TFA

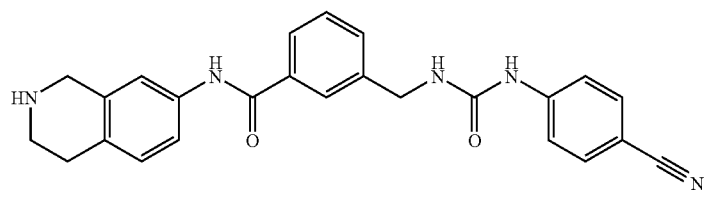

1

3-Methoxycarbonyl-benzyl-ammonium chloride (605 mg, 3.0 mmol) was dissolved in 6 mL DMF in a reaction vial. Si-dimethylamine (silica-bound dimethylamine; 3.3 g, 5 mmol) was added and the mixture was agitated for 1 hour. Subsequently, p-cyanophenylisocyanate (403.5 mg, 2.8 mmol) was added and the mixture was agitated overnight. SCX (strong cation exchanger; silica-bound benzenesulfonic acid; (568 mg, 0.5 mmol) was added and the mixture was agitated for 30 minutes. The solids were filtered, and the filtrate was evaporated to provide 843 mg (91% yield) of the desired urea, 3-[3-(4-cyano-phenyl)-ureidomethyl]-benzoic acid methyl ester, which was used directly. The intermediate urea was dissolved in 7 mL THF. A solution of lithium hydroxide (410 mg, 10 mmol) in 3 mL water was added. The resulting mixture was heated at 50° C. for 2 hours then cooled to room temperature. The organic phase was evaporated, and the remaining aqueous solution was neutralized. 3-[3-(4-Cyano-phenyl)-ureidomethyl]-benzoic acid (118 mg, 0.4 mmol) was isolated as a white solid by filtration (710 mg; 93% yield) and was used directly. The intermediate acid (118 mg, 0.4 mmol), EDC (115 mg, 0.6 mmol), and HOBt (67.6 mg, 0.5 mmol) were combined in a reaction vial and DMF (1 mL) then N-methylmorpholine (0.066 mL, 0.6 mmol) were added. The reaction mixture was agitated for 1 h, then 7-amino-3,4-dihydro-1H-isoquinoline-2-carboxylic acid tert-butyl ester (104.3 mg, 0.42 mmol) was added. Shaking was continued overnight. The reaction mixture was diluted to 6 mL with dichloromethane, washed with 1N HCl (3×2 mL), NaHCO$_3$ (satd. aq., 3×2 mL), and brine (1×2 mL), dried, and the solvents were evaporated to give 220 mg of the intermediate 7-{3-[3-(4-cyano-phenyl)-ureidomethyl]-benzoylamino}-3,4-dihydro-1H-isoquinoline-2-carboxylic acid tert-butyl ester, which was treated directly with a solution of TFA (0.6 mL) in dichloromethane (2 mL). The reaction mixture was stirred for 2 h, and then the solvents were evaporated. The residue was purified by preparative HPLC using an acetonitrile/water/formic acid gradient. The title compound was collected as a solid (137 mg, 77%-2 steps) following evaporation of the solvent; MS analysis electrospray, 426 (M+H).

Using the methods described in the above example, the following analogs were also synthesized:

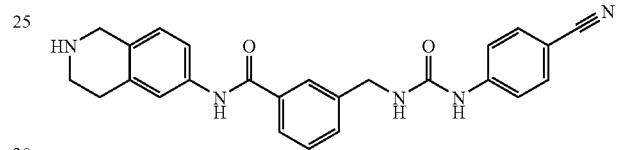

[2] 3-[3-(4-Cyano-phenyl)-ureidomethyl]-N-(1,2,3,4-tetrahydro-isoquinolin-6-yl)-benzamide; MS, electrospray, 426 (M+H)

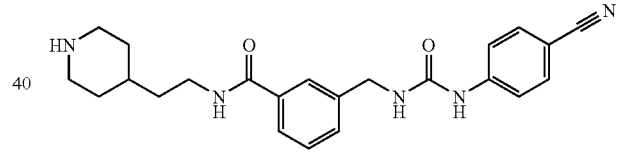

[3] 3-[3-(4-Cyano-phenyl)-ureidomethyl]-N-(2-piperidin-4-yl-ethyl)-benzamide; MS, electrospray, 406 (M+H)

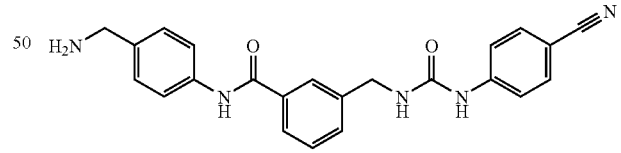

[4] N-(4-Aminomethyl-phenyl)-3-[3-(4-cyano-phenyl)-ureidomethyl]-benzamide; MS, electrospray, 400 (M+H)

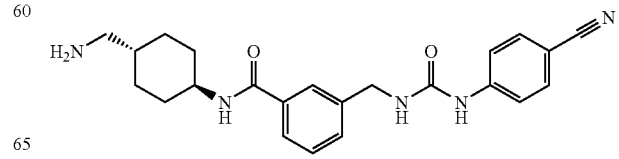

[5] N-(4-Aminomethyl-cyclohexyl)-3-[3-(4-cyano-phenyl)-ureidomethyl]-benzamide; MS, electrospray, 406 (M+H)

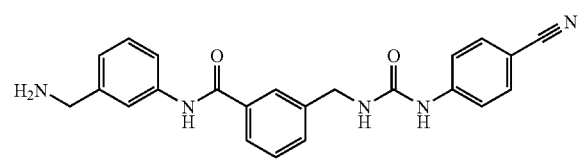

[6] N-(3-Aminomethyl-phenyl)-3-[3-(4-cyano-phenyl)-ureidomethyl]-benzamide; MS, electrospray, 400 (M+H)

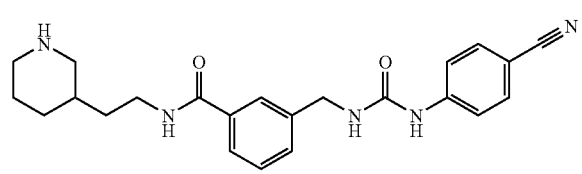

[7] 3-[3-(4-Cyano-phenyl)-ureidomethyl]-N-(2-piperidin-3-yl-ethyl)-benzamide; MS, electrospray, 406 (M+H)

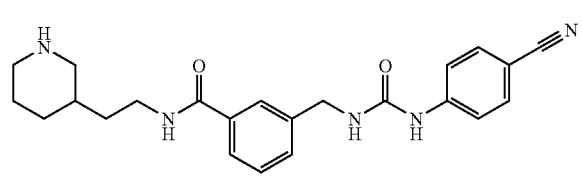

[8] 3-[3-(4-Cyano-phenyl)-ureidomethyl]-N-(2-piperidin-3-yl-ethyl)-benzamide; MS, electrospray, 406 (M+H)

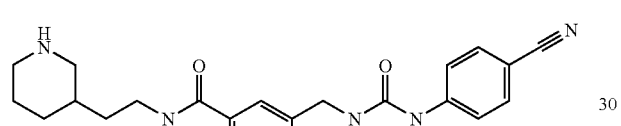

[9] 3-[3-(3,4-Dimethoxy-phenyl)-ureidomethyl]-N-(1,2,3,4-tetrahydro-isoquinolin-6-yl)-benzamide; MS, electrospray, 481 (M+H)

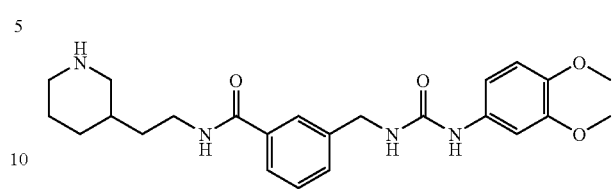

[10] 3-[3-(3,4-Dimethoxy-phenyl)-ureidomethyl]-N-(2-piperidin-3-yl-ethyl)-benzamide; MS, electrospray, 441 (M+H)

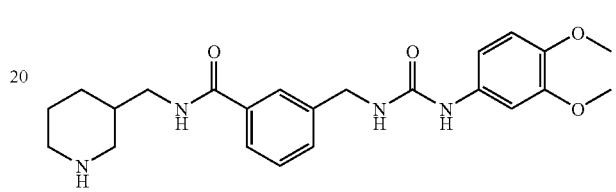

[11] 3-[3-(3,4-Dimethoxy-phenyl)-ureidomethyl]-N-piperidin-3-ylmethyl-benzamide; MS, electrospray, 427 (M+H)

Example 2

Synthesis of 3-[3-(4-cyano-phenyl)-ureidomethyl]-N-(4-dimethylamino-butyl)-benzamide (12)

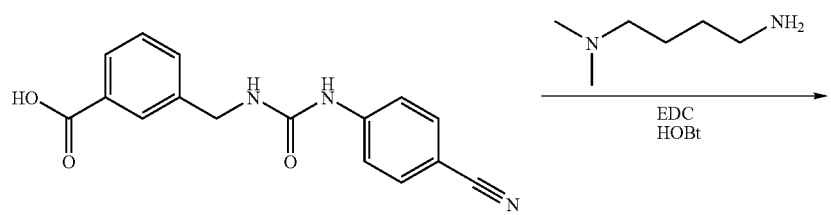

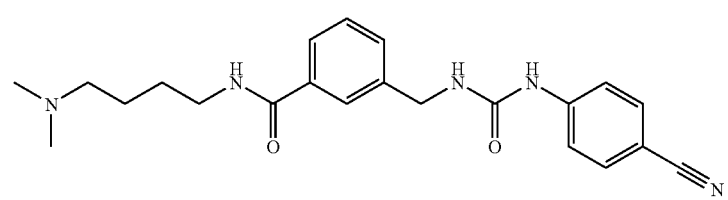

12

3-[3-(4-Cyano-phenyl)-ureidomethyl]-benzoic acid (30 mg, 0.1 mmol), prepared as described in Example 1, EDC (28.8 mg, 0.15 mmol), and HOBt (17.6 mg, 0.13 mmol) were combined in a reaction vial and DMF (1 mL) then N-methylmorpholine (0.017 mL, 0.15 mmol) were added. The reaction mixture was agitated for 30 minutes, then $N^1,N^1$-dimethyl-butane-1,4-diamine (14 mg, 0.12 mmol) was added. Shaking was continued overnight. The reaction mixture was purified by preparative HPLC using an acetonitrile/water/formic acid gradient. The title compound was collected as a formate salt (36 mg, 90% yield) following evaporation of the solvent; MS analysis electrospray, 394 (M+H).

Using the methods described in the above example, the following analogs were also synthesized:

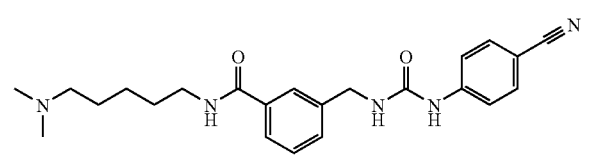

[13] 3-[3-(4-Cyano-phenyl)-ureidomethyl]-N-(3-dimethylamino-propyl)-benzamide; MS, electrospray, 380 (M+H)

[14] 3-[3-(4-Cyano-phenyl)-ureidomethyl]-N-(5-dimethylamino-pentyl)-benzamide; MS, electrospray, 408 (M+H)

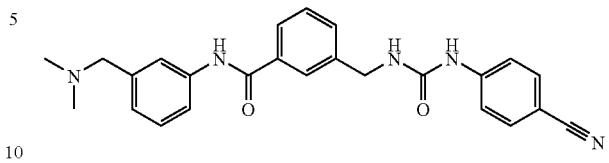

[15] 3-[3-(4-Cyano-phenyl)-ureidomethyl]-N-(3-dimethylaminomethyl-phenyl)-benzamide; MS, electrospray, 428 (M+H)

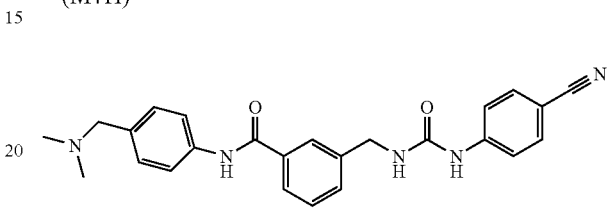

[16] 3-[3-(4-Cyano-phenyl)-ureidomethyl]-N-(4-dimethylaminomethyl-phenyl)-benzamide; MS, electrospray, 428 (M+H)

Example 3

Preparation of 3-[3-(3,4-dimethoxy-phenyl)-ureidomethyl]-N-(4-dimethylaminomethyl-phenyl)-benzamide (17)

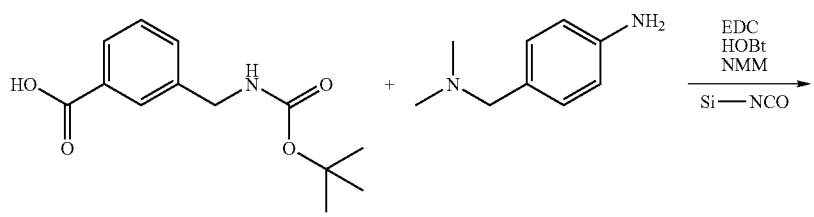

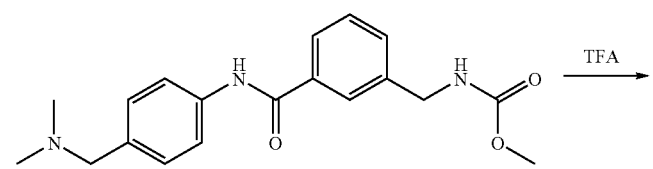

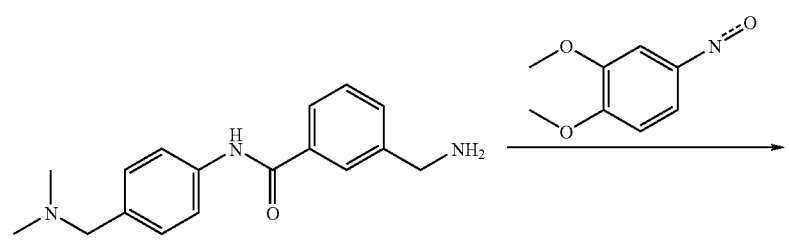

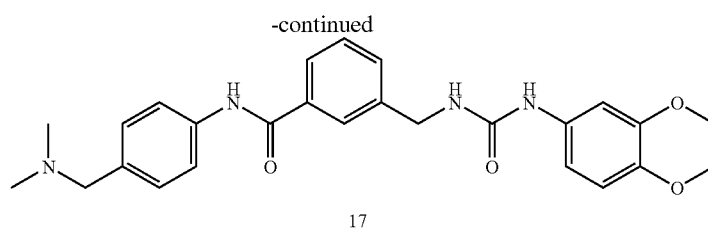

17

3-(tert-Butoxycarbonylamino-methyl)-benzoic acid, (754 mg, 3.0 mmol), EDC (958.5 mg, 5.0 mmol), and HOBt (540.5 mg, 5.0 mmol) were combined in a reaction vial and DMF (5 mL) then N-methylmorpholine (0.549 mL, 5.0 mmol) were added. The reaction mixture was agitated for 1 h, then 4-dimethylaminomethyl-phenylamine (451 mg, 3 mmol) was added as a solution in 1 mL DMF. Shaking was continued 48 h. The reaction mixture was diluted to 50 mL with dichloromethane, washed with $NaHCO_3$ (satd. aq., 1×25 mL, and brine (1×25 mL), dried and evaporated to a residue weighing approximately 2 g, which was taken up in 10 mL dichloromethane and treated with Si-isocyanate (silica-bound alkyl isocyanate; 1.2 g, 14.4 mmol). The resulting mixture was agitated overnight and the silica reagent was filtered. The filtrate was evaporated to provide the intermediate ([3-(4-dimethylaminomethyl-phenylcarbamoyl)-benzyl]-carbamic acid tert-butyl ester), which was treated directly with a solution of TFA (2 mL) in dichloromethane (5 mL). The reaction mixture was stirred for 2 h, then the solvents were evaporated and the residue was re-dissolved in dichloromethane (25 mL). This solution was washed with $NaHCO_3$ (satd. aq., 1×25 mL). To this wash was added 1 g $Na_2CO_3$ and the wash was extracted with dichloromethane (2×25 mL). The organic extracts were combined and washed with brine (1×25 mL), dried and evaporated to 160 mg of a solid (3-aminomethyl-N-(4-dimethylaminomethyl-phenyl)-benzamide-20%-2 steps) which was used directly. This intermediate (28.3 mg, 0.1 mmol) was dissolved in DMF (1 mL), and 4-isocyanato-1,2-dimethoxy-benzene (23.3 mg, 0.13 mmol) was added. The resulting mixture was agitated for 48 hours, then was purified directly by preparative HPLC using an acetonitrile/water/formic acid gradient. The title compound was collected as a formate salt (31 mg, 67% yield), MS analysis electrospray, 426 (M+H).

Using the methods described in the above example, the following analogs were also synthesized:

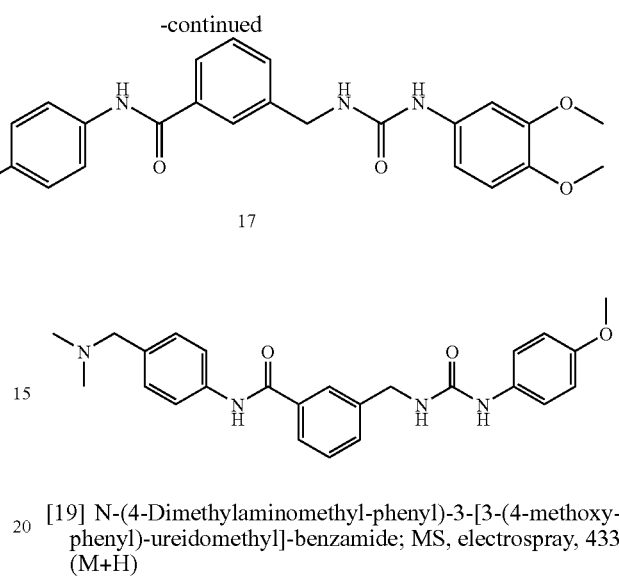

[18] 3-[3-(4-Acetyl-phenyl)-ureidomethyl]-N-(4-dimethylaminomethyl-phenyl)-benzamide; MS, electrospray, 445 (M+H)

[19] N-(4-Dimethylaminomethyl-phenyl)-3-[3-(4-methoxyphenyl)-ureidomethyl]-benzamide; MS, electrospray, 433 (M+H)

[20] 3-[3-(4-Chloro-phenyl)-ureidomethyl]-N-(4-dimethylaminomethyl-phenyl)-benzamide; MS, electrospray, 437 (M+H)

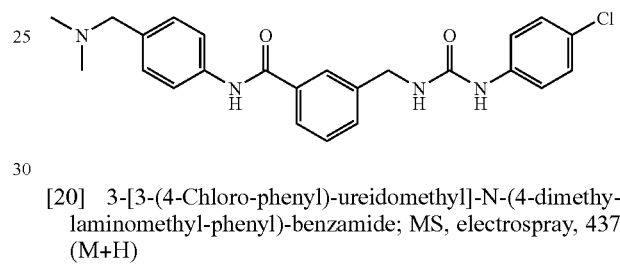

[21] N-(4-Dimethylaminomethyl-phenyl)-3-[3-(4-methoxy-2-methyl-phenyl)-ureidomethyl]-benzamide; MS, electrospray, 447 (M+H)

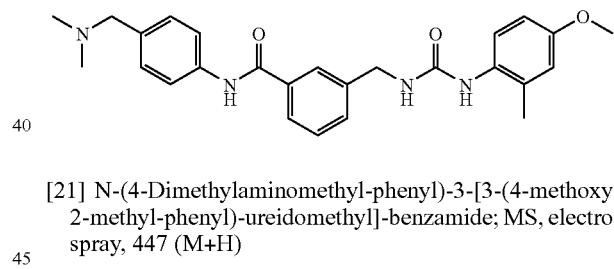

[22] 3-[3-(3-Cyano-phenyl)-ureidomethyl]-N-(4-dimethylaminomethyl-phenyl)-benzamide; MS, electrospray, 428 (M+H)

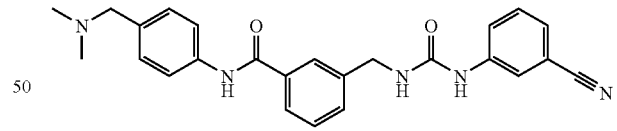

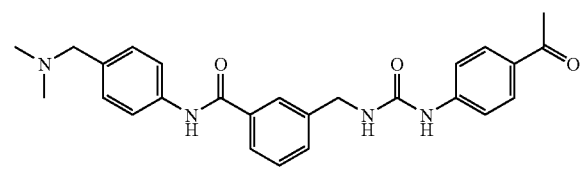

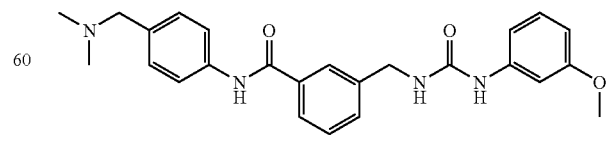

[23] N-(4-Dimethylaminomethyl-phenyl)-3-[3-(3-methoxyphenyl)-ureidomethyl]-benzamide; MS, electrospray, 433 (M+H)

Example 4

Synthesis of 3-[3-(3-chloro-4-cyano-phenyl)-ureidomethyl]-N-(3-dimethylaminomethyl-benzyl)-benzamide (24)

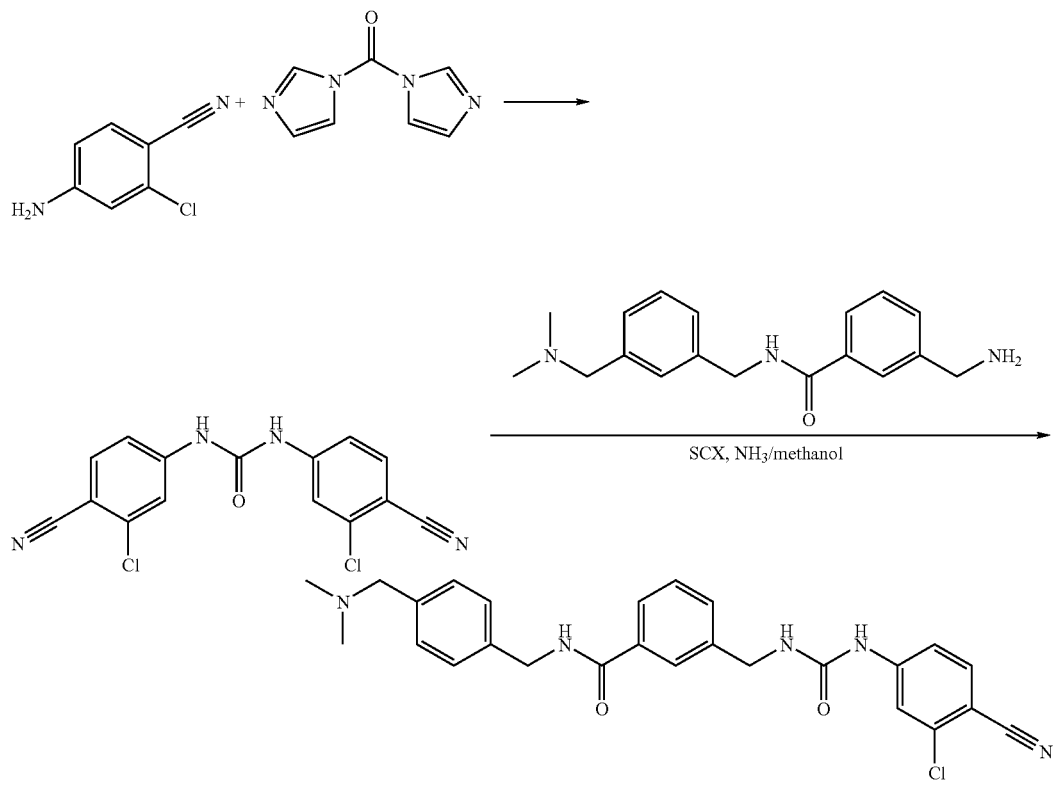

2-Chloro-4-aminobenzonitrile (305.2 mg, 2 mmol) and carbonyldiimidazole (324 mg, 2 mmol) were combined in a reaction vial, and THF (3 mL) was added. The resulting mixture was heated overnight at 60° C., and the product, 1,3-bis-(3-chloro-4-cyano-phenyl)-urea was isolated by filtration and washed with several portions of 1N HCl to provide 220 mg (73% yield). This intermediate (200 mg, 0.6 mmol) was dispersed in DMF (2 mL) in a microwave vial, and a solution of 3-aminomethyl-N-(3-dimethylaminomethyl-benzyl)-benzamide (200 mg, 0.7 mmol), prepared in a fashion analogous to 3-aminomethyl-N-(4-dimethylaminomethyl-phenyl)-benzamide (Example 3), in DMF (1 mL), was added. The vial was sealed and heated in a microwave at 150° C. for 70 min. The reaction mixture was purified directly by preparative HPLC using an acetonitrile/water/formic acid gradient providing 76 mg of product which was contaminated with the aniline by-product. To remove the aniline, the mixture was dissolved in a solution of methanol/acetonitrile (20/80, 10 mL) and divided into 10 portions each of which were loaded directly onto a Varian 50 mg SCX cartridge. Each cartridge was washed with 2×2 mL acetonitrile and 2×2 mL methanol, then treated with $NH_3$ in methanol (7N, 2 mL) to elute the pure title compound (60 mg, 18.4% yield), MS analysis electrospray, 462 (M+H).

Example 5

Synthesis of 3-[3-(4-amido-phenyl)-ureidomethyl]-N-(1,2,3,4-tetrahydro-isoquinolin-7-yl)-benzamide (25)

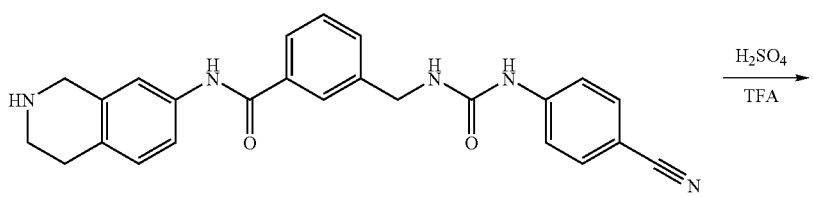

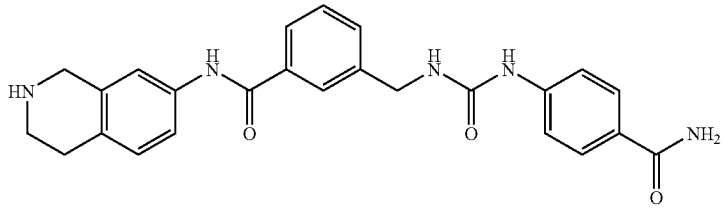

25

Compound I (20 mg, 0.047 mmol) (Example 1) was dissolved in 0.5 mL TFA, and 7 drops $H_2SO_4$ (conc) was added. The resulting mixture was agitated for 24 h. The TFA was evaporated, ice was added followed by 0.7 mL DMF and the mixture was purified directly by preparative HPLC using an acetonitrile/water/formic acid gradient providing the title compound (15 mg, 72% yield), MS analysis electrospray, 444 (M+H).

Using the methods described in the above example, the following analogs were also synthesized:

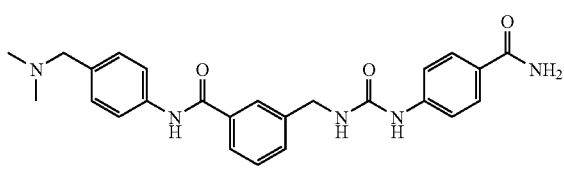

[26] 3-[3-(4-Amido-phenyl)-ureidomethyl]-N-(4-dimethylaminomethyl-phenyl)-benzamide; MS, electrospray, 446 (M+H)

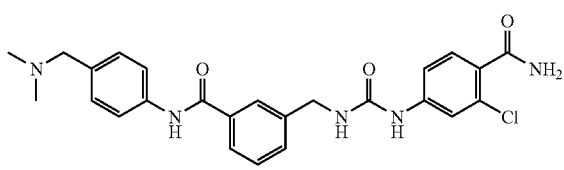

[27] 3-[3-(3-Chloro-4-amido-phenyl)-ureidomethyl]-N-(4-dimethylaminomethyl-phenyl)-benzamide; MS, electrospray, 480(M+H)

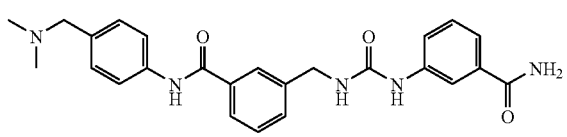

[28] 3-[3-(3-Amido-phenyl)-ureidomethyl]-N-(4-dimethylaminomethyl-phenyl)-benzamide; MS, electrospray, 446 (M+H)

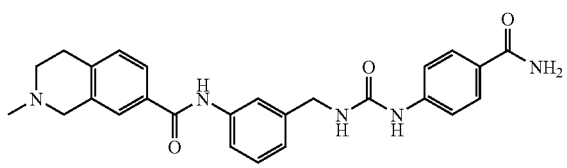

[29] 2-Methyl-1,2,3,4-tetrahydro-isoquinoline-7-carboxylic acid {3-[3-(4-amido-phenyl)-ureidomethyl]-phenyl}-amide; MS, electrospray, 458 (M+H)

Example 6

Synthesis of 2-methyl-1,2,3,4-tetrahydro-isoquinoline-7-carboxylic acid {3-[3-(4-cyano-phenyl)-ureidomethyl]-phenyl}-amide (30)

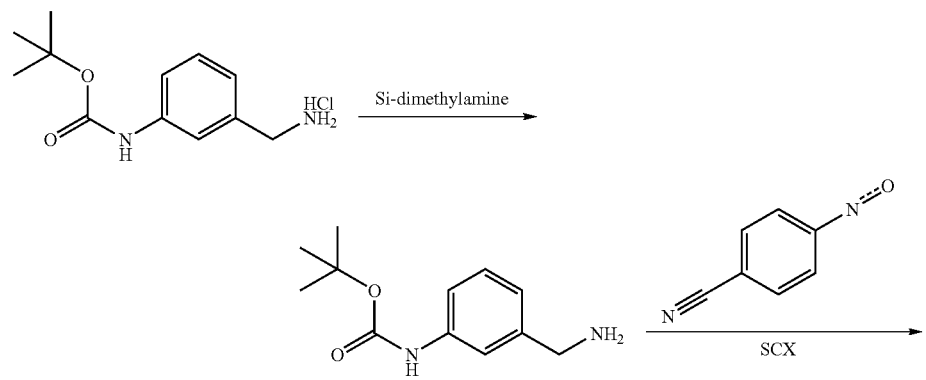

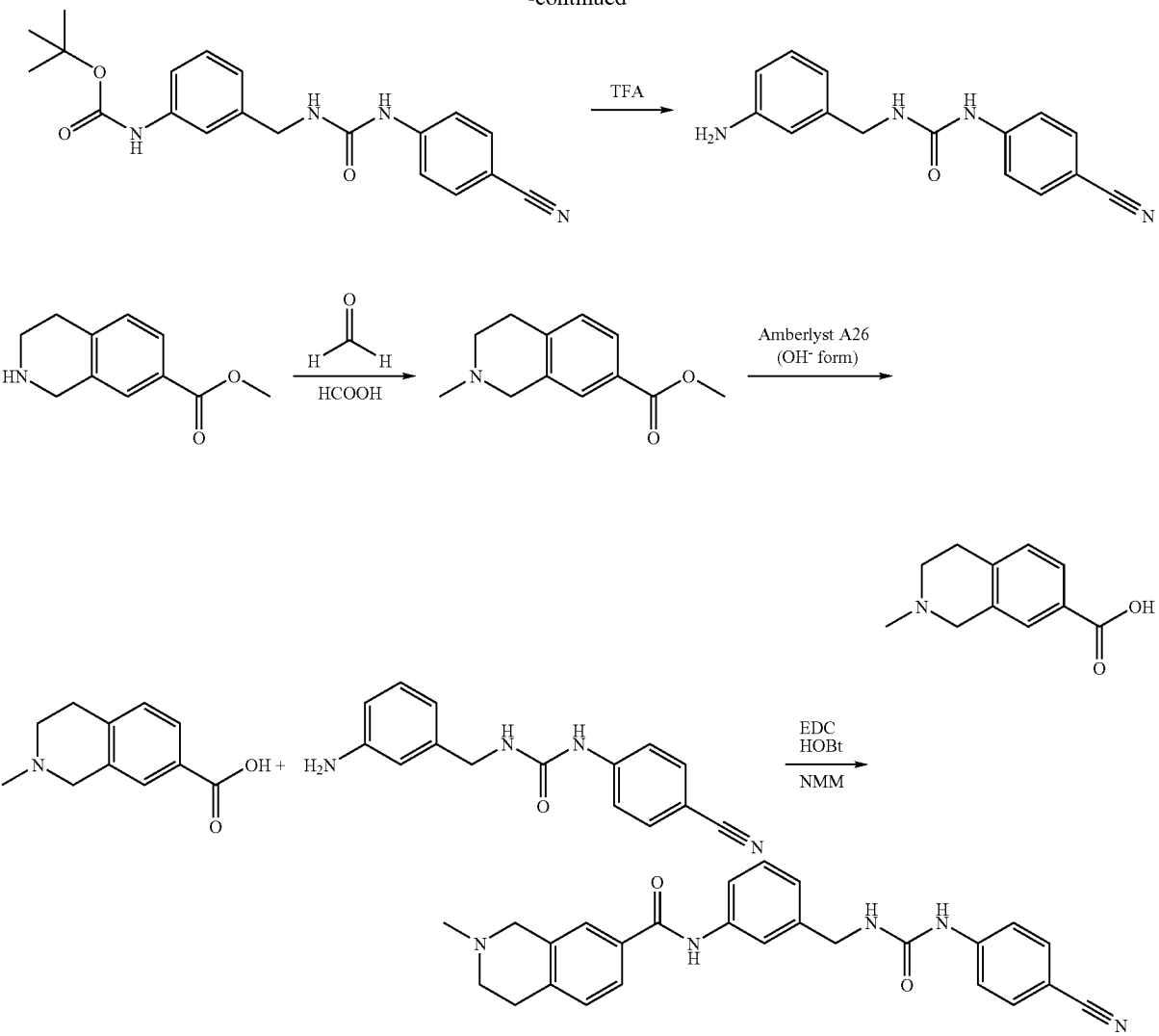

3-t-Butoxycarbonylamino-benzyl-ammonium chloride (103.5 mg, 0.4 mmol) was dissolved in 1 mL DMF in a reaction vial, and Si-dimethylamine (350 mg, 0.525 mmol) was added. The resulting mixture was agitated for 1 h, after which time p-cyanophenylisocyanate (52 mg, 0.36 mmol) was added and the reaction mixture was agitated 8 h. SCX (113 mg, 0.1 mmol) was added and the mixture was agitated an additional 30 minutes. The reaction mixture was filtered, the filrate was concentrated, and the residue was dissolved in 5 mL dichloromethane. TFA (1 mL) was added and the mixture was stirred at room temperature for 1.5 hours. The solvents were evaporated providing 96 mg of pure intermediate (1-(3-amino-benzyl)-3-(4-cyano-phenyl)-urea) which was used directly. Synthesis of the second reagent was carried out by treating 1,2,3,4-tetrahydro-isoquinoline-7-carboxylic acid methyl ester (139 mg, 0.727 mmol) with formaldehyde (1 mL, 37% aqueous) in formic acid (1 mL) and heating the resulting mixture for 62 h at 60° C. The reaction mixture was evaporated to dryness, and the residue was taken up in dichloromethane and evaporated (3×). The intermediate, 2-methyl-1,2,3,4-tetrahydro-isoquinoline-7-carboxylic acid methyl ester, was then dissolved in methanol (2 mL) and treated with Amberlyst® A26 (OH⁻ form) (polymer-supported hydroxide exchange resin; 2240 mg, 3 mmol), and the resulting mixture was agitated overnight, then heated in the microwave at 130° C. for 40 min. After cooling to room temperature, the resin was then filtered and washed with 1×2 mL DMF and 3×2 mL methanol. The product acid was eluted with a solution of 20% formic acid in methanol (3×2 mL). The eluant solvents were evaporated to provide the pure acid (2-methyl-1,2,3,4-tetrahydro-isoquinoline-7-carboxylic acid) as a formate salt (110 mg, 66%-2 steps). Coupling of the two reagents prepared above proceeded by dissolution of the acid (86 mg, 0.45 mmol), EDC (143.8 mg, 0.75 mmol), and HOBt (74 mg, 0.55 mmol) in DMF (1 mL). Subsequently N-methylmorpholine (0.1 mL, 0.9 mmol) was added and the resulting reaction mixture was agitated for 30 min. The urea (1-(3-amino-benzyl)-3-(4-cyano-phenyl)-urea) (110 mg, 0.413 mmol) was added and the resulting mixture was agitated for 48 h. The reaction mixture was purified directly by preparative HPLC using an acetonitrile/water/formic acid gradient providing the title compound as a formate salt (53 mg, 27% yield), MS analysis electrospray, 440 (M+H).

Example 7

Synthesis of 1,2,3,4-Tetrahydro-isoquinoline-6-carboxylic acid {3-[3-(4-cyano-phenyl)-ureidomethyl]-phenyl}-amide (31)

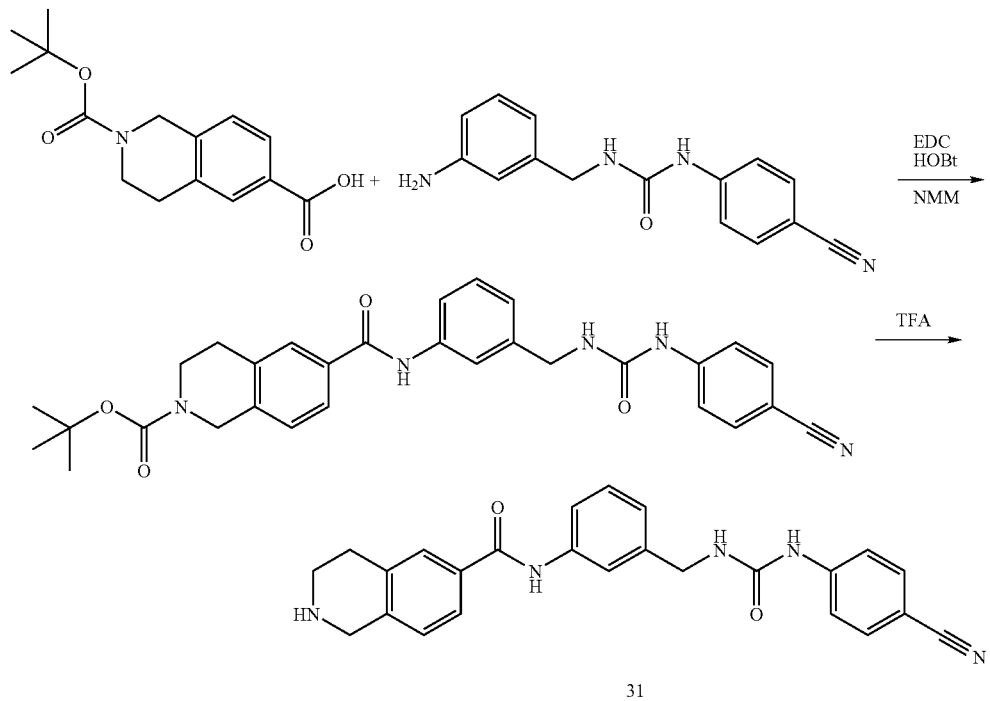

3,4-Dihydro-1H-isoquinoline-2,6-dicarboxylic acid 2-tert-butyl ester (50 mg, 0.18 mmol), EDC (38.3 mg, 0.2 mmol) and HOBt (24.3 mg, 0.18 mmol) were combined in a reaction vial, and DMF (1 mL) was added. To the solution thus formed, N-methylmorpholine (0.22 mL, 0.2 mmol) was added and the reaction mixture was agitated for 1 hour. The urea, 1-(3-amino-benzyl)-3-(4-cyano-phenyl)-urea (40 mg, 0.15 mmol), prepared as described above, was then added as a solution in DMF (0.3 mL), and the reaction mixture was agitated for 48 h. The reaction mixture was diluted to 6 mL with dichloromethane, washed with 1N HCl (3×2 mL), NaHCO₃ (satd. aq., 3×2 mL, and brine (1×2 mL), dried and evaporated to 59 mg of an oil (95% yield). This intermediate (6-{3-[3-(4-cyano-phenyl)-ureidomethyl]-phenylcarbamoyl}-3,4-dihydro-1H-isoquinoline-2-carboxylic acid tert-butyl ester) was dissolved in dichloromethane (1 mL) and TFA (0.4 mL) was added. The reaction mixture was stirred for 2 h, then the solvents were evaporated and the resulting residue was purified directly by preparative HPLC using an acetonitrile/water/formic acid gradient providing the title compound (20 mg, 48% yield), MS analysis electrospray, 426 (M+H).

Using the methods described in the above example, the following analog was also synthesized:

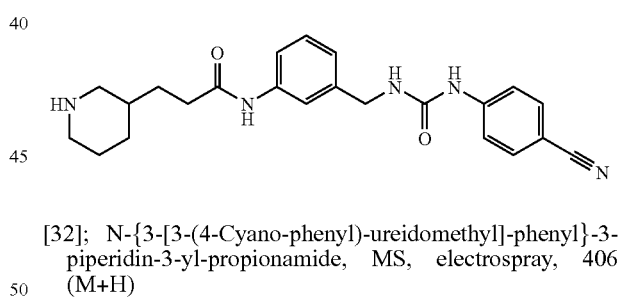

[32]; N-{3-[3-(4-Cyano-phenyl)-ureidomethyl]-phenyl}-3-piperidin-3-yl-propionamide, MS, electrospray, 406 (M+H)

Example 8

Synthesis of 3,4-dimethoxy-N-[3-(2-piperidin-3-yl-ethylcarbamoyl)-benzyl]-benzamide (33)

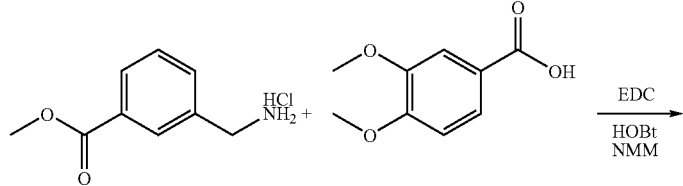

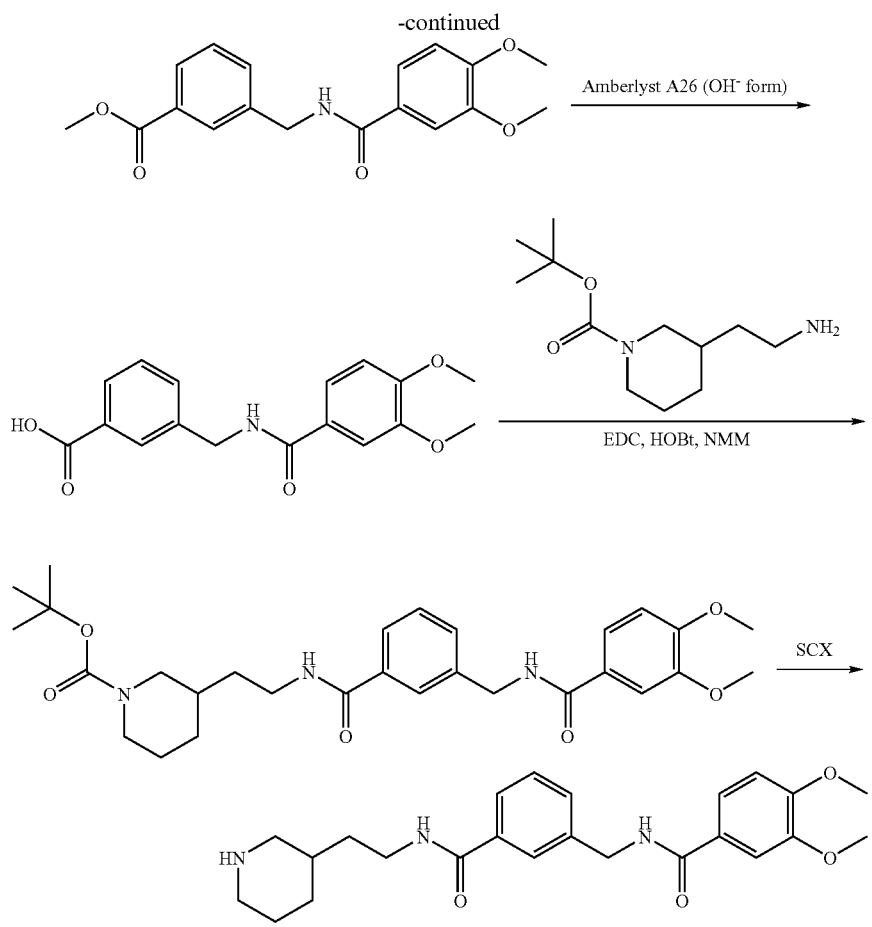

3,4-Dimethoxybenzoic acid (400.8 mg, 2.2 mmol), EDC (479 mg, 2.5 mmol) and HOBt (338 mg, 2.5 mmol) were combined in a reaction vial. DMF (2 mL) was added followed by Hunig's base (0.79 mL, 4.5 mmol). The resulting mixture was agitated for 1 hour. Subsequently, 3-methoxycarbonyl-benzyl-ammonium chloride (403.3 mg, 2 mmol) was added and the mixture was agitated 16 h. The reaction mixture was diluted with 10 mL dichloromethane, and the resulting mixture was washed with 1N HCl (2×10 mL), NaHCO$_3$ (satd. aq., 2×10 mL), and brine (1×10 mL), dried, and the solvents were evaporated to give 3-[(3,4-dimethoxy-benzoylamino)-methyl]-benzoic acid methyl ester (680 mg) as an oil which was used without purification. The ester was then dissolved in a mixture of methanol (6 mL) and DMF (1 mL) and treated with Amberlyst® A26 (OH$^{-\ form}$) (3730 mg, 5 mmol), and the resulting mixture was agitated for 36 h. The resin was then filtered and washed with 2×4 mL methanol, 1×4 mL DMF and 2×4 mL methanol. The product acid was eluted with a solution of 20% formic acid in methanol. The eluant solvents were evaporated, and the resulting solid was triturated in diethyl-ether. 3-[(3,4-dimethoxy-benzoylamino)-methyl]-benzoic acid was isolated by filtration (386 mg, 61%-2 steps) and carried forward. This intermediate (80 mg, 0.254 mmol) was combined with EDC (57.5 mg, 0.3 mmol) and HOBt (40.5 mg, 0.3 mmol) in a reaction vial, and N-methyl morpholine (0.034 mL, 0.3 mmol) was added. The resulting mixture was agitated for 30 min, after which time, 3-(2-amino-ethyl)-piperidine-1-carboxylic acid tert-butyl ester (64 mg, 0.28 mmol) was added and the resulting mixture was agitated overnight. The reaction mixture was diluted with 3 mL dichloromethane, and the resulting mixture was washed with 1N HCl (2×1 mL), NaHCO$_3$ (satd. aq., 2×1 mL), and brine (1×1 mL), dried, and the solvents were evaporated to 140 mg of the intermediate, 3-(2-{3-[(3,4-dimethoxy-benzoylamino)-methyl]-benzoylamino}-ethyl)-piperidine-1-carboxylic acid tert-butyl ester, which was redissolved in dichloromethane (2 mL). SCX (681 mg, 0.6 mmol) was added and the resulting mixture was agitated overnight. The reaction mixture was filtered and the solids were washed with dichloromethane (2×2 mL) and methanol (2×2 mL). The product was eluted with NH$_3$ in methanol (7N, 3×1 mL). The solvents were evaporated to provide 80 mg (74.3%-2 steps) of the title compound, MS analysis electrospray, 426 (M+H).

Using the methods described in the above example, the following analogs were also synthesized:

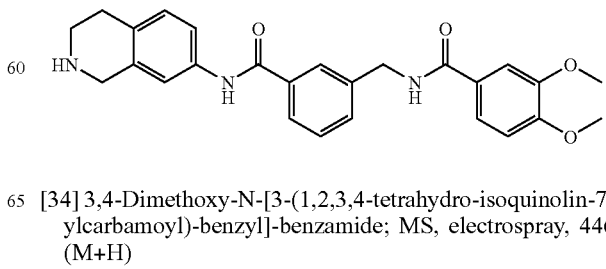

[34] 3,4-Dimethoxy-N-[3-(1,2,3,4-tetrahydro-isoquinolin-7-ylcarbamoyl)-benzyl]-benzamide; MS, electrospray, 446 (M+H)

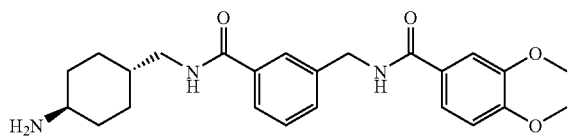

[35] N-{3-[(4-Amino-cyclohexylmethyl)-carbamoyl]-benzyl}-3,4-dimethoxy-benzamide; MS, electrospray, 426 (M+H)

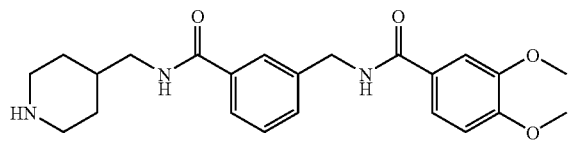

[36] 3,4-Dimethoxy-N-{3-[(piperidin-4-ylmethyl)-carbamoyl]-benzyl}-benzamide; MS, electrospray, 412 (M+H)

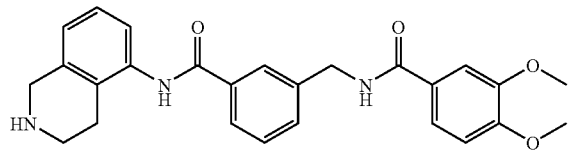

[37] 3,4-Dimethoxy-N-[3-(1,2,3,4-tetrahydro-isoquinolin-5-ylcarbamoyl)-benzyl]-benzamide; MS, electrospray, 446 (M+H)

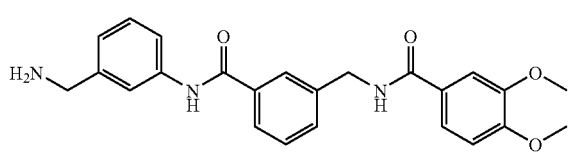

[38] N-[3-(3-Aminomethyl-phenylcarbamoyl)-benzyl]-3,4-dimethoxy-benzamide; MS, electrospray, 420 (M+H)

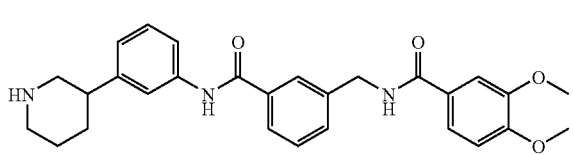

[39] 3,4-Dimethoxy-N-[3-(3-piperidin-3-yl-phenylcarbamoyl)-benzyl]-benzamide; MS, electrospray, 474 (M+H)

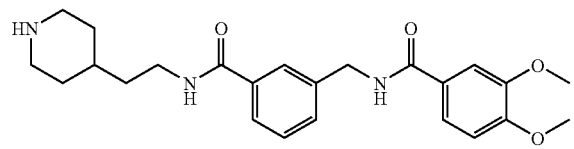

[40] 3,4-Dimethoxy-N-[3-(2-piperidin-4-yl-ethylcarbamoyl)-benzyl]-benzamide; MS, electrospray, 426 (M+H)

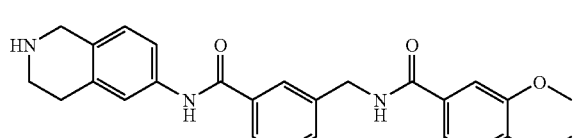

[41] 3,4-Dimethoxy-N-[3-(1,2,3,4-tetrahydro-isoquinolin-6-ylcarbamoyl)-benzyl]-benzamide; MS, electrospray, 446 (M+H)

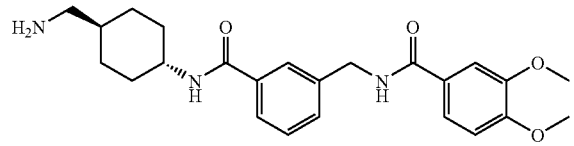

[42] N-[3-(4-Aminomethyl-cyclohexylcarbamoyl)-benzyl]-3,4-dimethoxy-benzamide; MS, electrospray, 426 (M+H)

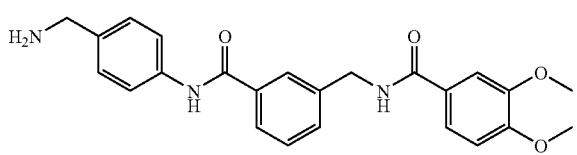

[43] N-[3-(4-Aminomethyl-phenylcarbamoyl)-benzyl]-3,4-dimethoxy-benzamide; MS, electrospray, 420 (M+H)

Example 9

Synthesis of 3,4-dimethoxy-N-{3-[2-(1-methyl-piperidin-3-yl)-ethylcarbamoyl]-benzyl}-benzamide (44)

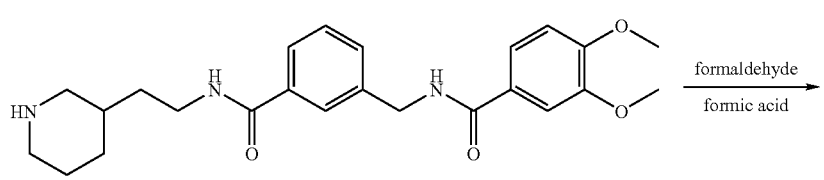

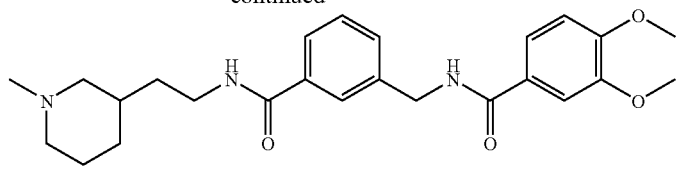

44

Compound 33 (80 mg, 0.188 mmol), (Example 8), was dissolved in formic acid (0.5 mL) and formaldehyde (0.5 mL, 37% aqueous solution) was added. The resulting mixture was heated at 70° C. overnight. The solvents were evaporated and the product was purified by preparative HPLC using an acetonitrile/water/formic acid gradient providing the title compound as a formate salt (23 mg, 28% yield), MS analysis electrospray, 440 (M+H).

Using the methods described in the above example, the following analog was also synthesized:

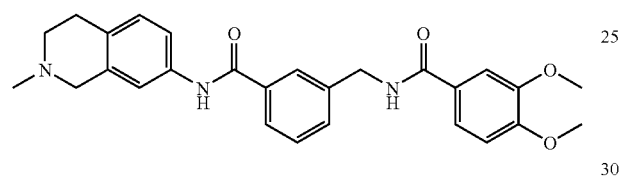

[45] 3,4-Dimethoxy-N-[3-(2-methyl-1,2,3,4-tetrahydro-isoquinolin-7-ylcarbamoyl)-benzyl]-benzamide; MS, electrospray, 460 (M+H)

Example 10

Synthesis of 7-{3-[(3,4-dimethoxy-benzoylamino)-methyl]-benzoylamino}-2,2-dimethyl-1,2,3,4-tetrahydro-isoquinolinium formate (46)

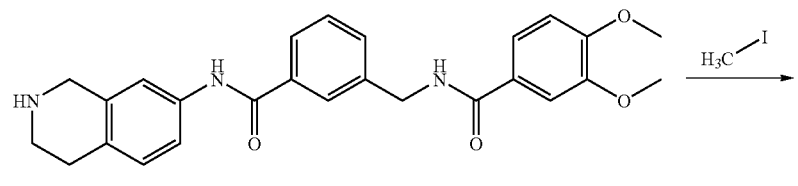

34

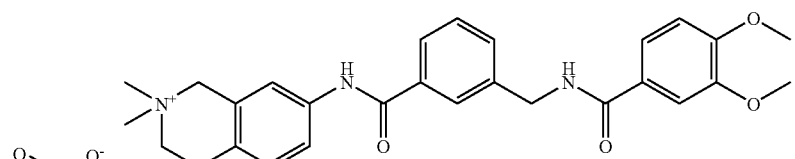

46

Compound 34 (50 mg, 0.112 mmol) was dissolved in 4 mL DMF. Methyl iodide (50 µL, 0.352 mmol) and triethylamine were added. The mixture was stirred at 90° C. overnight. The solvents were evaporated and the product was purified by preparative HPLC using an acetonitrile/water/formic acid gradient providing the title compound as a formate salt (32 mg, 55% yield); MS, electrospray, 474 (M+).

Example 11

Synthesis of N-{3-[2-(2,2-Dimethyl-propyl)-1,2,3,4-tetrahydro-isoquinolin-7-ylcarbamoyl]-benzyl}-3,4-dimethoxy-benzamide (47)

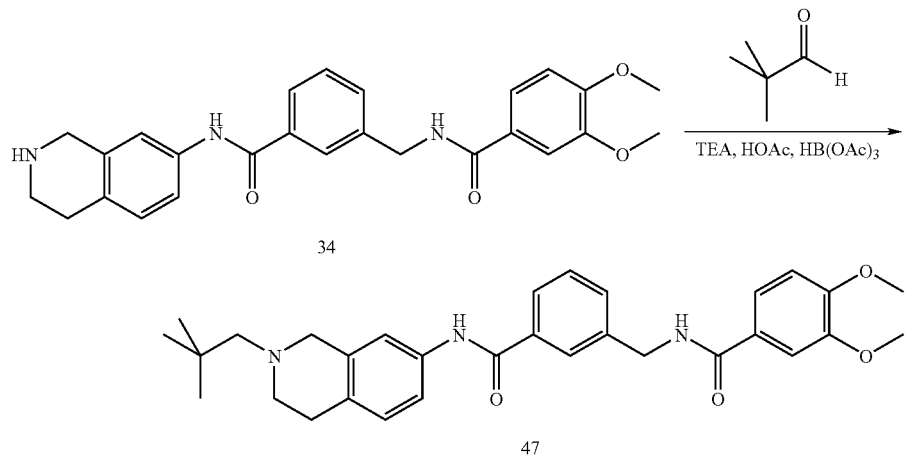

To a solution of trimethylacetaldehyde (0.1 mL, 0.887 mmol) and compound 34, (50 mg, 0.112 mmol) in 1.5 mL DMF were added triethylamine (75 µL, 0.532 mmol) and acetic acid (0.05 mL, 0.887 mmol). The mixture was stirred at room temperature for 30 min. Sodium triacetoxyborohydride (188 mg, 0.887 mmol) was added in one portion and the resulting mixture was stirred at room temperature for 5 h. The product was purified directly from the reaction mixture by preparative HPLC using an acetonitrile/water/formic acid gradient providing the title compound as yellow oil (14 mg, 24% yield); MS, electrospray, 516 (M+H).

Example 12

Synthesis of 3,4-dimethoxy-N-methyl-N-[3-(1,2,3,4-tetrahydro-isoquinolin-6-ylcarbamoyl)-benzyl]-benzamide (48)

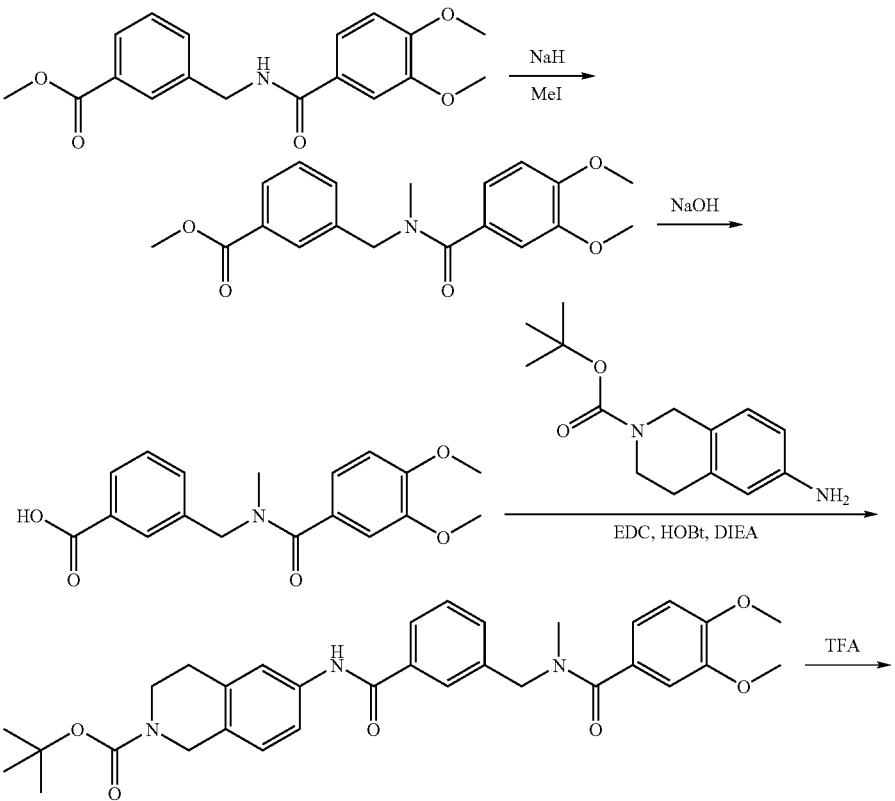

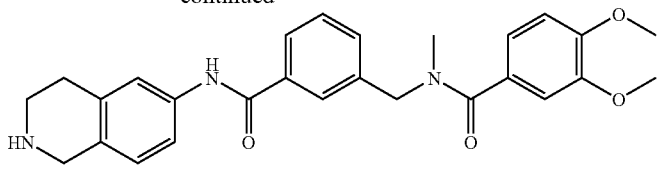

48

3-[(3,4-Dimethoxy-benzoylamino)-methyl]-benzoic acid methyl ester (100 mg, 0.32 mmol), was dissolved in 5 mL DMF. Iodomethane (20 mL, 0.32 mmol) and NaH (15 mg, 0.62 mmol) were added. The mixture was stirred at room temperature for 2 hours, then diluted with 15 mL water and extracted with 3×10 mL ethyl acetate. The combined organic solvent was dried with Na$_2$SO$_4$ and evaporated to give 80 mg of crude product which was used without purification. The intermediate, 3-{[(3,4-dimethoxy-benzoyl)-methyl-amino]-methyl}-benzoic acid methyl ester, was dissolved in methanol (20 mL). NaOH (2 mL, 4M, 8 mmol) was added and the mixture was stirred at room temperature overnight, then diluted with 20 mL water. The resulting solution was neutralized with 1N HCl and extracted with dichloromethane (3×15 mL). Evaporation of the solvent afforded 80 mg of crude product as yellow oil which was used without further purification. The intermediate, 3-{[(3,4-dimethoxy-benzoyl)-methyl-amino]-methyl}-benzoic acid (80 mg, 0.24 mmol) was combined with 6-amino-3,4-dihydro-1H-isoquinoline-2-carboxylic acid tert-butyl ester (70 mg, 0.28 mmol), EDC (80 mg, 0.51 mmol) and HOBt (80 mg, 0.59 mmol) in a reaction vial. DMF (2 mL) was added followed by Hunig's base (0.1 mL, 0.57 mmol). The mixture was stirred at room temperature for 16 h. The product was purified by preparative HPLC using an acetonitrile/water/formic acid gradient providing the intermediate, 6-(3-{[(3,4-dimethoxy-benzoyl)-methyl-amino]-methyl}-benzoylamino)-3,4-dihydro-1H-isoquinoline-2-carboxylic acid tert-butyl ester, as a yellow oil. This intermediate was dissolved in dichloromethane (4 mL), and trifluoroacetic (1 mL) was added thereafter. The mixture was stirred at room temperature for 2 h. The mixture was concentrated to give the title product as a TFA salt (119 mg, 65% yield, 4 steps); MS, electrospray, 460 (M+H).

Example 13

Synthesis of N-[3-(3-dimethylaminomethyl-phenylcarbamoyl)-benzyl]-3,4-dimethoxy-benzamide (49)

3-[(3,4-Dimethoxy-benzoylamino)-methyl]-benzoic acid (40 mg, 0.127 mmol), prepared as described in Example 8, was combined with EDC (38.3 mg, 0.2 mmol) and HOBt (24.3 mg, 0.18 mmol) in a reaction vial, and DMF (1 mL) was added followed by N-methylmorpholine (0.025 mL, 0.22 mmol). The resulting mixture was agitated for 1 h, then 3-dimethylaminomethyl-phenylamine (25.5 mg, 0.17 mmol) was added as a solution in DMF (0.5 mL), and the resulting mixture was agitated overnight. The product was purified directly by preparative HPLC using an acetonitrile/water/formic acid gradient providing the title compound as a formate salt (40 mg, 70% yield), MS analysis electrospray, 448 (M+H).

Using the methods described in the above example, the following analogs were also synthesized:

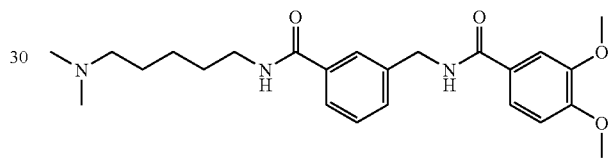

[50] N-[3-(5-Dimethylamino-pentylcarbamoyl)-benzyl]-3,4-dimethoxy-benzamide; MS, electrospray, 428 (M+H)

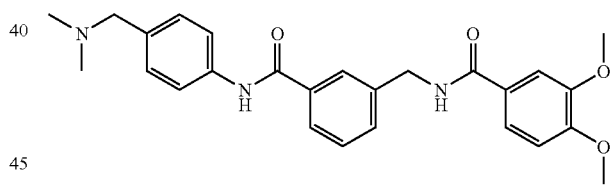

[51] N-[3-(4-Dimethylaminomethyl-phenylcarbamoyl)-benzyl]-3,4-dimethoxy-benzamide; MS, electrospray, 448 (M+H)

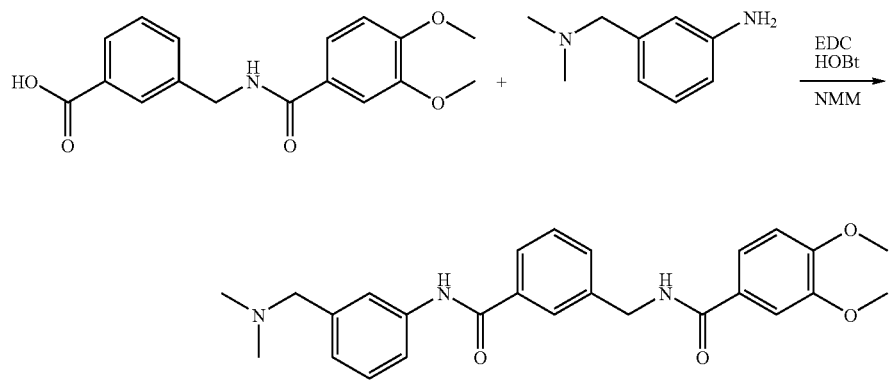

49

115 116

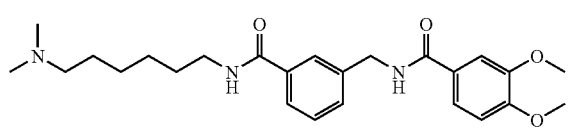

[52] N-[3-(6-Dimethylamino-hexylcarbamoyl)-benzyl]-3,4-dimethoxy-benzamide; MS, electrospray, 442 (M+H)

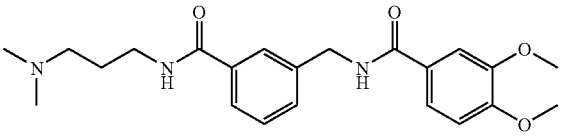

[54] N-[3-(3-Dimethylamino-propylcarbamoyl)-benzyl]-3,4-dimethoxy-benzamide; MS, electrospray, 400 (M+H)

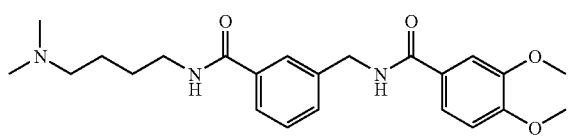

[53] N-[3-(4-Dimethylamino-butylcarbamoyl)-benzyl]-3,4-dimethoxy-benzamide; MS, electrospray, 414 (M+H)

[55] N-[3-(4-Dimethylamino-cyclohexylcarbamoyl)-benzyl]-3,4-dimethoxy-benzamide; MS, electrospray, 440 (M+H)

Example 14

Synthesis of 3-Chloro-N-[3-(4-dimethylaminomethyl-phenylcarbamoyl)-benzyl]-4-methoxy-benzamide (56)

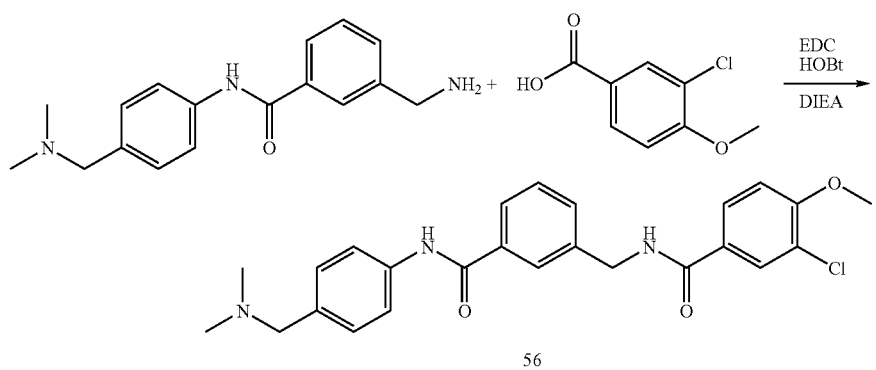

A reaction vial was charged with 3-chloro-4-methoxybenzoic acid (40 mg, 0.21 mmol), 3-aminomethyl-N-(4-dimethylaminomethyl-phenyl)-benzamide (40 mg, 0.14 mmol), EDC (40 mg, 0.25 mmol) and HOBt (40 mg, 0.29 mmol). DMF (2 mL) was added followed by Hunig's base (0.11 mL, 0.57 mmol). The mixture was stirred at room temperature for 16 h. The product was purified by preparative HPLC using an acetonitrile/water/formic acid gradient providing the title compound as a formate salt (20 mg, 31% yield); MS, electrospray, 452 (M+H).

Using the methods described in the above example, the following analogs were also synthesized:

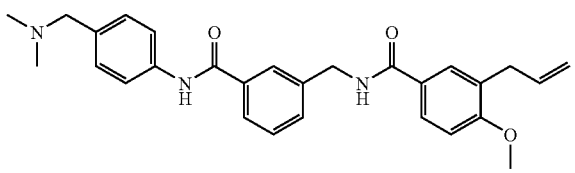

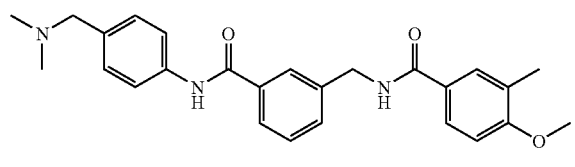

[57] 3-Allyl-N-[3-(4-dimethylaminomethyl-phenylcarbamoyl)-benzyl]-4-methoxy-benzamide; MS, electrospray, 458 (M+H)

[62] N-[3-(4-Dimethylaminomethyl-phenylcarbamoyl)-benzyl]-4-methoxy-3-methyl-benzamide; MS, electrospray, 432 (M+H)

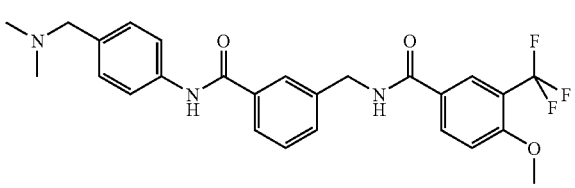

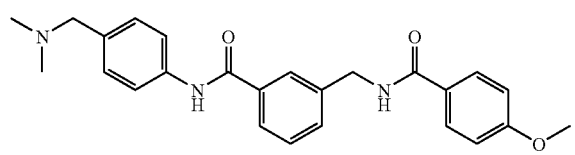

[58] N-[3-(4-Dimethylaminomethyl-phenylcarbamoyl)-benzyl]-4-methoxy-3-trifluoromethyl-benzamide; MS, electrospray, 485 (M+H)

[63] N-[3-(4-Dimethylaminomethyl-phenylcarbamoyl)-benzyl]-4-methoxy-benzamide; MS, electrospray, 418 (M+H)

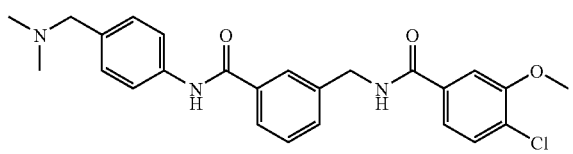

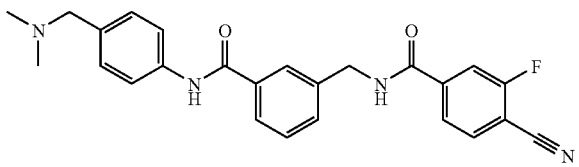

[59] 4-Chloro-N-[3-(4-dimethylaminomethyl-phenylcarbamoyl)-benzyl]-3-methoxy-benzamide; MS, electrospray, 452 (M−H)

[64] 4-Cyano-N-[3-(4-dimethylaminomethyl-phenylcarbamoyl)-benzyl]-3-fluoro-benzamide; MS, electrospray, 431 (M+H)

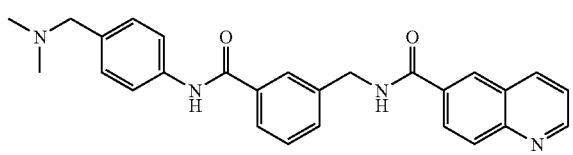

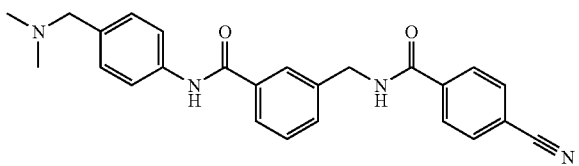

[60] Quinoline-6-carboxylic acid 3-(4-dimethylaminomethyl-phenylcarbamoyl)-benzylamide; MS, electrospray, 439 (M+H)

[65] 4-Cyano-N-[3-(4-dimethylaminomethyl-phenylcarbamoyl)-benzyl]-benzamide; MS, electrospray, 413 (M+H)

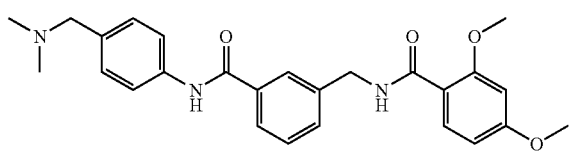

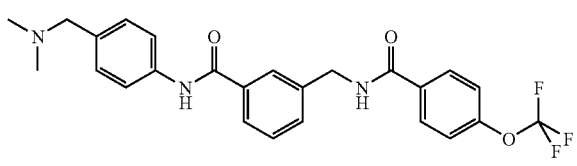

[61] N-[3-(4-Dimethylaminomethyl-phenylcarbamoyl)-benzyl]-2,4-dimethoxy-benzamide; MS, electrospray, 448 (M+H)

[66] N-[3-(4-Dimethylaminomethyl-phenylcarbamoyl)-benzyl]-4-trifluoromethoxy-benzamide; MS, electrospray, 472 (M+H)

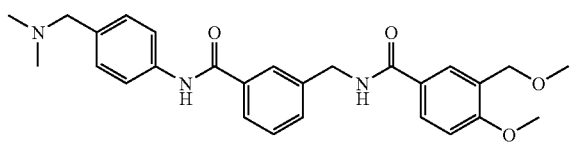

[67] N-[3-(4-Dimethylaminomethyl-phenylcarbamoyl)-benzyl]-4-methoxy-3-methoxymethyl-benzamide; MS, electrospray, 462 (M+H)

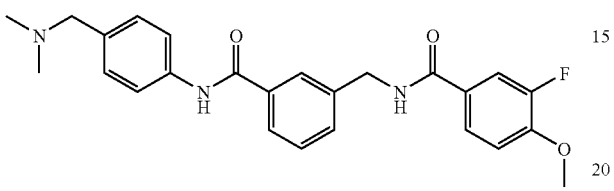

[68] N-[3-(4-Dimethylaminomethyl-phenylcarbamoyl)-benzyl]-3-fluoro-4-methoxy-benzamide; MS, electrospray, 436 (M–H)

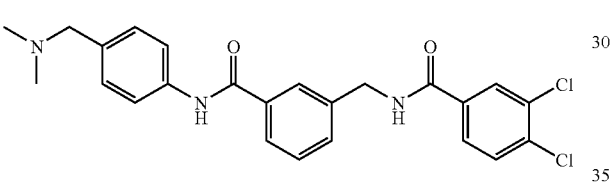

[69] 3,4-Dichloro-N-[3-(4-dimethylaminomethyl-phenylcarbamoyl)-benzyl]-benzamide; MS, electrospray, 457 (M+H)

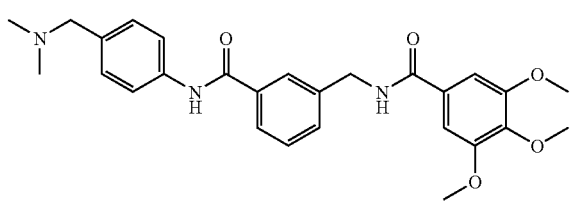

[70] N-[3-(4-Dimethylaminomethyl-phenylcarbamoyl)-benzyl]-3,4,5-trimethoxy-benzamide; MS, electrospray, 478 (M+H)

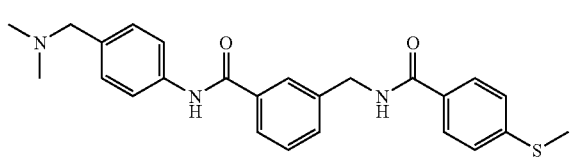

[71] N-[3-(4-Dimethylaminomethyl-phenylcarbamoyl)-benzyl]-4-methylsulfanyl-benzamide; MS, electrospray, 434 (M+H)

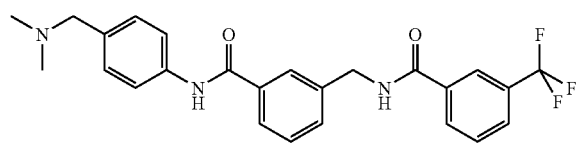

[72] N-[3-(4-Dimethylaminomethyl-phenylcarbamoyl)-benzyl]-3-trifluoromethyl-benzamide; MS, electrospray, 456 (M+H)

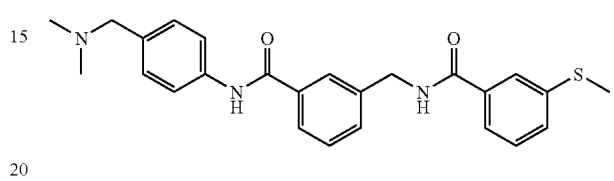

[73] N-[3-(4-Dimethylaminomethyl-phenylcarbamoyl)-benzyl]-3-methylsulfanyl-benzamide; MS, electrospray, 434 (M+H)

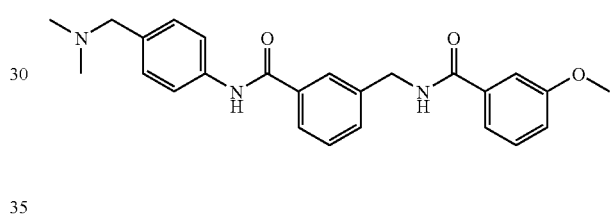

[74] N-[3-(4-Dimethylaminomethyl-phenylcarbamoyl)-benzyl]-3-methoxy-benzamide; MS, electrospray, 418 (M+H)

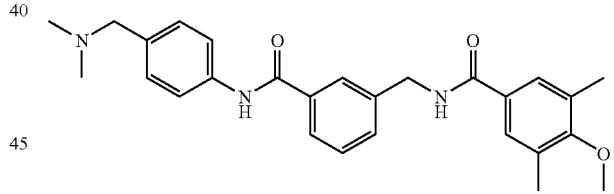

[75] N-[3-(4-Dimethylaminomethyl-phenylcarbamoyl)-benzyl]-4-methoxy-3,5-dimethyl-benzamide; MS, electrospray, 446 (M+H)

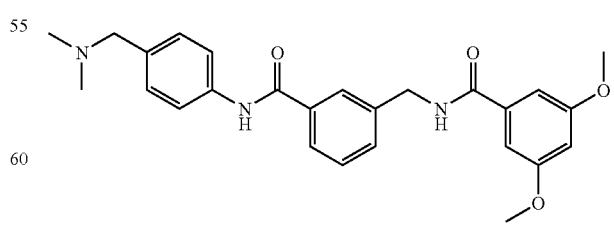

[76] N-[3-(4-Dimethylaminomethyl-phenylcarbamoyl)-benzyl]-3,5-dimethoxy-benzamide; MS, electrospray, 448 (M+H)

121

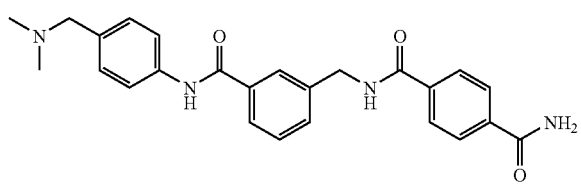

[77] N-[3-(4-Dimethylaminomethyl-phenylcarbamoyl)-benzyl]-terephthalamide; MS, electrospray, 431 (M+H)

122

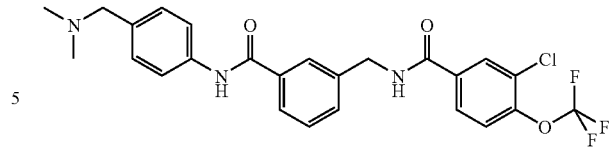

[78] 3-Chloro-N-[3-(4-dimethylaminomethyl-phenylcarbamoyl)-benzyl]-4-trifluoromethoxy-benzamide; MS, electrospray, 506 (M+H)

Example 15

Synthesis of-(4-Dimethylaminomethyl-phenylcarbamoyl)-benzyl]-3-ureido-benzamide (79)

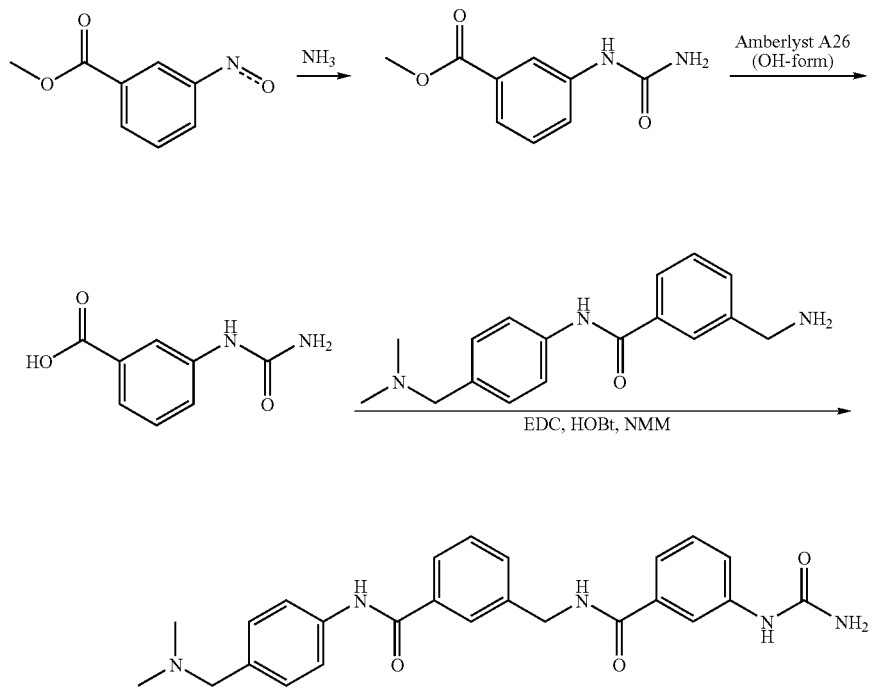

79

3-Isocyanato-benzoic acid methyl ester (500 mg, 2.82 mmol) was treated with 0.5 M $NH_3$ in dioxane (20 mL). The mixture was agitated for 48 h, and the product, 3-ureido-benzoic acid methyl ester (200 mg, 1.03 mmol), was isolated by filtration as a white solid (404 mg, 73.7%). This intermediate was dissolved in methanol (2 mL) and Amberlyst A26® ($OH^-$ form) was added. The resulting mixture was agitated overnight. The resin was then filtered and washed with methanol (3×2 mL). The product was eluted with a solution of 20% formic acid in methanol (3×2 mL) and the resin was washed with methanol (1 mL) and DMF (2×2 mL). The combined eluant solvents were evaporated to provide 139 mg (75% yield) of the urea 3-ureido-benzoic acid. This reagent was then coupled with 3-aminomethyl-N-(4-dimethylaminomethyl-phenyl)-benzamide using the same coupling procedure described in Example 14 to provide the title compound; MS, electrospray, 446 (M+H)

Example 16

Synthesis of N-[3-(4-Dimethylaminomethyl-phenyl-carbamoyl)-benzyl]-isophthalamide (80)

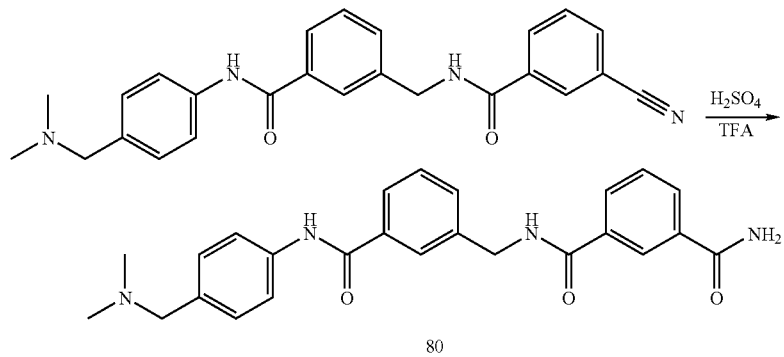

3-Cyano-N-[3-(4-dimethylaminomethyl-phenylcarbamoyl)-benzyl]-benzamide was prepared using the coupling procedure described in Example 14 from 3-cyanobenzoic acid and 3-aminomethyl-N-(4-dimethylaminomethyl-phenyl)-benzamide. Hydrolysis to the title compound was accomplished using the method described in Example 5; MS, electrospray, 431 (M+H)

Example 17

Synthesis of 1,2,3,4-Tetrahydro-isoquinoline-6-carboxylic acid {3-[(3,4-dimethoxy-benzoylamino)-methyl]-phenyl}-amide (81)

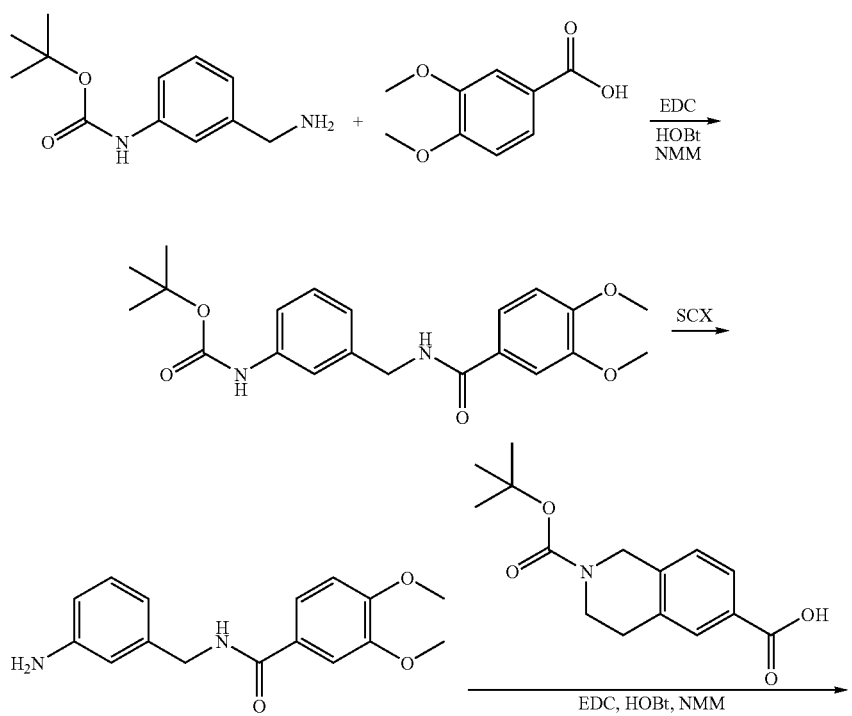

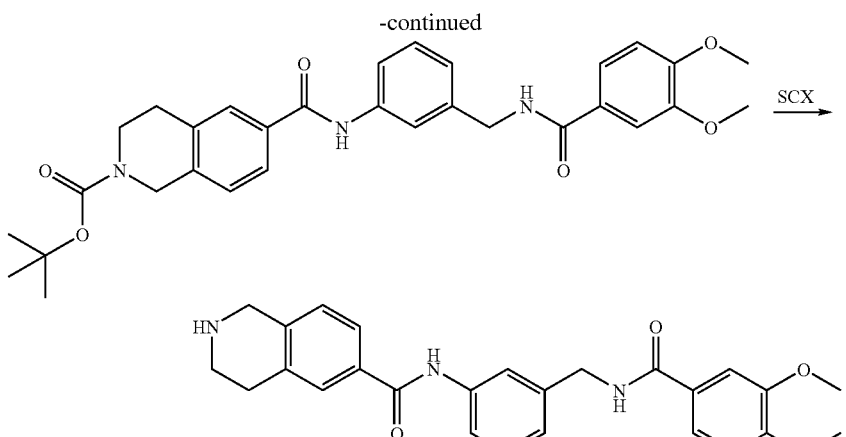

81

3,4-Dimethoxybenzoic acid (100 mg, 0.55 mmol) was dissolved in DMF (1 mL). EDC (124.6 mg, 0.65 mmol) and HOBt (81 mg, 0.6 mmol) were added, followed by N-methylmorpholine (0.71 mL, 0.65 mmol). The resulting solution was agitated for 1 h. 3-Aminomethylphenyl-carbamic acid tert-butyl ester (111 mg, 0.5 mmol) was then added and the resulting mixture was agitated overnight. The reaction mixture was diluted with 4 mL dichloromethane, and the resulting mixture was washed with 1 N HCl (2×5 mL), NaHCO₃ (saturated aqueous, 2×5 mL), and brine (1×5 mL), dried, and the solvents were evaporated to provide 190 mg (quantitative yield) of {3-[(3,4-dimethoxy-benzoylamino)-methyl]-phenyl}-carbamic acid tert-butyl ester, which was dissolved in dichloromethane (2 mL). SCX (1.14 g, 1.0 mmol) was added and the resulting mixture was agitated for 48 h. The reaction mixture was filtered and the solids were washed with dichloromethane (2×2 mL) and methanol (2×2 mL). The product was eluted with NH₃ in methanol (7 N, 2×2 mL). The solvents were evaporated to provide 112 mg (78% yield) of N-(3-amino-benzyl)-3,4-dimethoxy-benzamide as a white solid, which was used directly. 3,4-Dihydro-1H-isoquinoline-2,6-dicarboxylic acid 2-tert-butyl ester (19.1 mg, 0.069 mmol), EDC (19.2 mg, 0.1 mmol), and HOBt (12.2 mg, 0.09 mmol) were combined in a reaction tube, and DMF (1 mL) was added. To the resulting solution was added N-methylmorpholine (0.013 mL, 0.12 mmol), and the mixture was agitated for 1 h. The intermediate prepared above, N-(3-amino-benzyl)-3,4-dimethoxy-benzamide (17 mg, 0.059 mmol), was then added as a solution in DMF (0.3 mL), and the reaction mixture was agitated overnight. The reaction mixture was diluted with 6 mL dichloromethane, and the resulting mixture was washed with 1 N HCl (2×2 mL), NaHCO₃ (saturated aqueous, 2×2 mL), and brine (1×2 mL), dried, and concentrated to 32 mg of 6-{3-[(3,4-dimethoxy-benzoylamino)-methyl]-phenylcarbamoyl}-3,4-dihydro-1H-isoquinoline-2-carboxylic acid tert-butyl ester as an oil, which was redissolved in dichloromethane (1 mL) and treated with SCX (284 mg, 0.25 mmol). The resulting mixture was agitated overnight. The reaction mixture was filtered and the solids were washed with dichloromethane (2×2 mL) and methanol (2×2 mL). The product was eluted with NH₃ in methanol (7 N, 2×2 mL), and the eluant was evaporated. The resulting residue was purified by preparative HPLC using an acetonitrile/water/formic acid gradient providing the title compound as a formate salt (20 mg, 77% yield-2 steps), MS analysis electrospray, 446 (M+H).

Using the methods described in the above example, the following analog was also synthesized:

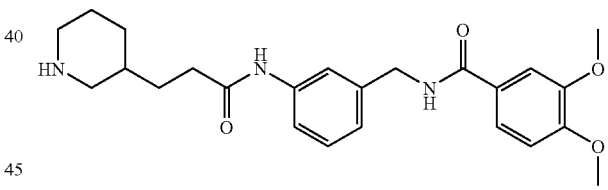

[82] 3,4-Dimethoxy-N-[3-(3-piperidin-3-yl-propionylamino)-benzyl]-benzamide; MS, electrospray, 426 (M+H)

Example 18

Synthesis of 2-methyl-1,2,3,4-tetrahydro-isoquinoline-6-carboxylic acid {3-[(3,4-dimethoxy-benzoylamino)-methyl]-phenyl}-amide (83)

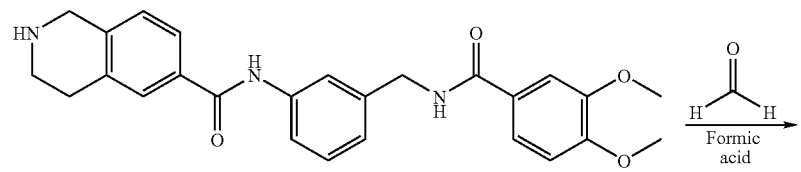

81

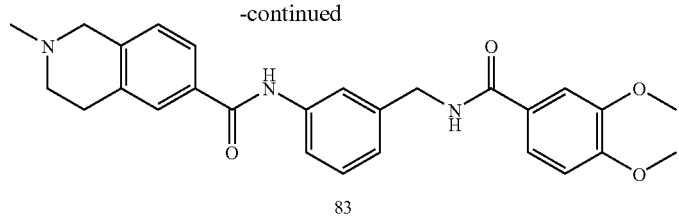

83

Compound 81, the synthesis of which is described in Example 17, was methylated using the procedure described in Example 9 to provide the title compound, MS, electrospray, 460 (M+H).

Using the methods described in the above example, the following analog was also synthesized:

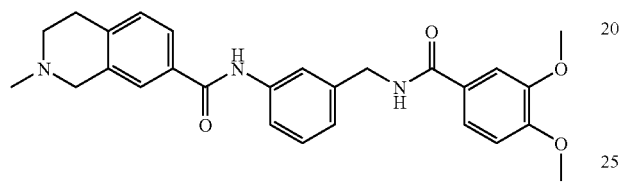

[84] 2-Methyl-1,2,3,4-tetrahydro-isoquinoline-7-carboxylic acid {3-[(3,4-dimethoxy-benzoylamino)-methyl]-phenyl}-amide; MS, electrospray, 460 (M+H)

Example 19

Synthesis of N-{3-[(3,4-Dimethoxy-phenylcarbamoyl)-methyl]-phenyl}-3-piperidin-3-yl-propionamide (85)

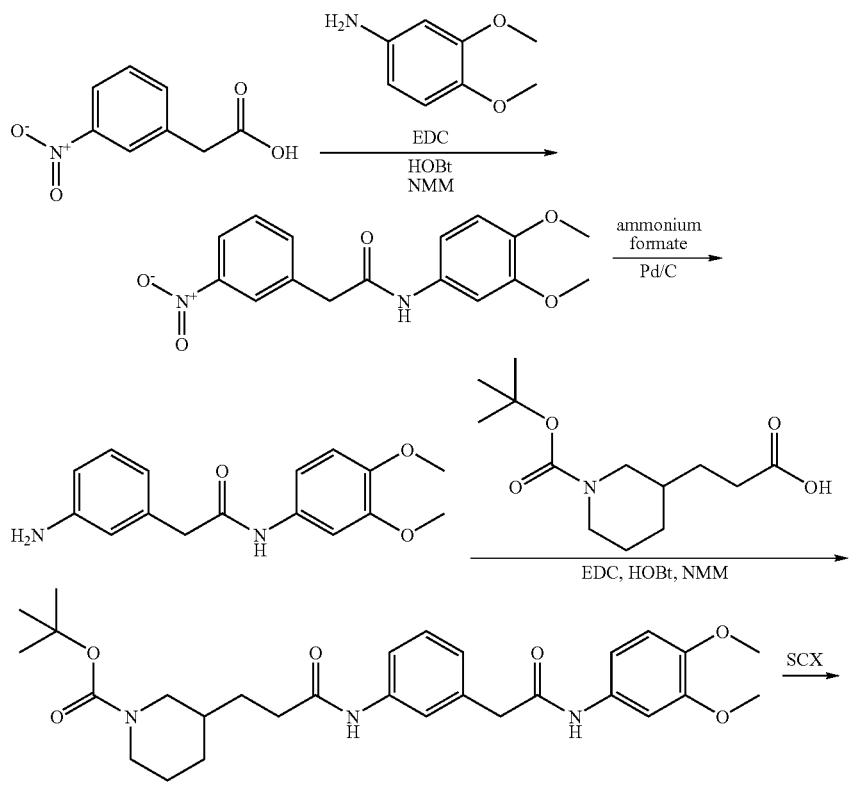

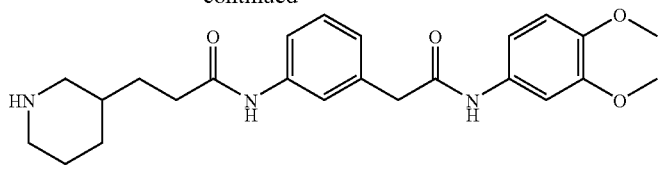

85

3-Nitrophenylacetic acid (136 mg, 0.75 mmol), EDC (240 mg, 1.25 mmol) and HOBt (135 mg, 1 mmol) were combined in a reaction vial, and DMF (1 mL) was added, followed by N-methylmorpholine (0.137 mL, 1.25 mmol). The resulting solution was agitated for 1 h, after which time 3,4-dimethoxyaniline (115 mg, 0.75 mmol) was added and the reaction mixture was agitated overnight. The reaction mixture was then diluted with 6 mL dichloromethane, and the resulting mixture was washed with 1 N HCl (2×2 mL), NaHCO$_3$ (satd. aq., 2×2 mL), and brine (1×2 mL), dried, and the solvents were evaporated to 216 mg of a dark oil. The product was purified by preparative HPLC using an acetonitrile/water/formic acid gradient to provide 36 mg (15% yield) of the intermediate N-(3,4-dimethoxy-phenyl)-2-(3-nitrophenyl)-acetamide. This intermediate (36 mg, 0.114 mmol) was dissolved in methanol (1 mL) and ammonium formate (69 mg, 1.1 mmol) and then Pd/C (5 mg) was added. The reaction vial was sealed and heated to 45° C. overnight. The reaction mixture was filtered, and the mother liquors were diluted with ethyl acetate (10 mL). This mixture was washed with water (2×5 mL) and brine (1×5 mL), dried and concentrated to provide 10 mg (31% yield) of the desired intermediate 2-(3-amino-phenyl)-N-(3,4-dimethoxy-phenyl)-acetamide, which was used directly. Subsequently, 3-(2-carboxyethyl)-piperidine-1-carboxylic acid tert-butyl ester (12.9 mg, 0.05 mmol), EDC (11.5 mg, 0.06 mmol) and HOBt (8.1 mg, 0.06 mmol) were combined in a reaction vial, and DMF (1 mL) was added, followed by N-methylmorpholine (0.007 mL, 0.06 mmol). The resulting solution was agitated for 30 minutes, after which time the intermediate prepared above, 2-(3-amino-phenyl)-N-(3,4-dimethoxy-phenyl)-acetamide (10 mg, 0.035 mmol) was added. The reaction mixture was agitated overnight, then diluted with 5 mL dichloromethane, and the resulting mixture was washed with 1N HCl (2×2 mL), NaHCO$_3$ (saturated aqueous, 1×2 mL), and brine (1×2 mL), dried, and concentrated to 19 mg (72%) of an amber oil, which was dissolved in dichloromethane (1 mL) and treated with SCX (136 mg, 0.12 mmol). The resulting mixture was agitated overnight. The reaction mixture was then filtered and the solids were washed with dichloromethane (2×2 mL) and methanol (2×2 mL). The product was eluted with NH$_3$ in methanol (7 N, 2×2 mL), and the solvents were evaporated. The resulting residue was purified by preparative HPLC using an acetonitrile/water/formic acid gradient providing the title compound as a formate salt (6.5 mg, 38% yield), MS analysis electrospray, 426 (M+H).

Using the methods described in the above example, the following analogs were also synthesized:

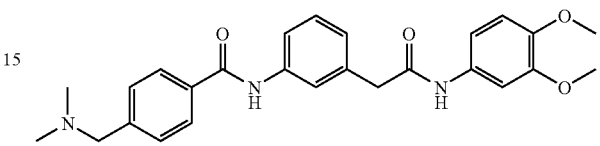

[86] N-{3-[(3,4-Dimethoxy-phenylcarbamoyl)-methyl]-phenyl}-4-dimethylaminomethyl-benzamide; MS, electrospray, 448 (M+H)

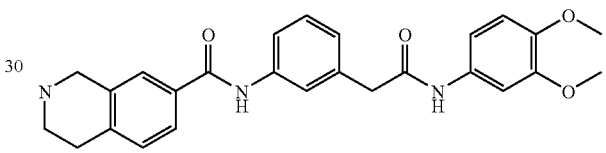

[87] 1,2,3,4-Tetrahydro-isoquinoline-7-carboxylic acid {3-[(3,4-dimethoxy-phenylcarbamoyl)-methyl]-phenyl}-amide; MS, electrospray, 446 (M+H)

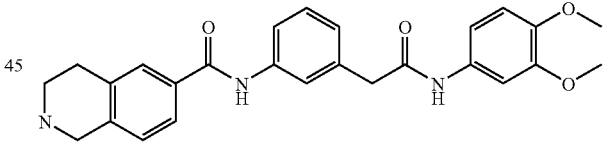

[88] 1,2,3,4-Tetrahydro-isoquinoline-6-carboxylic acid {3-[(3,4-dimethoxy-phenylcarbamoyl)-methyl]-phenyl}-amide; MS, electrospray, 446 (M−H)

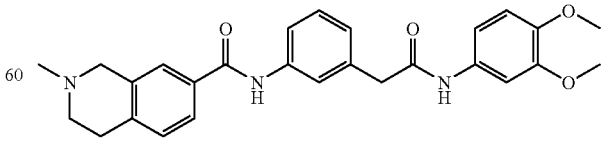

[89] 2-Methyl-1,2,3,4-tetrahydro-isoquinoline-7-carboxylic acid {3-[(3,4-dimethoxy-phenylcarbamoyl)-methyl]-phenyl}-amide; MS, electrospray, 460 (M+H)

Example 20

Synthesis of N-(3,4-Dimethoxy-phenyl)-3-[3-(3-piperidin-3-yl-propionylamino)-phenyl]-propionamide (90)

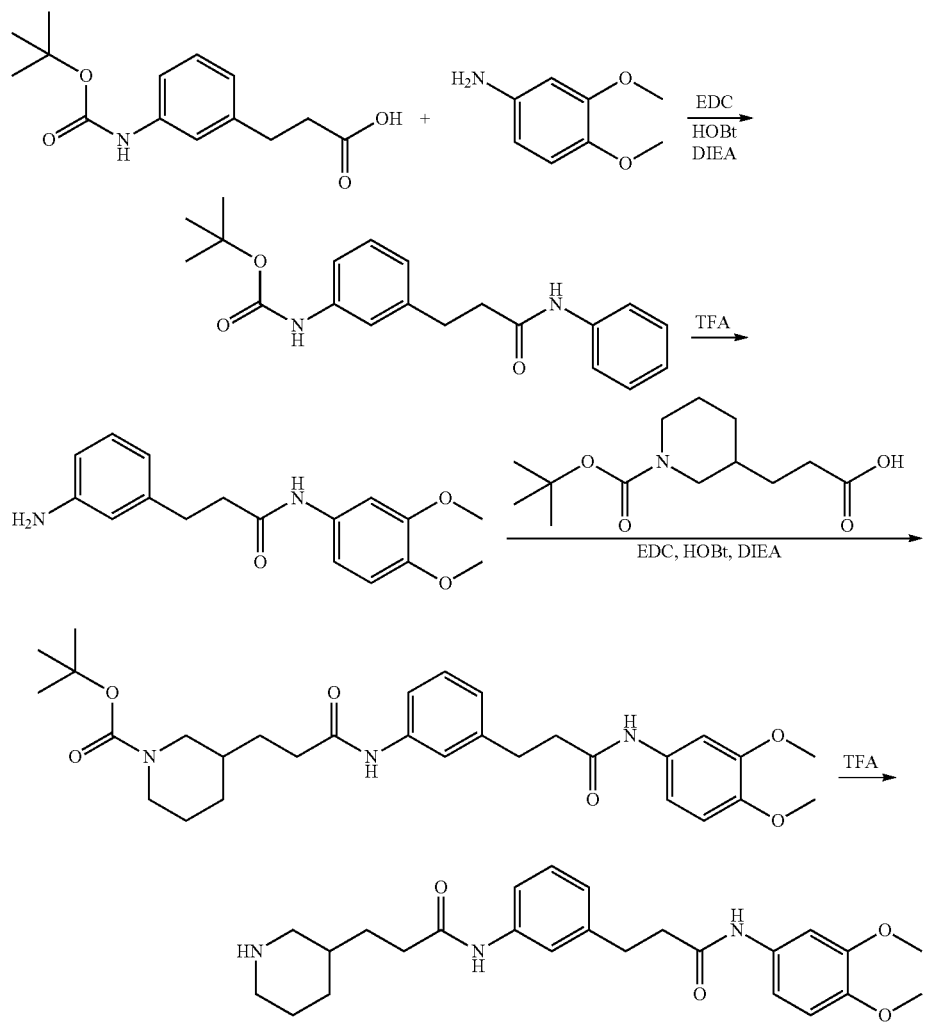

A reaction vial was charged with 3-(3-tert-butoxycarbonylamino-phenyl)-propionic acid (90 mg, 0.34 mmol), 3,4-dimethoxylaniline (90 mg, 0.59 mmol), EDC (100 mg, 0.64 mmol) and HOBt (100 mg, 0.74 mmol). DMF (2 mL) was added, followed by Hunig's base (0.3 mL, 1.72 mmol). The mixture was stirred at room temperature overnight, and then diluted with 10 mL water. The resulting mixture was extracted with 3×10 mL ethyl acetate. The organic layers were combined and washed with water and brine, dried with $Na_2SO_4$, and evaporated to give 150 mg crude {3-[2-(3,4-dimethoxy-phenylcarbamoyl)-ethyl]-phenyl}-carbamic acid tert-butyl ester which was used without purification. The ester intermediate was dissolved in dichloromethane (4 mL), and TFA (1 mL) was added. The resulting mixture was stirred at room temperature for 2 h, then concentrated to provide the product, 3-(3-amino-phenyl)-N-(3,4-dimethoxy-phenyl)-propionamide, as a TFA salt which was used without further purification (100 mg, 71% yield, 2 steps). This intermediate (100 mg, 0.33 mmol) was then combined with 3-(2-carboxy-ethyl)-piperidine-1-carboxylic acid tert-butyl ester (100 mg, 0.39 mmol), EDC (100 mg, 0.64 mmol) and HOBt (100 mg, 0.74 mmol) in a reaction vial. DMF (2 mL) was added, followed by Hunig's base (0.3 mL, 1.72 mmol). The mixture was stirred at room temperature overnight. The product was purified directly from the reaction mixture by preparative HPLC using an acetonitrile/water/formic acid gradient to afford the product, 3-(2-{3-[2-(3,4-dimethoxy-phenylcarbamoyl)-ethyl]-phenylcarbamoyl}-ethyl)-piperidine-1-carboxylic acid tert-butyl ester, as yellow oil (50 mg, 28% yield). This intermediate was then dissolved in dichloromethane (4 mL), and TFA (1 mL) was added. The resulting mixture was stirred at room temperature for 2 hours then concentrated to provide the title compound as a TFA salt (27 mg, 66% yield); MS, electrospray, 440 (M+H).

Example 21

Synthesis of N-(4-Cyano-phenyl)-3-[3-(3-piperidin-3-yl-propionylamino)-phenyl]-propionamide (91)

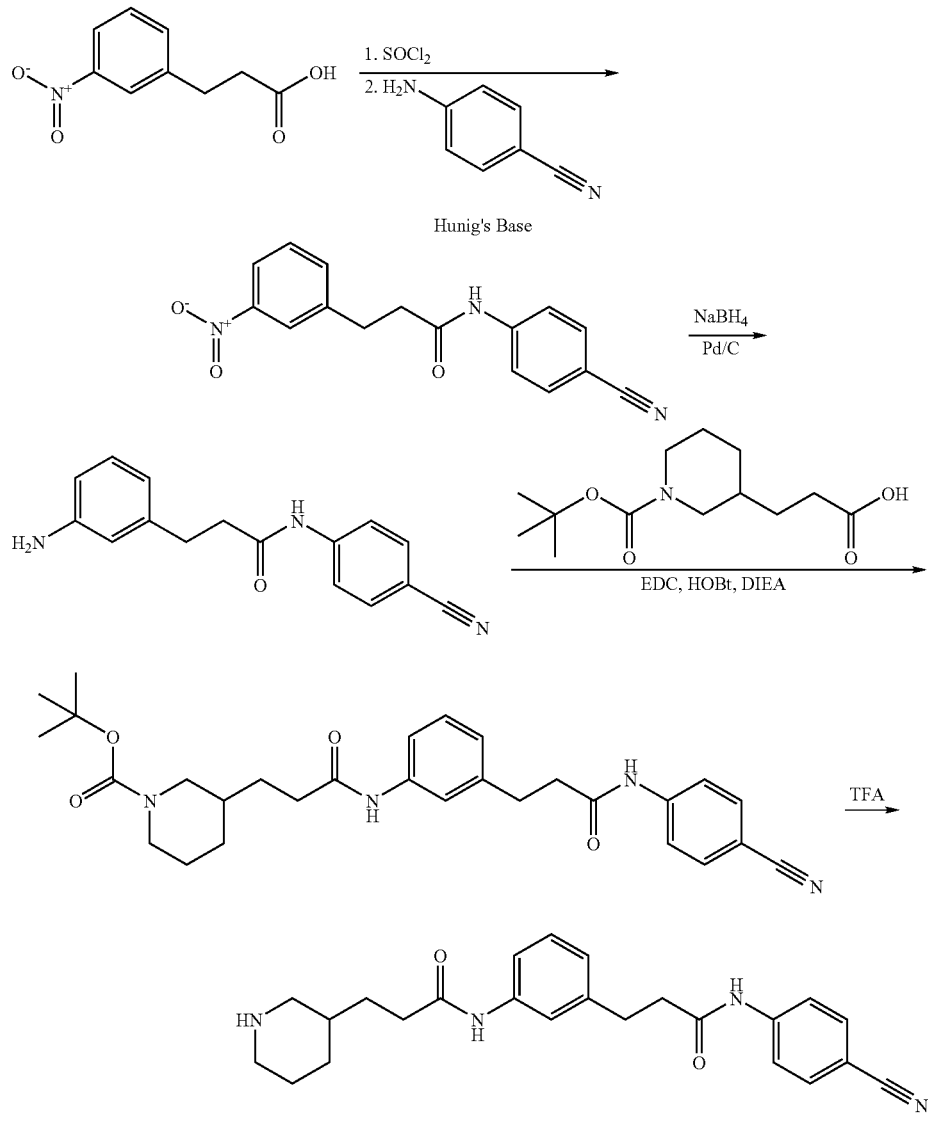

91

3-Nitrophenyl-propionic acid (992 mg, 5.08 mmol) was suspended in toluene (10 mL). Thionyl chloride (1.82 mL, 25.0 mmol) was added dropwise and the resulting mixture was stirred at 110° C. for 1 h. The reaction mixture was concentrated and the residue was dissolved in dry dichloromethane (15 mL). To this solution was added 4-aminobenzonitrile (590 mg, 5.2 mmol) and Hunig's base (1.85 mL, 10.0 mmol). The reaction mixture was stirred for 4 h then diluted with ethyl acetate (150 mL) and quenched with NH$_4$Cl (150 mL satd. aq.) The organic fraction was isolated and washed with brine (50 mL), dried with MgSO$_4$ and concentrated. The residue was purified by flash chromatography using an ethyl acetate/hexane gradient to provide 1.273 g of N-(4-cyano-phenyl)-3-(3-nitro-phenyl)-propionamide (85% yield). This intermediate (103 mg, 0.35 mmol) was dissolved in methanol (5 mL) under an atmosphere of argon, and sodium borohydride (26.3 mg, 0.7 mmol) and Pd/C (20 mg) were added. The resulting mixture was stirred at room temperature for 1 h, filtered through celite, and concentrated. The residue was suspended in NH$_4$Cl (20 mL, saturated aqueous), and this mixture was extracted with ethyl acetate (2×20 mL). The combined organic fractions were washed with brine (20 mL), dried and concentrated to provide 3-(3-amino-phenyl)-N-(4-cyano-phenyl)-propionamide (80 mg, 87% yield) which was used without further purification. This intermediate was converted to the title compound as described in example 20. MS, electrospray, 405 (M+H).

Using the methods described in the above example, the following analogs were also synthesized:

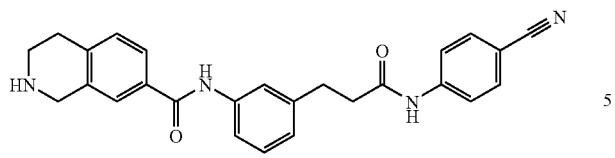

[92]; 1,2,3,4-Tetrahydro-isoquinoline-7-carboxylic acid {3-[2-(4-cyano-phenylcarbamoyl)-ethyl]-phenyl}-amide; MS, electrospray, 425 (M+H)

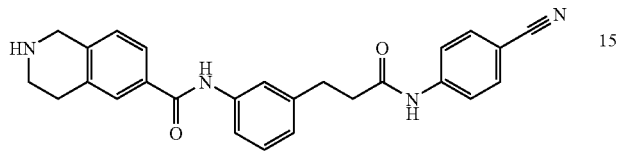

[93]; 1,2,3,4-Tetrahydro-isoquinoline-6-carboxylic acid {3-[2-(4-cyano-phenylcarbamoyl)-ethyl]-phenyl}-amide; MS, electrospray, 425 (M+H)

Example 22

N-[3-(2-Benzyl-1,2,3,4-tetrahydro-isoquinolin-7-ylcarbamoyl)-benzyl]-3,4-dimethoxy-benzamide (94)

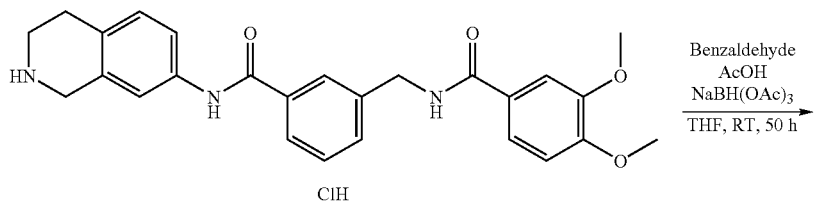

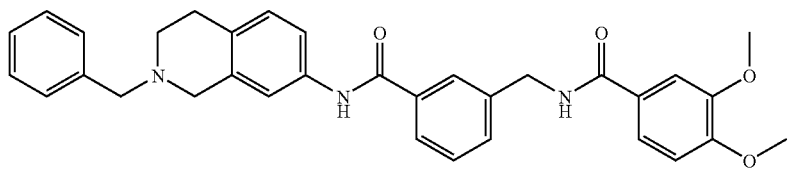

Suspended 3,4-Dimethoxy-N-[3-(1,2,3,4-tetrahydro-isoquinolin-7-ylcarbamoyl)-benzyl]-benzamide hydrochloride (50.0 mg, 0.104 mmol) in 2 mL of THF. To this was added AcOH (0.06 mL, 1.0 mmol) and benzaldehyde (0.016 mL, 0.150 mmol). The mixture stirred for 1 h. To this was added NaBH(OAc)$_3$ (63.3 mg, 0.300 mmol). The mixture stirred for 50 h. LC-MS analysis indicated the desired product. Concentrated the mixture to dryness. Redissolved in CH$_2$Cl$_2$/MeOH and applied to a SiO$_2$ prep plate. Eluted with (10% MeOH/1% NH3/CH$_2$Cl$_2$) to give 40.6 mg of N-[3-(2-Benzyl-1,2,3,4-tetrahydro-isoquinolin-7-ylcarbamoyl)-benzyl]-3,4-dimethoxy-benzamide. MS, electrospray 536.4 (M+H).

The following compounds were made by the method described in Example 22.

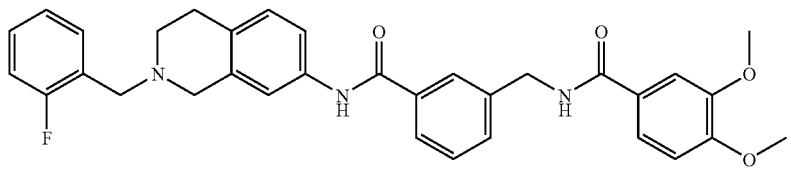

[95] N-{3-[2-(2-Fluoro-benzyl)-1,2,3,4-tetrahydro-isoquinolin-7-ylcarbamoyl]-benzyl}-3,4-dimethoxy-benzamide. MS, electrospray 554.5 (M+H).

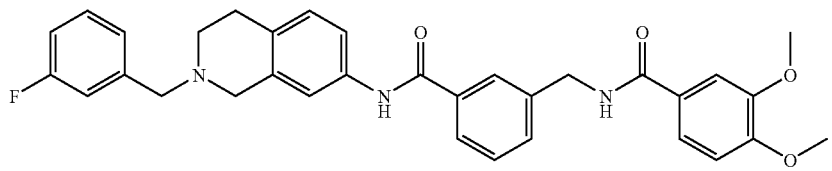

[96] N-{3-[2-(3-Fluoro-benzyl)-1,2,3,4-tetrahydro-isoquinolin-7-ylcarbamoyl]-benzyl}-3,4-dimethoxy-benzamide. MS, electrospray 554.5 (M+H).

[97] N-{3-[2-(3-Fluoro-benzyl)-1,2,3,4-tetrahydro-isoquinolin-7-ylcarbamoyl]-benzyl}-3,4-dimethoxy-benzamide. MS, electrospray 554.5 (M+H).

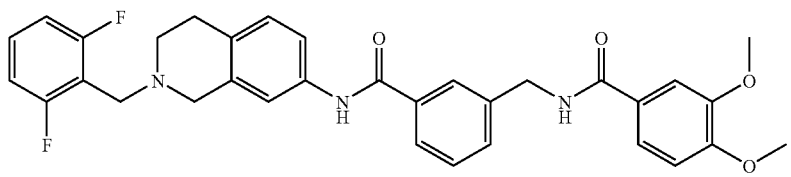

[98] N-{3-[2-(2,6-Difluoro-benzyl)-1,2,3,4-tetrahydro-isoquinolin-7-ylcarbamoyl]-benzyl}-3,4-dimethoxy-benzamide. MS, electrospray 552.5 (M+H).

[99] N-{3-[2-(2,3-Difluoro-benzyl)-1,2,3,4-tetrahydro-isoquinolin-7-ylcarbamoyl]-benzyl}-3,4-dimethoxy-benzamide. MS, electrospray 552.5 (M+H).

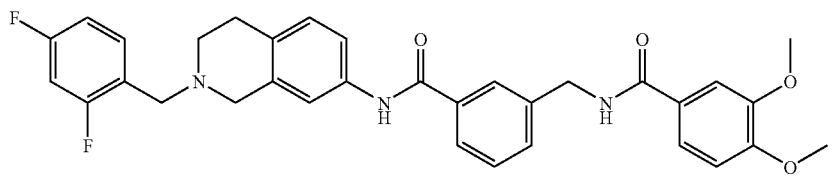

[100] N-{3-[2-(2,4-Difluoro-benzyl)-1,2,3,4-tetrahydro-isoquinolin-7-ylcarbamoyl]-benzyl}-3,4-dimethoxy-benzamide. MS, electrospray 552.5 (M+H).

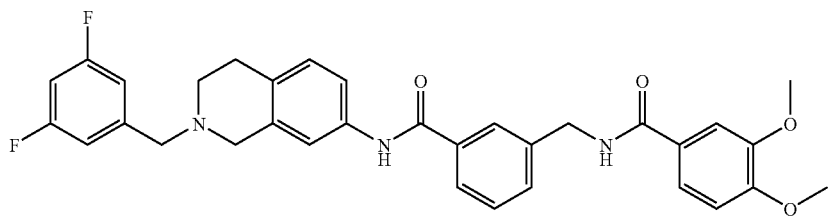

[101] N-{3-[2-(3,5-Difluoro-benzyl)-1,2,3,4-tetrahydro-isoquinolin-7-ylcarbamoyl]-benzyl}-3,4-dimethoxy-benzamide. MS, electrospray 552.5 (M+H).

Example 23

3,4-Dimethoxy-N-[3-(5-methyl-4,5,6,7-tetrahydro-thiazolo[5,4-c]pyridin-2-ylcarbamoyl)-benzyl]-benzamide (102)

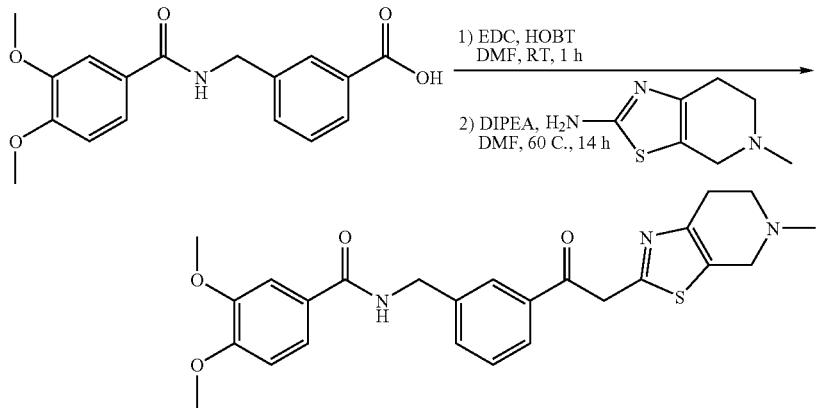

Dissolved 3-[(3,4-dimethoxy-benzoylamino)-methyl]-benzoic acid (100 mg, 0.317 mmol), EDC (105 mg, 0.55 mmol) and hydroxybenzotriazole (84.2 mg, 0.55 mmol) in 1 mL of DMF. The mixture was stirred for 1 h. To this was added DIPEA (0.12 mL, 0.64 mmol) and 5-methyl-4,5,6,7-tetrahydro-thiazolo[5,4-c]pyridin-2-ylamine (107 mg, 0.63 mmol). The mixture was placed in a 60° C. bath with an Ar stream blowing over it. The mixture stirred 14 h resulting in a concentrated residue. LC-MS analysis indicated the desired product. Dissolved in 5 mL of DMF/$H_2O$ and purified via prep HPLC (5%-95% $CH_3CN/H_2O$) to give 121.9 mg of 3,4-dimethoxy-N-[3-(5-methyl-4,5,6,7-tetrahydro-thiazolo[5,4-c]pyridin-2-ylcarbamoyl)-benzyl]-benzamide. MS, electrospray 467.4 (M+H).

Example 24

3,4-Dimethoxy-N-[3-(5,6,7,8-tetrahydro-[1,6]naph-thyridin-3-ylcarbamoyl)-benzyl]-benzamide (103)

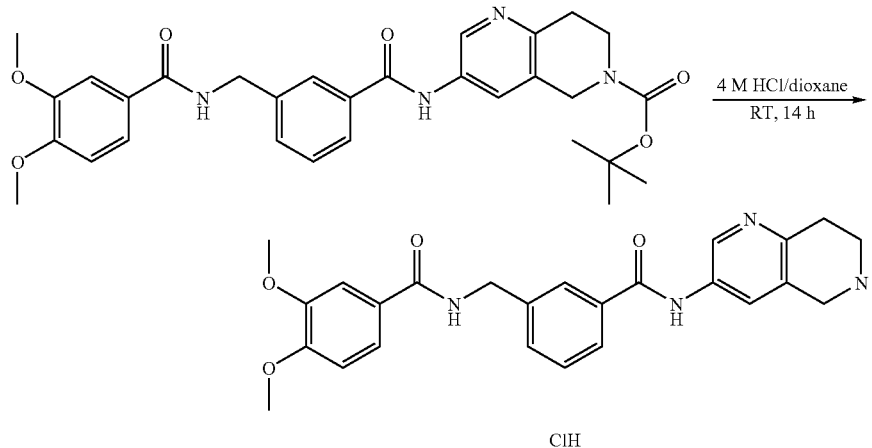

3-{3-[(3,4-Dimethoxy-benzoylamino)-methyl]-benzoylamino}-7,8-dihydro-5H-[1,6]naphthyridine-6-carboxylic acid tert-butyl ester was prepared by the method described in Example 23.

Dissolved 3-{3-[(3,4-dimethoxy-benzoylamino)-methyl]-benzoylamino}-7,8-dihydro-5H-[1,6]naphthyridine-6-carboxylic acid tert-butyl ester (120 mg, 0.22 mmol) in 3 mL $CH_2Cl_2$ and added HCl in dioxane (1.00 mL/4.0 mmol). The mixture was stirred overnight resulting in a heterogenous mixture. Concentrated the mixture to dryness to give 100.7 mg of the desired product. MS, electrospray 447.4 (M+H).

Example 25

(7-{3-[(3,4-Dimethoxy-benzoylamino)-methyl]-benzoylamino}-3,4-dihydro-1H-isoquinolin-2-yl)-acetic acid methyl ester (104)

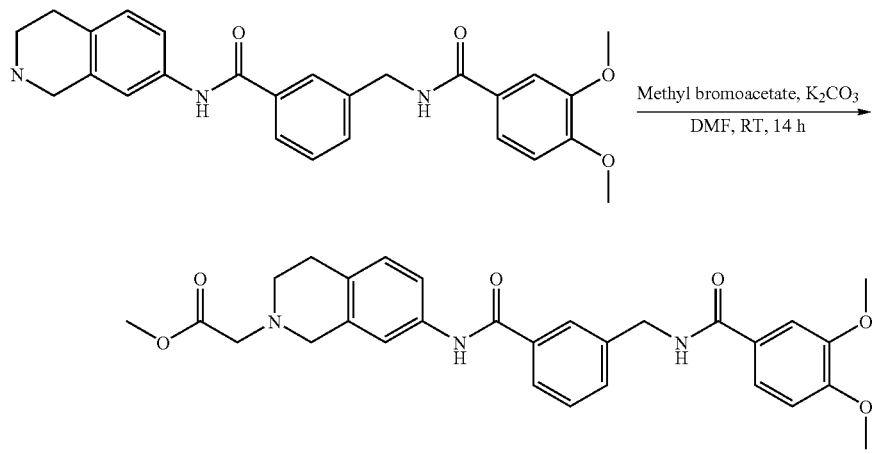

Dissolved 3,4-dimethoxy-N-[3-(1,2,3,4-tetrahydro-isoquinolin-7-ylcarbamoyl)-benzyl]-benzamide (50.0 mg, 0.12 mmol) in 1 mL of DMF. To the mixture was added methyl bromoacetate (0.02 mL, 0.20 mmol) and $K_2CO_3$ (50 mg, 0.36 mmol). The mixture was stirred at room temperature overnight. LC-MS indicated the desired product. Dissolved in 5 mL of DMF and purified via prep HPLC (5%-95% $CH_3CN/H_2O$) to give 37 mg (7-{3-[(3,4-dimethoxy-benzoylamino)-methyl]-benzoylamino}-3,4-dihydro-1H-isoquinolin-2-yl)-acetic acid methyl ester. MS, electrospray 590.6 (M+H).

The following compounds were prepared by the method shown in Example 25.

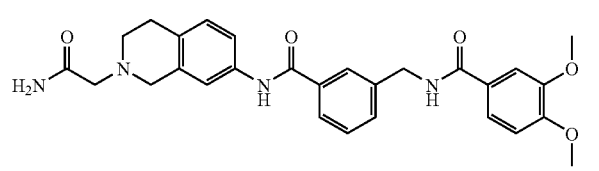
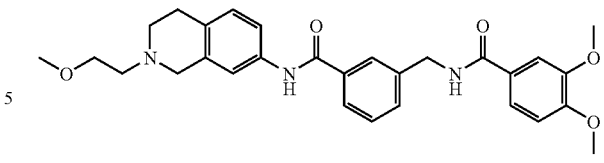

[106] 3,4-Dimethoxy-N-{3-[2-(2-methoxy-ethyl)-1,2,3,4-tetrahydro-isoquinolin-7-ylcarbamoyl]-benzyl}-benzamide. MS, electrospray 504.5 (M+H).

Example 26

N-{3-[2-(2-Cyano-ethyl)-1,2,3,4-tetrahydro-isoquinolin-7-ylcarbamoyl]-benzyl}-3,4-dimethoxy-benzamide (107)

[105] N-[3-(2-Carbamoylmethyl-1,2,3,4-tetrahydro-isoquinolin-7-ylcarbamoyl)-benzyl]-3,4-dimethoxy-benzamide. MS, electrospray 503.5 (M+H).

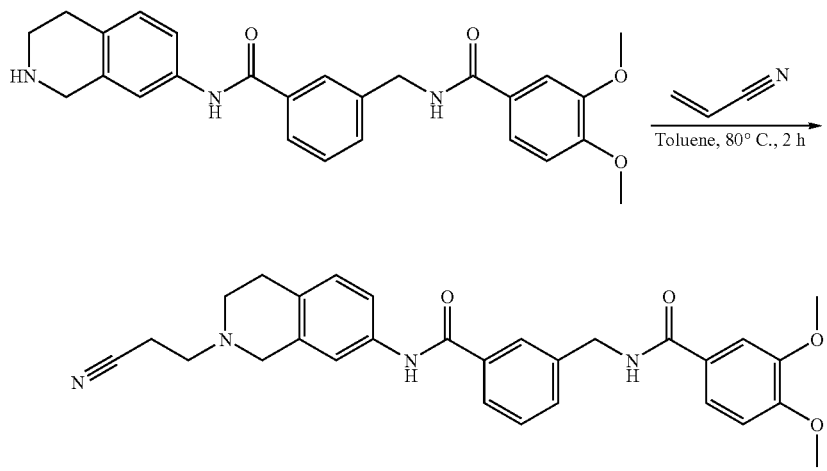

Dissolved 3,4-dimethoxy-N-[3-(1,2,3,4-tetrahydro-isoquinolin-7-ylcarbamoyl)-benzyl]-benzamide (50.0 mg, 0.12 mmol) in 3 mL of toluene and added acrylonitrile (0.04 mL, 0.600 mmol). The mixture was heated at 80° C. for 2 h. LC-MS indicated the desired material. Concentrated to dryness and applied to a SiO₂ prep plate. Eluted with (5% MeOH/ 1% NH₃/CH₂Cl₂) to give 40.8 mg of N-{3-[2-(2-Cyano-ethyl)-1,2,3,4-tetrahydro-isoquinolin-7-ylcarbamoyl]-benzyl}-3,4-dimethoxy-benzamide. MS, electrospray 499.5 (M+H).

Example 27

N-{3-[2-(2,2-Difluoro-ethyl)-1,2,3,4-tetrahydro-isoquinolin-7-ylcarbamoyl]-benzyl}-3,4-dimethoxy-benzamide (108)

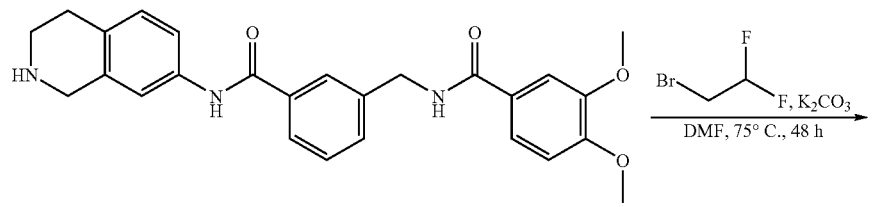

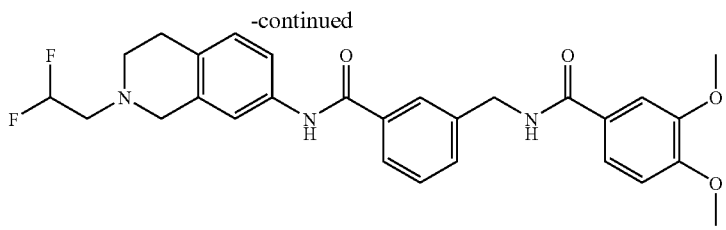

Dissolved 3,4-dimethoxy-N-[3-(1,2,3,4-tetrahydro-isoquinolin-7-ylcarbamoyl)-benzyl]-benzamide (50.0 mg, 0.12 mmol) in 1 mL of DMF. Added 2-bromo-1,1-difluoro-ethane and (0.02 mL, 0.20 mmol) K₂CO₃ (50.0 mg, 0.36 mmol). The mixture was stirred at room temperature overnight. LC-MS indicated low conversion to alkylated product. Heated the mixture to 60° C. for 8 h with continued low conversion, thereafter it was heated to 75° C. for 48 h. LC-MS indicated the desired product. Dissolved in 5 mL of DMF and purified via prep HPLC (5%-95% CH₃CN/H2O) to give 28.1 mg of N-{3-[2-(2,2-difluoro-ethyl)-1,2,3,4-tetrahydro-isoquinolin-7-ylcarbamoyl]-benzyl}-3,4-dimethoxy-benzamide. MS, electrospray 510.4 (M+H).

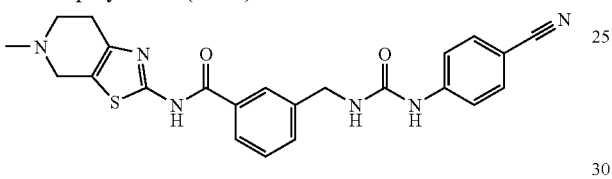

[109] 3-[3-(4-Cyano-phenyl)-ureidomethyl]-N-(5-methyl-4,5,6,7-tetrahydro-thiazolo[5,4-c]pyridin-2-yl)-benzamide. Prepared by the method described in Example 23. MS, electrospray 447.3 (M+H).

Example 28

4-Methoxy-3-methyl-N-[3-(2-methyl-1,2,3,4-tetrahydro-isoquinolin-7-ylcarbamoyl)-benzyl]-benzamide (110)

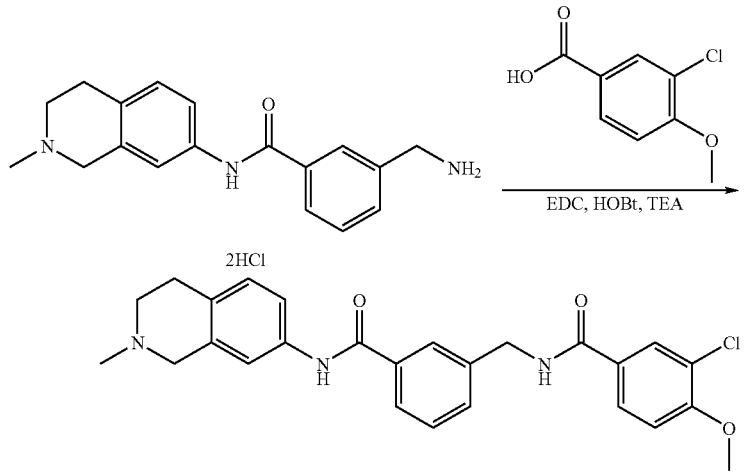

A solution of 3-chloro-4-methoxybenzoic acid dihydrochloride (29 mg, 150 mmol), EDC (30 mg, 150 mmol), HOBt (22 mg, 150 mmol), and TEA (0.057 mL, 408 mmol) in anhydrous DMF (5 mL) was stirred at room temperature for 30 min. To this was added 3-aminomethyl-N-(2-methyl-1,2,3,4-tetrahydro-isoquinolin-7-yl)-benzamide. (50 mg, 136 mmol) and the solution stirred at room temperature for 24 h. The reaction was diluted EtOAc (100 mL) and quenched with sat. NH₄Cl (100 mL). The organic fraction was dried (Na₂SO₄). The residue was purified by flash chromatography using a methanol/methylene chloride gradient to provide 31 mg of 3-chloro-4-methoxy-N-[3-(2-methyl-1,2,3,4-tetrahydro-isoquinolin-7-ylcarbamoyl)-benzyl]-benzamide. MS, electrospray, 464 (M+H).

The following compounds were prepared by the method described in Example 26.

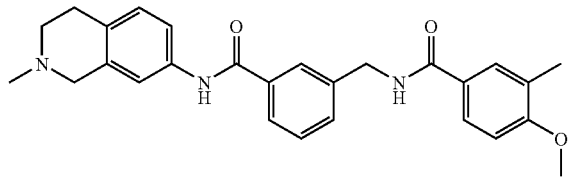

[111] 4-Methoxy-3-methyl-N-[3-(2-methyl-1,2,3,4-tetrahydro-isoquinolin-7-ylcarbamoyl)-benzyl]-benzamide. MS, electrospray, 444 (M+H)

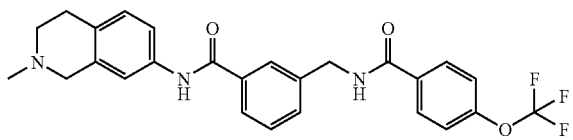

[112] 4-Trifluoromethoxy-N-[3-(2-methyl-1,2,3,4-tetrahydro-isoquinolin-7-ylcarbamoyl)-benzyl]-benzamide. MS, electrospray, 484 (M+H)

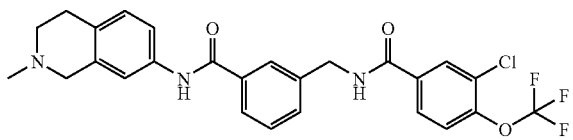

[113] 3-Chloro-N-[3-(2-methyl-1,2,3,4-tetrahydro-isoquinolin-7-ylcarbamoyl)-benzyl]-4-trifluoromethoxy-benzamide. MS, electrospray, 518 (M+H)

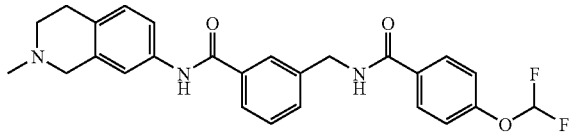

[114] 4-Difluoromethoxy-N-[3-(2-methyl-1,2,3,4-tetrahydro-isoquinolin-7-ylcarbamoyl)-benzyl]-benzamide. MS, electrospray, 466 (M+H)

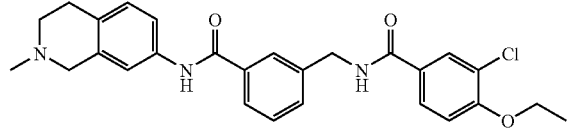

[115] 3-Chloro-4-ethoxy-N-[3-(2-methyl-1,2,3,4-tetrahydro-isoquinolin-7-ylcarbamoyl)-benzyl]-benzamide. MS, electrospray, 478 (M+H)

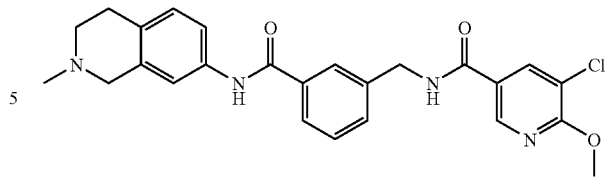

[116] 5-Chloro-6-methoxy-N-[3-(2-methyl-1,2,3,4-tetrahydro-isoquinolin-7-ylcarbamoyl)-benzyl]-nicotinamide. MS, electrospray, 465 (M+H)

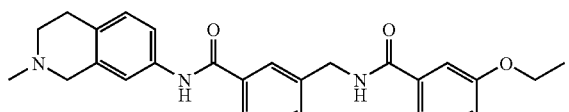

[117] 3,4-Diethoxy-N-[3-(2-methyl-1,2,3,4-tetrahydro-isoquinolin-7-ylcarbamoyl)-benzyl]-benzamide. MS, electrospray, 488 (M+H)

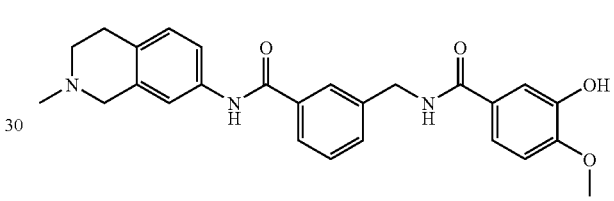

[118] 3-Hydroxy-4-methoxy-N-[3-(2-methyl-1,2,3,4-tetrahydro-isoquinolin-7-ylcarbamoyl)-benzyl]-benzamide. MS, electrospray, 446 (M+H)

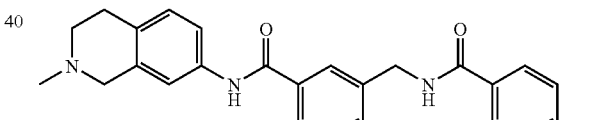

[119] 6-Hydroxy-N-[3-(2-methyl-1,2,3,4-tetrahydro-isoquinolin-7-ylcarbamoyl)-benzyl]-nicotinamide. MS, electrospray, 417 (M+H)

The following compounds were prepared by the method described in Example 22.

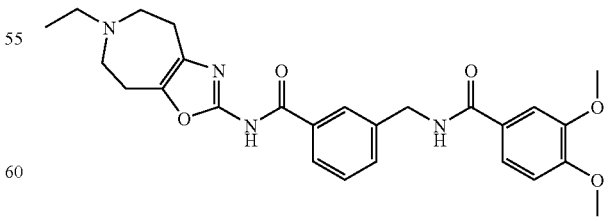

[120] N-[3-(6-Ethyl-5,6,7,8-tetrahydro-4H-oxazolo[4,5-d]azepin-2-ylcarbamoyl)-benzyl]-3,4-dimethoxy-benzamide. Prepared by the method described in Example 22. MS, electrospray 479.4 (M+H).

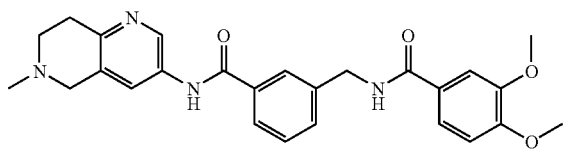

[121] 3,4-Dimethoxy-N-[3-(6-methyl-5,6,7,8-tetrahydro-[1,6]naphthyridin-3-ylcarbamoyl)-benzyl]-benzamide. MS, electrospray 461.39 (M+H).

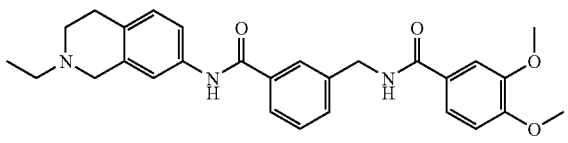

[122] N-[3-(2-Ethyl-1,2,3,4-tetrahydro-isoquinolin-7-ylcarbamoyl)-benzyl]-3,4-dimethoxy-benzamide. MS, electrospray 474.4 (M+H).

The following compounds were prepared by the method described in Example 28.

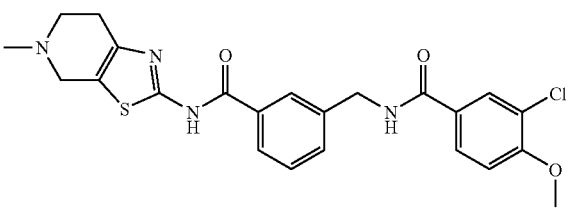

[123] 3-Chloro-4-methoxy-N-[3-(5-methyl-4,5,6,7-tetrahydro-thiazolo[5,4-c]pyridin-2-ylcarbamoyl)-benzyl]-benzamide. MS, electrospray, 471 (M+H)

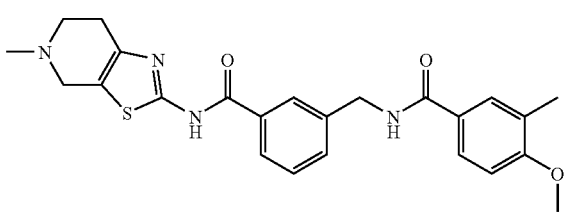

[124] 4-Methoxy-3-methyl-N-[3-(5-methyl-4,5,6,7-tetrahydro-thiazolo[5,4-c]pyridin-2-ylcarbamoyl)-benzyl]-benzamide. MS, electrospray, 451 (M+H)

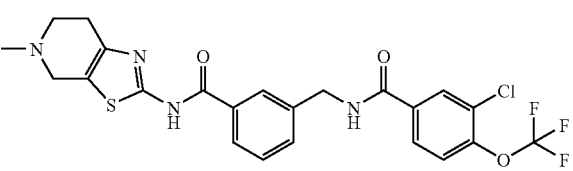

[125] 3-Chloro-N-[3-(5-methyl-4,5,6,7-tetrahydro-thiazolo[5,4-c]pyridin-2-ylcarbamoyl)-benzyl]-4-trifluoromethoxy-benzamide. MS, electrospray, 525 (M+H)

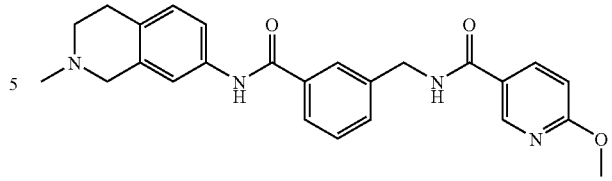

[126] 6-Methoxy-N-[3-(2-methyl-1,2,3,4-tetrahydro-isoquinolin-7-ylcarbamoyl)-benzyl]-nicotinamide. MS, electrospray, 431 (M+H)

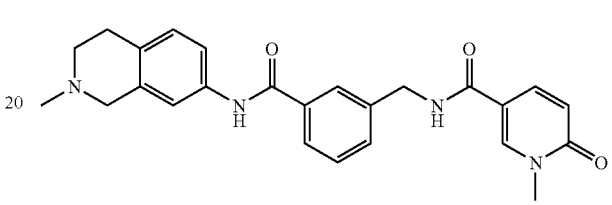

[127] 1-Methyl-6-oxo-1,6-dihydro-pyridine-3-carboxylic acid 3-(2-methyl-1,2,3,4-tetrahydro-isoquinolin-7-ylcarbamoyl)-benzylamide. MS, electrospray, 431 (M+H)

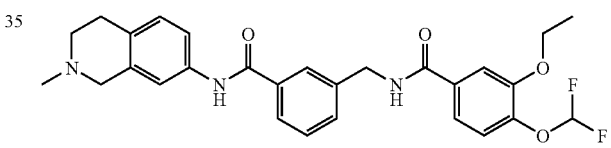

[128] 4-Difluoromethoxy-3-ethoxy-N-[3-(2-methyl-1,2,3,4-tetrahydro-isoquinolin-7-ylcarbamoyl)-benzyl]-benzamide. MS, electrospray, 510 (M+H)

[129] N-[3-(5-Benzyl-4,5,6,7-tetrahydro-thiazolo[5,4-c]pyridin-2-ylcarbamoyl)-benzyl]-3,4-dimethoxy-benzamide. Prepared by the method described in 23. MS, electrospray 543.5 (M+H).

The following compounds were prepared by the method described in Example 22.

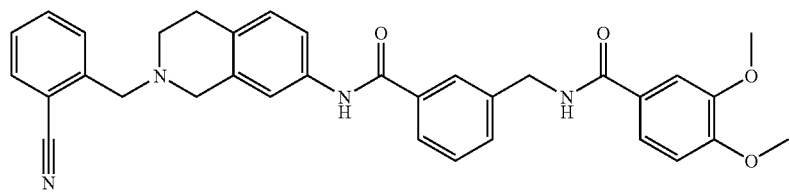

[130] N-{3-[2-(2-Cyano-benzyl)-1,2,3,4-tetrahydro-isoquinolin-7-ylcarbamoyl]-benzyl}-3,4-dimethoxy-benzamide. MS, electrospray 561.5 (M+H).

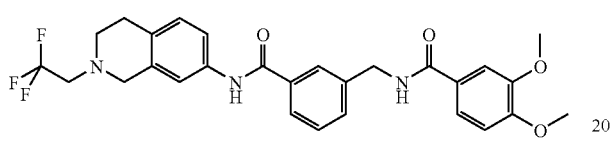

[131] 3,4-Dimethoxy-N-{3-[2-(2,2,2-trifluoro-ethyl)-1,2,3,4-tetrahydro-isoquinolin-7-ylcarbamoyl]-benzyl}-benzamide. MS, electrospray 528.4 (M+H).

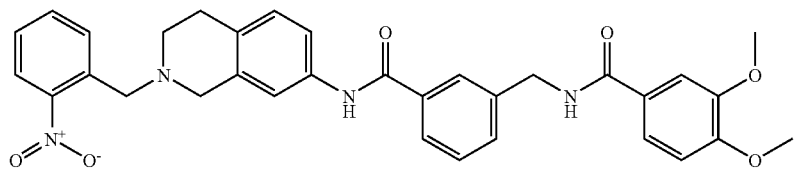

[132] 3,4-Dimethoxy-N-{3-[2-(2-nitro-benzyl)-1,2,3,4-tetrahydro-isoquinolin-7-ylcarbamoyl]-benzyl}-benzamide. MS, electrospray 581.9 (M+H).

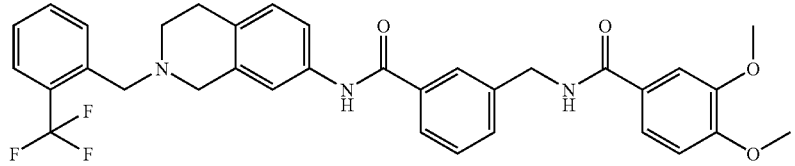

[133] 3,4-Dimethoxy-N-{3-[2-(2-trifluoromethyl-benzyl)-1,2,3,4-tetrahydro-isoquinolin-7-ylcarbamoyl]-benzyl}-benzamide. MS, electrospray 605.0 (M+H).

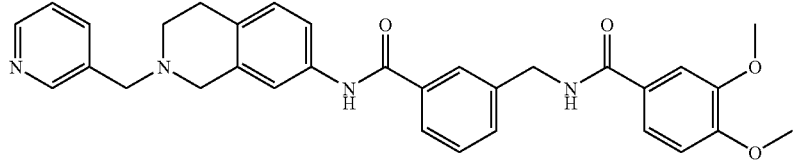

[134] 3,4-Dimethoxy-N-[3-(2-pyridin-3-ylmethyl-1,2,3,4-tetrahydro-isoquinolin-7-ylcarbamoyl)-benzyl]-benzamide. MS, electrospray 537.9 (M+H).

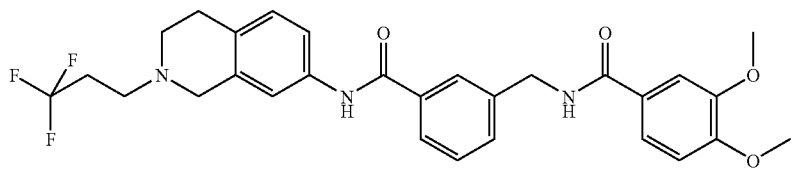

[135] 3,4-Dimethoxy-N-{3-[2-(3,3,3-trifluoro-propyl)-1,2,3,4-tetrahydro-isoquinolin-7-ylcarbamoyl]-benzyl}-benzamide. MS, electrospray 542.6 (M+H).

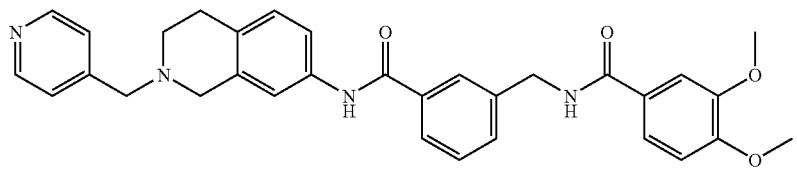

[136] 3,4-Dimethoxy-N-[3-(2-pyridin-4-ylmethyl-1,2,3,4-tetrahydro-isoquinolin-7-ylcarbamoyl)-benzyl]-benzamide. MS, electrospray 537.9 (M+H).

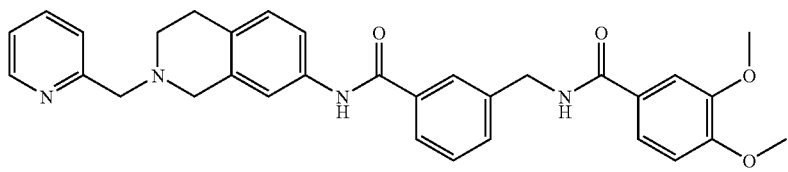

[137] 3,4-Dimethoxy-N-[3-(2-pyridin-2-ylmethyl-1,2,3,4-tetrahydro-isoquinolin-7-ylcarbamoyl)-benzyl]-benzamide. MS, electrospray 537.9 (M+H).

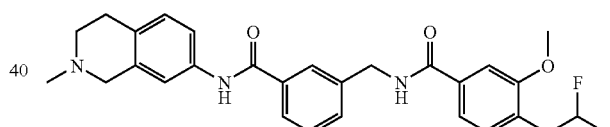

[138] N-{3-[2-(2-Fluoro-ethyl)-1,2,3,4-tetrahydro-isoquinolin-7-ylcarbamoyl]-benzyl}-3,4-dimethoxy-benzamide. Prepared by the method described in Example 27. MS, electrospray 492.5 (M+H).

The following compounds were prepared by the method described in Example 28.

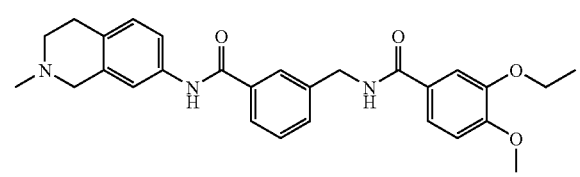

[139] 3-Ethoxy-4-methoxy-N-[3-(2-methyl-1,2,3,4-tetrahydro-isoquinolin-7-ylcarbamoyl)-benzyl]-benzamide. MS, electrospray, 474 (M+H).

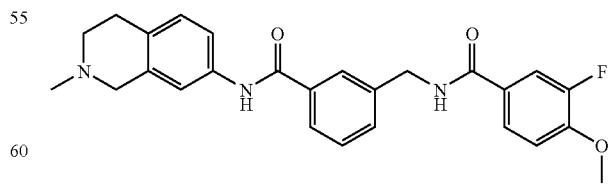

[140] 4-Difluoromethoxy-3-methoxy-N-[3-(2-methyl-1,2,3,4-tetrahydro-isoquinolin-7-ylcarbamoyl)-benzyl]-benzamide. MS, electrospray, 496 (M+H).

[141] 3-Fluoro-4-methoxy-N-[3-(2-methyl-1,2,3,4-tetrahydro-isoquinolin-7-ylcarbamoyl)-benzyl]-benzamide. MS, electrospray, 448 (M+H).

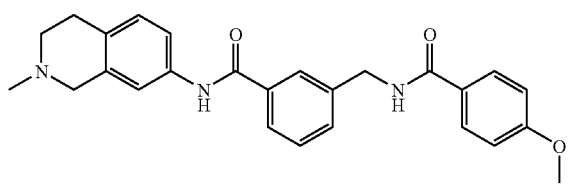

[142] 4-Methoxy-N-[3-(2-methyl-1,2,3,4-tetrahydro-isoquinolin-7-ylcarbamoyl)-benzyl]-benzamide. MS, electrospray, 430 (M+H).

The following compounds were prepared by the methods described in Example 23 and Example 24.

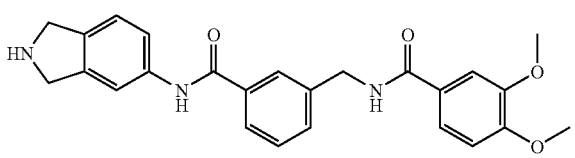

[143] N-[3-(2,3-Dihydro-1H-isoindol-5-ylcarbamoyl)-benzyl]-3,4-dimethoxy-benzamide. MS, electrospray 432.4 (M+H).

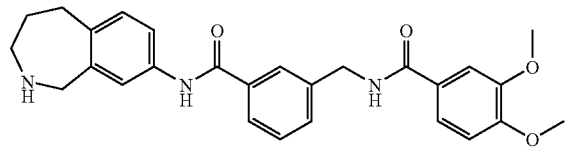

[144] 3,4-Dimethoxy-N-[3-(2,3,4,5-tetrahydro-1H-benzo[c]azepin-8-ylcarbamoyl)-benzyl]-benzamide. MS, electrospray 460.4 (M+H).

Example 29

3,4-Dimethoxy-N-[3-(4,5,6,7-tetrahydro-thiazolo[5,4-c]pyridin-2-ylcarbamoyl)-benzyl]-benzamide (145)

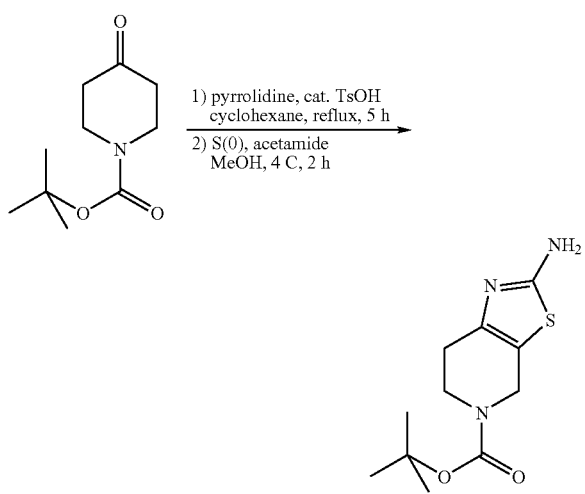

Dissolved 4-Oxo-piperidine-1-carboxylic acid tert-butyl ester (15.0 g, 75.28 mmol) in 75 mL of cyclohexane. To this was added pyrrolidine (6.70 mL, 79.00 mmol) and a catalytic amount of TsOH. The mixture was refluxed with a Dean-Stark trap until no water was collected (5 h). The mixture was filtered and concentrated to an oily brown residue. The residue was dissolved in 25 mL of anhydrous MeOH. To this mixture was added S(0) (2.40 g). The mixture was cooled in and ice bath and acetamide (3.19 g, 76.00 mmol) was added in portions. After 2 h and warming to room temperature a thick tan ppt. appeared. Filtered the material and washed with cold MeOH to give 10.04 g. A second ppt., 3.64 g, was collected. $^1$H NMR indicated identical material and these were combined to give 2-amino-6,7-dihydro-4H-thiazolo[5,4-c]pyridine-5-carboxylic acid tert-butyl ester.

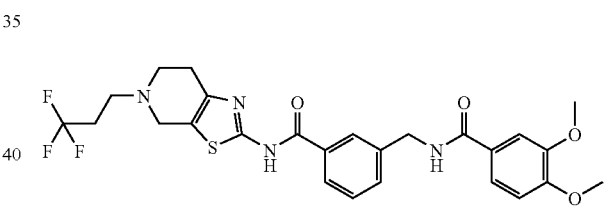

[145] 3,4-Dimethoxy-N-[3-(4,5,6,7-tetrahydro-thiazolo[5,4-c]pyridin-2-ylcarbamoyl)-benzyl]-benzamide was prepared by the methods described in Example 23 and Example 24. MS, electrospray 453.3 (M+H).

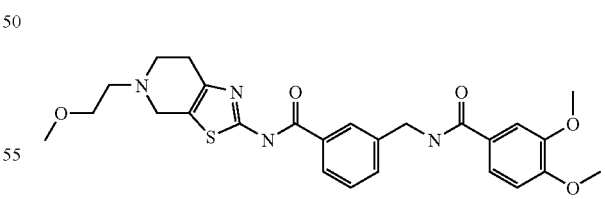

[146] 3,4-Dimethoxy-N-{3-[5-(3,3,3-trifluoro-propyl)-4,5,6,7-tetrahydro-thiazolo[5,4-c]pyridin-2-ylcarbamoyl]-benzyl}-benzamide. Prepared by the method described in Example 22. MS, electrospray 549.5 (M+H).

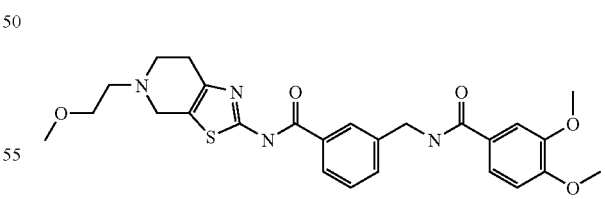

[147] 3,4-Dimethoxy-N-{3-[5-(2-methoxy-ethyl)-4,5,6,7-tetrahydro-thiazolo[5,4-c]pyridin-2-ylcarbamoyl]-benzyl}-benzamide. Prepared by the method described in Example 25. MS, electrospray 511.4 (M+H).

The following compounds were prepared by the method described in Example 27.

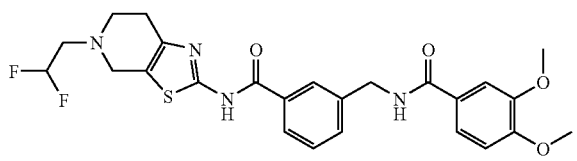

[148] N-{3-[5-(2,2-Difluoro-ethyl)-4,5,6,7-tetrahydro-thiazolo[5,4-c]pyridin-2-ylcarbamoyl]-benzyl}-3,4-dimethoxy-benzamide. MS, electrospray 517.4 (M+H).

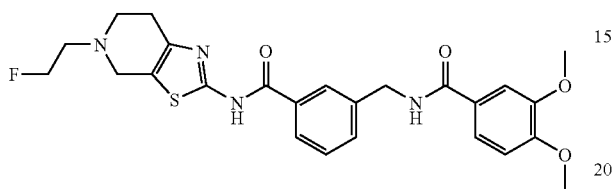

[149] N-{3-[5-(2-Fluoro-ethyl)-4,5,6,7-tetrahydro-thiazolo[5,4-c]pyridin-2-ylcarbamoyl]-benzyl}-3,4-dimethoxy-benzamide. MS, electrospray 499.4 (M+H).

The following compounds were prepared by the methods described in Examples 23 and 24.

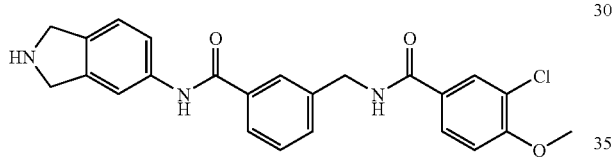

[150] 3-Chloro-N-[3-(2,3-dihydro-1H-isoindol-5-ylcarbamoyl)-benzyl]-4-methoxy-benzamide. MS, electrospray 436.3 (M+H).

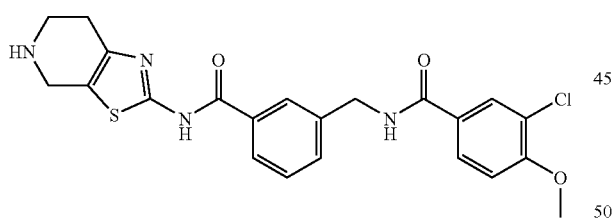

[151] 3-Chloro-4-methoxy-N-[3-(4,5,6,7-tetrahydro-thiazolo[5,4-c]pyridin-2-ylcarbamoyl)-benzyl]-benzamide. MS, electrospray 457.3 (M+H).

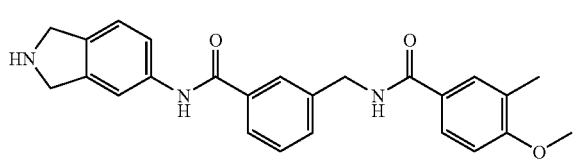

[152] N-[3-(2,3-Dihydro-1H-isoindol-5-ylcarbamoyl)-benzyl]-4-methoxy-3-methyl-benzamide. MS, electrospray 416.3 (M+H).

[153] 4-Methoxy-3-methyl-N-[3-(4,5,6,7-tetrahydro-thiazolo[5,4-c]pyridin-2-ylcarbamoyl)-benzyl]-benzamide. MS, electrospray 437.3 (M+H).

Example 30

N-[3-(5-Dimethylaminomethyl-thiazol-2-ylcarbamoyl)-benzyl]-3,4-dimethoxy-benzamide (154)

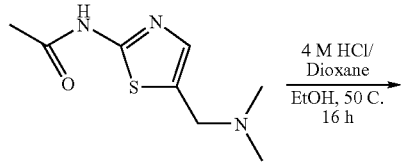

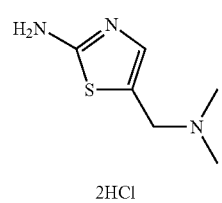

Bubbled dimethyl amine through glacial acetic acid for 1 h. 2-Acetamido thiazole (5.00 g, 35.2 mmol) was dissolved in 8 mL of formalin (37%) and 10 mL of dimethyl amine/AcOH solution was added. The mixture was heated at 100° C. overnight. Added 25 mL of $H_2O$ and the solution was made basic with $K_2CO_3$. Extract with 5×50 mL of $CH_2Cl_2$ and dried with $MgSO_4$. Concentrated the organic phase to a brown residue. Treated residue with 40 mL of EtOH and 2 mL conc. HCl, resulting in a golden brown ppt. Filtered and washed with 2×50 mL of EtOH to give 6.76 g. of N-(5-dimethylaminomethyl-thiazol-2-yl)-acetamide hydrochloride.

Dissolved N-(5-dimethylaminomethyl-thiazol-2-yl)-acetamide hydrochloride (300 mg, 1.27 mmol) in 5 mL of EtOH. Added 2 mL of 4 M HCl in dioxane and heated at 50° C. for 16 h. LC-MS analysis indicated complete acetyl removal. Concentrated to give 5-dimethylaminomethyl-thiazol-2-ylamine dihydrochloride.

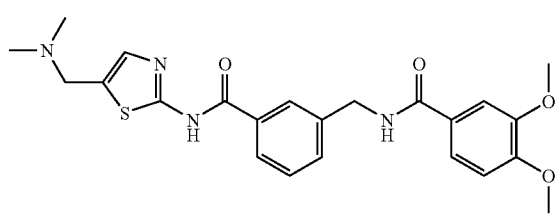

[154] N-[3-(5-Dimethylaminomethyl-thiazol-2-ylcarbamoyl)-benzyl]-3,4-dimethoxy-benzamide. was prepared by the method described in Example 23. MS, electrospray 456 (M+H)

Example 31

4,5,6,7-Tetrahydro-thiazolo[5,4-c]pyridine-2-carboxylic acid {3-[(3,4-dimethoxy-benzoylamino)-methyl]-phenyl}-amide (155)

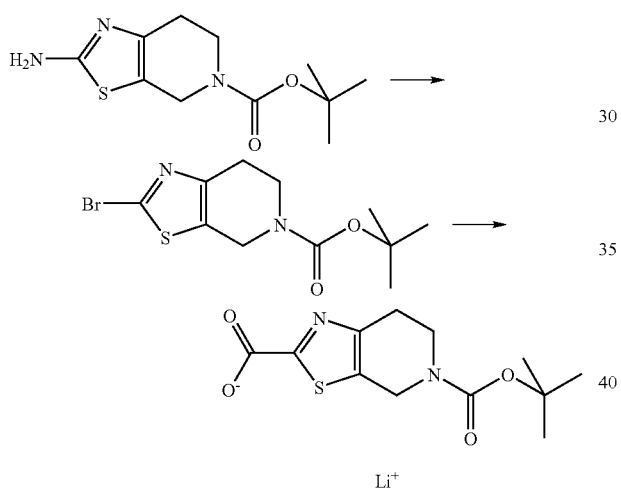

Suspended CuBr$_2$ (905 mg, 4.05 mmol) in 5 mL of DMF and added i-butylnitrite (0.57 mL), 4.86 mmol). To this was added 2-amino-6,7-dihydro-4H-thiazolo[5,4-c]pyridine-5-carboxylic acid tert-butyl ester (860 mg, 3.36 mmol) and the mixture was stirred for 2 h at 60° C. LC-MS analysis indicated the desired bromide. Concentrated the mixture to a brown-red residue. Dissolved the residue in CH$_2$Cl$_2$ and purified via SiO$_2$ chromatography (EtOAc/hexanes 0-20%) to give 650 mg of 2-bromo-6,7-dihydro-4H-thiazolo[5,4-c]pyridine-5-carboxylic acid tert-butyl ester.

Dissolved 2-bromo-6,7-dihydro-4H-thiazolo[5,4-c]pyridine-5-carboxylic acid tert-butyl ester (650 mg, 2.036) in dry THF and the mixture was cooled to −78° C. To this was added n-BuLi in a dropwise fashion. The mixture was stirred for 30 min at 4° C. and then was re-cooled to −78° C. and solid CO$_2$ was added in one portion. The mixture was warmed to room temperature, stirred for 1 h and was concentrated to give 132.5 mg of lithium 5-tert-butoxycarbonyl-4,5,6,7-tetrahydro-thiazolo[5,4-c]pyridine-2-carboxylate.

[155] 4,5,6,7-Tetrahydro-thiazolo[5,4-c]pyridine-2-carboxylic acid {3-[(3,4-dimethoxy-benzoylamino)-methyl]-phenyl}-amide was prepared by the method described in Example 23. MS, electrospray 453 (M+H).

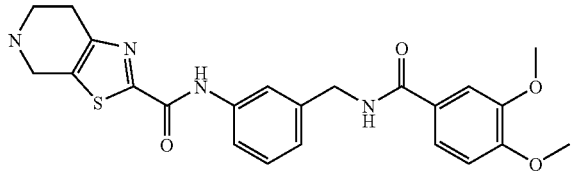

[156] 3,4-Dimethoxy-N-[3-(11-methyl-3-thia-5,11-diazatricyclo[6.2.1.02,6]undeca-2(6),4-dien-4-ylcarbamoyl)-benzyl]-benzamide. Prepared by the method described in Example 23. MS, electrospray 493.5 (M+H).

Example 32

N-[3-(4-Dimethylaminomethyl-thiazol-2-ylcarbamoyl)-benzyl]-3,4-dimethoxy-benzamide (157)

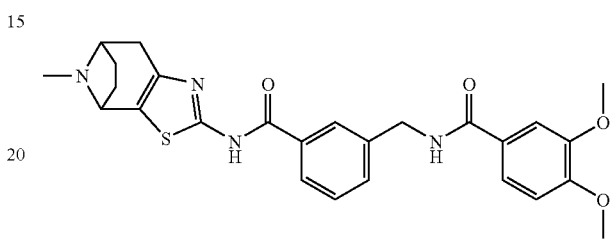

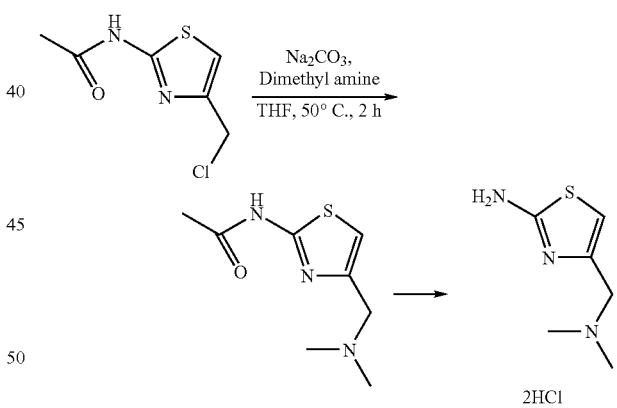

Dissolved N-(4-chloromethyl-thiazol-2-yl)-acetamide (250 mg, 1.31 mmol) in 5 mL of THF. To this was added Na$_2$CO$_3$ (250 mg). Bubbled dimethyl amine in for 15 min. Sealed the flask and heated at 50° C. for 2 h. LC-MS analysis indicated the desired adduct. Filtered the mixture through diatomaceous earth and washed plug with 2×10 mL of THF. Concentrated to dryness to give 274 mg of N-(4-dimethylaminomethyl-thiazol-2-yl)-acetamide.

Dissolved N-(4-dimethylaminomethyl-thiazol-2-yl)-acetamide (274 mg, 1.38 mmol) in 5 mL of EtOH. Added 2 mL of 4 M HCl in dioxane and heated at 50° C. for 16 h. LC-MS analysis indicated complete acetyl removal. Concentrated to give 274 mg of 4-dimethylaminomethyl-thiazol-2-ylamine dihydrochloride.

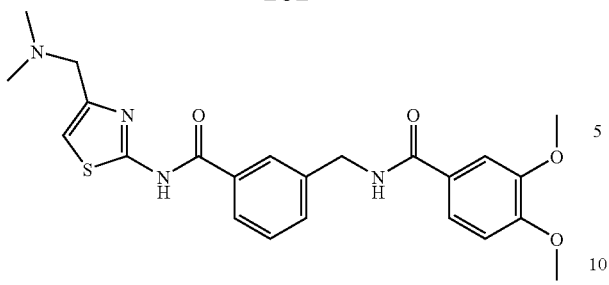

[157] N-[3-(4-Dimethylaminomethyl-thiazol-2-lcarbamoyl)-benzyl]-3,4-dimethoxy-benzamide was prepared by the method described in Example 23. MS, electrospray 455 (M+H)

The following compounds prepared by the method described in Example 23.

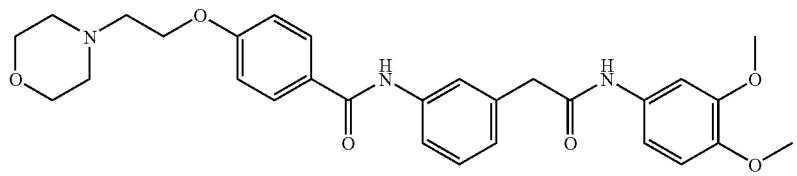

[158] N-{3-[(3,4-Dimethoxy-phenylcarbamoyl)-methyl]-phenyl}-4-(2-morpholin-4-yl-ethoxy)-benzamide. MS, electrospray 520.6 (M+H).

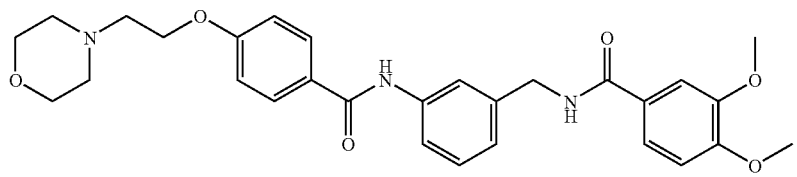

[159] 3,4-Dimethoxy-N-{3-[4-(2-morpholin-4-yl-ethoxy)-benzoylamino]-benzyl}-benzamide. MS, electrospray 520.6 (M+H).

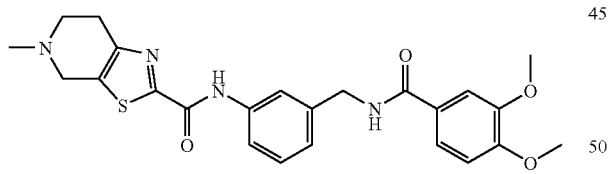

[160] 5-Methyl-4,5,6,7-tetrahydro-thiazolo[5,4-c]pyridine-2-carboxylic acid {3-[(3,4-dimethoxy-benzoylamino)-methyl]-phenyl}-amide. Prepared by the method described in Example 22. MS, electrospray 467.3 (M+H).

The following compounds prepared by the method described in Example 23.

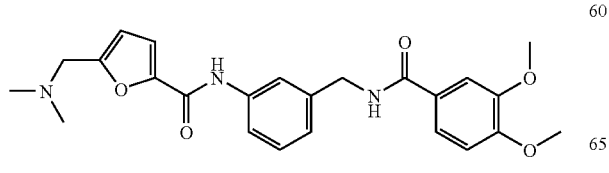

[161] 5-Dimethylaminomethyl-furan-2-carboxylic acid {3-[(3,4-dimethoxy-benzoylamino)-methyl]-phenyl}-amide. MS, electrospray 438.6 (M+H).

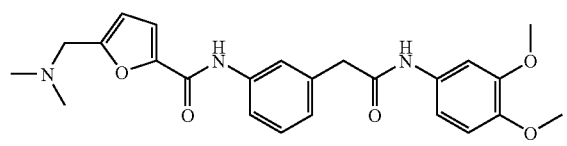

[162] 5-Dimethylaminomethyl-furan-2-carboxylic acid {3-[(3,4-dimethoxy-phenylcarbamoyl)-methyl]-phenyl}-amide. MS, electrospray 438.6 (M+H).

Example 33

N-{3-[4-(2-Amino-ethyl)-thiazol-2-ylcarbamoyl]-benzyl}-3,4-dimethoxy-benzamide (163)

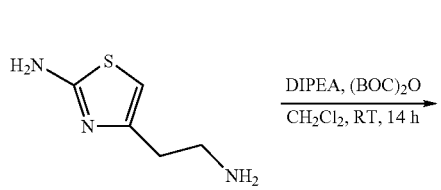

-continued

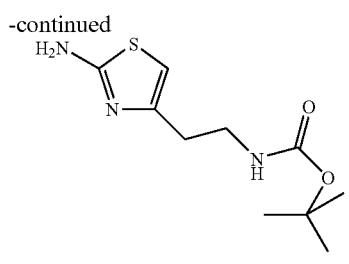

Suspended 4-(2-amino-ethyl)-thiazol-2-ylamine (500 mg, 3.49 mmol) in 10 mL of $CH_2Cl_2$ and DIPEA (0.74 mL. 4.00 mmol) was added. The mixture became homogeneous and BOC anhydride (762 mg, 3.49 mmol) was added. The mixture stirred overnight. LC-MS analysis indicated the desired product along with some over protection. Diluted with 50 mL of EtOAc. Quenched with 20 mL of saturated $NH_4Cl$. Washed with 2×20 mL of $H_2O$ and 1×20 mL of brine. Dried organic phase with $MgSO_4$, filtered and concentrated to obtain 589 mg. $^1H$ NMR indicated mostly the desired [2-(2-Amino-thiazol-4-yl)-ethyl]-carbamic acid tert-butyl ester

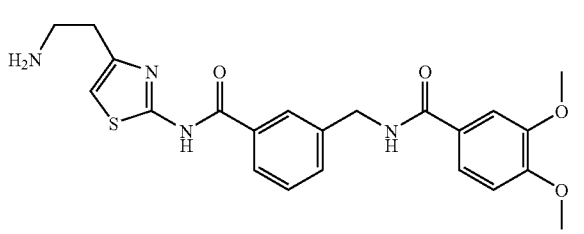

[163] N-{3-[4-(2-Amino-ethyl)-thiazol-2-ylcarbamoyl]-benzyl}-3,4-dimethoxy-benzamide was prepared by the method described in Example 23 and Example 24. MS, electrospray 441.4 (M+H).

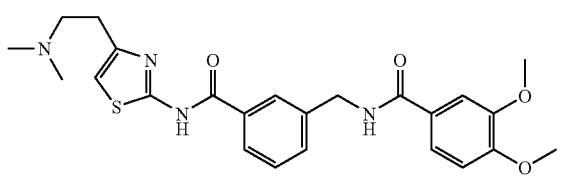

[164] N-{3-[4-(2-Dimethylamino-ethyl)-thiazol-2-ylcarbamoyl]-benzyl}-3,4-dimethoxy-benzamide. Prepared by the method described in Example 22. MS, electrospray 469.5 (M+H)

The following compounds were prepared by the method described in Example 23 and Example 24.

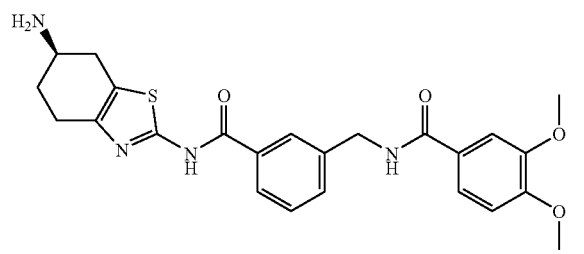

[165] N-[3-((R)-6-Amino-4,5,6,7-tetrahydro-benzothiazol-2-ylcarbamoyl)-benzyl]-3,4-dimethoxy-benzamide. MS, electrospray 467.5 (M+H).

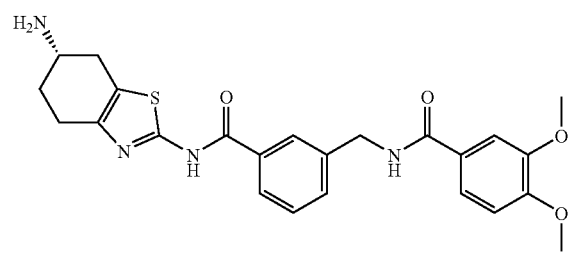

[166] N-[3-((S)-6-Amino-4,5,6,7-tetrahydro-benzothiazol-2-ylcarbamoyl)-benzyl]-3,4-dimethoxy-benzamide. MS, electrospray 467.5 (M+H).

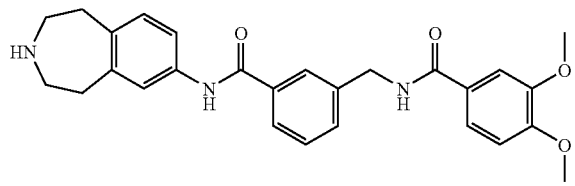

[167] 3,4-Dimethoxy-N-[3-(2,3,4,5-tetrahydro-1H-benzo[d]azepin-7-ylcarbamoyl)-benzyl]-benzamide. MS, electrospray 460.6 (M+H).

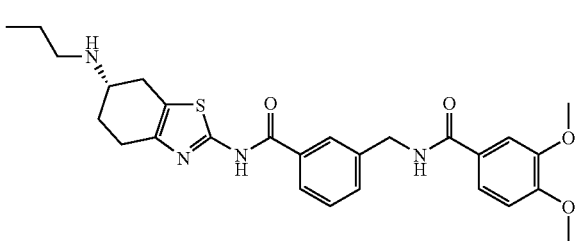

[168] 3,4-Dimethoxy-N-[3-((S)-6-propylamino-4,5,6,7-tetrahydro-benzothiazol-2-ylcarbamoyl)-benzyl]-benzamide. Prepared by the method described in Example 23. MS, electrospray 509.6 (M+H).

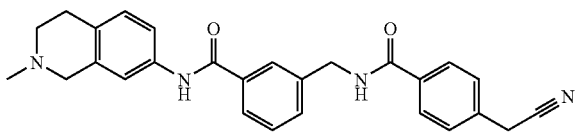

[169] 4-Methylcyano-N-[3-(2-methyl-1,2,3,4-tetrahydro-isoquinolin-7-ylcarbamoyl)-benzyl]-benzamide. Prepared by the method described in Example 28. MS, electrospray 439.5 (M+H).

The following compounds were prepared by the method described in Example 23 and Example 24.

165

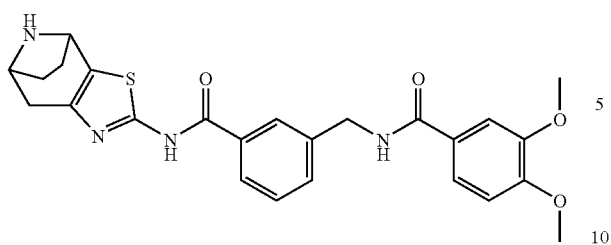

[170] 3,4-Dimethoxy-N-[3-(3-thia-5,11-diaza-tricyclo[6.2.1.02,6]undeca-2(6),4-dien-4-ylcarbamoyl)-benzyl]-benzamide

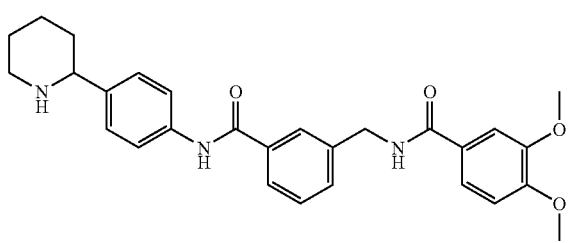

[171] 3,4-Dimethoxy-N-[3-(4-piperidin-2-yl-phenylcarbamoyl)-benzyl]-benzamide. MS, electrospray 474.6 (M+H).

166

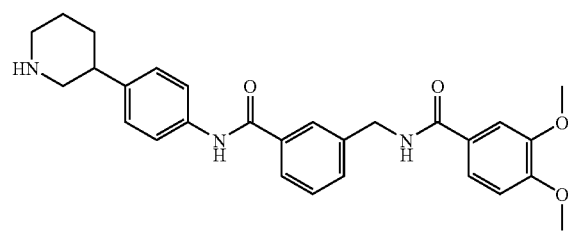

[172] 3,4-Dimethoxy-N-[3-(4-piperidin-2-yl-phenylcarbamoyl)-benzyl]-benzamide. MS, electrospray 474.6 (M+H).

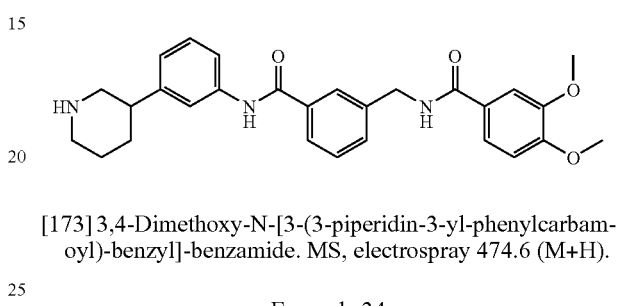

[173] 3,4-Dimethoxy-N-[3-(3-piperidin-3-yl-phenylcarbamoyl)-benzyl]-benzamide. MS, electrospray 474.6 (M+H).

Example 34

N-[3-((R)-6-Amino-4,5,6,7-tetrahydro-benzothiazol-2-ylcarbamoyl)-benzyl]-3-chloro-4-methoxy-benzamide (174)

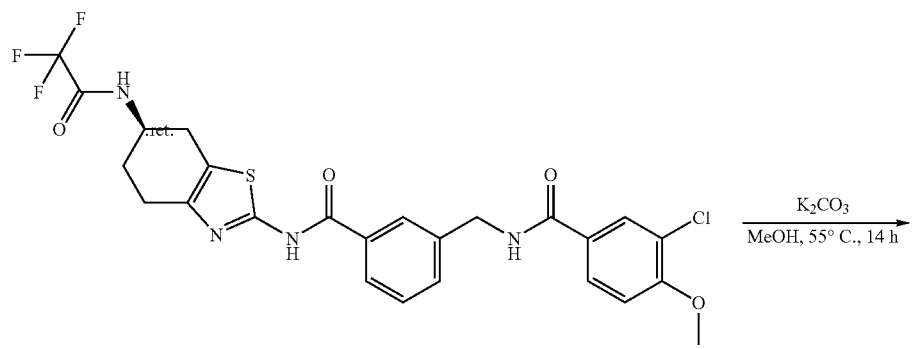

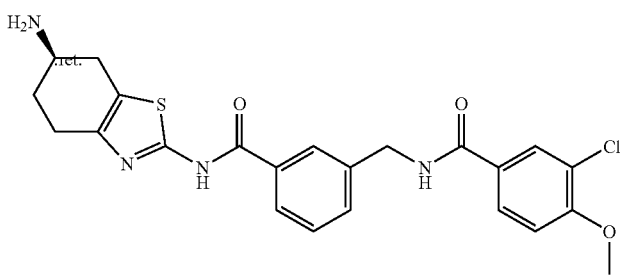

3-Chloro-4-methoxy-N-{3-[(R)-6-(2,2,2-trifluoro-acetylamino)-4,5,6,7-tetrahydro-benzothiazol-2-ylcarbamoyl]-benzyl}-benzamide was prepared by the method described in Example 23.

Dissolved 3-chloro-4-methoxy-N-{3-[(R)-6-(2,2,2-trifluoro-acetylamino)-4,5,6,7-tetrahydro-benzothiazol-2-ylcarbamoyl]-benzyl}-benzamide (520 mg, 0.92 mmol) in 5 mL of MeOH and added 5 mL of H$_2$O. To this was added K$_2$CO$_3$ (500 mg, 3.62 mmol) and the mixture was heated overnight at 55° C. LC-MS analysis indicated the desired material. Dissolved in 5 mL of DMF and purified via prep HPLC (5%-70% CH$_3$CN/H$_2$O) to give 334.6 mg of N-[3-((R)-6-Amino-4,5,6,7-tetrahydro-benzothiazol-2-ylcarbamoyl)-benzyl]-3-chloro-4-methoxy-benzamide. MS, electrospray 471.2 (M+H).

The following compounds were prepared by the method described in Example 23 and Example 34.

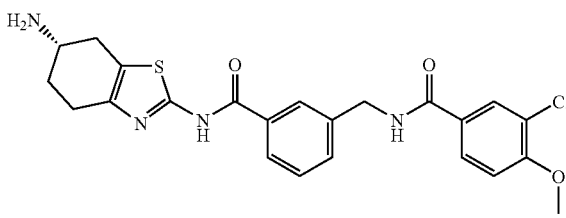

[175] N-[3-((S)-6-Amino-4,5,6,7-tetrahydro-benzothiazol-2-ylcarbamoyl)-benzyl]-3-chloro-4-methoxy-benzamide. MS, electrospray 471.2 (M+H).

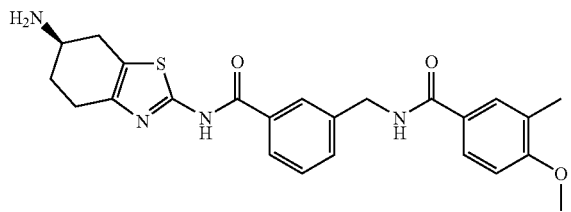

[176] N-[3-((R)-6-Amino-4,5,6,7-tetrahydro-benzothiazol-2-ylcarbamoyl)-benzyl]-4-methoxy-3-methyl-benzamide. MS, electrospray 451.5 (M+H).

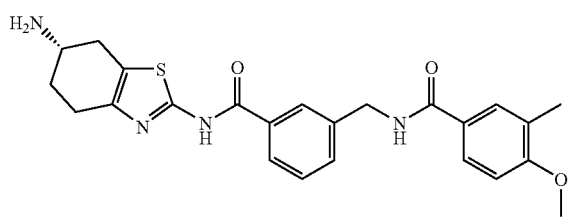

[177] N-[3-((S)-6-Amino-4,5,6,7-tetrahydro-benzothiazol-2-ylcarbamoyl)-benzyl]-4-methoxy-3-methyl-benzamide. MS, electrospray 451.5 (M+H).

The following compounds were prepared by the method described in Example 23

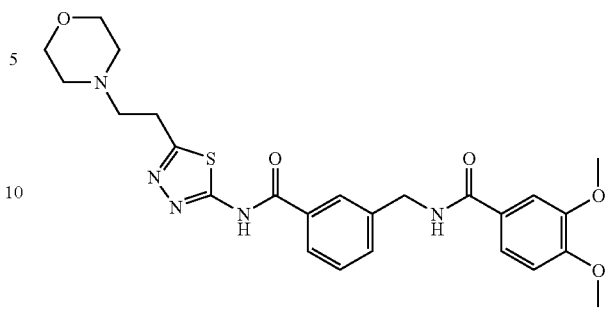

[178] 3,4-Dimethoxy-N-{3-[5-(2-morpholin-4-yl-ethyl)-[1,3,4]thiadiazol-2-ylcarbamoyl]-benzyl}-benzamide. MS, electrospray 512.6 (M+H).

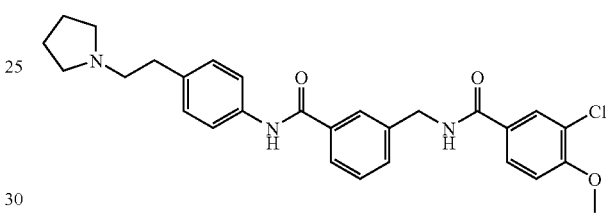

[179] 3-Chloro-4-methoxy-N-{3-[4-(2-pyrrolidin-1-yl-ethyl)-phenylcarbamoyl]-benzyl}-benzamide. MS, electrospray 492.6 (M+H).

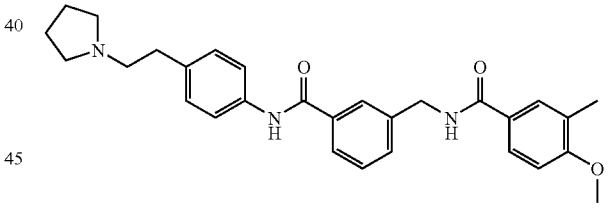

[180] 4-Methoxy-3-methyl-N-{3-[4-(2-pyrrolidin-1-yl-ethyl)-phenylcarbamoyl]-benzyl}-benzamide. MS, electrospray 472.3 (M+H).

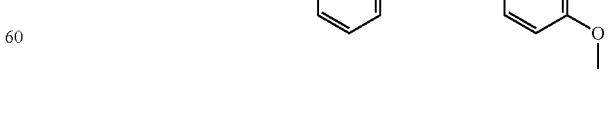

[181] N-[3-((R)-2-Amino-4,5,6,7-tetrahydro-benzothiazol-6-ylcarbamoyl)-benzyl]-4-methoxy-3-methyl-benzamide. MS, electrospray 539.6 (M+H).

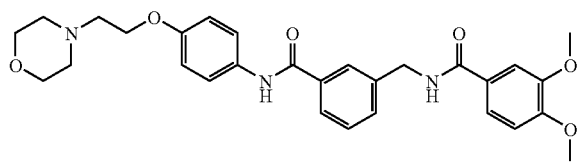

[182] 3,4-Dimethoxy-N-{3-[4-(2-morpholin-4-yl-ethoxy)-phenylcarbamoyl]-benzyl}-benzamide. MS, electrospray 520.7 (M+H).

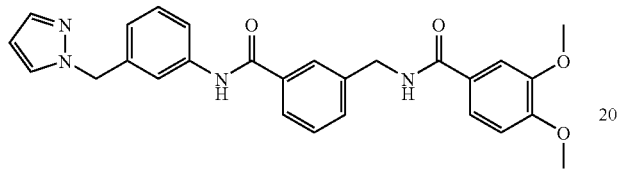

[183] 3,4-Dimethoxy-N-[3-(3-pyrazol-1-ylmethyl-phenylcarbamoyl)-benzyl]-benzamide. MS, electrospray 471.6 (M+H).

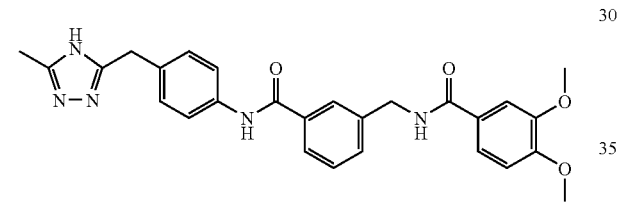

[184] 3,4-Dimethoxy-N-{3-[4-(5-methyl-4H-[1,2,4]triazol-3-ylmethyl)-phenylcarbamoyl]-benzyl}-benzamide. MS, electrospray 486.6 (M+H).

The following compounds were prepared by the method described in Example 22.

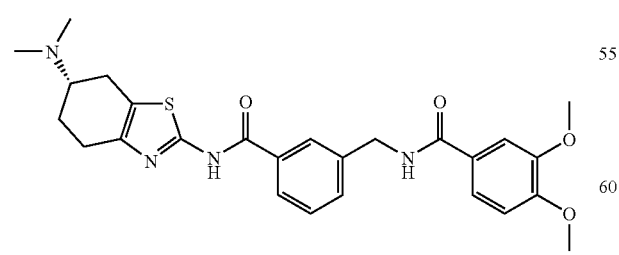

[185] N-[3-((S)-6-Dimethylamino-4,5,6,7-tetrahydro-benzothiazol-2-ylcarbamoyl)-benzyl]-3,4-dimethoxy-benzamide. MS, electrospray 495.6 (M+H).

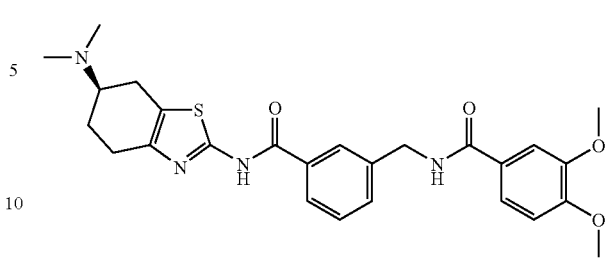

[186] N-[3-((R)-6-Dimethylamino-4,5,6,7-tetrahydro-benzothiazol-2-ylcarbamoyl)-benzyl]-3,4-dimethoxy-benzamide. MS, electrospray 495.6 (M+H).

Example 35

3,4-Dimethoxy-N-[3-((S)-6-morpholin-4-yl-4,5,6,7-tetrahydro-benzothiazol-2-ylcarbamoyl)-benzyl]-benzamide (187)

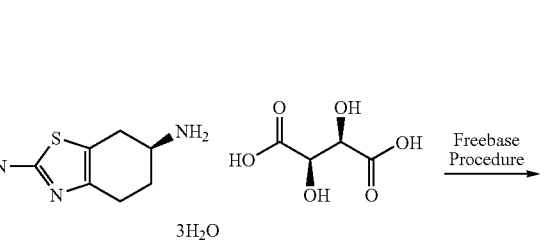

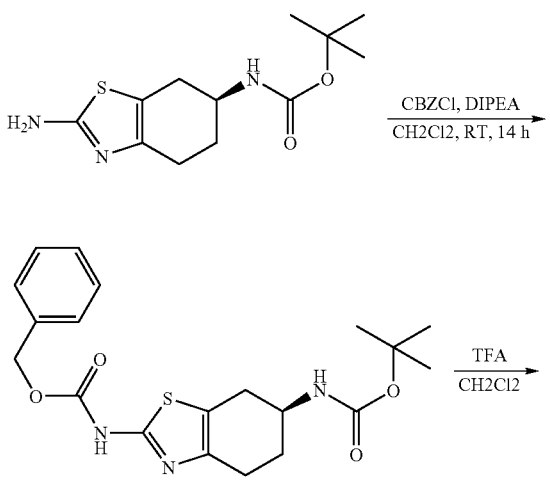

-continued

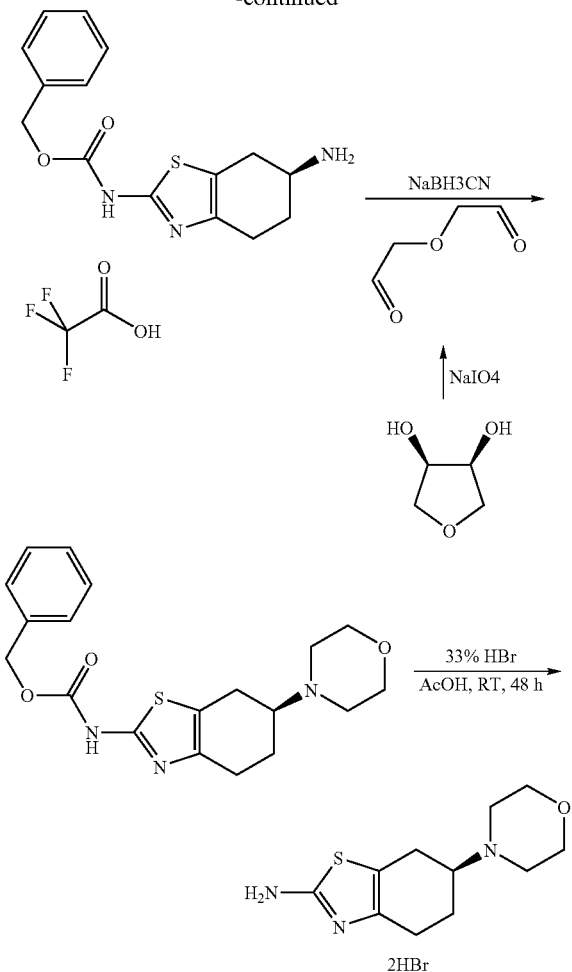

Dissolved (S)-4,5,6,7-tetrahydro-benzothiazole-2,6-diamine tartrate trihydrate (80.0 g, 214.25 mmol) in 50 mL of 2 M HCl, giving a dark gray solution. To this was added decolorizing charcoal (20 g). The mixture stirred for 30 min. Filtered the mixture and washed with 20 mL H₂O. The filtrate was heated at 50° C. with stirring. Solid NaOH was added slowly until the pH was basic. Cooling to room temperature followed by refrigeration for 2 h gave a white ppt. Filtered the white ppt and placed it in a vacuum drying oven overnight at 40° C. Collected the material giving 25.19 g of (S)-4,5,6,7-tetrahydro-benzothiazole-2,6-diamine. ¹H NMR showed pure freebase.

Suspended (S)-4,5,6,7-tetrahydro-benzothiazole-2,6-diamine (20.0 g, 118.2 mmol) in 200 mL of CH₂Cl₂ and DIPEA (36.9 mL, 200.0 mmol) was added. The mixture remained heterogeneous and BOC-ON (29.2 g, 118.7 mmol) was added. The mixture stirred overnight. LC-MS analysis indicated the desired product along with one major DAD peaks. Diluted with 200 mL CH₂Cl₂. Quenched with 100 mL of saturated NH₄Cl. Washed with 2×100 mL of H₂O and 1×100 mL of brine. Dried organic phase with MgSO₄, filtered and concentrated. Applied to a SiO₂ column and purified (50% EtOAC/hexanes then 0-5% MeOH/CH₂Cl₂) to give mixed fractions and pure product. Repurified the mixed fractions to give 32.6 ((S)-2-Amino-4,5,6,7-tetrahydro-benzothiazol-6-yl)-carbamic acid tert-butyl ester.

Dissolved ((S)-2-Amino-4,5,6,7-tetrahydro-benzothiazol-6-yl)-carbamic acid tert-butyl ester (32.6 g, 121.02 mmol) in 300 mL of CH₂Cl₂. To this was added DIPEA (41.8 mL, 240 mmol). The mixture was cooled to 4° C. To this was added the benzyl chloroformate (17.8 mL, 125 mmol). The mixture stirred overnight. TLC analysis indicated some starting material remaining. Added 0.3 eq more of chloroformate and 0.3 eq. more of DIPEA. Stirred for 4 h. TLC indicated remaining starting material Quenched with 200 mL of saturated NH₄Cl. Washed with 2×200 mL of H₂O, 200 mL of Na₂CO₃ and 1×200 mL of brine. Dried organic phase with MgSO₄, filtered and concentrated. Applied to a SiO₂ column and purified (5:5 CH₂Cl₂/hexanes to 9:1 CH₂Cl₂/MeOH) to give two main fractions. ¹H NMR analysis indicated that both fractions were acceptable and they were combined to give 44.5 g of ((S)-6-tert-butoxycarbonylamino-4,5,6,7-tetrahydro-benzothiazol-2-yl)-carbamic acid benzyl ester. 3.06 g of S.M recovered 9%.

Dissolved ((S)-6-tert-butoxycarbonylamino-4,5,6,7-tetrahydro-benzothiazol-2-yl)-carbamic acid benzyl ester in 20 mL of CH₂Cl₂. Added 20 mL of TFA. Stirred for 1 h. LC-MS analysis indicated complete deprotection of BOC group. Concentrated to give 46.0 g of ((S)-6-amino-4,5,6,7-tetrahydro-benzothiazol-2-yl)-carbamic acid benzyl ester trifluoroacetate as pale yellow solid.

Dissolved sodium periodate (47.1 g, 220 mmol) in 400 mL of H₂O. The mixture was placed in an ice bath at 4° C. and (3S,4R)-tetrahydro-furan-3,4-diol (18.4 mL, 224.5 mmol) was added. Over a period of a few minutes, a thick white ppt. formed. The mixture stirred for 20 h. Added 200 mL of CH₃CN. The mixture was filtered and the ppt. rinsed with 200 mL of CH₃CN. The filtrate containing (2-oxo-ethoxy)-acetaldehyde was used directly in the next reaction.

Dissolved ((S)-6-amino-4,5,6,7-tetrahydro-benzothiazol-2-yl)-carbamic acid benzyl ester trifluoroacetate (10.0 g, 23.9 mmol) in crude dialdehyde solution. The mixture stirred for 30 min. To this was added NaBH₃CN (18.8 g, 299.16 mmol). The mixture was sealed and stirred for 36 h. LC-MS analysis indicated the desired morpholine product. Filtered the heterogeneous mixture and concentrated the filtrate. Dissolved residue in 5% HCl/MeOH and passed through pre-rinsed 50×2-200 Dowex acidic ion exchange resin. The column was rinsed with 1×150 mL of 5% HCl, 2×150 mL H₂O, 2×125 mL of MeOH. The compound was liberated with 4×150 mL elutions of 10% NH₄OH/MeOH and concentrated.

Dissolved ppt. from initial reaction. in 5% HCl/MeOH and passed through Dowex acidic ion exchange resin. The column was rinsed with 1×150 mL of 5% HCl, 2×150 mL H₂O, 2×125 mL of MeOH. The compound was liberated with 4×150 mL elutions of 10% NH₄OH/MeOH. Concentrated with previous batch to give 4.62 g. Observed white residue ion exchange medium. Rinsed with 4×100 mL of CH₂Cl₂ to give an additional 3.4 g. Combined to give 8.02 g of ((S)-6-morpholin-4-yl-4,5,6,7-tetrahydro-benzothiazol-2-yl)-carbamic acid benzyl ester.

Dissolved ((S)-6-morpholin-4-yl-4,5,6,7-tetrahydro-benzothiazol-2-yl)-carbamic acid benzyl ester (7.46 g, 20.00 mmol) in 25 mL of 33% HBr/AcOH. Stirred mixture for 48 h. LC-MS indicated complete deprotection. Added 200 mL of Et₂O resulting in a pale orange ppt. Filtered to give 7.46 mg of (S)-6-Morpholin-4-yl-4,5,6,7-tetrahydro-benzothiazol-2-ylaminedihydrobromide a light brown solid.

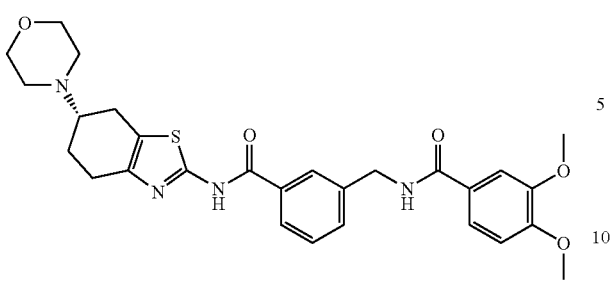

[187] 3,4-Dimethoxy-N-[3-((S)-6-morpholin-4-yl-4,5,6,7-tetrahydro-benzothiazol-2-ylcarbamoyl)-benzyl]-benzamide. Prepared by the method described in Example 23. MS, electrospray 537.6 (M+H).

Example 36

3,4-Dimethoxy-N-[3-((R)-6-morpholin-4-yl-4,5,6,7-tetrahydro-benzothiazol-2-ylcarbamoyl)-benzyl]-benzamide (188)

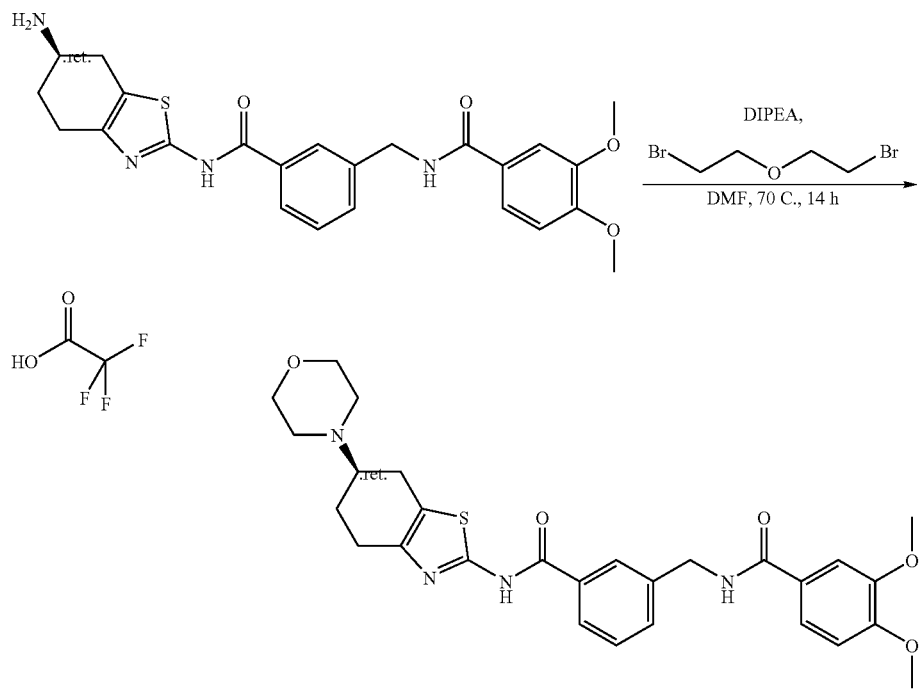

Dissolved N-[3-((R)-6-Amino-4,5,6,7-tetrahydro-benzothiazol-2-ylcarbamoyl)-benzyl]-3,4-dimethoxy-benzamide trifluoroacetate (50.0 mg, 0.09 mmol) in 1.5 mL of dry DMF. To this was added DIPEA (0.05 mL, 0.26 mmol) and the 1-bromo-2-(2-bromo-ethoxy)-ethane (0.02 mL, 0.12 mmol). The mixture was heated at 70° C. overnight. LC-MS analysis indicted the desired material. Dissolved in 5 mL of DMF and purified via prep HPLC (5%-95% CH$_3$CN/H$_2$O) to give the desired product with one major impurity. Applied to a SiO2 prep plate. Eluted with (10% MeOH/1% NH$_3$/CH$_2$Cl$_2$) to give 18.9 mg of N-[3-((R)-6-Amino-4,5,6,7-tetrahydro-benzothiazol-2-ylcarbamoyl)-benzyl]-3,4-dimethoxy-benzamide. MS, electrospray 537.6 (M+H).

The following compounds were prepared by the methods described in Example 23 and Example 34.

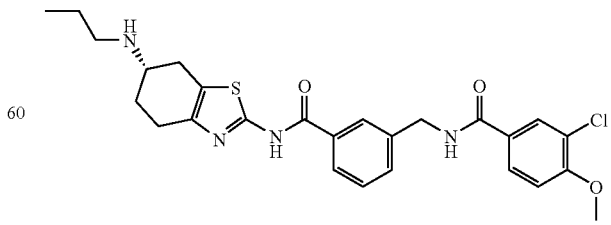

[189] 3-Chloro-4-methoxy-N-[3-((S)-6-propylamino-4,5,6,7-tetrahydro-benzothiazol-2-ylcarbamoyl)-benzyl]-benzamide. MS, electrospray 513.2 (M+H).

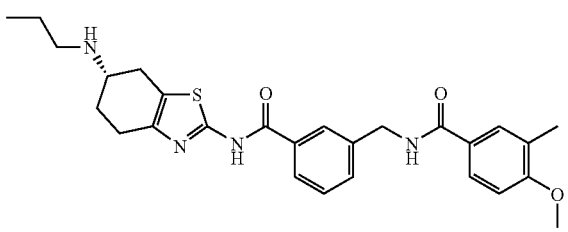

[190] 4-Methoxy-3-methyl-N-[3-((S)-6-propylamino-4,5,6,7-tetrahydro-benzothiazol-2-ylcarbamoyl)-benzyl]-benzamide. MS, electrospray 493.3 (M+H).

The following compounds were prepared by the method described in Example 22.

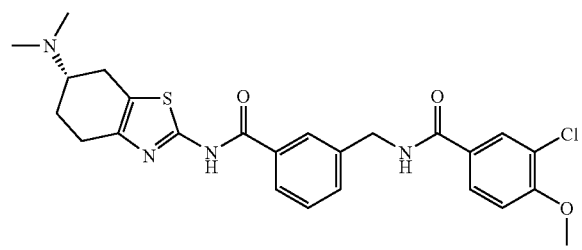

[191] 3-Chloro-N-[3-((S)-6-dimethylamino-4,5,6,7-tetrahydro-benzothiazol-2-ylcarbamoyl)-benzyl]-4-methoxy-benzamide. MS, electrospray 499.9 (M+H).

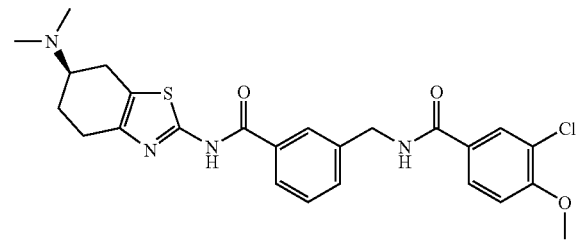

[192] 3-Chloro-N-[3-((R)-6-dimethylamino-4,5,6,7-tetrahydro-benzothiazol-2-ylcarbamoyl)-benzyl]-4-methoxy-benzamide. MS, electrospray 499.9 (M+H).

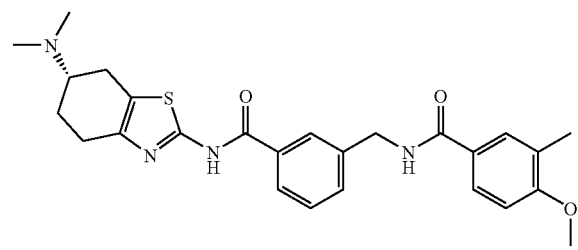

[193] N-[3-((S)-6-Dimethylamino-4,5,6,7-tetrahydro-benzothiazol-2-ylcarbamoyl)-benzyl]-4-methoxy-3-methyl-benzamide. MS, electrospray 480.0 (M+H).

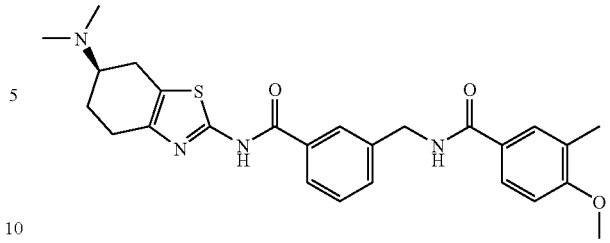

[194] N-[3-((R)-6-Dimethylamino-4,5,6,7-tetrahydro-benzothiazol-2-ylcarbamoyl)-benzyl]-4-methoxy-3-methyl-benzamide. MS, electrospray 480.0 (M+H).

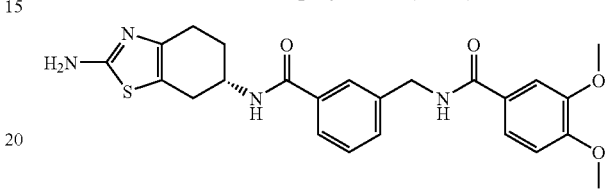

[195] N-[3-((S)-2-Amino-4,5,6,7-tetrahydro-benzothiazol-6-ylcarbamoyl)-benzyl]-3,4-dimethoxy-benzamide. Prepared by the method described in Example 23. MS, electrospray 467.8 (M+H).

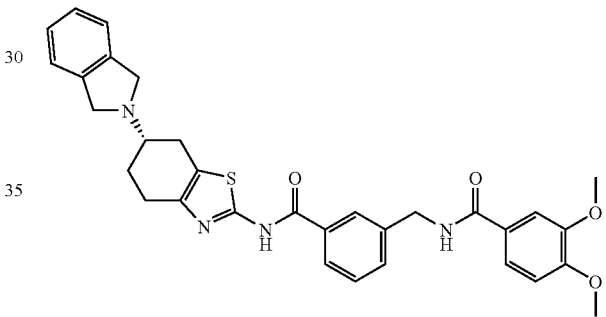

[196] N-{3-[(S)-6-(1,3-Dihydro-isoindol-2-yl)-4,5,6,7-tetrahydro-benzothiazol-2-ylcarbamoyl]-benzyl}-3,4-dimethoxy-benzamide Prepared by the method described in Example 36. MS, electrospray 570.1 (M+H).

Example 37

N-{3-[(S)-6-(1,1-Dioxo-1□6-thiomorpholin-4-yl)-4,5,6,7-tetrahydro-benzothiazol-2-ylcarbamoyl]-benzyl}-3,4-dimethoxy-benzamide (197)

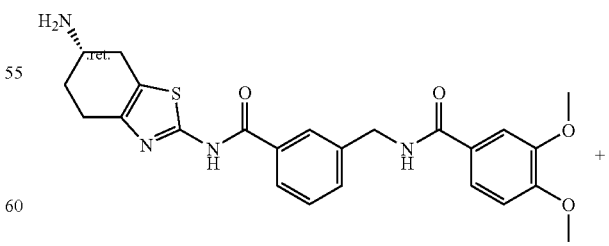

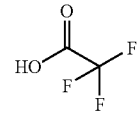

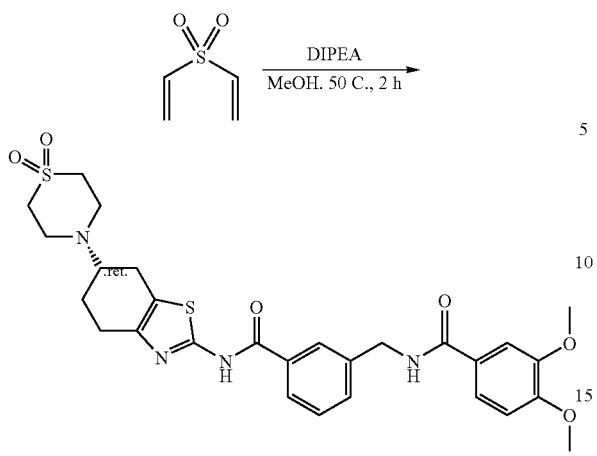

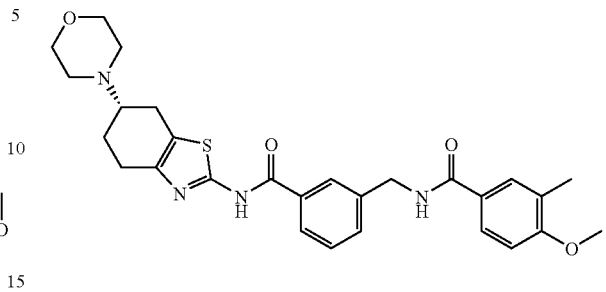

[199] 3-Chloro-4-methoxy-N-[3-((S)-6-morpholin-4-yl-4,5,6,7-tetrahydro-benzothiazol-2-ylcarbamoyl)-benzyl]-benzamide. MS, electrospray 541.4 (M+H).

Dissolved N-[3-((R)-6-Amino-4,5,6,7-tetrahydro-benzothiazol-2-ylcarbamoyl)-benzyl]-3,4-dimethoxy-benzamide trifluoroacetate (135.0 mg, 0.23 mmol) in dry 2 mL of MeOH. To this was added DIPEA (0.46 mL, 0.25 mmol) and divinyl sulfone (0.03 mL, 0.25 mmol). The mixture was heated at 50° C. for 1 h. LC-MS analysis indicated only partial cyclization. Heated the mixture an additional hour. LC-MS indicated remaining starting material. Added another equivalent of vinyl sulfone. After 1 h at 50° C., the reaction was almost complete. LC-MS for another hour indicated complete conversion. Dissolved in 5 mL of DMF and purified via Prep HPLC (5%-95% CH₃CN/H₂O) to give 84.1 mg of N-{3-[(S)-6-(1,1-Dioxo-1☐6-thiomorpholin-4-yl)-4,5,6,7-tetrahydro-benzothiazol-2-ylcarbamoyl]-benzyl}-3,4-dimethoxy-benzamide. MS, electrospray 560.0 (M+H).

[200] 4-Methoxy-3-methyl-N-[3-((S)-6-morpholin-4-yl-4,5,6,7-tetrahydro-benzothiazol-2-ylcarbamoyl)-benzyl]-benzamide. MS, electrospray 521.6 (M+H).

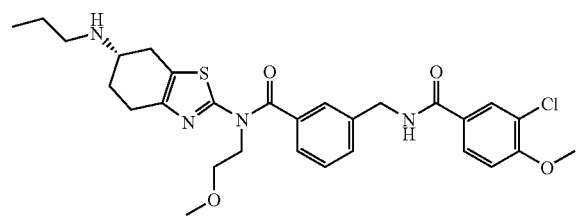

[201] 3-Chloro-4-methoxy-N-{3-[(2-methoxy-ethyl)-((S)-6-propylamino-4,5,6,7-tetrahydro-benzothiazol-2-yl)-carbamoyl]-benzyl}-benzamide. Prepared by the method described in Example 25. MS, electrospray 571.5 (M+H).

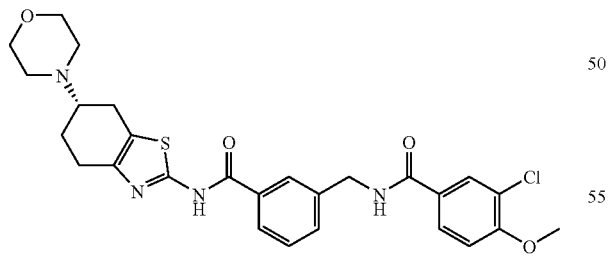

[198] N-[3-(2-Amino-indan-5-ylcarbamoyl)-benzyl]-3,4-dimethoxy-benzamide. Prepared by the methods described in Example 23 and Example 24. MS, electrospray 446.8 (M+H).

The following compounds were prepared by the method described in Example 23.

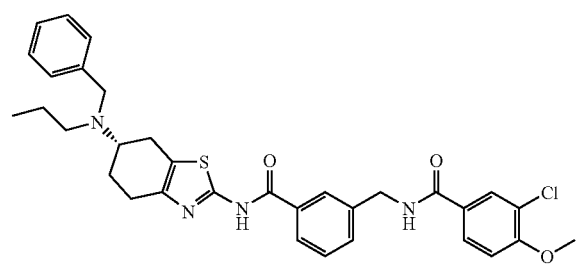

[202] N-{3-[(S)-6-(Benzyl-propyl-amino)-4,5,6,7-tetrahydro-benzothiazol-2-ylcarbamoyl]-benzyl}-3-chloro-4-methoxy-benzamide. Prepared by the method described in Example 22. MS, electrospray 571.5 (M+H).

Example 38

Synthesis of 3,4-Dimethoxy-N-{3-[5-(2-morpholin-4-yl-ethyl)-thiazol-2-ylcarbamoyl]-benzyl}-benzamide (203)

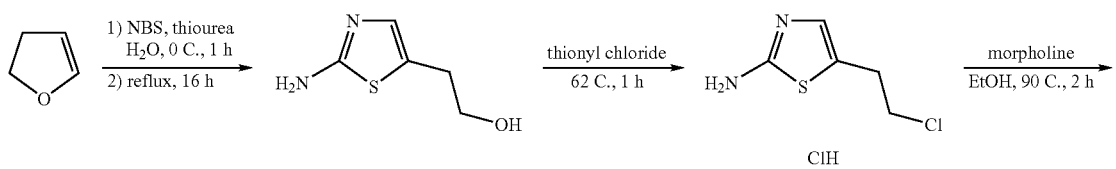

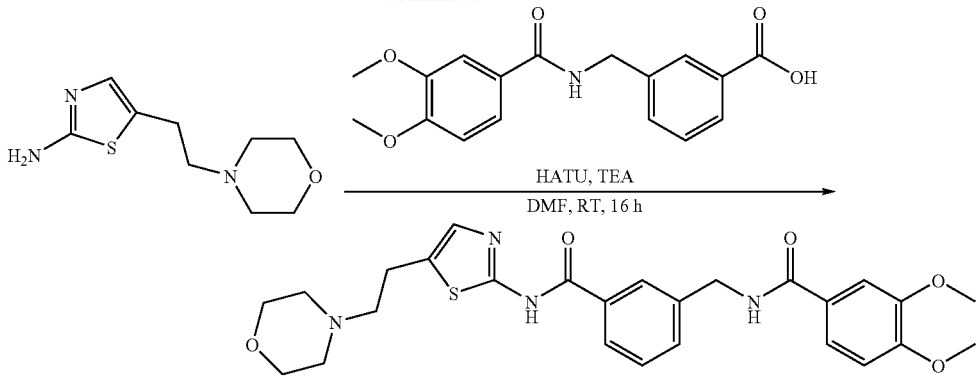

To an ice cold suspension of NBS (1.182 g, 6.72 mmol) in water (8 mL) was added 2,3-dihyofuran (0.75 mL, 9.92 mmol) slowly. The resulting solution was stirred at 0° C. for 1 h, followed by addition of thiourea (0.505 g, 6.63 mmol). The mixture was heated under reflux under nitrogen atmosphere overnight to form a yellow clear solution. The mixture was extracted with EtOAc (3×5 mL) and the aqueous solution was treated with ammonium hydroxide to pH 12. The solution was extracted with $CH_2Cl_2$ (2×5 mL), followed by extraction with EtOAc (8×10 mL). The $CH_2Cl_2$ layer contains small amount of product and large amount of impurities, which was discarded. The EtOAc layers were combined, dried, and concentrated to give 1.123 g 2-(2-amino-thiazol-5-yl)-ethanol To a suspension of 2-(2-amino-thiazol-5-yl)-ethanol (0.844 g, 5.853 mmol) was added thionyl chloride (3 mL). The mixture was heated at 62° C. for 1 h. The volatiles were removed under reduced vacuum. The residue was co-evaporated with toluene (3×5 mL) to give 0.963 g of 5-(2-chloroethyl)-thiazol-2-ylamine crude 5-(2-chlorothyl)-2-thiazolamine monohydrochloride as brown oil.

To a solution of above intermediate (402 mg, 2.47 mmol) in ethanol (10 mL) was added morpholine (2.153 g, 24.7 mmol). The mixture was heated at 90° C. for 2 h. The reaction mixture was concentrated and purified by column chromatography (10% methanol in $CH_2Cl_2$) to give 371 mg of 5-(2-morpholin-4-yl-ethyl)-thiazol-2-ylamine as a yellow oil.

To a solution of 3-[(3,4-dimethoxy-benzoylamino)-methyl]-benzoic acid (211 mg, 0.67 mmol) in DMF (2 mL) was added HATU (356 mg, 0.94 mmol) and TEA (203 mg, 2 mmol). The mixture was stirred at room temperature for 20 minutes, followed by addition of above intermediate (157 mg, 0.74 mmol). After stirring at room temperature overnight, the mixture was diluted with water (6 mL), extracted with EtOAc (3×4 mL). The organic layers were combined, dried and concentrated. The residue was purified by column chromatography to give 112 mg of 3,4-dimethoxy-N-{3-[5-(2-morpholin-4-yl-ethyl)-thiazol-2-ylcarbamoyl]-benzyl}-benzamide as a yellow oil. MS, electrospray, 511 (M+H)

Example 39

3,4-Dimethoxy-N-[3-(4-morpholin-4-ylmethyl-thiazol-2-ylcarbamoyl)-benzyl]-benzamide (204)

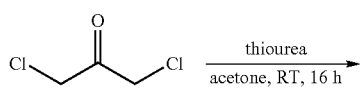

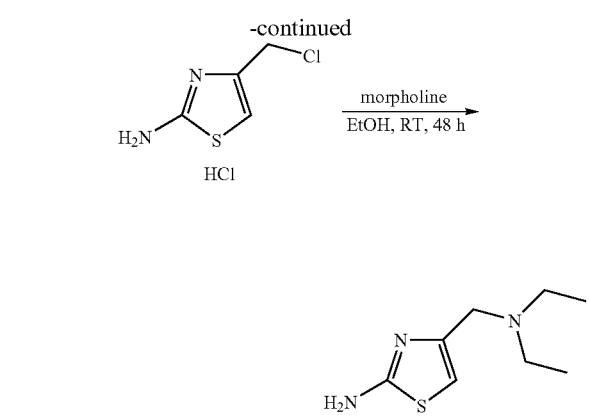

A solution of 1,3-dichloroacetone (917 mg, 7.23 mmol) in acetone (6 mL) was added a solution of thiourea (550 mg, 7.23 mmol) in acetone (30 mL) at a fairly fast speed. The mixture was stirred at room temperature overnight. The formed solid was filtered and the filtrate was concentrated to give 524 mg of (2-amino-thiazol-4-yl)-methanol monohydrochloride as colorless oil.

The above intermediate (491 mg, 2.65 mmol) was dissolved in ethanol (10 mL) followed by addition of morpholine (1.155 g, 13.3 mmol). The mixture was stirred at room temperature for 48 h. The ethanol was removed and the residue was dissolved in EtOAc. The formed solid was filtered. The filtrate was concentrated and the residue crystallized in solvent of $CH_2Cl_2$/methanol(10:1) to give 487 mg of 4-morpholin-4-ylmethyl-thiazol-2-ylamine as light yellow crystals.

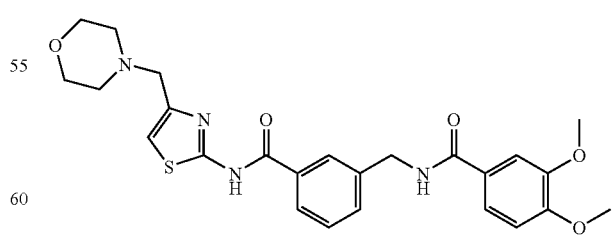

[204] 3,4-Dimethoxy-N-[3-(4-morpholin-4-ylmethyl-thiazol-2-ylcarbamoyl)-benzyl]-benzamide. Prepared by the method described in Example 39. MS, electrospray, 497 (M+H)

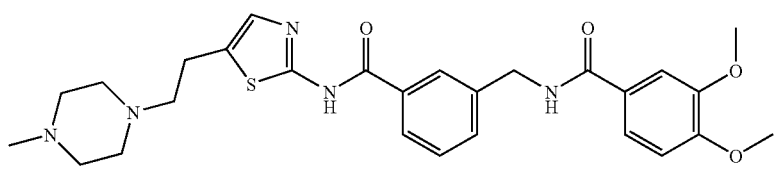

[205] 3,4-Dimethoxy-N-(3-{5-[2-(4-methyl-piperazin-1-yl)-ethyl]-thiazol-2-yl carbamoyl}-benzyl)-benzamide. Prepared by the method described in Example 38. MS, electrospray, 524 (M+H)

Example 40

2-Bromo-4,5-dimethoxy-N-[3-(2-methyl-1,2,3,4-tetrahydro-isoquinolin-7-ylcarbamoyl)-benzyl]-benzamide (206)

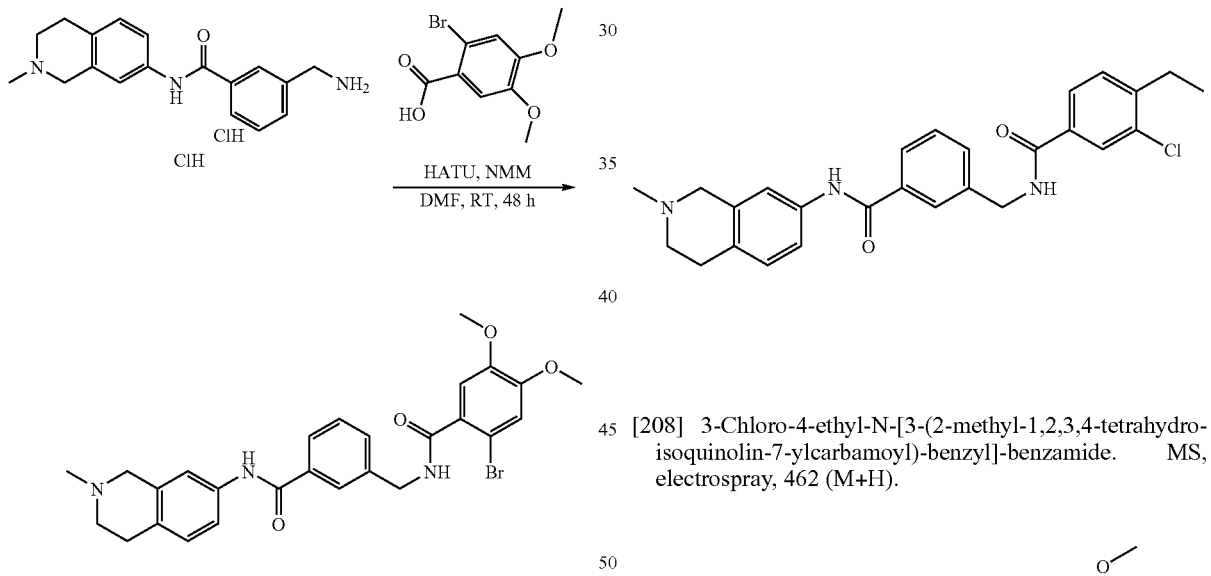

Dissolved 3-(2-methyl-1,2,3,4-tetrahydro-isoquinolin-7-ylcarbamoyl)benzylamine dihydrochloride (36.8 mg, 0.10 mmol) in DMF (1.0 mL) and added 4-methylmorpholine (0.044 mL, 0.4 mmol). Dissolved HATU (57.0 mg, 0.15 mmol) in 1.0 mL DMF and added to the 2-bromo-4,5-dimethoxybenzoic acid (25.5 mg, 0.12 mmol) and stirred to dissolve. Added the amine to the 2-bromo-4,5-dimethoxybenzoic acid solution and shook at room temperature 48 hours. The solvent was removed under reduced pressure. The residue was dissolved in 10% water/DMSO (900 uL). Purified by prep HPLC to give 22.0 mg of 2-bromo-4,5-dimethoxy-N-[3-(2-methyl-1,2,3,4-tetrahydro-isoquinolin-7-ylcarbamoyl)-benzyl]-benzamide. MS, electrospray, 538 (M+H).

The following compounds were prepared by the method described in Example 40.

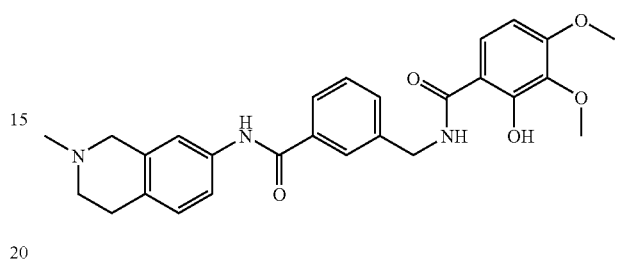

[207] 2-Hydroxy-3,4-dimethoxy-N-[3-(2-methyl-1,2,3,4-tetrahydro-isoquinolin-7-ylcarbamoyl)-benzyl]-benzamide. MS, electrospray, 476 (M+H).

[208] 3-Chloro-4-ethyl-N-[3-(2-methyl-1,2,3,4-tetrahydro-isoquinolin-7-ylcarbamoyl)-benzyl]-benzamide. MS, electrospray, 462 (M+H).

[209] 2,4,5-trimethoxy-N-[3-(2-methyl-1,2,3,4-tetrahydro-isoquinolin-7-ylcarbamoyl)-benzyl]-benzamide. MS, electrospray, 490 (M+H).

Example 41

3-[1-Benzyl-3-(4-cyano-phenyl)-ureidomethyl]-N-(5-methyl-4,5,6,7-tetrahydro-thiazolo[5,4-c]pyridin-2-yl)-benzamide (210)

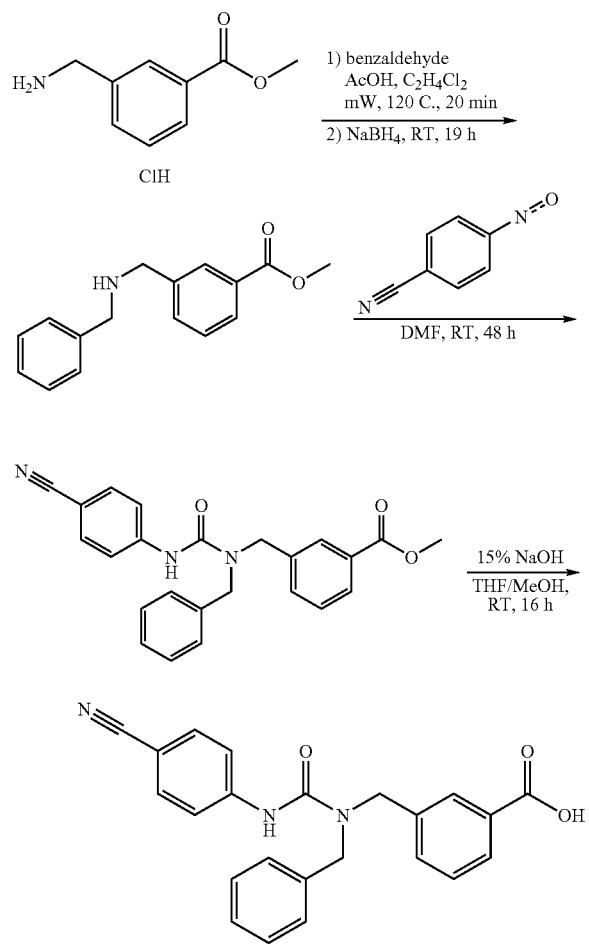

Suspended 3-aminomethyl-benzoic acid methyl ester hydrochloride (100 mg. 0.99 mmol) in 3 mL of dichloroethane in a microwave tube and added 100 uL of AcOH. To this was added benzaldehyde (0.10 mL, 1.00 mmol). The mixture was sealed and heated at 120° C. for 20 minutes resulting in a homogeneous solution. 2 mL of MeOH was added and the mixture was treated with NaBH$_4$ (56.8 mg, 1.50 mmol) resulting in gas evolution. The mixture stirred for 19 h. The mixture was quenched with careful addition of 5% HCl resulting in a bi-phasic mixture. The aqueous phase was removed and treated with 50×2-200 Dowex acidic ion exchange resin. The product was liberated with 10% NH$_3$ in MeOH and concentrated to give 197 mg of 3-(benzylamino-methyl)-benzoic acid methyl ester, partially contaminated with starting benzyl amine (15%).

Dissolved 3-(benzylamino-methyl)-benzoic acid methyl ester (197 mg, 0.77 mmol) in 5 mL of DMF. To this was added 4-cyanophenyl isocyanate (112 mg, 0.78 mmol). The mixture stirred for 48. LC-MS analysis indicated the desired urea. The mixture was diluted with 100 mL EtOAc, washed with 3×50 mL of H$_2$O and 1×20 mL of brine. The organic phase was dried with MgSO$_4$, filtered and concentrated. The resulting residue was applied to a SiO$_2$ prep plate and eluted with 50% EtOAc/hexanes to give two fractions-one clear band and a tail. LC-MS analysis indicated both band and tail were composed of the product. Both fractions were combined to give 105.7 mg of 3-[1-benzyl-3-(4-cyano-phenyl)-ureidomethyl]-benzoic acid methyl ester.

Dissolved to 3-[1-benzyl-3-(4-cyano-phenyl)-ureidomethyl]-benzoic acid methyl ester (106 mg, 0.27 mmol) in 1:1 mixture of THF/MeOH (4 mL). To this was added a 15% NaOH solution and the mixture stirred overnight at room temperature. LC-MS analysis indicated the desired carboxylic acid. Concentrated the mixture and the residue was suspended in 5 mL of H$_2$O and made acidic by the addition of 5% HCl, resulting in a white ppt., which was filtered and dried to give 101.6 mg of 3-[1-benzyl-3-(4-cyano-phenyl)-ureidomethyl]-benzoic acid.

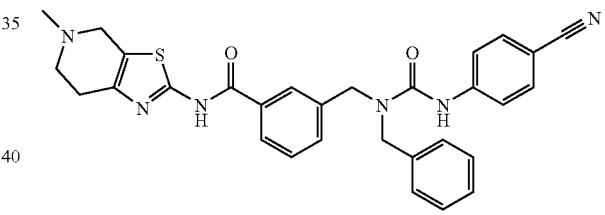

[210] 3-[1-Benzyl-3-(4-cyano-phenyl)-ureidomethyl]-N-(5-methyl-4,5,6,7-tetrahydro-thiazolo[5,4-c]pyridin-2-yl)-benzamide was prepared by the method described in Example 23. MS, electrospray, 537, (M+H).

Example 42

3,4-Dimethoxy-N-[3-(2-morpholin-4-yl-indan-5-ylcarbamoyl)-benzyl]-benzamide (211)

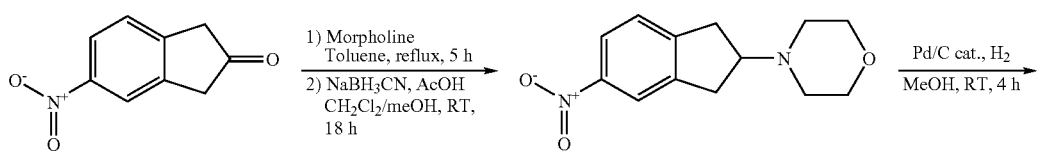

-continued

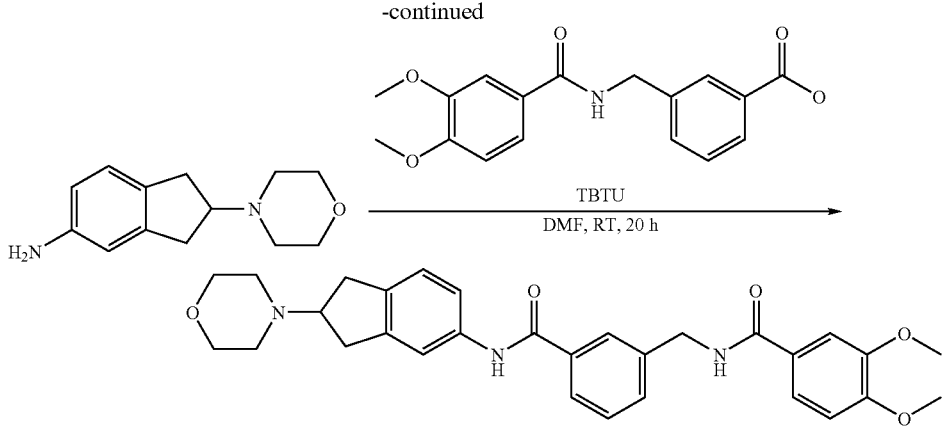

Morpholine (0.13 mL, 1.5 mmol) was added to a suspension of nitroindanone (177 mg, 1.00 mmol) in 10 mL of toluene. The mixture was heated to reflux with stirring. A dark solution was obtained, and water was seen collecting in the condenser. After 3 h the solution was cooled. An aliquot was evaporated to dryness and the enamine was verified by $^1$H NMR. A dark solid separated from the solution on cooling. The bulk reaction mixture was evaporated to remove most of the solvent. 5 mL of methanol was added, which did not dissolve solid residue. 5 mL CH$_2$Cl$_2$ was added, which did dissolve most of the material. NaBH$_3$CN (62.8 mg, 1.00 mmol) was added, followed by HOAc (1.00 mL). Stirring was continued overnight. Evaporated the solvent to dryness and partitioned the resulting residue between Na$_2$CO$_3$ and CH$_2$Cl$_2$. The aqueous phase was extracted with more CH$_2$Cl$_2$. The combined organic layers were dried over MgSO$_4$ and evaporated. The residue was purified by column chromatography, CH$_2$Cl$_2$AMeOH gradient 1-10%, isolating 215 mg of 4-(5-nitro-indan-2-yl)-morpholine as a tan crystalline solid.

To a solution of 4-(5-nitro-indan-2-yl)-morpholine (210 mg, 0.85 mmol) in 20 mL of methanol was added Pd/C 10% (20 mg). The mixture was placed under a H$_2$ atmosphere with stirring for 2 h. TLC showed 2 spots. CH$_2$Cl$_2$ was added to dissolve the ppt. that had formed and the hydrogenation continued further 2 h. The catalyst was removed by filtering, and the filtrate evaporated to give 188 mg of 2-morpholin-4-yl-indan-5-ylamine. The crude amine was used in the next step without purification.

To a suspension of the 3-[(3,4-dimethoxy-benzoylamino)-methyl]-benzoic acid (100 mg, 0.32 mmol) and 2-morpholin-4-yl-indan-5-ylamine (84 mg, 0.38 mmol) 1.5 mL of DMF. To this was added TBTU (122 mg, 0.38 mmol), and the vial warmed until a clear solution was obtained. The solution was stirred at room temperature. Stirring continued for 20 h total. Diluted with EtOAc and washed with Na$_2$CO$_3$, water and brine. The organic layer was dried over MgSO$_4$, evaporated and purified by column chromatography, CH$_2$Cl$_2$/MeOH gradient 1-10%, to give 103 mg of 3,4-dimethoxy-N-[3-(2-morpholin-4-yl-indan-5-ylcarbamoyl)-benzyl]-benzamide. MS, electrospray, 516, (M+H).

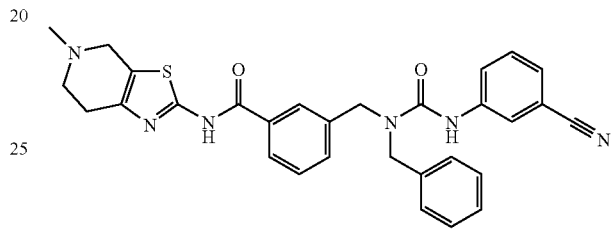

[212] 3-[1-Benzyl-3-(3-cyano-phenyl)-ureidomethyl]-N-(5-methyl-4,5,6,7-tetrahydro-thiazolo[5,4-c]pyridin-2-yl)-benzamide. Prepared by the methods described in Example 41 and Example 23. MS, electrospray, 537 (M+H).

Example 43

N-Benzyl-3,4-dimethoxy-N-[3-(5-methyl-4,5,6,7-tetrahydro-thiazolo[5,4-c]pyridin-2-ylcarbamoyl)-benzyl]-benzamide (213)

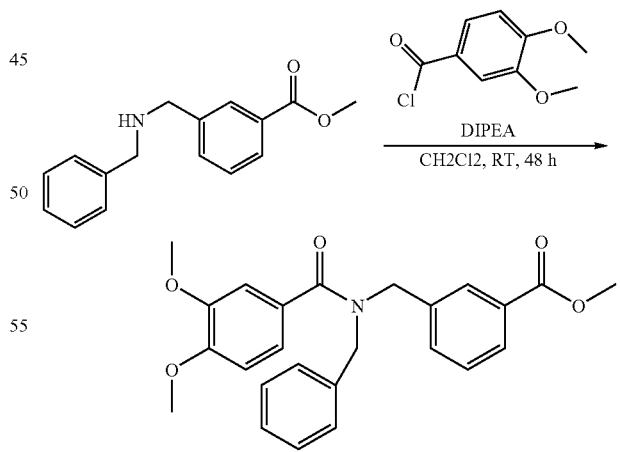

Dissolved 3-(benzylamino-methyl)-benzoic acid methyl ester (163 mg, 0.64 mmol) in 5 mL of CH$_2$Cl$_2$. To this was added 3-4-dimethoxybenzyl chloroformate (150 mg, 0.75 mmol) and DIPEA (0.19 mL, 1.00 mmol). The mixture stirred for 48 h. LC-MS analysis indicated some product formed. The mixture was diluted with 50 mL EtOAc, quenched with 20 mL of saturated NH$_4$Cl and washed with 2×20 mL of Na$_2$CO$_3$ and 1×20 mL of brine. The organic phase was dried with MgSO$_4$, filtered and concentrated. The residue was applied to a SiO$_2$ prep plate and eluted with 50% EtOAc/hexanes to give 52.0 mg of 3-{[Benzyl-(3,4-dimethoxy-benzoyl)-amino]-methyl}-benzoic acid methyl ester.

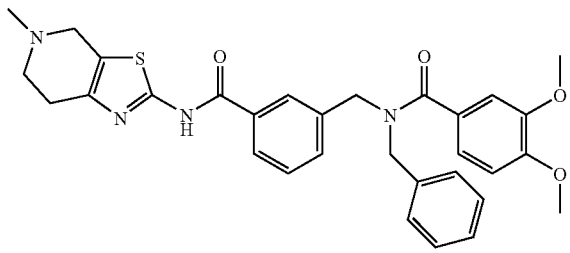

[213] N-Benzyl-3,4-dimethoxy-N-[3-(5-methyl-4,5,6,7-tetrahydro-thiazolo[5,4-c]pyridin-2-ylcarbamoyl)-benzyl]-benzamide was prepared by the methods described in Example 41 and Example 23. MS, electrospray, 557 (M+H).

Example 44

3-[3-(3-Ethynyl-phenyl)-ureidomethyl]-N-(5-methyl-4,5,6,7-tetrahydro-thiazolo[5,4-c]pyridin-2-yl)-benzamide (214)

3-Aminomethyl-N-(5-methyl-4,5,6,7-tetrahydro-thiazolo[5,4-c]pyridin-2-yl)-benzamide was prepared by the methods described in Example 23 and Example 24.

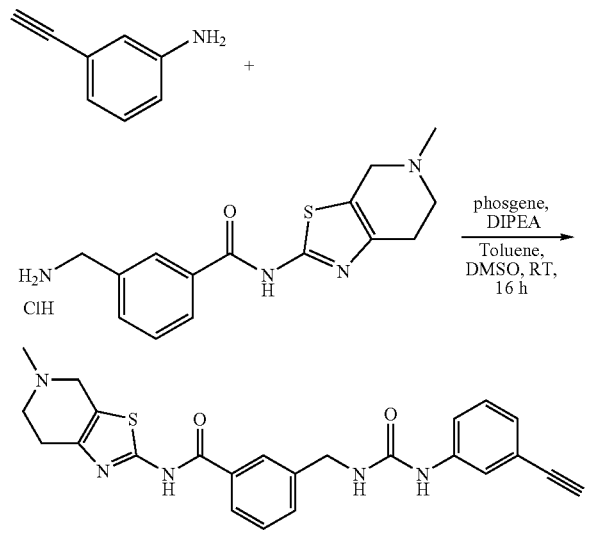

3-Ethynlaniline (0.15 mL, 1.43 mmol) was added to a 20% solution of phosgene in toluene (4.04 mmol) followed by DIPEA (0.50 mL, 2.71 mmol). The reaction mixture was stirred at room temperature for 3 h. To this was added 3-aminomethyl-N-(5-methyl-4,5,6,7-tetrahydro-thiazolo[5,4-c]pyridin-2-yl)-benzamide (250 mg, 0.69 mmol) and 1 mL of DMSO. The reaction mixture was stirred overnight at room temperature, then diluted with EtOAc (100 mL), washed with water (2×100 mL), dried with Na$_2$SO$_4$ and concentrated to provide 300 mg of a yellow solid. LC-MS indicated this was a mixture of primarily desired product and the symmetrical urea of ethynyl aniline. This material was triturated with methanol which enriched the ppt in desired product (now approximately 40%) and removed the residual amine. This solid was then partitioned between ethyl acetate and 2 N HCl. The aqueous phase was separated, neutralized, and extracted with ethyl acetate to provide a mixture ~9:1 of the desired product and urea (25 mg yellow solid). This material was further purified by prep HPLC to provide 3 mg of 3-[3-(3-ethynyl-phenyl)-ureidomethyl]-N-(5-methyl-4,5,6,7-tetrahydro-thiazolo[5,4-c]pyridin-2-yl)-benzamide. MS, electrospray, 447 (M+H).

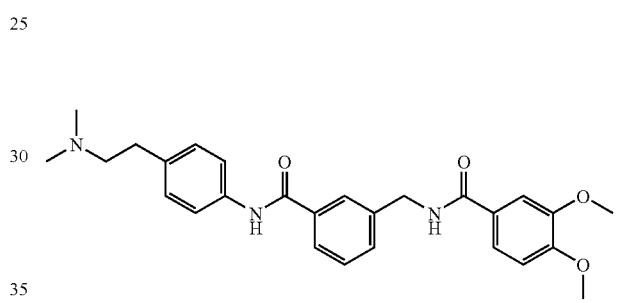

[215] N-{3-[4-(2-Dimethylamino-ethyl)-phenylcarbamoyl]-benzyl}-3,4-dimethoxy-benzamide was prepared by the method described in Example 23. MS, electrospray, 463 (M+H)

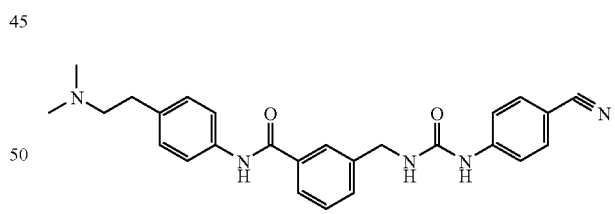

[216] 3-[3-(4-Cyano-phenyl)-ureidomethyl]-N-[4-(2-dimethylamino-ethyl)-phenyl]-benzamide was prepared by the method described in Example 23. MS, electrospray, 443 (M+H)

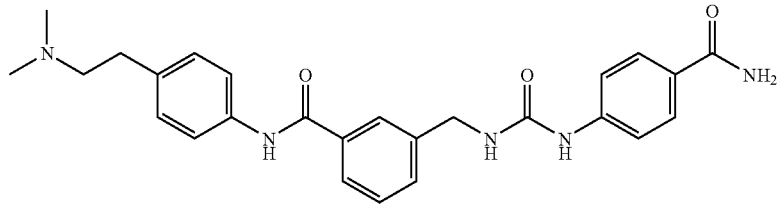

3-[3-(4-carboxamide-phenyl)-ureidomethyl]-N-[4-(2-dimethylamino-ethyl)-phenyl]-benzamide. was prepared by the method described in Example 23. MS, electrospray, 461 (M+H)

Assessment Of Biological Activity

Molecular Assay

The activity of ROCKII (1-543) kinase was measured utilizing Cambrex PKLight ATP Detection Reagent, a homogeneous assay technology using luciferin-luciferase to quantify residual ATP. The assay was performed in 384-well low-volume, white, non-binding surface microtiter plates (Corning). The assay buffer was 25 mM HEPES, pH 7.5, 10 mM $MgCl_2$, 50 mM KCl, 0.2% BSA, 0.01% CHAPS, 100 µM $Na_3VO_4$ and 0.5 mM DTT. Test compounds, dissolved in neat DMSO at 500 µg/mL, were serially diluted for dose response for a final starting concentration of 3 µg/mL in 1% DMSO of assay buffer. ROCKII (1-543) (62,408 Da) was diluted in assay buffer to a final concentration of 7.5 nM in a total volume of 15 µL. Positive controls were reaction mixtures containing no test compound; negative controls (blanks) were reaction mixtures containing no kinase. After 15 minutes of pre-incubation of the test compounds with the kinase, a mixture of ATP and peptide substrate (AKRRRLSSLRA) in assay buffer was added to each well for a final concentration of 750 nM ATP and 500 nM peptide, respectively. After 90 minutes of incubation of the kinase reaction at 28° C. temperature, 10 µL of PKLight ATP Detection Reagent (warmed to room temperature previously) was added to each well. The assay plate was incubated at room temperature for additional 15 minutes and then read on an Analyst in luminescence mode. Dose-response experiments for each of the test compounds were conducted in quadruplet. $IC_{50}$ values of test compounds represent 50% response of the positive control from the dose-response curve.

Representative compounds of the present invention were tested for activity in this assay and all had $IC_{50}$ values <10 µM. Preferred compounds have an $IC_{50}$<1 µM and more preferred compounds have an $IC_{50}$<0.1 µM in this assay. As examples the following data were obtained for the compounds named below:

| Name | Rock2 $IC_{50}$ (nM) |
|---|---|
| 3,4-Dimethoxy-N-[3-((S)-6-morpholin-4-yl-4,5,6,7-tetrahydro-benzothiazol-2-ylcarbamoyl)-benzyl]-benzamide | 1 |
| N-[3-((R)-6-Dimethylamino-4,5,6,7-tetrahydro-benzothiazol-2-ylcarbamoyl)-benzyl]-3,4-dimethoxy-benzamide | 1 |
| 3-Chloro-4-methoxy-N-[3-((S)-6-propylamino-4,5,6,7-tetrahydro-benzothiazol-2-ylcarbamoyl)-benzyl]-benzamide | 2 |
| 3-Chloro-4-methoxy-N-[3-(4,5,6,7-tetrahydro-thiazolo[5,4-c]pyridin-2-ylcarbamoyl)-benzyl]-benzamide | 4 |
| N-[3-(2,3-Dihydro-1H-isoindol-5-ylcarbamoyl)-benzyl]-3,4-dimethoxy-benzamide | 6 |
| N-[3-(2-Amino-indan-5-ylcarbamoyl)-benzyl]-3,4-dimethoxy-benzamide | 12 |
| N-{3-[(S)-6-(1,1-Dioxo-thiomorpholin-4-yl)-4,5,6,7-tetrahydro-benzothiazol-2-ylcarbamoyl]-benzyl}-3,4-dimethoxy-benzamide | 13 |
| 3,4-Dimethoxy-N-[3-(2,3,4,5-tetrahydro-1H-benzo[d]azepin-7-ylcarbamoyl)-benzyl]-benzamide | 15 |
| 3,4-Dimethoxy-N-(3-{5-[2-(4-methyl-piperazin-1-yl)-ethyl]-thiazol-2-ylcarbamoyl}-benzyl)-benzamide | 20 |
| 4,5,6,7-Tetrahydro-thiazolo[5,4-c]pyridine-2-carboxylic acid {3-[(3,4-dimethoxy-benzoylamino)-methyl]-phenyl}-amide | 22 |
| 3,4-Dimethoxy-N-[3-(6-methyl-5,6,7,8-tetrahydro-[1,6]naphthyridin-3-ylcarbamoyl)-benzyl]-benzamide | 61 |

| Name | Rock2 $IC_{50}$ (nM) |
|---|---|
| 3-Chloro-4-methoxy-N-{3-[(2-methoxy-ethyl)-((S)-6-propylamino-4,5,6,7-tetrahydro-benzothiazol-2-yl)-carbamoyl]-benzyl}-benzamide | 72 |
| 3,4-Dimethoxy-N-{3-[2-(2-methoxy-ethyl)-1,2,3,4-tetrahydro-isoquinolin-7-ylcarbamoyl]-benzyl}-benzamide | 99 |
| 4-Methoxy-3-methyl-N-{3-[4-(2-pyrrolidin-1-yl-ethyl)-phenylcarbamoyl]-benzyl}-benzamide | 120 |
| 3,4-Dimethoxy-N-{3-[4-(2-morpholin-4-yl-ethoxy)-phenylcarbamoyl]-benzyl}-benzamide | 58 |
| N-[3-(2-Ethyl-1,2,3,4-tetrahydro-isoquinolin-7-ylcarbamoyl)-benzyl]-3,4-dimethoxy-benzamide | 27 |
| 3-[3-(4-Cyano-phenyl)-ureidomethyl]-N-(5-methyl-4,5,6,7-tetrahydro-thiazolo[5,4-c]pyridin-2-yl)-benzamide | 10 |

Methods of Therapeutic Use

In accordance with the invention, there are provided novel methods of using the compounds of formula (I). The compounds disclosed herein effectively inhibit Rho kinase. The inhibition of Rho kinase is an attractive means for preventing and treating a variety of cardiovascular diseases or conditions associated with Rho kinase activation. Thus, the compounds are useful for the treatment of diseases and conditions as described in the Background section, including the following conditions and diseases: hypertension, atherosclerosis, restenosis, stroke, myocardial infarction, heart failure, coronary artery disease, peripheral artery disease, coronary vasospasm, cerebral vasospasm, ischemia/reperfusion injury, pulmonary hypertension, angina, erectile dysfunction, renal disease and organ failure. As disclosed in the Background section, the compounds of the invention will also be useful for treating diseases or conditions associated with smooth muscle hyper reactivity or with activated Rho kinase under other pathophysiological conditions. These diseases include but are not limited to asthma, glaucoma, cancer, Alzheimer's disease, multiple sclerosis, spinal cord injury, neuropathic pain, rheumatoid arthritis, psoriasis and inflammatory bowel disease.

These disorders have been well characterized in man, but also exist with a similar etiology in other mammals, and can be treated by pharmaceutical compositions of the present invention.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of formula I

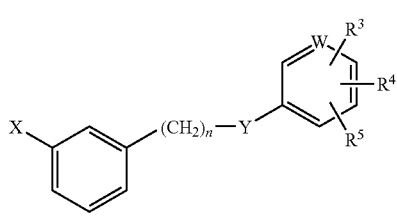

wherein:

X is —C(O)NR$^1$R$^2$ or —NHC(O)R$^1$;

Y is —N(R$^8$)C(O)NR$^9$—, —N(R$^8$)C(O)— or —C(O)N(R$^8$)—;

W is C or N;

n is 1 or 2;

R$^1$ is selected from:

a)
b)
c)
d)
e)
f)
g)
h)
i)
j)
k)
l)
m)
n)

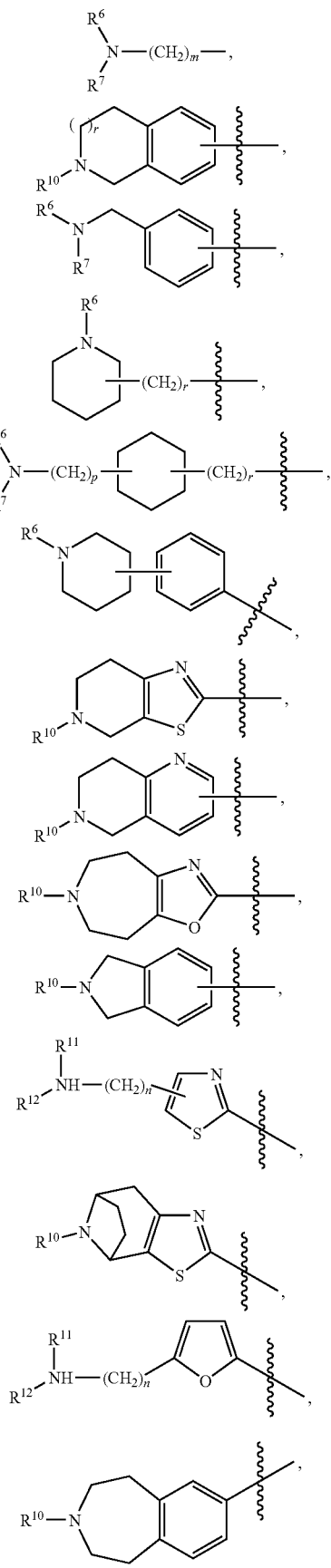

-continued o) 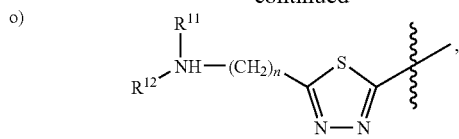

p) 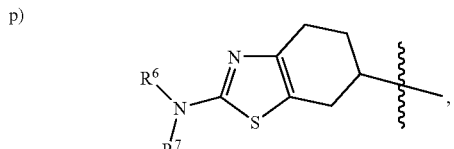

q) 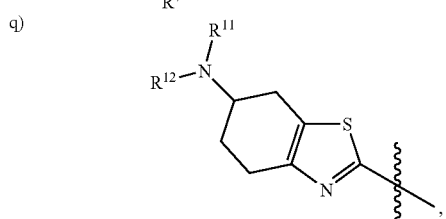

r) 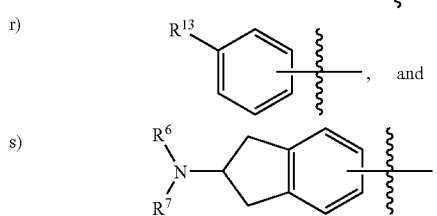, and s) 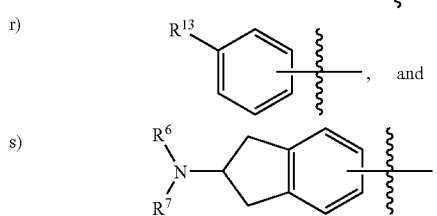;

R² is selected from H, C₁₋₆alkyl and methoxyC₂₋₄alkyl;
R³, R⁴, and R⁵ are independently selected from:
H, C₁₋₆alkyl, C₂₋₆alkenyl, C₂₋₆alkynyl, C₁₋₆alkoxy, C₁₋₆alkoxyC₁₋₆alkyl, Cl, F, Br, —CN, —CH₂CN, —CF₃, —OCHF₂, —OCF₃, —C(O)NH₂, —C(O)C₁₋₃alkyl, —NHC(O)NH₂, and —SC₁₋₃alkyl; or
R³ and R⁴ together with the benzene ring they are bonded to form a quinoline ring;
R⁶ and R⁷ are independently selected from H and C₁₋₆alkyl, or R⁶ and R⁷, together with the nitrogen to which they are bound, may form a morpholine ring;
R⁸ and R⁹ are independently selected from H, C₁₋₃alkyl and benzyl;
R¹⁰ is selected from H, C₁₋₆alkyl, —CH₂pyridyl, —CH₂CO₂C₁₋₄alkyl, —CH₂C(O)NH₂, —CH₂CH₂OC₁₋₄alkyl, —CH₂CH₂CN, —CH₂CHF₂, —(CH₂)₁₋₂CF₃, —CH₂CH₂F, —CH(CO₂Me)CH₂CO₂C₁₋₄alkyl, and benzyl, wherein said benzyl group is optionally substituted with one to two groups selected from R³ and R⁴;
R¹¹ and R¹² are independently selected from H and C₁₋₆alkyl; or R¹¹ and R¹², together with the nitrogen they are attached to, form a morpholine ring, a 4-methyl-1-piperazinyl ring, a thiomorpholine ring, optionally with a dioxo substituent at the sulfur atom, or a 1,3-dihydroisoindole ring;
R¹³ is selected from —(CH₂)ᵣN(R⁶)(R⁷), —OCH₂CH₂(4-morpholinyl), —CH₂CH₂(1-pyrrolidinyl), —CH₂(1-pyrazolyl) and —CH₂-(5-methyl-4H-[1,2,4]triazol-3-yl);
m is 3-6;
r is 0-2; and
p is 0-1;
with the proviso that if Y =—C(O)NR⁸— and n=1, then X is not —C(O)NR¹R² and if Y is —N(R⁸)C(O)NR⁹—, then n is not 2;
or a tautomer or a salt thereof.

2. The compound of formula (I) according to claim 1, wherein:

W is C;

R¹ is selected from:

a) 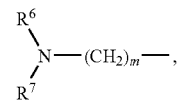, b) 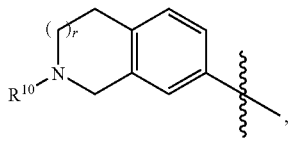, c) 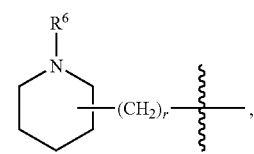, d) 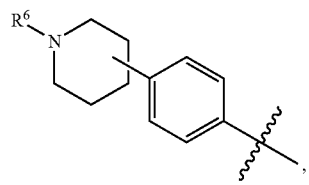, e) 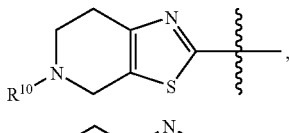, f) 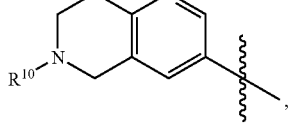, g) 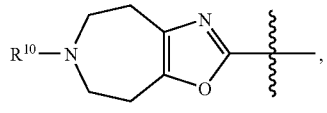, h) 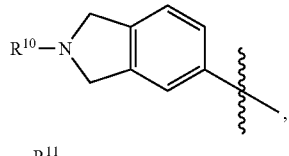, i) 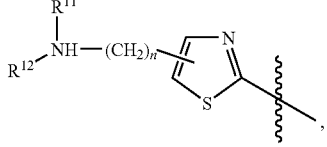, j) 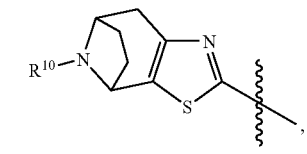, k) 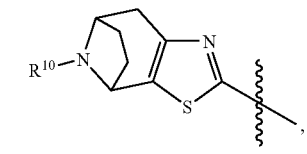

195

-continued l) 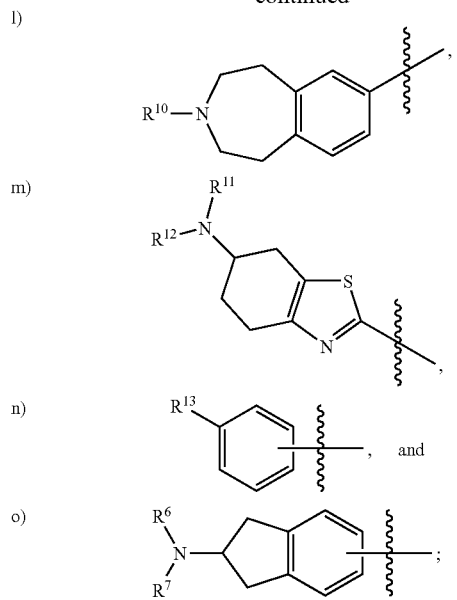

m, n, o) 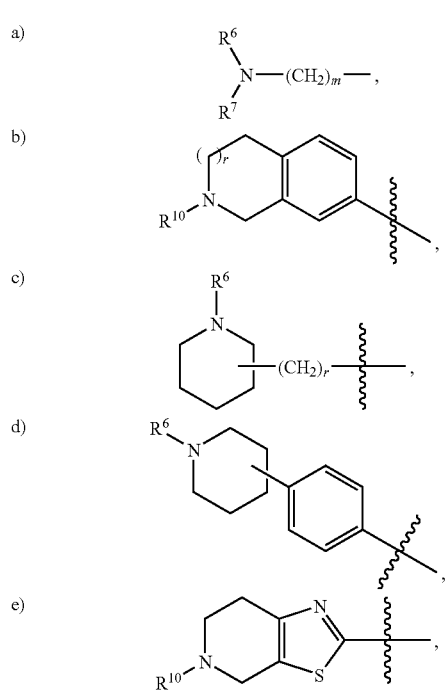

R² is H;

R³, R⁴, and R⁵ are independently selected from:

H, $C_{1-6}$alkyl, $C_{2-6}$alkenyl, $C_{2-6}$alkynyl, $C_{1-6}$alkoxy, $C_{1-6}$alkoxy$C_{1-6}$alkyl, Cl, F, Br, —CN, —$CH_2CN$, —$CF_3$, —$OCHF_2$, —$OCF_3$, —C(O)$NH_2$, —C(O)$C_{1-3}$alkyl, —NHC(O)$NH_2$, and —S$C_{1-3}$alkyl; and R⁸ and R⁹ are H.

3. The compound of formula (I) according to claim 1, wherein:

W is C;

R¹ is selected from:

196

-continued f) – m) 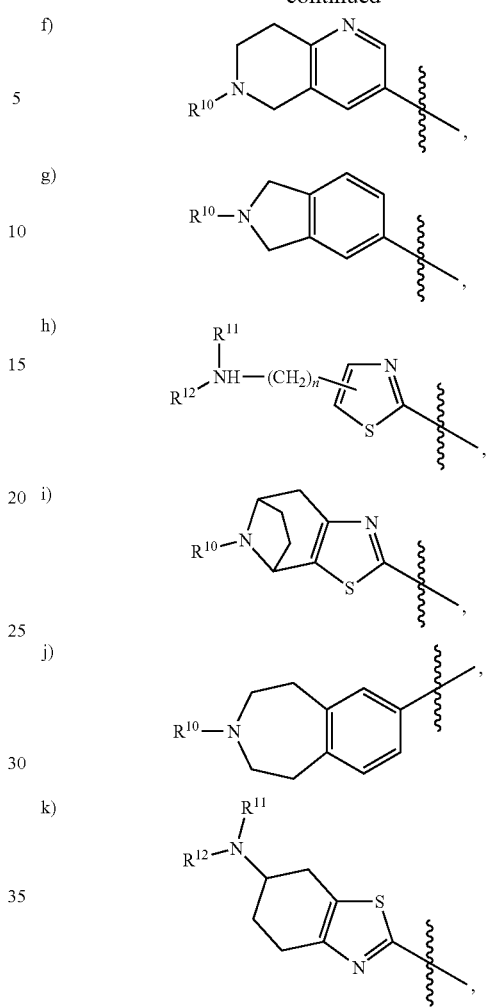

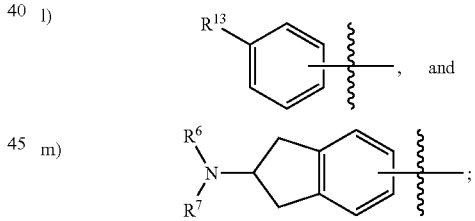

R² is H;

R³, R⁴, and R⁵ are independently selected from:

H, $C_{1-6}$alkyl, $C_{2-6}$alkenyl, $C_{2-6}$alkynyl, $C_{1-6}$alkoxy, $C_{1-6}$alkoxy$C_{1-6}$alkyl, Cl, F, Br, —CN, —$CH_2CN$, —$CF_3$, —$OCHF_2$, —$OCF_3$, —C(O)$NH_2$, —C(O)$C_{1-3}$alkyl, —NHC(O)$NH_2$, and —S$C_{1-3}$alkyl;

R⁸ and R⁹ are H; and

R¹³ is selected from —OCH₂CH₂(4-morpholinyl), —CH₂CH₂(1-pyrrolidinyl), —CH₂(1-pyrazolyl) and —CH₂-(5-methyl-4H-[1,2,4]triazol-3-yl).

4. The compound of formula (I) according to claim 1, wherein:

W is C;

$R^1$ is selected from:

a) 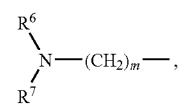

b) 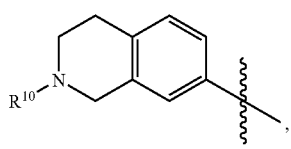

c) 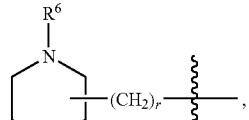

d) 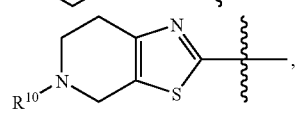

e) 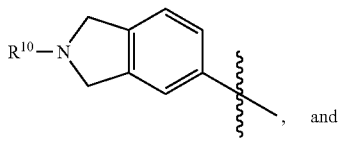, and h) 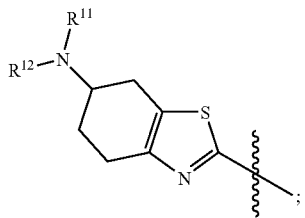;

$R^2$ is H;
$R^3$, $R^4$, and $R^5$ are independently selected from:
H, $C_{1-6}$alkyl, $C_{2-6}$alkenyl, $C_{2-6}$alkynyl, $C_{1-6}$alkoxy, $C_{1-6}$alkoxyC$_{1-6}$alkyl, Cl, F, Br, —CN, —CH$_2$CN, —CF$_3$, —OCHF$_2$, —OCF$_3$, —C(O)NH$_2$, —C(O)C$_{1-3}$alkyl, —NHC(O)NH$_2$, and —SC$_{1-3}$alkyl;
$R^8$ and $R^9$ are H; and
$R^{13}$ is selected from —OCH$_2$CH$_2$(4-morpholinyl), —CH$_2$CH$_2$(1-pyrrolidinyl), —CH$_2$(1-pyrazolyl) and —CH$_2$-(5-methyl-4H-[1,2,4]triazol-3-yl).

5. The compound of formula (I) according to claim 1, wherein:
X is —C(O)NR$^1$R$^2$;
Y is —NHC(O)—;
W is C;
n is 1;
$R^1$ is

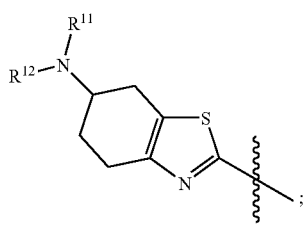;

$R^2$ is H;
$R^3$, $R^4$, and $R^5$ are independently selected from:
H, $C_{1-6}$alkyl, $C_{2-6}$alkenyl, $C_{2-6}$alkynyl, $C_{1-6}$alkoxy, $C_{1-6}$alkoxyC$_{1-6}$alkyl, Cl, F, Br, —CN, —CH$_2$CN, —CF$_3$, —OCHF$_2$, —OCF$_3$, —C(O)NH$_2$, —C(O)C$_{1-3}$alkyl, —NHC(O)NH$_2$, and —SC$_{1-3}$alkyl; and
$R^{11}$ and $R^{12}$ are independently selected from H and $C_{1-6}$alkyl; or $R^{11}$ and $R^{12}$, together with the nitrogen they are attached to, form a morpholine ring, a 4-methyl-1-piperazinyl ring, a thiomorpholine ring, optionally with a dioxo substituent at the sulfur atom, or a 1,3-dihydroisoindole ring.

6. A compound selected from:
3-[3-(4-cyano-phenyl)-ureidomethyl]-N-(1,2,3,4-tetrahydro-isoquinolin-7-yl)-benzamide;
3-[3-(4-cyano-phenyl)-ureidomethyl]-N-(1,2,3,4-tetrahydro-isoquinolin-6-yl)-benzamide;
3-[3-(4-cyano-phenyl)-ureidomethyl]-N-(2-piperidin-4-yl-ethyl)-benzamide;
N-(4-aminomethyl-phenyl)-3-[3-(4-cyano-phenyl)-ureidomethyl]-benzamide;
N-(4-aminomethyl-cyclohexyl)-3-[3-(4-cyano-phenyl)-ureidomethyl]-benzamide;
N-(3-aminomethyl-phenyl)-3-[3-(4-cyano-phenyl)-ureidomethyl]-benzamide;
3-[3-(4-cyano-phenyl)-ureidomethyl]-N-(2-piperidin-3-yl-ethyl)-benzamide;
3-[3-(3-cyano-phenyl)-ureidomethyl]-N-(2-piperidin-3-yl-ethyl)-benzamide;
3-[3-(3,4-dimethoxy-phenyl)-ureidomethyl]-N-(1,2,3,4-tetrahydro-isoquinolin-6-yl)-benzamide;
3-[3-(3,4-dimethoxy-phenyl)-ureidomethyl]-N-(2-piperidin-3-yl-ethyl)-benzamide;
3-[3-(3,4-dimethoxy-phenyl)-ureidomethyl]-N-piperidin-3-ylmethyl-benzamide;
3-[3-(4-cyano-phenyl)-ureidomethyl]-N-(4-dimethylamino-butyl)-benzamide;
3-[3-(4-cyano-phenyl)-ureidomethyl]-N-(3-dimethylamino-propyl)-benzamide;
3-[3-(4-cyano-phenyl)-ureidomethyl]-N-(5-dimethylamino-pentyl)-benzamide;
3-[3-(4-cyano-phenyl)-ureidomethyl]-N-(3-dimethylaminomethyl-phenyl)-benzamide;
3-[3-(4-cyano-phenyl)-ureidomethyl]-N-(4-dimethylaminomethyl-phenyl)-benzamide;
3-[3-(3,4-dimethoxy-phenyl)-ureidomethyl]-N-(4-dimethylaminomethyl-phenyl)-benzamide;
3-[3-(4-acetyl-phenyl)-ureidomethyl]-N-(4-dimethylaminomethyl-phenyl)-benzamide;
N-(4-dimethylaminomethyl-phenyl)-3-[3-(4-methoxy-phenyl)-ureidomethyl]-benzamide;
3-[3-(4-chloro-phenyl)-ureidomethyl]-N-(4-dimethylaminomethyl-phenyl)-benzamide;
N-(4-dimethylaminomethyl-phenyl)-3-[3-(4-methoxy-2-methyl-phenyl)-ureidomethyl]-benzamide;
3-[3-(3-cyano-phenyl)-ureidomethyl]-N-(4-dimethylaminomethyl-phenyl)-benzamide;
N-(4-dimethylaminomethyl-phenyl)-3-[3-(3-methoxy-phenyl)-ureidomethyl]-benzamide;
3-[3-(3-chloro-4-cyano-phenyl)-ureidomethyl]-N-(3-dimethylaminomethyl-benzyl)-benzamide;
3-[3-(4-amido-phenyl)-ureidomethyl]-N-(1,2,3,4-tetrahydro-isoquinolin-7-yl)-benzamide;
3-[3-(4-amido-phenyl)-ureidomethyl]-N-(4-dimethylaminomethyl-phenyl)-benzamide;
3-[3-(3-chloro-4-amido-phenyl)-ureidomethyl]-N-(4-dimethylaminomethyl-phenyl)-benzamide;
3-[3-(3-amido-phenyl)-ureidomethyl]-N-(4-dimethylaminomethyl-phenyl)-benzamide;

2-methyl-1,2,3,4-tetrahydro-isoquinoline-7-carboxylic acid {3-[3-(4-amido-phenyl)-ureidomethyl]-phenyl}-amide;
2-methyl-1,2,3,4-tetrahydro-isoquinoline-7-carboxylic acid{3-[3-(4-cyano-phenyl)-ureidomethyl]-phenyl}-amide;
1,2,3,4-tetrahydro-isoquinoline-6-carboxylic acid {3-[3-(4-cyano-phenyl)-ureidomethyl]-phenyl}-amide;
N-{3-[3-(4-cyano-phenyl)-ureidomethyl]-phenyl}-3-piperidin-3-yl-propionamide;
3,4-dimethoxy-N-[3-(2-piperidin-3-yl-ethylcarbamoyl)-benzyl]-benzamide;
3,4-dimethoxy-N-[3-(1,2,3,4-tetrahydro-isoquinolin-7-ylcarbamoyl)-benzyl]-benzamide;
N-{3-[(4-amino-cyclohexylmethyl)-carbamoyl]-benzyl}-3,4-dimethoxy-benzamide;
3,4-dimethoxy-N-{3-[(piperidin-4-ylmethyl)-carbamoyl]-benzyl}-benzamide;
3,4-dimethoxy-N-[3-(1,2,3,4-tetrahydro-isoquinolin-5-ylcarbamoyl)-benzyl]-benzamide;
N-[3-(3-aminomethyl-phenylcarbamoyl)-benzyl]-3,4-dimethoxy-benzamide;
3,4-dimethoxy-N-[3-(3-piperidin-3-yl-phenylcarbamoyl)-benzyl]-benzamide;
3,4-dimethoxy-N-[3-(2-piperidin-4-yl-ethylcarbamoyl)-benzyl]-benzamide;
3,4-dimethoxy-N-[3-(1,2,3,4-tetrahydro-isoquinolin-6-ylcarbamoyl)-benzyl]-benzamide;
N-[3-(4-aminomethyl-cyclohexylcarbamoyl)-benzyl]-3,4-dimethoxy-benzamide;
N-[3-(4-aminomethyl-phenylcarbamoyl)-benzyl]-3,4-dimethoxy-benzamide;
3,4-dimethoxy-N-{3-[2-(1-methyl-piperidin-3-yl)-ethylcarbamoyl]-benzyl}-benzamide;
3,4-dimethoxy-N-[3-(2-methyl-1,2,3,4-tetrahydro-isoquinolin-7-ylcarbamoyl)-benzyl]-benzamide;
7-{3-[(3,4-dimethoxy-benzoylamino)-methyl]-benzoylamino}-2,2-dimethyl-1,2,3,4-tetrahydro-isoquinolinium formate;
N-{3-[2-(2,2-dimethyl-propyl)-1,2,3,4-tetrahydro-isoquinolin-7-ylcarbamoyl]-benzyl}-3,4-dimethoxy-benzamide;
3,4-dimethoxy-N-methyl-N-[3-(1,2,3,4-tetrahydro-isoquinolin-6-ylcarbamoyl)-benzyl]-benzamide;
N-[3-(3-dimethylaminomethyl-phenylcarbamoyl)-benzyl]-3,4-dimethoxy-benzamide;
N-[3-(5-dimethylamino-pentylcarbamoyl)-benzyl]-3,4-dimethoxy-benzamide;
N-[3-(4-dimethylaminomethyl-phenylcarbamoyl)-benzyl]-3,4-dimethoxy-benzamide;
N-[3-(6-dimethylamino-hexylcarbamoyl)-benzyl]-3,4-dimethoxy-benzamide;
N-[3-(4-dimethylamino-butylcarbamoyl)-benzyl]-3,4-dimethoxy-benzamide;
N-[3-(3-dimethylamino-propylcarbamoyl)-benzyl]-3,4-dimethoxy-benzamide;
N-[3-(4-dimethylamino-cyclohexylcarbamoyl)-benzyl]-3,4-dimethoxy-benzamide;
3-chloro-N-[3-(4-dimethylaminomethyl-phenylcarbamoyl)-benzyl]-4-methoxy-benzamide;
3-allyl-N-[3-(4-dimethylaminomethyl-phenylcarbamoyl)-benzyl]-4-methoxy-benzamide;
N-[3-(4-dimethylaminomethyl-phenylcarbamoyl)-benzyl]-4-methoxy-3-trifluoromethyl-benzamide;
4-chloro-N-[3-(4-dimethylaminomethyl-phenylcarbamoyl)-benzyl]-3-methoxy-benzamide;
quinoline-6-carboxylic acid 3-(4-dimethylaminomethyl-phenylcarbamoyl)-benzylamide;
N-[3-(4-dimethylaminomethyl-phenylcarbamoyl)-benzyl]-2,4-dimethoxy-benzamide;
N-[3-(4-dimethylaminomethyl-phenylcarbamoyl)-benzyl]-4-methoxy-3-methyl-benzamide;
N-[3-(4-dimethylaminomethyl-phenylcarbamoyl)-benzyl]-4-methoxy-benzamide;
4-cyano-N-[3-(4-dimethylaminomethyl-phenylcarbamoyl)-benzyl]-3-fluoro-benzamide;
4-cyano-N-[3-(4-dimethylaminomethyl-phenylcarbamoyl)-benzyl]-benzamide;
N-[3-(4-dimethylaminomethyl-phenylcarbamoyl)-benzyl]-4-trifluoromethoxy-benzamide;
N-[3-(4-dimethylaminomethyl-phenylcarbamoyl)-benzyl]-4-methoxy-3-methoxymethyl-benzamide;
N-[3-(4-dimethylaminomethyl-phenylcarbamoyl)-benzyl]-3-fluoro-4-methoxy-benzamide;
3,4-dichloro-N-[3-(4-dimethylaminomethyl-phenylcarbamoyl)-benzyl]-benzamide;
N-[3-(4-dimethylaminomethyl-phenylcarbamoyl)-benzyl]-3,4,5-trimethoxy-benzamide;
N-[3-(4-dimethylaminomethyl-phenylcarbamoyl)-benzyl]-4-methylsulfanyl-benzamide;
N-[3-(4-dimethylaminomethyl-phenylcarbamoyl)-benzyl]-3-trifluoromethyl-benzamide;
N-[3-(4-dimethylaminomethyl-phenylcarbamoyl)-benzyl]-3-methylsulfanyl-benzamide;
N-[3-(4-dimethylaminomethyl-phenylcarbamoyl)-benzyl]-3-methoxy-benzamide;
N-[3-(4-dimethylaminomethyl-phenylcarbamoyl)-benzyl]-4-methoxy-3,5-dimethyl-benzamide;
N-[3-(4-dimethylaminomethyl-phenylcarbamoyl)-benzyl]-3,5-dimethoxy-benzamide;
N-[3-(4-dimethylaminomethyl-phenylcarbamoyl)-benzyl]-terephthalamide;
3-chloro-N-[3-(4-dimethylaminomethyl-phenylcarbamoyl)-benzyl]-4-trifluoromethoxy-benzamide;
N-[3-(4-dimethylaminomethyl-phenylcarbamoyl)-benzyl]-3-ureido-benzamide;
N-[3-(4-dimethylaminomethyl-phenylcarbamoyl)-benzyl]-isophthalamide;
1,2,3,4-tetrahydro-isoquinoline-6-carboxylic acid {3-[(3,4-dimethoxy-benzoylamino)-methyl]-phenyl}-amide;
3,4-dimethoxy-N-[3-(3-piperidin-3-yl-propionylamino)-benzyl]-benzamide;
2-methyl-1,2,3,4-tetrahydro-isoquinoline-6-carboxylic acid {3-[(3,4-dimethoxy-benzoylamino)-methyl]-phenyl}-amide;
2-methyl-1,2,3,4-tetrahydro-isoquinoline-7-carboxylic acid {3-[(3,4-dimethoxy-benzoylamino)-methyl]-phenyl}-amide;
N-{3-[(3,4-dimethoxy-phenylcarbamoyl)-methyl]-phenyl}-3-piperidin-3-yl-propionamide;
N-{3-[(3,4-dimethoxy-phenylcarbamoyl)-methyl]-phenyl}-4-dimethylaminomethyl-benzamide;
1,2,3,4-tetrahydro-isoquinoline-7-carboxylic acid {3-[(3,4-dimethoxy-phenylcarbamoyl)-methyl]-phenyl}-amide;
1,2,3,4-tetrahydro-isoquinoline-6-carboxylic acid {3-[(3,4-dimethoxy-phenylcarbamoyl)-methyl]-phenyl}-amide;
2-methyl-1,2,3,4-tetrahydro-isoquinoline-7-carboxylic acid {3-[(3,4-dimethoxy-phenylcarbamoyl)-methyl]-phenyl}-amide;
N-(3,4-dimethoxy-phenyl)-3-[3-(3-piperidin-3-yl-propionylamino)-phenyl]-propionamide;

N-(4-cyano-phenyl)-3-[3-(3-piperidin-3-yl-propiony-lamino)-phenyl]-propionamide;
1,2,3,4-tetrahydro-isoquinoline-7-carboxylic acid {3-[2-(4-cyano-phenylcarbamoyl)-ethyl]-phenyl}-amide;
1,2,3,4-tetrahydro-isoquinoline-6-carboxylic acid {3-[2-(4-cyano-phenylcarbamoyl)-ethyl]-phenyl}-amide;
3,4-dimethoxy-N-[3-(1-methyl-piperidin-4-ylcarbamoyl)-benzyl]-benzamide;
N-[3-(2-benzyl-1,2,3,4-tetrahydro-isoquinolin-7-ylcarbamoyl)-benzyl]-3,4-dimethoxy-benzamide;
N-{3-[2-(2-fluoro-benzyl)-1,2,3,4-tetrahydro-isoquinolin-7-ylcarbamoyl]-benzyl}-3,4-dimethoxy-benzamide;
N-{3-[2-(3-fluoro-benzyl)-1,2,3,4-tetrahydro-isoquinolin-7-ylcarbamoyl]-benzyl}-3,4-dimethoxy-benzamide;
N-{3-[2-(4-fluoro-benzyl)-1,2,3,4-tetrahydro-isoquinolin-7-ylcarbamoyl]-benzyl}-3,4-dimethoxy-benzamide;
N-{3-[2-(2,6-difluoro-benzyl)-1,2,3,4-tetrahydro-isoquinolin-7-ylcarbamoyl]-benzyl}-3,4-dimethoxy-benzamide;
N-{3-[2-(2,3-difluoro-benzyl)-1,2,3,4-tetrahydro-isoquinolin-7-ylcarbamoyl]-benz}-3,4-dimethoxy-benzamide;
N-{3-[2-(2,4-difluoro-benzyl)-1,2,3,4-tetrahydro-isoquinolin-7-ylcarbamoyl]-benz}-3,4-dimethoxy-benzamide;
N-{3-[2-(3,5-difluoro-benzyl)-1,2,3,4-tetrahydro-isoquinolin-7-ylcarbamoyl]-benz}-3,4-dimethoxy-benzamide;
3,4-dimethoxy-N-[3-(5-methyl-4,5,6,7-tetrahydro-thiazolo[5,4-c]pyridin-2-ylcarbamoyl)-benzyl]-benzamide;
3,4-dimethoxy-N-[3)5,6,7,8-tetrahydro-[1,6]naphthyridin-3-ylcarbamoyl)-benzyl]-benzamide;
(7-{3-[(3,4-dimethoxy-benzoylamino)-methyl]-benzoylamino}-3,4-dihydro-1H-isoquinolin-2-yl)-acetic acid methyl ester;
N-[3-(2-carbamoylmethyl-1,2,3,4-tetrahydro-isoquinolin-7-ylcarbamoyl)-benzyl]-3,4-dimethoxy-benzamide;
3,4-dimethoxy-N-{3-[2-(2-methoxy-ethyl)-1,2,3,4-tetrahydro-isoquinolin-7-ylcarbamoyl]-benzyl}-benzamide;
N-{3-[2-(2-cyano-ethyl)-1,2,3,4-tetrahydro-isoquinolin-7-ylcarbamoyl]-benzyl}-3,4-dimethoxy-benzamide;
N-{3-[2-(2,2-difluoro-ethyl)-1,2,3,4-tetrahydro-isoquinolin-7-ylcarbamoyl]-benzyl}-3,4-dimethoxy-benzamide;
3-[3-(4-cyano-phenyl)-ureidomethyl]-N-(5-methyl-4,5,6,7-tetrahydro-thiazolo[5,4-c]pyridin-2-yl)-benzamide;
3-chloro-4-methoxy-N-[3-(2-methyl-1,2,3,4-tetrahydro-isoquinolin-7-ylcarbamoyl)-benzyl]-benzamide;
4-methoxy-3-methyl-N-[3-(2-methyl-1,2,3,4-tetrahydro-isoquinolin-7-ylcarbamoyl)-benzyl]-benzamide;
4-trifluoromethoxy-N-[3-(2-methyl-1,2,3,4-tetrahydro-isoquinolin-7-ylcarbamoyl)-benzyl]-benzamide;
3-chloro-N-[3-(2-methyl-1,2,3,4-tetrahydro-isoquinolin-7-ylcarbamoyl)-benzyl]-4-trifluoromethoxy-benzamide;
4-difluoromethoxy-N-[3-(2-methyl-1,2,3,4-tetrahydro-isoquinolin-7-ylcarbamoyl)-benzyl]-benzamide;
3-chloro-4-ethoxy-N-[3-(2-methyl-1,2,3,4-tetrahydro-isoquinolin-7-ylcarbamoyl)-benzyl]-benzamide;
5-chloro-6-methoxy-N-[3-(2-methyl-1,2,3,4-tetrahydro-isoquinolin-7-ylcarbamoyl)-benzyl]-nicotinamide;
3,4-diethoxy-N-[3-(2-methyl-1,2,3,4-tetrahydro-isoquinolin-7-ylcarbamoyl)-benzyl]-benzamide;
3-hydroxy-4-methoxy-N-[3-(2-methyl-1,2,3,4-tetrahydro-isoquinolin-7-ylcarbamoyl)-benzyl]-benzamide;
6-hydroxy-N-[3-(2-methyl-1,2,3,4-tetrahydro-isoquinolin-7-ylcarbamoyl)-benzyl]-nicotinamide;
N-[3-(6-ethyl-5,6,7,8-tetrahydro-4H-oxazolo[4,5-d]azepin-2-ylcarbamoyl)-benzyl]-3,4-dimethoxy-benzamide;
3,4-dimethoxy-N-[3-(6-methyl-5,6,7,8-tetrahydro-[1,6]naphthyridin-3-ylcarbamoyl)-benzyl]-benzamide;
N-[3-(2-ethyl-1,2,3,4-tetrahydro-isoquinolin-7-ylcarbamoyl)-benzyl]-3,4-dimethoxy-benzamide;
3-chloro-4-methoxy-N-[3-(5-methyl-4,5,6,7-tetrahydro-thiazolo[5,4-c]pyridin-2-ylcarbamoyl)-benzyl]-benzamide;
4-methoxy-3-methyl-N-[3-(5-methyl-4,5,6,7-tetrahydro-thiazolo[5,4-c]pyridin-2-ylcarbamoyl)-benzyl]-benzamide;
3-chloro-N-[3-(5-methyl-4,5,6,7-tetrahydro-thiazolo[5,4-c]pyridin-2-ylcarbamoyl)-benzyl]-4-trifluoromethoxy-benzamide;
6-methoxy-N-[3-(2-methyl-1,2,3,4-tetrahydro-isoquinolin-7-ylcarbamoyl)-benzyl]-nicotinamide;
1-methyl-6-oxo- 1,6-dihydro-pyridine-3-carboxylic acid 3-(2-methyl-1,2,3,4-tetrahydro-isoquinolin-7-ylcarbamoyl)-benzylamide;
4-difluoromethoxy-3-ethoxy-N-[3-(2-methyl-1,2,3,4-tetrahydro-isoquinolin-7-ylcarbamoyl)-benzyl]-benzamide;
N-[3-(5-benzyl-4,5,6,7-tetrahydro-thiazolo[5,4-c]pyridin-2-ylcarbamoyl)-benzyl]-3,4-dimethoxy-benzamide;
N-{3-[2-(2-cyano-benzyl)-1,2,3,4-tetrahydro-isoquinolin-7-ylcarbamoyl]-benzyl}-3,4-dimethoxy-benzamide;
3,4-dimethoxy-N-{3-[2-(2,2,2-trifluoro-ethyl)-1,2,3,4-tetrahydro-isoquinolin-7-ylcarbamoyl]-benzyl}-benzamide;
3,4-dimethoxy-N-{3-[2-(2-nitro-benzyl)-1,2,3,4-tetrahydro-isoquinolin-7-ylcarbamoyl]-benzyl}-benzamide;
3,4-dimethoxy-N-{3-[2-(2-trifluoromethyl-benzyl)-1,2,3,4-tetrahydro-isoquinolin-7-ylcarbamoyl]-benzyl}-benzamide;
3,4-dimethoxy-N-[3-(2-pyridin-3-ylmethyl-1,2,3,4-tetrahydro-isoquinolin-7-ylcarbamoyl)-benzyl]-benzamide;
3,4-dimethoxy-N-{3-[2-(3,3,3-trifluoro-propyl)-1,2,3,4-tetrahydro-isoquinolin-7-ylcarbamoyl]-benzyl}-benzamide;
3,4-dimethoxy-N-[3-(2-pyridin-4-ylmethyl-1,2,3,4-tetrahydro-isoquinolin-7-ylcarbamoyl)-benzyl]-benzamide;
3,4-dimethoxy-N-[3-(2-pyridin-2-ylmethyl-1,2,3,4-tetrahydro-isoquinolin-7-ylcarbamoyl)-benzyl]-benzamide;
N-{3-[2-(2-fluoro-ethyl)-1,2,3,4-tetrahydro-isoquinolin-7-ylcarbamoyl]-benzyl}-3,4-dimethoxy-benzamide;
3-ethoxy-4-methoxy-N-[3-(2-methyl-1,2,3,4-tetrahydro-isoquinolin-7-ylcarbamoyl)-benzyl]-benzamide;
4-difluoromethoxy-3-methoxy-N-[3-(2-methyl-1,2,3,4-tetrahydro-isoquinolin-7-ylcarbamoyl)-benzyl]-benzamide;
3-fluoro-4-methoxy-N-[3-(2-methyl-1,2,3,4-tetrahydro-isoquinolin-7-ylcarbamoyl)-benzyl]-benzamide;
4-methoxy-N-[3-(2-methyl-1,2,3,4-tetrahydro-isoquinolin-7-ylcarbamoyl)-benzyl]-benzamide;

N-[3-(2,3-dihydro-1H-isoindol-1-5-ylcarbamoyl)-benzyl]-3,4-dimethoxy-benzamide;
3,4-dimethoxy-N-[3-(2,3,4,5-tetrahydro-1H-benzo[c]azepin-8-ylcarbamoyl)-benzyl]-benzamide;
3,4-dimethoxy-N-[3-(4,5,6,7-tetrahydro-thiazolo[5,4-c]pyridin-2-ylcarbamoyl)-benzyl]-benzamide;
3,4-dimethoxy-N-{3-[5-(3,3,3-trifluoro-propyl)-4,5,6,7-tetrahydro-thiazolo[5,4-c]pyridin-2-ylcarbamoyl]-benzyl}-benzamide;
3,4-dimethoxy-N-{3-[5-(2-methoxy-ethyl)-4,5,6,7-tetrahydro-thiazolo[5,4-c]pyridin-2-ylcarbamoyl]-benzyl}-benzamide;
N-{3-[5-(2,2-difluoro-ethyl)-4,5,6,7-tetrahydro-thiazolo[5,4-c]pyridin-2-ylcarbamoyl]-benzyl}-3,4-dimethoxy-benzamide;
N-{3-[5-(2-fluoro-ethyl)-4,5,6,7-tetrahydro-thiazolo[5,4-c]pyridin-2-ylcarbamoyl]-benz}-3,4-dimethoxy-benzamide;
3-chloro-N-[3-(2,3-dihydro-1H-isoindol-1-5-ylcarbamoyl)-benzyl]-4-methoxy-benzamide;
3-chloro-4-methoxy-N-[3-(4,5,6,7-tetrahydro-thiazolo[5,4-c]pyridin-2-ylcarbamoyl)-benzyl]-benzamide;
N-[3-(2,3-dihydro- 1H-isoindol-5-ylcarbamoyl)-benzyl]-4-methoxy-3-methyl-benzamide;
4-methoxy-3-methyl-N-[3-(4,5,6,7-tetrahydro-thiazolo[5,4-c]pyridin-2-ylcarbamoyl)-benzyl]-benzamide;
N-[3-(5-dimethylaminomethyl-thiazol-2-ylcarbamoyl)-benzyl]-3,4-dimethoxy-benzamide;
4,5,6,7-tetrahydro-thiazolo[5,4-c]pyridine-2-carboxylic acid {3-[(3,4-dimethoxy-benzoylamino)-methyl]-phenyl}-amide;
3,4-dimethoxy-N-[3-(11-methyl-3-thia-5,11-diaza-tricyclo[6.2.1.02,6]undeca-2(6),4-dien-4-ylcarbamoyl)-benzyl]-benzamide;
N-[3-(4-dimethylaminomethyl-thiazol-2-ylcarbamoyl)-benzyl]-3,4-dimethoxy-benzamide;
N-{3-[(3,4-dimethoxy-phenylcarbamoyl)-methyl]-phenyl}-4-(2-morpholin-4-yl-ethoxy)-benzamide;
3,4-dimethoxy-N-{3-[4-(2-morpholin-4-yl-ethoxy)-benzoylamino]-benzyl}-benzamide;
5-methyl-4,5,6,7-tetrahydro-thiazolo[5,4-c]pyridine-2-carboxylic acid {3-[(3,4-dimethoxy-benzoylamino)-methyl]-phenyl}-amide;
5-dimethylaminomethyl-furan-2-carboxylic acid {3-[(3,4-dimethoxy-benzoylamino)-methyl]-phenyl}-amide;
5-dimethylaminomethyl-furan-2-carboxylic acid {3-[(3,4-dimethoxy-phenylcarbamoyl)-methyl]phenyl}-amide;
N-{3-[4-(2-amino-ethyl)-thiazol-2-ylcarbamoyl]-benzyl}-3,4-dimethoxy-benzamide;
N-{3-[4-(2-dimethylamino-ethyl)-thiazol-2-ylcarbamoyl]-benzyl}-3,4-dimethoxy-benzamide;
N-[3-((R)-6-amino-4,5,6,7-tetrahydro-benzothiazol-2-ylcarbamoyl)-benzyl]-3,4-dimethoxy-benzamide;
N-[3-((S)-6-amino-4,5,6,7-tetrahydro-benzothiazol-2-ylcarbamoyl)-benzyl]-3,4-dimethoxy-benzamide;
3,4-dimethoxy-N-[3-(2,3,4,5-tetrahydro-1H-benzo[d]azepin-7-ylcarbamoyl)-benzyl]-benzamide;
3,4-dimethoxy-N-[3-((S)-6-propylamino-4,5,6,7-tetrahydro-benzothiazol-2-ylcarbamoyl)-benzyl]-benzamide;
4-methylcyano-N-[3-(2-methyl-1,2,3,4-tetrahydro-isoquinolin-7-ylcarbamoyl)-benzyl]-benzamide;
3,4-dimethoxy-N-[3-(3-thia-5,11-diaza-tricyclo[6.2.1.02,6]undeca-2(6),4-dien-4-ylcarbamoyl)-benzyl]-benzamide;
3,4-dimethoxy-N-[3-(4-piperidin-2-yl-phenylcarbamoyl)-benzyl]-benzamide;
3,4-dimethoxy-N-[3-(4-piperidin-2-yl-phenylcarbamoyl)-benzyl]-benzamide;
3,4-dimethoxy-N-[3-(3-piperidin-3-yl-phenylcarbamoyl)-benzyl]-benzamide;
N-[3-((R)-6-amino-4,5,6,7-tetrahydro-benzothiazol-2-ylcarbamoyl)-benzyl]-3-chloro-4-methoxy-benzamide;
N-[3-((S)-6-amino-4,5,6,7-tetrahydro-benzothiazol-2-ylcarbamoyl)-benzyl]-3-chloro-4-methoxy-benzamide;
N-[3-((R)-6-amino-4,5,6,7-tetrahydro-benzothiazol-2-ylcarbamoyl)-benzyl]-4-methoxy-3-methyl-benzamide;
N-[3-((S)-6-amino-4,5,6,7-tetrahydro-benzothiazol-2-ylcarbamoyl)-benzyl]-4-methoxy-3-methyl-benzamide;
3,4-dimethoxy-N-{3-[5-(2-morpholin-4-yl-ethyl)-[1,3,4]thiadiazol-2-ylcarbamoyl]-benzyl}-benzamide;
3-chloro-4-methoxy-N-{3-[4-(2-pyrrolidin-1-yl-ethyl)-phenylcarbamoyl]-benzyl}-benzamide;
4-methoxy-3-methyl-N-{3-[4-(2-pyrrolidin-1-yl-ethyl)-phenylcarbamoyl]-benzyl}-benzamide;
N-[3-((R)-2-amino-4,5,6,7-tetrahydro-benzothiazol-6-ylcarbamoyl)-benzyl]-4-methoxy-3-methyl-benzamide;
3,4-dimethoxy-N-{3-[4-(2-morpholin-4-yl-ethoxy)-phenylcarbamoyl]-benzyl}-benzamide;
3,4-dimethoxy-N-[3-(3-pyrazol-1-ylmethyl-phenylcarbamoyl)-benzyl]-benzamide;
3,4-dimethoxy-N-{3-[4-(5-methyl-4H-[1,2,4]triazol-3-ylmethyl)-phenylcarbamoyl]-benzyl}-benzamide;
N-[3-((S)-6-dimethylamino-4,5,6,7-tetrahydro-benzothiazol-2-ylcarbamoyl)-benzyl]-3,4-dimethoxy-benzamide;
N-[3-((R)-6-dimethylamino-4,5,6,7-tetrahydro-benzothiazol-2-ylcarbamoyl)-benzyl]-3,4-dimethoxy-benzamide;
3,4-dimethoxy-N-[3-((S)-6-morpholin-4-yl-4,5,6,7-tetrahydro-benzothiazol-2-ylcarbamoyl)-benzyl]-benzamide;
3,4-dimethoxy-N-[3-((R)-6-morpholin-4-yl-4,5,6,7-tetrahydro-benzothiazol-2-ylcarbamoyl)-benzyl]-benzamide;
3-chloro-4-methoxy-N-[3-((S)-6-propylamino-4,5,6,7-tetrahydro-benzothiazol-2-ylcarbamoyl)-benzyl]-benzamide;
4-methoxy-3-methyl-N-[3-((S)-6-propylamino-4,5,6,7-tetrahydro-benzothiazol-2-ylcarbamoyl)-benzyl]-benzamide;
3-chloro-N-[3-((S)-6-dimethylamino-4,5,6,7-tetrahydro-benzothiazol-2-ylcarbamoyl)-benzyl]-4-methoxy-benzamide;
3-chloro-N-[3-((R)-6-dimethylamino-4,5,6,7-tetrahydro-benzothiazol-2-ylcarbamoyl)-benzyl]-4-methoxy-benzamide;
N-[3-((S)-6-dimethylamino-4,5,6,7-tetrahydro-benzothiazol-2-ylcarbamoyl)-benzyl]-4-methoxy-3-methyl-benzamide;
N-[3-((R)-6-dimethylamino-4,5,6,7-tetrahydro-benzothiazol-2-ylcarbamoyl)-benzyl]-4-methoxy-3-methyl-benzamide;
N-[3-((S)-2-amino-4,5,6,7-tetrahydro-benzothiazol-6-ylcarbamoyl)-benzyl]-3,4-dimethoxy-benzamide;
N-{3-[(S)-6-(1,3-dihydro-isoindol-2-yl)-4,5,6,7-tetrahydro-benzothiazol-2-ylcarbamoyl]-benzyl}-3,4-dimethoxy-benzamide;
N-{3-[(S)-6-(1,1-dioxo-thiomorpholin-4-yl)-4,5,6,7-tetrahydro-benzothiazol-2-ylcarbamoyl]-benzyl}-3,4-dimethoxy-benzamide;
N-[3-(2-amino-indan-5-ylcarbamoyl)-benzyl]-3,4-dimethoxy-benzamide;

3-chloro-4-methoxy-N-[3-((S)-6-morpholin-4-yl-4,5,6,7-tetrahydro-benzothiazol-2ylcarbamoyl)-benzyl]-benzamide;
4-methoxy-3-methyl-N-[3-((S)-6-morpholin-4-yl-4,5,6,7-tetrahydro-benzothiazol-2ylcarbamoyl)-benzyl]-benzamide;
3-chloro-4-methoxy-N-{3-[(2-methoxy-ethyl)-((S)-6-propylamino-4,5,6,7-tetrahydro-benzothiazol-2-yl)-carbamoyl]-benzyl}-benzamide;
N-{3-[(S)-6-(benzyl-propyl-amino)-4,5,6,7-tetrahydro-benzothiazol-2-ylcarbamoyl]-benzyl}-3-chloro-4-methoxy-benzamide;
3,4-dimethoxy-N-{3-[5-(2-morpholin-4-yl-ethyl)-thiazol-2-ylcarbamoyl]-benzyl}-benzamide;
3,4-dimethoxy-N-[3-(5-morpholin-4-ylmethyl-thiazol-2-ylcarbamoyl)-benzyl]-benzamide;
3,4-dimethoxy-N-(3-{5-[2-(4-methyl-piperazin-1-yl)-ethyl]-thiazol-2-ylcarbamoyl}-benzyl)-benzamide;
2-bromo-4,5-dimethoxy-N-[3-(2-methyl-1,2,3,4-tetrahydro-isoquinolin-7-ylcarbamoyl)-benzyl]-benzamide;
2-hydroxy-3,4-dimethoxy-N-[3-(2-methyl-1,2,3,4-tetrahydro-isoquinolin-7-ylcarbamoyl)-benzyl]-benzamide;
3-chloro-4-ethyl-N-[3-(2-methyl-1,2,3,4-tetrahydro-isoquinolin-7-ylcarbamoyl)-benzyl]-benzamide;
2,4,5-trimethoxy-N-[3-(2-methyl-1,2,3,4-tetrahydro-isoquinolin-7-ylcarbamoyl)-benzyl]-benzamide;
3-[1-benzyl-3-(4-cyano-phenyl)-ureidomethyl]-N-(5-methyl-4,5,6,7-tetrahydro-thiazolo[5,4-c]pyridin-2-yl)-benzamide;
3,4-dimethoxy-N-[3-(2-morpholin-4-yl-indan-5-ylcarbamoyl)-benzyl]-benzamide;
3-[1-benzyl-3-(3-cyano-phenyl)-ureidomethyl]-N-(5-methyl-4,5,6,7-tetrahydro-thiazolo[5,4-c]pyridin-2-yl)-benzamide;
N-benzyl-3,4-dimethoxy-N-[3-(5-methyl-4,5,6,7-tetrahydro-thiazolo[5,4-c]pyridin-2-ylcarbamoyl)-benzyl]-benzamide;
3-[3-(3-ethynyl-phenyl)-ureidomethyl]-N-(5-methyl-4,5,6,7-tetrahydro-thiazolo[5,4-c]pyridin-2-yl)-benzamide;
N-{3-[4-(2-Dimethylamino-ethyl)-phenylcarbamoyl]-benzyl}-3,4-dimethoxy-benzamide;
3-[3-(4-Cyano-phenyl)-ureidomethyl]-N-[4-(2-dimethylamino-ethyl)-phenyl]-benzamide; and
3-[3-(4-carboxamide-phenyl)-ureidomethyl]-N-[4-(2-dimethylamino-ethyl)-phenyl]-benzamide;
or a tautomer or a salt of any of the above compounds.

7. The compound according to claim 6 selected from:
3-[3-(4-cyano-phenyl)-ureidomethyl]-N-(1,2,3,4-tetrahydro-isoquinolin-7-yl)-benzamide;
3-[3-(4-cyano-phenyl)-ureidomethyl]-N-(2-piperidin-4-yl-ethyl)-benzamide;
3-[3-(4-cyano-phenyl)-ureidomethyl]-N-(2-piperidin-3-yl-ethyl)-benzamide;
3-[3-(3-cyano-phenyl)-ureidomethyl]-N-(2-piperidin-3-yl-ethyl)-benzamide;
3-[3-(3,4-dimethoxy-phenyl)-ureidomethyl]-N-(2-piperidin-3-yl-ethyl)-benzamide;
3-[3-(3,4-dimethoxy-phenyl)-ureidomethyl]-N-piperidin-3-ylmethyl-benzamide;
3-[3-(4-cyano-phenyl)-ureidomethyl]-N-(4-dimethylamino-butyl)-benzamide;
3-[3-(4-cyano-phenyl)-ureidomethyl]-N-(3-dimethylamino-propyl)-benzamide;
3-[3-(4-cyano-phenyl)-ureidomethyl]-N-(5-dimethylamino-pentyl)-benzamide;
3-[3-(4-amido-phenyl)-ureidomethyl]-N-(1,2,3,4-tetrahydro-isoquinolin-7-yl)-benzamide;
2-methyl-1,2,3,4-tetrahydro-isoquinoline-7-carboxylic acid {3-[3-(4-amido-phenyl)-ureidomethyl]-phenyl}-amide;
2-methyl-1,2,3,4-tetrahydro-isoquinoline-7-carboxylic acid {3-[3-(4-cyano-phenyl)-ureidomethyl]-phenyl}-amide;
N-{3-[3-(4-cyano-phenyl)-ureidomethyl]-phenyl}-3-piperidin-3-yl-propionamide;
3,4-dimethoxy-N-[3-(2-piperidin-3-yl-ethylcarbamoyl)-benzyl]-benzamide;
3,4-dimethoxy-N-[3-(1,2,3,4-tetrahydro-isoquinolin-7-ylcarbamoyl)-benzyl]-benzamide;
3,4-dimethoxy-N-{3-[(piperidin-4-ylmethyl)-carbamoyl]-benzyl}-benzamide;
3,4-dimethoxy-N-[3-(2-piperidin-4-yl-ethylcarbamoyl)-benzyl]-benzamide;
3,4-dimethoxy-N-{3-[2-(1-methyl-piperidin-3-yl)-ethylcarbamoyl]-benzyl}-benzamide;
3,4-dimethoxy-N-[3-(2-methyl-1,2,3,4-tetrahydro-isoquinolin-7-ylcarbamoyl)-benzyl]-benzamide;
N-{3-[2-(2,2-dimethyl-propyl)-1,2,3,4-tetrahydro-isoquinolin-7-ylcarbamoyl]-benzyl}-3,4-dimethoxy-benzamide;
N-[3-(5-dimethylamino-pentylcarbamoyl)-benzyl]-3,4-dimethoxy-benzamide;
N-[3-(6-dimethylamino-hexylcarbamoyl)-benzyl]-3,4-dimethoxy-benzamide;
N-[3-(4-dimethylamino-butylcarbamoyl)-benzyl]-3,4-dimethoxy-benzamide;
N-[3-(3-dimethylamino-propylcarbamoyl)-benzyl]-3,4-dimethoxy-benzamide;
3,4-dimethoxy-N-[3-(3-piperidin-3-yl-propionylamino)-benzyl]-benzamide;
2-methyl-1,2,3,4-tetrahydro-isoquinoline-6-carboxylic acid {3-[(3,4-dimethoxy-benzoylamino)-methyl]-phenyl}-amide;
2-methyl-1,2,3,4-tetrahydro-isoquinoline-7-carboxylic acid {3-[(3,4-dimethoxy-benzoylamino)-methyl]-phenyl}-amide;
N-{3-[(3,4-dimethoxy-phenylcarbamoyl)-methyl]-phenyl}-3-piperidin-3-yl-propionamide;
1,2,3,4-tetrahydro-isoquinoline-7-carboxylic acid {3-[(3,4-dimethoxy-phenylcarbamoyl)-methyl]-phenyl}-amide;
2-methyl-1,2,3,4-tetrahydro-isoquinoline-7-carboxylic acid {3-[(3,4-dimethoxy-phenylcarbamoyl)-methyl]-phenyl}-amide;
N-(3,4-dimethoxy-phenyl)-3-[3-(3-piperidin-3-yl-propionylamino)-phenyl]-propionamide
N-(4-cyano-phenyl)-3-[3-(3-piperidin-3-yl-propionylamino)-phenyl]-propionamide;
1,2,3,4-tetrahydro-isoquinoline-7-carboxylic acid {3-[2-(4-cyano-phenylcarbamoyl)-ethyl]-phenyl}-amide;
3,4-dimethoxy-N-[3-(1-methyl-piperidin-4-ylcarbamoyl)-benzyl]-benzamide;
N-[3-(2-benzyl-1,2,3,4-tetrahydro-isoquinolin-7-ylcarbamoyl)-benzyl]-3,4-dimethoxy-benzamide;
N-{3-[2-(2-fluoro-benzyl)-1,2,3,4-tetrahydro-isoquinolin-7-ylcarbamoyl]-benzyl}-3,4-dimethoxy-benzamide;
N-{3-[2-(3-fluoro-benzyl)-1,2,3,4-tetrahydro-isoquinolin-7-ylcarbamoyl]-benzyl}-3,4-dimethoxy-benzamide;

N-{3-[2-(4-fluoro-benzyl)-1,2,3,4-tetrahydro-isoquinolin-7-ylcarbamoyl]-benzyl}-3,4-dimethoxy-benzamide;

N-{3-[2-(2,6-difluoro-benzyl)-1,2,3,4-tetrahydro-isoquinolin-7-ylcarbamoyl]-benzyl}-3,4-dimethoxy-benzamide;

N-{3-[2-(2,3-difluoro-benzyl)-1,2,3,4-tetrahydro-isoquinolin-7-ylcarbamoyl]-benzyl}-3,4-dimethoxy-benzamide;

N-{3-[2-(2,4-difluoro-benzyl)-1,2,3,4-tetrahydro-isoquinolin-7-ylcarbamoyl]-benzyl}-3,4-dimethoxy-benzamide;

N-{3-[2-(3,5-difluoro-benzyl)-1,2,3,4-tetrahydro-isoquinolin-7-ylcarbamoyl]-benzyl}-3,4-dimethoxy-benzamide;

3,4-dimethoxy-N-[3-(5-methyl-4,5,6,7-tetrahydro-thiazolo[5,4-c]pyridin-2-ylcarbamoyl)-benzyl]-benzamide;

(7-{3-[(3,4-dimethoxy-benzoylamino)-methyl]-benzoylamino}-3,4-dihydro-1H-isoquinolin-2-yl)-acetic acid methyl ester;

N-[3-(2-carbamoylmethyl-1,2,3,4-tetrahydro-isoquinolin-7-ylcarbamoyl)-benzyl]-3,4-dimethoxy-benzamide;

3,4-dimethoxy-N-{3-[2-(2-methoxy-ethyl)-1,2,3,4-tetrahydro-isoquinolin-7-ylcarbamoyl]-benzyl}-benzamide;

N-{3-[2-(2-cyano-ethyl)-1,2,3,4-tetrahydro-isoquinolin-7-ylcarbamoyl]-benzyl}-3,4-dimethoxy-benzamide;

N-{3-[2-(2,2-difluoro-ethyl)-1,2,3,4-tetrahydro-isoquinolin-7-ylcarbamoyl]-benzyl}-3,4-dimethoxy-benzamide;

3-[3-(4-cyano-phenyl)-ureidomethyl]-N-(5-methyl-4,5,6,7-tetrahydro-thiazolo[5,4-c]pyridin-2-yl)-benzamide;

3-chloro-4-methoxy-N-[3-(2-methyl-1,2,3,4-tetrahydro-isoquinolin-7-ylcarbamoyl)-benzyl]-benzamide;

4-methoxy-3-methyl-N-[3-(2-methyl-1,2,3,4-tetrahydro-isoquinolin-7-ylcarbamoyl)-benzyl]-benzamide;

4-trifluoromethoxy-N-[3-(2-methyl-1,2,3,4-tetrahydro-isoquinolin-7-ylcarbamoyl)-benzyl]-benzamide;

3-chloro-N-[3-(2-methyl-1,2,3,4-tetrahydro-isoquinolin-7-ylcarbamoyl)-benzyl]-4-trifluoromethoxy-benzamide;

4-difluoromethoxy-N-[3-(2-methyl-1,2,3,4-tetrahydro-isoquinolin-7-ylcarbamoyl)-benzyl]-benzamide;

3-chloro-4-ethoxy-N-[3-(2-methyl-1,2,3,4-tetrahydro-isoquinolin-7-ylcarbamoyl)-benzyl]-benzamide;

5-chloro-6-methoxy-N-[3-(2-methyl-1,2,3,4-tetrahydro-isoquinolin-7-ylcarbamoyl)-benzyl]-nicotinamide;

3,4-diethoxy-N-[3-(2-methyl-1,2,3,4-tetrahydro-isoquinolin-7-ylcarbamoyl)-benzyl]-benzamide;

3-hydroxy-4-methoxy-N-[3-(2-methyl-1,2,3,4-tetrahydro-isoquinolin-7-ylcarbamoyl)-benzyl]-benzamide;

6-hydroxy-N-[3-(2-methyl-1,2,3,4-tetrahydro-isoquinolin-7-ylcarbamoyl)-benzyl]-nicotinamide;

N-[3-(2-ethyl-1,2,3,4-tetrahydro-isoquinolin-7-ylcarbamoyl)-benzyl]-3,4-dimethoxy-benzamide;

3-chloro-4-methoxy-N-[3-(5-methyl-4,5,6,7-tetrahydro-thiazolo[5,4-c]pyridin-2-ylcarbamoyl)-benzyl]-benzamide;

4-methoxy-3-methyl-N-[3-(5-methyl-4,5,6,7-tetrahydro-thiazolo[5,4-c]pyridin-2-ylcarbamoyl)-benzyl]-benzamide;

3-chloro-N-[3-(5-methyl-4,5,6,7-tetrahydro-thiazolo[5,4-c]pyridin-2-ylcarbamoyl)-benzyl]-4-trifluoromethoxy-benzamide;

6-methoxy-N-[3-(2-methyl-1,2,3,4-tetrahydro-isoquinolin-7-ylcarbamoyl)-benzyl]-nicotinamide;

1-methyl-6-oxo-1,6-dihydro-pyridine-3-carboxylic acid 3-(2-methyl-1,2,3,4-tetrahydro-isoquinolin-7-ylcarbamoyl)-benzylamide;

4-difluoromethoxy-3-ethoxy-N-[3-(2-methyl-1,2,3,4-tetrahydro-isoquinolin-7-ylcarbamoyl)-benzyl]-benzamide;

N-[3-(5-benzyl-4,5,6,7-tetrahydro-thiazolo[5,4-c]pyridin-2-ylcarbamoyl)-benzyl]-3,4-dimethoxy-benzamide;

N-{3-[2-(2-cyano-benzyl)-1,2,3,4-tetrahydro-isoquinolin-7-ylcarbamoyl]-benzyl}-3,4-dimethoxy-benzamide;

3,4-dimethoxy-N-{3-[2-(2,2,2-trifluoro-ethyl)-1,2,3,4-tetrahydro-isoquinolin-7-ylcarbamoyl]-benzyl}-benzamide;

3,4-dimethoxy-N-{3-[2-(2-nitro-benzyl)-1,2,3,4-tetrahydro-isoquinolin-7-ylcarbamoyl]-benzyl}-benzamide;

3,4-dimethoxy-N-{3-[2-(2-trifluoromethyl-benzyl)-1,2,3,4-tetrahydro-isoquinolin-7-ylcarbamoyl]-benzyl}-benzamide;

3,4-dimethoxy-N-[3-(2-pyridin-3-ylmethyl-1,2,3,4-tetrahydro-isoquinolin-7-ylcarbamoyl)-benzyl]-benzamide;

3,4-dimethoxy-N-{3-[2-(3,3,3-trifluoro-propyl)-1,2,3,4-tetrahydro-isoquinolin-7-ylcarbamoyl]-benzyl}-benzamide;

3,4-dimethoxy-N-[3-(2-pyridin-4-ylmethyl-1,2,3,4-tetrahydro-isoquinolin-7-ylcarbamoyl)-benzyl]-benzamide;

3,4-dimethoxy-N-[3-(2-pyridin-2-ylmethyl-1,2,3,4-tetrahydro-isoquinolin-7-ylcarbamoyl)-benzyl]-benzamide;

N-{3-[2-(2-fluoro-ethyl)-1,2,3,4-tetrahydro-isoquinolin-7-ylcarbamoyl]-benzyl}-3,4-dimethoxy-benzamide;

3-ethoxy-4-methoxy-N-[3-(2-methyl-1,2,3,4-tetrahydro-isoquinolin-7-ylcarbamoyl)-benzyl]-benzamide;

4-difluoromethoxy-3-methoxy-N-[3-(2-methyl-1,2,3,4-tetrahydro-isoquinolin-7-ylcarbamoyl)-benzyl]-benzamide;

3-fluoro-4-methoxy-N-[3-(2-methyl-1,2,3,4-tetrahydro-isoquinolin-7-ylcarbamoyl)-benzyl]-benzamide;

4-methoxy-N-[3-(2-methyl-1,2,3,4-tetrahydro-isoquinolin-7-ylcarbamoyl)-benzyl]-benzamide;

N-[3-(2,3-dihydro-1H-isoindol-5-ylcarbamoyl)-benzyl]-3,4-dimethoxy-benzamide;

3,4-dimethoxy-N-[3-(4,5,6,7-tetrahydro-thiazolo[5,4-c]pyridin-2-ylcarbamoyl)-benzyl]-benzamide;

3,4-dimethoxy-N-{3-[5-(3,3,3-trifluoro-propyl)-4,5,6,7-tetrahydro-thiazolo[5,4-c]pyridin-2-ylcarbamoyl]-benzyl}-benzamide;

3,4-dimethoxy-N-{3-[5-(2-methoxy-ethyl)-4,5,6,7-tetrahydro-thiazolo[5,4-c]pyridin-2-ylcarbamoyl]-benzyl}-benzamide;

N-{3-[5-(2,2-difluoro-ethyl)-4,5,6,7-tetrahydro-thiazolo[5,4-c]pyridin-2-ylcarbamoyl]-benzyl}-3,4-dimethoxy-benzamide;

N-{3-[5-(2-fluoro-ethyl)-4,5,6,7-tetrahydro-thiazolo[5,4-c]pyridin-2-ylcarbamoyl]-benzyl}-3,4dimethoxy-benzamide;

3-chloro-N-[3-(2,3-dihydro-1H-isoindol-5-ylcarbamoyl)-benzyl]-4-methoxy-benzamide;

3-chloro-4-methoxy-N-[3-(4,5,6,7-tetrahydro-thiazolo[5,4-c]pyridin-2-ylcarbamoyl)-benzyl]benzamide;

N-[3-(2,3-dihydro-1H-isoindol-5-ylcarbamoyl)-benzyl]-4-methoxy-3-methyl-benzamide;

4-methoxy-3-methyl-N-[3-(4,5,6,7-tetrahydro-thiazolo[5,4-c]pyridin-2-ylcarbamoyl)-benzyl]-benzamide;
4,5,6,7-tetrahydro-thiazolo[5,4-c]pyridine-2-carboxylic acid {3-[(3,4-dimethoxy-benzoylamino)methyl]-phenyl}-amide;
5-methyl-4,5,6,7-tetrahydro-thiazolo[5,4-c]pyridine-2-carboxylic acid {3-[(3,4-dimethoxy-benzoylamino)-methyl]-phenyl}-amide;
N-[3-((R)-6-amino-4,5,6,7-tetrahydro-benzothiazol-2-ylcarbamoyl)-benzyl]-3,4-dimethoxy-benzamide;
N-[3-((S)-6-amino-4,5,6,7-tetrahydro-benzothiazol-2-ylcarbamoyl)-benzyl]-3,4-dimethoxy-benzamide;
3,4-dimethoxy-N-[3-((S)-6-propylamino-4,5,6,7-tetrahydro-benzothiazol-2-ylcarbamoyl)-benzyl]-benzamide;
4-methylcyano-N-[3-(2-methyl-1,2,3,4-tetrahydro-isoquinolin-7-ylcarbamoyl)-benzyl]-benzamide;
N-[3-((R)-6-amino-4,5,6,7-tetrahydro-benzothiazol-2-ylcarbamoyl)-benzyl]-3-chloro-4-methoxy-benzamide;
N-[3-((S)-6-amino-4,5,6,7-tetrahydro-benzothiazol-2-ylcarbamoyl)-benzyl]-3-chloro-4-methoxy-benzamide;
N-[3-((R)-6-amino-4,5,6,7-tetrahydro-benzothiazol-2-ylcarbamoyl)-benzyl]-4-methoxy-3-methyl-benzamide;
N-[3-((S)-6-amino-4,5,6,7-tetrahydro-benzothiazol-2-ylcarbamoyl)-benzyl]-4-methoxy-3-methyl-benzamide;
N-[3-((S)-6-dimethylamino-4,5,6,7-tetrahydro-benzothiazol-2-ylcarbamoyl)-benzyl]-3,4-dimethoxy-benzamide;
N-[3-((R)-6-dimethylamino-4,5,6,7-tetrahydro-benzothiazol-2-ylcarbamoyl)-benzyl]-3,4-dimethoxy-benzamide;
3,4-dimethoxy-N-[3-((S)-6-morpholin-4-yl-4,5,6,7-tetrahydro-benzothiazol-2-ylcarbamoyl)-benzyl]-benzamide;
3,4-dimethoxy-N-[3-((R)-6-morpholin-4-yl-4,5,6,7-tetrahydro-benzothiazol-2-ylcarbamoyl)-benzyl]-benzamide;
3-chloro-4-methoxy-N-[3-((S)-6-propylamino-4,5,6,7-tetrahydro-benzothiazol-2-ylcarbamoyl)benzyl]-benzamide;
4-methoxy-3-methyl-N-[3-((S)-6-propylamino-4,5,6,7-tetrahydro-benzothiazol-2-ylcarbamoyl)benzyl]-benzamide;
3-chloro-N-[3-((S)-6-dimethylamino-4,5,6,7-tetrahydro-benzothiazol-2-ylcarbamoyl)-benzyl]-4-methoxy-benzamide;
3-chloro-N-[3-((R)-6-dimethylamino-4,5,6,7-tetrahydro-benzothiazol-2-ylcarbamoyl)-benzyl]-4-methoxy-benzamide;
N-[3-((S)-6-dimethylamino-4,5,6,7-tetrahydro-benzothiazol-2-ylcarbamoyl)-benzyl]-4-methoxy3-methyl-benzamide;
N-[3-((R)-6-dimethylamino-4,5,6,7-tetrahydro-benzothiazol-2-ylcarbamoyl)-benzyl]-4-methoxy3-methyl-benzamide;
N-{3-[(S)-6-(1,3-dihydro-isoindol-2-yl)-4,5,6,7-tetrahydro-benzothiazol-2-ylcarbamoyl]benzyl}-3,4-dimethoxy-benzamide;
N-{3-[(S)-6-(1,1-dioxo-thiomorpholin-4-yl)-4,5,6,7-tetrahydro-benzothiazol-2-ylcarbamoyl]benzyl}-3,4-dimethoxy-benzamide;
N-[3-(2-amino-indan-5-ylcarbamoyl)-benzyl]-3,4-dimethoxy-benzamide;
3-chloro-4-methoxy-N-[3-((S)-6-morpholin-4-yl-4,5,6,7-tetrahydro-benzothiazol-2-ylcarbamoyl)-benzyl]-benzamide;
4-methoxy-3-methyl-N-[3-((S)-6-morpholin-4-yl-4,5,6,7-tetrahydro-benzothiazol-2-ylcarbamoyl)-benzyl]-benzamide;
3-chloro-4-methoxy-N-{3-[(2-methoxy-ethyl)-((S)-6-propylamino-4,5,6,7-tetrahydro-benzothiazol-2-yl)-carbamoyl]-benzyl}-benzamide;
N-{3-[(S)-6-(benzyl-propyl-amino)-4,5,6,7-tetrahydro-benzothiazol-2-ylcarbamoyl]-benzyl}-3chloro-4-methoxy-benzamide;
2-bromo-4,5-dimethoxy-N-[3-(2-methyl-1,2,3,4-tetrahydro-isoquinolin-7-ylcarbamoyl)-benzyl]-benzamide;
2-hydroxy-3,4-dimethoxy-N-[3-(2-methyl-1,2,3,4-tetrahydro-isoquinolin-7-ylcarbamoyl)benzyl]-benzamide;
3-chloro-4-ethyl-N-[3-(2-methyl-1,2,3,4-tetrahydro-isoquinolin-7-ylcarbamoyl)-benzyl]-benzamide;
2,4,5-trimethoxy-N-[3-(2-methyl-1,2,3,4-tetrahydro-isoquinolin-7-ylcarbamoyl)-benzyl]-benzamide;
3-[1-benzyl-3-(4-cyano-phenyl)-ureidomethyl]-N-(5-methyl-4,5,6,7-tetrahydro-thiazolo[5,4-c]pyridin-2-yl)-benzamide;
3,4-dimethoxy-N-[3-(2-morpholin-4-yl-indan-5-ylcarbamoyl)-benzyl]-benzamide;
3-[1-benzyl-3-(3-cyano-phenyl)-ureidomethyl]-N-(5-methyl-4,5,6,7-tetrahydro-thiazolo[5,4c]-pyridin-2-yl)-benzamide;
N-benzyl-3,4-dimethoxy-N-[3-(5-methyl-4,5,6,7-tetrahydro-thiazolo[5,4-c]pyridin-2-ylcarbamoyl)-benzyl]-benzamide; and
3-[3-(3-ethynyl-phenyl)-ureidomethyl]-N-(5-methyl-4,5,6,7-tetrahydro-thiazolo[5,4-c]pyridin-2-yl)-benzamide;
or a tautomer or a salt of any of the above compounds.

8. The compound according to claim 6 selected from:
N-[3-((R)-6-amino-4,5,6,7-tetrahydro-benzothiazol-2-ylcarbamoyl)-benzyl]-3,4-dimethoxy-benzamide;
N-[3-((S)-6-amino-4,5,6,7-tetrahydro-benzothiazol-2-ylcarbamoyl)-benzyl]-3,4-dimethoxy-benzamide;
3,4-dimethoxy-N-[3-((S)-6-propylamino-4,5,6,7-tetrahydro-benzothiazol-2-ylcarbamoyl)-benzyl]-benzamide;
N-[3-((R)-6-amino-4,5,6,7-tetrahydro-benzothiazol-2-ylcarbamoyl)-benzyl]-3-chloro-4-methoxy-benzamide;
N-[3-((S)-6-amino-4,5,6,7-tetrahydro-benzothiazol-2-ylcarbamoyl)-benzyl]-3-chloro-4-methoxy-benzamide;
N-[3-((R)-6-amino-4,5,6,7-tetrahydro-benzothiazol-2-ylcarbamoyl)-benzyl]-4-methoxy-3-methyl-benzamide;
N-[3-((S)-6-amino-4,5,6,7-tetrahydro-benzothiazol-2-ylcarbamoyl)-benzyl]-4-methoxy-3-methyl-benzamide;
N-[3-((S)-6-dimethylamino-4,5,6,7-tetrahydro-benzothiazol-2-ylcarbamoyl)-benzyl]-3,4-dimethoxy-benzamide;
N-[3-((R)-6-dimethylamino-4,5,6,7-tetrahydro-benzothiazol-2-ylcarbamoyl)-benzyl]-3,4-dimethoxy-benzamide;
3,4-dimethoxy-N-[3-((S)-6-morpholin-4-yl-4,5,6,7-tetrahydro-benzothiazol-2-ylcarbamoyl)-benzyl]-benzamide;
3,4-dimethoxy-N-[3-((R)-6-morpholin-4-yl-4,5,6,7-tetrahydro-benzothiazol-2-ylcarbamoyl)-benzyl]-benzamide;
3-chloro-4-methoxy-N-[3-((S)-6-propylamino-4,5,6,7-tetrahydro-benzothiazol-2-ylcarbamoyl)-benzyl]-benzamide;
4-methoxy-3-methyl-N-[3-((S)-6-propylamino-4,5,6,7-tetrahydro-benzothiazol-2-ylcarbamoyl)-benzyl]-benzamide;

3-chloro-N-[3-((S)-6-dimethylamino-4,5,6,7-tetrahydro-benzothiazol-2-ylcarbamoyl)-benzyl]-4-methoxy-benzamide;

3-chloro-N-[3-((R)-6-dimethylamino-4,5,6,7-tetrahydro-benzothiazol-2-ylcarbamoyl)-benzyl]-4-methoxy-benzamide;

N-[3-((S)-6-dimethylamino-4,5,6,7-tetrahydro-benzothiazol-2-ylcarbamoyl)-benzyl]-4-methoxy-3-methyl-benzamide;

N-[3-((R)-6-dimethylamino-4,5,6,7-tetrahydro-benzothiazol-2-ylcarbamoyl)-benzyl]-4-methoxy-3-methyl-benzamide;

N-{3-[(S)-6-(1,3-dihydro-isoindol-2-yl)-4,5,6,7-tetrahydro-benzothiazol-2-ylcarbamoyl]-benzyl}-3,4-dimethoxy-benzamide;

N-{3[-(S)-6-(1,1-dioxo-thiomorpholin-4-yl)-4,5,6,7-tetrahydro-benzothiazol-2-ylcarbamoyl]-benzyl}-3,4-dimethoxy-benzamide;

3-chloro-4-methoxy-N-[3-((S)-6-morpholin-4-yl-4,5,6,7-tetrahydro-benzothiazol-2-ylcarbamoyl)-benzyl]-benzamide;

4-methoxy-3-methyl-N-[3-(S)-6-morpholin-4-yl-4,5,6,7-tetrahydro-benzothiazol-2-ylcarbamoyl)-benzyl]-benzamide; and N-{3-[(S)-6-(benzyl-propyl-amino)-4,5,6,7-tetrahydro-benzothiazol-2-ylcarbamoyl]-benzyl}-3-chloro-4-methoxy-benzamide;

or a tautomer or a salt of any of the above compounds.

9. A method of treating a cardiovascular disease or condition in an individual, comprising administering to the individual an effective amount of a compound as recited in claim 1.

10. The method of claim 9, wherein the cardiovascular disease or condition is selected from the group consisting of hypertension, atherosclerosis, restenosis, stroke, heart failure, coronary vasospasm, cerebral vasospasm, ischemia/reperfusion injury, pulmonary hypertension, angina, myocardial infarction, peripheral artery disease, and coronary artery disease, and combinations thereof.

11. A pharmaceutical composition comprising an effective amount of a compound according to claim 1, or a tautomer or a salt thereof, and a pharmaceutically acceptable excipient or carrier.

* * * * *